(12) United States Patent
Dimarchi et al.

(10) Patent No.: US 8,980,830 B2
(45) Date of Patent: Mar. 17, 2015

(54) PEPTIDE COMPOUNDS EXHIBITING GLUCAGON ANTAGONIST AND GLP-1 AGONIST ACTIVITY

(75) Inventors: Richard D. Dimarchi, Carmel, IN (US); Bin Yang, Bloomington, IN (US); Chenguang Ouyang, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 501 days.

(21) Appl. No.: 12/740,206

(22) PCT Filed: Oct. 27, 2008

(86) PCT No.: PCT/US2008/081333
§ 371 (c)(1),
(2), (4) Date: Apr. 28, 2010

(87) PCT Pub. No.: WO2009/058734
PCT Pub. Date: May 7, 2009

(65) Prior Publication Data
US 2011/0098217 A1    Apr. 28, 2011

Related U.S. Application Data

(60) Provisional application No. 60/983,766, filed on Oct. 30, 2007, provisional application No. 61/090,441, filed on Aug. 20, 2008.

(51) Int. Cl.
*C07K 14/605* (2006.01)
*C07K 7/02* (2006.01)
*A61K 38/26* (2006.01)
(Continued)

(52) U.S. Cl.
CPC ............... *C07K 14/605* (2013.01); *A61K 38/16* (2013.01); *C07K 7/02* (2013.01); *A61K 38/22* (2013.01); *A61K 38/26* (2013.01); *A61K 38/00* (2013.01)
USPC ............ 514/6.9; 514/4.9; 514/21.3; 530/326; 530/324; 530/323; 530/308

(58) Field of Classification Search
None
See application file for complete search history.

(56) References Cited

U.S. PATENT DOCUMENTS

| 4,275,152 A | 6/1981 | Esders et al. |
| 5,359,030 A | 10/1994 | Ekwuribe |

(Continued)

FOREIGN PATENT DOCUMENTS

| CA | 2024855 | 3/1992 |
| EP | 0220958 | 5/1987 |

(Continued)

OTHER PUBLICATIONS

De, et al., "Investigation of the feasibility of an amide-based prodrug under physiological conditions," Int. J. Pept. Res. Ther., 14, pp. 255-262 (2008).

(Continued)

*Primary Examiner* — Kevin S Orwig
(74) *Attorney, Agent, or Firm* — Barnes & Thornburg LLP

(57) ABSTRACT

Glucagon analogs are disclosed that exhibit both glucagon antagonist and GLP-1 agonist activity. In one embodiment, the glucagon antagonist/GLP-1 agonist comprises a modified amino acid sequence of native glucagon, in which the first one to five N-terminal amino acids of native glucagon is deleted and in which the alpha helix is stabilized.

22 Claims, 15 Drawing Sheets

(51) Int. Cl.
*A61K 38/16* (2006.01)
*A61K 38/22* (2006.01)
*A61P 3/04* (2006.01)
*A61P 3/10* (2006.01)
*A61K 38/00* (2006.01)

(56) References Cited

U.S. PATENT DOCUMENTS

| | | |
|---|---|---|
| 5,510,459 A | 4/1996 | Smith et al. |
| 5,512,549 A | 4/1996 | Chen et al. |
| 5,545,618 A | 8/1996 | Buckley et al. |
| 5,665,705 A | 9/1997 | Merrifield et al. |
| 5,783,674 A | 7/1998 | Geysin et al. |
| 6,191,102 B1 | 2/2001 | DiMarchi et al. |
| 6,583,111 B1 | 6/2003 | DiMarchi et al. |
| 6,677,136 B2 | 1/2004 | Marshall et al. |
| 7,192,922 B2 | 3/2007 | Shannon et al. |
| 7,211,557 B2 | 5/2007 | DiMarchi et al. |
| 7,326,688 B2 | 2/2008 | O'Harte et al. |
| 7,576,059 B2 | 8/2009 | Jonassen et al. |
| 8,053,560 B2 | 11/2011 | Sheffer et al. |
| 2002/0049164 A1 | 4/2002 | Demuth et al. |
| 2003/0021795 A1 | 1/2003 | Houston et al. |
| 2003/0143183 A1 | 7/2003 | Knudsen et al. |
| 2003/0195157 A1 | 10/2003 | Natarajan et al. |
| 2003/0204063 A1 | 10/2003 | Gravel et al. |
| 2004/0002468 A1 | 1/2004 | Wadsworth et al. |
| 2004/0235710 A1 | 11/2004 | DeFilippis et al. |
| 2005/0070469 A1 | 3/2005 | Bloom et al. |
| 2005/0095679 A1 | 5/2005 | Prescott et al. |
| 2005/0124550 A1 | 6/2005 | Peri |
| 2005/0153890 A1 | 7/2005 | Pan et al. |
| 2005/0288248 A1 | 12/2005 | Pan et al. |
| 2006/0003417 A1 | 1/2006 | Pan et al. |
| 2006/0003935 A1 | 1/2006 | Pan et al. |
| 2006/0084604 A1 | 4/2006 | Kitaura et al. |
| 2006/0171920 A1 | 8/2006 | Shechter et al. |
| 2006/0210534 A1 | 9/2006 | Lee et al. |
| 2006/0252916 A1 | 11/2006 | DiMarchi et al. |
| 2006/0286129 A1 | 12/2006 | Sarubbi |
| 2007/0042956 A1 | 2/2007 | Johansen et al. |
| 2007/0173452 A1 | 7/2007 | DiMarchi et al. |
| 2007/0203058 A1 | 8/2007 | Lau et al. |
| 2007/0287670 A1 | 12/2007 | Natarajan et al. |
| 2008/0113905 A1 | 5/2008 | DiMarchi et al. |
| 2008/0125574 A1 | 5/2008 | Sheffer et al. |
| 2008/0312157 A1 | 12/2008 | Levy et al. |
| 2008/0318837 A1 | 12/2008 | Quay et al. |
| 2009/0036364 A1 | 2/2009 | Levy et al. |
| 2009/0054305 A1 | 2/2009 | Schlein et al. |
| 2009/0062192 A1 | 3/2009 | Christensen et al. |
| 2009/0074769 A1 | 3/2009 | Glaesner et al. |
| 2009/0137456 A1 | 5/2009 | DiMarchi et al. |
| 2009/0192072 A1 | 7/2009 | Pillutla et al. |
| 2010/0190699 A1 | 7/2010 | DiMarchi et al. |
| 2010/0190701 A1 | 7/2010 | Day et al. |
| 2010/0204105 A1 | 8/2010 | Riber et al. |
| 2011/0065633 A1 | 3/2011 | DiMarchi et al. |
| 2011/0098217 A1 | 4/2011 | DiMarchi et al. |
| 2011/0166062 A1 | 7/2011 | DiMarchi et al. |
| 2011/0190200 A1 | 8/2011 | DiMarchi et al. |
| 2011/0257092 A1 | 10/2011 | DiMarchi et al. |
| 2011/0288003 A1 | 11/2011 | DiMarchi et al. |

FOREIGN PATENT DOCUMENTS

| | | |
|---|---|---|
| EP | 0479210 | 4/1992 |
| EP | 0708179 | 4/1996 |
| EP | 0815135 | 9/1996 |
| EP | 1695983 B1 | 8/2006 |
| EP | 2036539 A1 | 3/2009 |
| EP | 2036923 A1 | 3/2009 |
| EP | 2398483 | 8/2010 |
| EP | 2300035 | 1/2012 |
| JP | 2003/192698 | 7/2003 |
| WO | WO91/11457 | 8/1991 |
| WO | WO96/29342 | 9/1996 |
| WO | WO 9707814 | 3/1997 |
| WO | 97/29180 | 8/1997 |
| WO | WO9746584 | 12/1997 |
| WO | 98/11126 | 3/1998 |
| WO | 98/19698 | 5/1998 |
| WO | WO 9824464 | 6/1998 |
| WO | WO 9946283 | 9/1999 |
| WO | WO99/67278 | 12/1999 |
| WO | WO 0020592 | 4/2000 |
| WO | 00/34331 | 6/2000 |
| WO | WO00/42026 | 7/2000 |
| WO | WO 0058360 | 10/2000 |
| WO | 01/83527 | 11/2001 |
| WO | WO 0181919 | 11/2001 |
| WO | 01/98331 | 12/2001 |
| WO | WO 0210195 | 2/2002 |
| WO | WO0213801 | 2/2002 |
| WO | 02/48183 | 6/2002 |
| WO | WO 02100390 | 12/2002 |
| WO | WO03/011892 | 2/2003 |
| WO | 03/020201 | 3/2003 |
| WO | WO03022304 | 3/2003 |
| WO | WO 03026635 | 4/2003 |
| WO | 03/035099 | 5/2003 |
| WO | WO03/058203 | 7/2003 |
| WO | WO 03082898 | 10/2003 |
| WO | 03/103572 | 12/2003 |
| WO | WO 03103697 | 12/2003 |
| WO | WO 03105760 | 12/2003 |
| WO | WO04000354 | 12/2003 |
| WO | 2004/022004 | 3/2004 |
| WO | WO 2004/067548 | 8/2004 |
| WO | WO 2004078777 | 9/2004 |
| WO | 2004/093823 | 11/2004 |
| WO | 2004/105781 | 12/2004 |
| WO | 2004/105790 | 12/2004 |
| WO | WO 2004103390 | 12/2004 |
| WO | WO 2005082928 | 9/2005 |
| WO | WO 2006086769 | 8/2006 |
| WO | WO 2006121904 | 11/2006 |
| WO | WO2006124529 | 11/2006 |
| WO | WO2006134340 A2 | 12/2006 |
| WO | WO2007/124461 | 1/2007 |
| WO | 2007/022123 | 2/2007 |
| WO | WO 2007028632 | 3/2007 |
| WO | WO2007028633 | 3/2007 |
| WO | WO 2007 056362 | 5/2007 |
| WO | 2007/100535 | 9/2007 |
| WO | WO 2007109354 | 9/2007 |
| WO | WO 2008021560 | 2/2008 |
| WO | WO 2008022015 | 2/2008 |
| WO | WO2008023050 | 2/2008 |
| WO | WO 2008076933 | 6/2008 |
| WO | 2008/086086 | 7/2008 |
| WO | 2008/101017 | 8/2008 |
| WO | WO2009030738 A1 | 3/2009 |
| WO | WO2009030774 A1 | 3/2009 |
| WO | WO2009034117 A1 | 3/2009 |
| WO | WO2009034118 A1 | 3/2009 |
| WO | WO2009034119 A1 | 3/2009 |
| WO | WO2009035540 A2 | 3/2009 |
| WO | 2009/058662 | 5/2009 |
| WO | 2009/058734 | 5/2009 |
| WO | 2009/059278 | 5/2009 |
| WO | 2009/095479 | 8/2009 |
| WO | WO/2009/099763 | 8/2009 |
| WO | 2009/155257 | 12/2009 |
| WO | 2009/155258 | 12/2009 |
| WO | 2010/011439 | 1/2010 |
| WO | 2010/071807 | 6/2010 |
| WO | 2010/080605 | 7/2010 |
| WO | 2010/096052 | 8/2010 |
| WO | 2010/148089 | 12/2010 |
| WO | 2011/075393 | 6/2011 |
| WO | WO 2011087671 | 7/2011 |
| WO | WO 2011087672 | 7/2011 |

(56) References Cited

FOREIGN PATENT DOCUMENTS

| WO | 2011/094337 | 8/2011 |
|---|---|---|
| WO | WO2011119657 | 9/2011 |
| WO | WO2011143208 | 11/2011 |
| WO | WO2011143209 | 11/2011 |
| WO | WO2011163012 | 12/2011 |
| WO | WO2011163473 | 12/2011 |

OTHER PUBLICATIONS

Madsen, et al., "Structure-activity and protraction relationship of long-acting glucagon-like peptide-1 derivatives: Importance of fatty acid length, polarity, and bulkiness," J. Med. Chem., 50, pp. 6126-6132 (2007).
PCT International Search Report for PCT/US2011/041601 completed by the US Searching Authority on Nov. 10, 2011.
Ahn, Jung-Mo et al., "Development of potent truncated glucagon antagonists," Journal of Medicinal Chemistry, vol. 44, No. 9, Apr. 26, 2001, pp. 1372-1379 (abstract).
Ahn, J.M. et al., "A new approach to search for the bioactive conformation of glucagon: positional cyclization scanning," Journal of Medicinal Chemistry, vol. 44, No. 19, Sep. 13, 2001, pp. 3109-3116 (abstract).
Trivedi, Dev et al., "Design and synthesis of conformationally constrained glucagon analogues," Journal of Medicinal Chemistry, vol. 43, No. 9, May 4, 2000, pp. 1714-1722 (abstract).
PCT International Search Report for PCT/US2008/081333 completed by the US Searching Authority on Mar. 12, 2009.
Unson, et al. "Glucagon antagonists: contribution to binding and activity of the amino-terminal sequence 1-5, position 12 and the putative alpha-helical segment 19-27" J. Biol. Chem v264, p. 789-794, Jan. 15, 1989 p. 792, para1, Table 1.
Evans et al., "Effect of β-Endorphin C-Terminal Peptides on Glucose Uptake in Isolated Skeletal Muscles of the Mouse," Peptides, vol. 18, No. 1, pp. 165-167, (1997).
"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.
Chabenne et al., Optimization of the native glucagon sequence for medicinal purposes, J. Diabetes. Sci. Technol., 4(6): 1322-31, Nov. 1, 2010.
Day et al., Charge inversion at position 68 of the glucagon and glucagon-like peptide-1 receptors supports selectivity in hormone action. J. Pept. Sci., 17(3): 218-25, Nov. 30, 2010.
De et al., Synthesis and characterization of ester-based prodrugs of glucagon-like peptide 1, Biopolymers, 94(4): 448-56 (2010).
De, Design of peptide-based prodrug chemistry and its application to glucagon-like peptide 1. Masters Thesis Aug. 2007. [Retrieved from the Internet on Jun. 16, 2009: <https://scholarworks iu.edu/dspace/browse?value=De%2C+ArnabBtype=author>]; p. 8, para 2; p. 16, para 3; p. 40, para 1; p. 66, para 2; p. 77, para 1-2; p. 79, para 1.
Gelfanov, et al., Discover and Structural Optimization of High Affinity Co-Agonists at the Glucagon and GLP-1 Receptors, Understanding Biology Using Peptides, Springer, pp. 763-764, Jun. 23, 2005.
GenBank entry AAH05278. Jul. 15, 2006. [Retrieved from the Internet Jun. 18, 2009: ~http://www._ncbi._nim.n ih.gov/protein/13528972>].
Habegger et al., The metabolic actions of glucagon revisited, Nat. Rev. Endocrinol., 6(12): 689-97, Oct. 19, 2010.
Harris, J. Milton, Final Word: PEGylation—A "Sunset" Technology? <http://licence.icopyright.net/user/viewFreeUse.act?fuid=OTU1NjY3OA%3D%3D>, BioPharm International, Jun. 1, 2004.
Heppner et al., Glucagon regulation of energy metabolism, Physiol Behav., 100(5): 545-8, Apr. 8, 2010.
Hruby et al., "The Design and Biological Activities of Glucagon Agonists and Antagonists, and Their Use in Examining the Mechanisms of Glucose Action," Curr. Med. Chem.-Imm., Endoc. & Metab. Agents, 2001, 1, pp. 199-215.

Jonathan Day et al., "A New Glucagon and GLP-1 Co-Agonist Eliminates Obesity in Rodents," Nature Chemical Biology, vol. 5, No. 10, Oct. 2009, pp. 749-757.
Joshi et al, "Studies on the Mechanism of Aspartic Acid Cleavage and Glutamine Deamidation in the Acidic Degradation of Glucagon," Journal of Pharmaceutical Sciences, vol. 94, No. 9, Sep. 2005, pp. 1912-1927.
Joshi et al., "The Degradation Pathways of Glucagon in Acidic Solutions," International Journal of Pharmaceutics, 203 (2000), pp. 115-125.
Joshi et al., "The Estimation of Glutaminyl Deamidation and Aspartyl Cleavage Rates in Glucagon," International Journal of Pharmaceutics, 273 (2004), pp. 213-219.
Krstenansky et al., "Importance of the C-terminal α-helical structure for glucagon's biological activity," Int. J. Peptide Protein Res., 32, 1988, 468-475.
Lee et al., "Synthesis, Characterization, and Pharmacokinetic Studies of PEGylated Glucagon-like Peptide-1," Bioconjugate Chem., 2005, vol. 16, No. 2, pp. 377-382.
Levy et al., Optimization of the C-terminal Sequence in Glucagon to Maximize Receptor Affinity, Poster Presentation, Jun. 19, 2005.
Levy et al., Optimization of the C-terminal Sequence in Glucagon to Maximize Receptor Affinity, Understanding Biology Using Peptides, American Peptide Society, Apr. 2006.
Li et al., Crystallization and preliminary X-ray analysis of anti-obesity peptide hormone oxyntomodulin, Protein & Peptide Letters, 15(2): 232-4 (2008).
Li et al., Design, synthesis and crystallization of a novel glucagon analog as a therapeutic agent, Acta Crystallogr. Sect. F Struct. Biol. Cryst. Commun., 63(Pt 7):599-601, Jun. 15, 2007.
Li et al., Structural Basis for Enhanced Solublity of a C-Terminally Extended Glucagon Analog, Biopolymers., 96(4): 480 (2011).
M.J. Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.
Marita P. Feldkaemper et al., "Localization and Regulation of Glucagon Receptors in the Chick Eye and Preproglucagon and Glucagon Receptor Expression in the Mouse Eye," Experimental Eye Research, Academic Press Ltd., London, vol. 79, No. 3, Sep. 1, 2004, pp. 321-329.
McKee et al., Receptor Binding and Adenylate Cyclase Activities of Glucagon Analogues Modified in the N-Terminal Region, Biochemistry, 25: 1650-6 (1986).
Nogueiras et al., Direct control of peripheral lipid deposition by CNS GLP-1 receptor signaling is mediated by the sympathetic nervous system and blunted in diet-induced obesity, J. Neurosci., 29(18): 5916-25, May 6, 2009.
Ouyang et al., Discovery of Bi-Functional Peptides Balanced in Glucagon Antagonism & GLP-1 Agonism. A Search for the Molecular Basis in the Inversion of Activity at Homologous Receptors, 71st Scientific sessions of American Diabetes Association 2011—Post-Conference Review and Analysis.
Pan et al., Design of a Long Acting Peptide Functioning as Both a Glucagon-like Peptide-1 Receptor Agonist and a Glucagon Receptor Agonist, J. Biol. Chem., 281(18): 12506-15, Table 1, May 5, 2006.
Patterson et al., A novel human-based receptor antagonist of sustained action reveals body weight control by endogenous GLP-1, ACS Chem Biol., 6(2): 135-45 Nov. 4, 2010.
Patterson et al., Functional association of the N-terminal residues with the central region in glucagon-related peptides, J. Peptide Sci., First published online Jun. 10, 2011.
PCT International Search Report for PCT/US2008/050099 completed by the US Searching Authority on Sep. 1, 2008.
PCT International Search Report for PCT/US2008/053857 completed by the US Searching Authority on Sep. 16, 2008.
PCT International Search Report for PCT/US2008/080973 completed by the US Searching Authority on Jun. 6, 2009.
PCT International Search Report for PCT/US2009/031593 completed by the US Searching Authority on Jun. 18, 2009.
Robberecht, P. et al., "Receptor Occupancy and Adenylate Cyclase Activation in Rat Liver and Heart Membranes by 10 Glucagon Analogs Modified in Position 2, 3, 4, 25, 27 and/or 29," Regulatory Peptides, 21 (1988), 117-128.

(56) References Cited

OTHER PUBLICATIONS

Sapse et al., The Role of Sale Bridge Formation in Glucagon: An Experimental and Theoretical Study of Glucagon Analogs and Peptide Fragments of Glucagon, *Molec. Med.,* 8(5): 251-62, May 1, 2002.

Stigsnaes et al., "Characterisation and Physical Stability of PEGylated Glucagon," *International Journal of Pharmaceutics,* 330 (2007), pp. 87-98.

Traylor et al., Identification of the High Potency Glucagon Agonist with Enhanced Biophysical Stability and Aqueous Solubility, Poster Abstract PY 10, pp. 505-506, Jun. 10, 2005.

Tschoep et al., A Novel Glucagon/GLP-1 Co-Agonist Eliminates Obesity in Rodents, Diabetes, 58 (Supp. 1): A83 (2009).

Unson et al., Positively Charged Residues at Positions 12, 17, and 18 of Glucagon Ensure Maximum Biological Potency, *J. Biol. Chem.,* 273(17): 10308-12 (1998).

Ward et al., In vitro and in vivo evaluation of native glucagon and glucagon analog (MAR-D28) during aging: lack of cytotoxicity and preservation of hyperglycemic effect, J. Diabetes Sci. Technol., 4(6):1311-21, Nov. 1, 2010.

Wynne et al., "Subcutaneous Oxyntomodulin Reduces Body Weight in Overweight and Obese Subjects," *Diabetes,* vol. 54, Aug. 2005, pp. 2390-2395.

Yang et al., Synthesis and Biological Assessment of Sulfonic Acid-Based Glucagon Antagonists, Understanding Biology Using Peptides, American Peptide Symposia, 9(Part 6): 305-6 (2006).

Zhang et al., Design and synthesis of novel GLP1 analogues with significantly prolonged time action, Biopolymers., 80(4): 555 (2005).

Azizeh et al., "Topographical amino acid substitution in position 10 of glucagon leads to antagonists/partial agonists with greater binding differences," J. Med. Chem., vol. 39, No. 13, Jun. 21, 1996, pp. 2449-2455.

Azizeh et al., "Pure glucagon antagonists: biological activities and cAMP accumulation using phosphodiesterase inhibitors," Peptides 1997, vol. 18, No. 5, pp. 633-641.

Phillips et al., "Supramolecular Protein Engineering: Design of Zinc-Stapled Insulin Hexamers as a Long Acting Depot," J. Biol. Chem., vol. 285, No. 16, Apr. 16, 2010, pp. 11755-11759.

Murphy, et al., "Potent Long-Acting Alkylated Analogs of Growth Hormone-Releasing Factor," Pept. Res., vol. 1. No. 1, pp. 36-41 (1988).

Perret et al., "Mutational analysis of the glucagon receptor: similarities with the vasoactive intestinal peptide (VIP)/pituitary adenylate cyclase-activating peptide (PACAP)/secretin receptors for recognition of the ligand's third residue," J. Biochem., 362 (2002), pp. 389-394.

Gysin et al., "Design and Synthesis of Glucagon Partial Agonists and Antagonists," Biochemistry, 25, (1986), pp. 8278-8284.

PCT International Search Report for PCT/US2009/047437 completed by the US Searching Authority on Nov. 3, 2009.

Supplemental European Search Report issued in connection with EP Application No. 09767567.2 issued on Jun. 17, 2011.

Extended EP Search Report completed by the EP Searching Authority on Apr. 6, 2011 in connection with EP Patent Application No. 08845852.6.

DatabaseEMBL, Richard DiMarchi and David Smiley, "Human Glucagon Peptide SEQ ID No. 1," XP002631582, retrieved from EBI, Database Accession No. AGB07042, Abstract, Jul. 16, 2007.

Day et al., "A new glucagon and GLP-1 co-agonist eliminates obesity in rodents", Nature Chemical Biology (2009), 5(10), 749-757.

Day, J.; Patterson, J.; Gelfanov, V. and DiMarchi, Richard Molecularbasis for Specificity in Biological Action at the Homologous Glucagon and GLP-1 Receptors, (2009) Proceedings of the $21^{st}$ American Peptide Society 142-143.

De, A. and DiMarchi, R. Synthesis & Analysis of Peptide Hormone-based prodrugs, (2009) Proceedings of the 21st American Peptide Society 160-161.

De, Arnab; DiMarchi, Richard D. Investigation of the feasibility of an amide-based prodrug under physiological conditions. International Journal of Peptide Research and Therapeutics (2008), 14(4), 393.

De, A. and DiMarchi, R. Synthesis & Characterization of Ester-Based Prodrugs of Glucagon-Like Peptide 1, Peptide Science (2010) 94(4) 448-456.

DiMarchi, Richard, "The Use of Bioproducts in the Treatments of Metabolic Diseases" presentation slides for the Keystone Symposia (Jan. 25, 2009, Banff, Alberta).

Finan, B.; Gelfanov, V. and DiMarchi, R. Assessment of a Tat-Derived Peptide as a Vector for Hormonal Transport, (2009) Proceedings of the 21st American Peptide Society 321-322.

Kukuch, A.; Patterson, J.; DiMarchi, R. and Tolbert, T. Immunoglobulin Fc-based Peptide Fusion Proteins as a Basis for Optimizing In Vivo Pharmacology, (2009) Proceedings of the $21^{st}$ American Peptide Society 177-178.

Ma, T.; Day, J.; Gelfanov, V. and DiMarchi, R. Discovery and Structural Optimization of High Affinity Co-Agonists at the Glucagon and GLP-1 Receptors, (2009) Proceedings of the $21^{st}$ American Peptide Society 146-147.

Ouyang et al., "Synthesis and Characterization of Peptides with Glucagon Antagonism and GLP-1 Agonism," poster presentation at the $21^{st}$ American Peptide Symposium (Jun. 7-12, 2009, Bloomington, IN).

Tschoep et al., "A Novel Glucagon/GLP-1 Co-Agonist Eliminates Obesity in Rodents," American Diabetes Association Abstract No. 313-OR (2009).

Tschoep, Matthias, "A Novel Glucagon/GLP-1 Co-Agonist Eliminates Obesity in Rodents" presentation slides for the 2009 American Diabetes Association meeting (Jun. 5-9, 2009, New Orleans, LA).

Tschoep, Matthias, "Afferent Gut Hormones in the Control of Energy Balance and Metabolism" presentation slides for the 21st American Peptide Symposium (Jun. 7-12, 2009, Bloomington, IN).

Ward, B.; Finan, B.; Gelfanov, V. and DiMarchi, R. Exploring the N-terminal Hydrophobic Faces of Glucagon and Glucagon-like Peptide-1, (2009) Proceedings of the $21^{st}$ American Peptide Society 153-154.

Yang, B. and DiMarchi, R.D. (2005). A Novel Approach to Resin-based Cysteine Alkylation Peptides: Chemistry, Structure and Biology, Proceedings of the XIX American Peptide Symposium, (88-89).

Irwin et al., "Early administration of the glucose-dependent insulinotropic polypeptide receptor antagonist ($Pro^3$) GIP prevents the development of diabetes and related metabolic abnormalities associated with genetically inherited obesity in *ob/ob* mice," Diabetologia 50:1532-1540 (2007).

Kulkarni, "GIP: No Longer the Neglected Incretin Twin?," Science Translational Medicine 2(49): p. 47, Sep. 15, 2010.

Montrose-Rafizadeh et al., "High Potency Antagonists of the Pancreatic Glucagon-like Peptide-1 Receptor," Journal of Biological Chemistry, 272(34) 21201-21206 (1997).

Sturm et al., "Structure-Function Studies on Positions 17, 18, and 21 Replacement Analogues of Glucagon: The Importance of Charged Residues and Salt Bridges in Glucagon Biological Activity," J Med Chem 1998, 41, 2693-2700.

Habi et al., Peptide Science, vol. 80, Issue 4, pp. 608 and 579 (abstracts only), 2005.

Habi, "Special Issue: Program and Abstracts for the 19th American Peptide Symposium, 2005, Abstracts of Poster Section C," (pp. 574-603) Article first published online: Jun. 10, 2005 | DOI: 10.1002/bip.20325.

Blache et al., "Development of an oxyntomodulin/glicentin C-terminal radioimmunoassay using a "thiol-maleoyl" coupling method for preparing the immunogen," Anal Biochem 1988 173(1):151-159 (1988), abstract only.

Vijayalakshmi et al., "Comparison of Helix-Stabilizing Effects of α, α-dialkyl Glycines with Linear and Cycloalkyl Side Chains", *Biopolymers* 53: 84-98 (Jan. 21, 2000).

Andrews et al., "Forming Stable Helical Peptides Using Natural and Artificial Amino Acids", *Tetrahedron* 55: 11711-11743, (1999).

Battersby et al., "Diketopiperazine Formation and N-Terminal Degradation in Recombinant Human Growth Hormone", *International Journal of Peptide & Protein Research* 44: 215-222, (1994).

(56) References Cited

OTHER PUBLICATIONS

Eriksson et al., "hPEPT1 Affinity and Translocation of Selected Gln-Sar and Glu-Sar Dipeptide Derivatives", *Molecular Pharmaceutics* vol. 2, No. 3: 242-249 (May 10, 2005).
Garcia-Aparicio et al., "Design and Discovery of a Novel Dipeptidyl-peptidase IV (CD26)-Based Prodrug Approach", *J. Med. Chem.* 49: 5339-5351 (2006).
Goolcharran et al., "Comparison of the Rates of Deamidation, Diketopiperazine Formation, and Oxidation in Recombinant Human Vascular Endothelial Growth Factor and Model Peptides", *AAPS Pharmsci 2000* 2(1) article 5: 1-6 (Mar. 17, 2000).
Santos et al., Cyclization-Activated Prodrugs. Synthesis, Reactivity and Toxicity of Dipeptide Esters of Paracetamol, *Bioorganic & Medicinal Chemistry Letters* 15: 1595-1598 (2005).
Schafmeister et al., "An All-Hydrocarbon Cross-Linking System for Enhancing the Helicity and Metaboli Stability of Peptides", *J. Am. Chem. Soc.* 122: 5891-5892 (2000).
Walensky et al., "Activation of Apoptosis in Vivo by a Hydrocarbon-Stapled BH3 Helix", *Science* 205: 1466-1470 (Sep. 3, 2004).
Lebl, Michal, "Peptides: Breaking Away: The Proceedings of the Twenty-First American Peptide Symposium", *Prompt Scientific Publishing* (2009).
"Legacy Products—'Back to the Future'," presentation to Eli Lilly and Co., Sep. 22, 2005.
"Application of Chemical Biotechnology to Optimization of Endocrine Hormones," Carothers Lecture, Mar. 22, 2007.
"The Emergence of Chemical Biotechnology & Its Application to Optimization of Endocrine Hormones," UMBC presentation, Mar. 26, 2008.
"Emergence of Chemical Biotechnology," Eli Lilly and Co. presentation, Jun. 22, 2009.
"Novel Glucagon-Like Chimera Peptides—Virtues of Combinatorial Pharmacology," Keystone Conference, Apr. 12-17, 2010, Whistler, B.C.
"Novel Glucagon-Like Chimera Peptides—Virtues of Combinatorial Pharmacology," AAPS May 2010.
"Two for the Money" Gut Hormone Hybrids, Tschoep, ADA meeting, Jun. 25-29, 2010, Orlando, FL.
"Biotechnology—A Basis for Better Health & Economic Prosperity," Ohio State University presentation, Aug. 28, 2010.
"Novel Glucagon-Based Peptides—Virtues of Combinatorial Pharmacology," European Peptide Symposium, Sep. 5-9, 2010, Copenhagen, Denmark.
"Biotechnology—A Basis for Better Health & Economic Prosperity," Indiana University television presentation, Nov. 2010.
"Novel Glucagon-Based Peptides—Virtues of Combinatorial Pharmacology," University of Michigan, Oct. 13, 2010.
"Novel Glucagon-Based Peptides—Virtues of Combinatorial Pharmacology," Yale University, May 13, 2011.
"Speaking From the Gut: From Gastrointestinal Hormones to Combinatorial Therapies," Presentation to American Diabetes Association, Jun. 25, 2011.
"The Pursuit of Transformational Medicines," presentation to American Peptide Symposium, Jun. 25-30, 2011, San Diego, CA.
"The Pursuit of Transformational Medicines," NP2D presentation, Dec. 4, 2011.
"The Pursuit of Transformational Medicines," Keystone presentation, Jan. 29-Feb. 3, 2012, Santa Fe, NM.
"Novel Glucagon Peptides That Demonstrate the Virtues of Combinatorial Pharmacology," University of Toledo, Mar. 22, 2012.
Althage et al.,JBC "Targeted Ablation of GIP-Producing Cells in Transgenic mice reduces obesity and insulin resistance induced by a high fat diet" 2008).
Chia et al., "Exogenous glucose-dependent insulinotropic polypeptide worsens post-prandial hyperglycemia in type 2 diabetes," Diabetes, 58: 1342-1349 (2009).
Drucker, "Glucagon Gene Expression in Vertebrate Brain," The Journal of Biological Chemistry, vol. 263, No. 27, pp. 13475-13478, 1988.
Drucker, "The biology of incretin hormones," Cell Metabolism 3:153-165 (2006).
PCT International Search Report for PCT/US2009/034448 completed by the US Searching Authority on Jun. 4, 2010.
PCT International Search Report for PCT/US2009/068678 completed by the US Searching Authority on May 5, 2010.
Pan et al., "Synthesis of Cetuximab-Immunoliposomes via a Cholesterol-Based Membrane Anchor for Targeting of EGFR," Bioconjugate Chem., 18, pp. 101-108, 2007.
PCT International Search Report for PCT/US2009/047447 completed by the US Searching Authority on Mar. 19, 2010.
Collie et al., "Purification and sequence of rat oxyntomodulin," Proc. Natl. Acad. Sci. USA, vol. 91, pp. 9362-9366, Sep. 1994.
Sueiras-Diaz et al., "Structure-Activity Studies on the N-Terminal Region of Glucagon," J. Med. Chem., 27, pp. 310-315, 1984.
Hjorth et al., "glucagon and Glucagon-like Peptide 1: Selective Receptor Recognition via Distinct Peptide Epitopes," The Journal of Biological Chemistry, vol. 269, No. 48, pp. 30121-30124, Dec. 2, 1994.
Unson et al., "Role of Histidine-1 in Glucagon Action," Archives of Biochemistry and Biophysics, vol. 300, No. 2, pp. 747-750, Feb. 1, 1993.
Sato, H., "Enzymatic procedure for site-specific pegylation of proteins," Advanced Drug Delivery Reviews 54, pp. 487-504 (2002).
"Novel Glucagon-Like Chimera Peptides—Virtues of Combinatorial Pharmacology," University of Cincinnati, Jun. 2010.
"Molecular Miracles," Indiana University, Apr. 13, 2011.
"Novel Glucagon-Based Peptides—Virtues of Combinatorial Pharmacology," Aug. 31, 2011, Berlin.
Ward, "Fatty Acid Acylation of Peptides: Developing strategies to enhance medicines for treating metabolic disorders," Jan. 14, 2009.
DiMarchi, "Peptides—Development of Prodrug Chemistry," RBF Symposium Feb. 1-4, 2011 India.
Tschoep, "CNS Integration of Systems Metabolism: Target Opportunities for Diabetes Prevention and Therapy," RBF Symposium Feb. 1-4, 2011 India.
Yang et al., "Synthesis and Biological Assessment of Sulfonic Acid-Based Glucagon Antagonists," American Peptide Society, 2005.
Yang et al., "A Novel Approach to Resin-Based Cysteine Alkylation," American Peptide Society, 2005.
Yang et al., "Synthesis and Biological Assessment of Sulfonic Acid-Based Glucagon Antagonists," poster presentation to American Peptide Society, 2005.
Yang et al., "A Novel Approach to Resin-Based Cysteine Alkylation," poster presentation to American Peptide Society, 2005.
PCT International Search Report for PCT/US2010/038825 completed by the US Searching Authority on Sep. 15, 2010.
PCT International Search Report for PCT/US2010/059724 completed by the US Searching Authority on Jun. 14, 2011.
Wibowo, Synthesis, Purification , and Biological Activity of AIB Substituted Glucagon and GLP-1 Peptide Analogues (2005-2006) vol. 45, 707=738, accessed https://scholarworks.iu.edu/dspce/handle/2022/326 on Jul. 17, 2012.
O'Brien, Assay for DPPIV Activity using Homogenous, Luminescent Method, Cell Notes 2005, 11:8-11.
Hansen et al., "Incretin hormones and insulin sensitivity," Trends in Endocrinology and Metabolism, vol. 16, No. 4, May/Jun. 2005, pp. 135-136.
Jen Holst "The Physiology of Glucagon-like Peptide-1", Physiological Reviews, V. 87, No. 4, pp. 1409-1439 (Oct. 2007).
Database Geneseq [Online] Feb. 16, 2012, Human glucagonanalog peptide SEQ:495, XP002710329, EBI accession No. GSP: AZQ99373, Database accession No. AZQ99373.
Azizeh et al., "The role of phenylalanine at position 6 in glucagon's mechanism of biological action: multiple replacement analogues of glucagon" J Med Chem 1997, 40, 2555-2562.
Supplemental EP Search report for EP09800752 completed on Jul. 20, 2011.
"Novel Glucagon-Like Chimera Peptides—Virtues of Combinatorial Pharmacology," AAPS 2005 San Francisco.
Zhou et al., "Peptide and protein drugs: I. Therapeutic applications, absorption and parenteral administration," International Journal of Pharmaceutics vol. 75 p. 97-111 (Sep. 20, 1991).

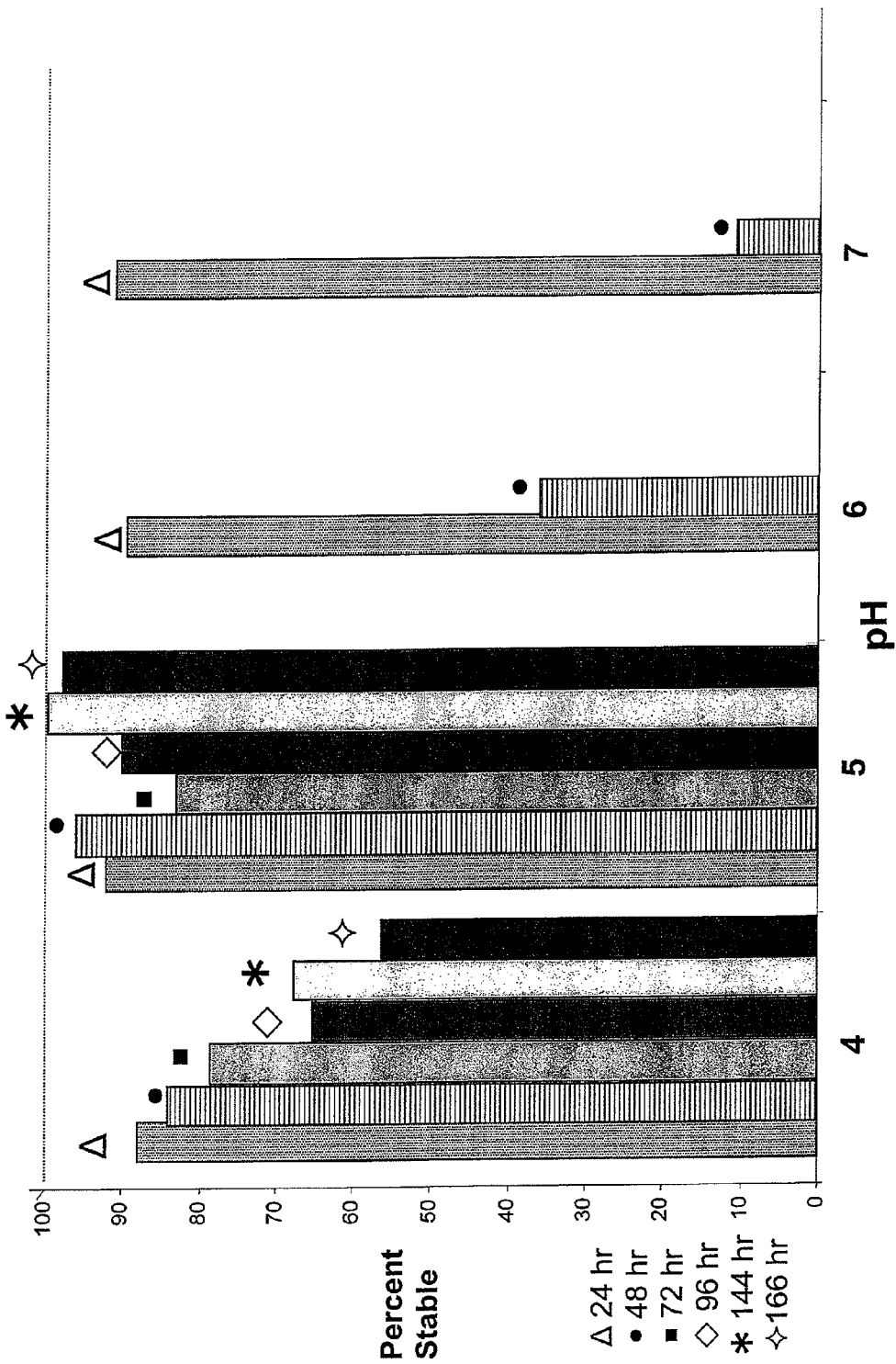

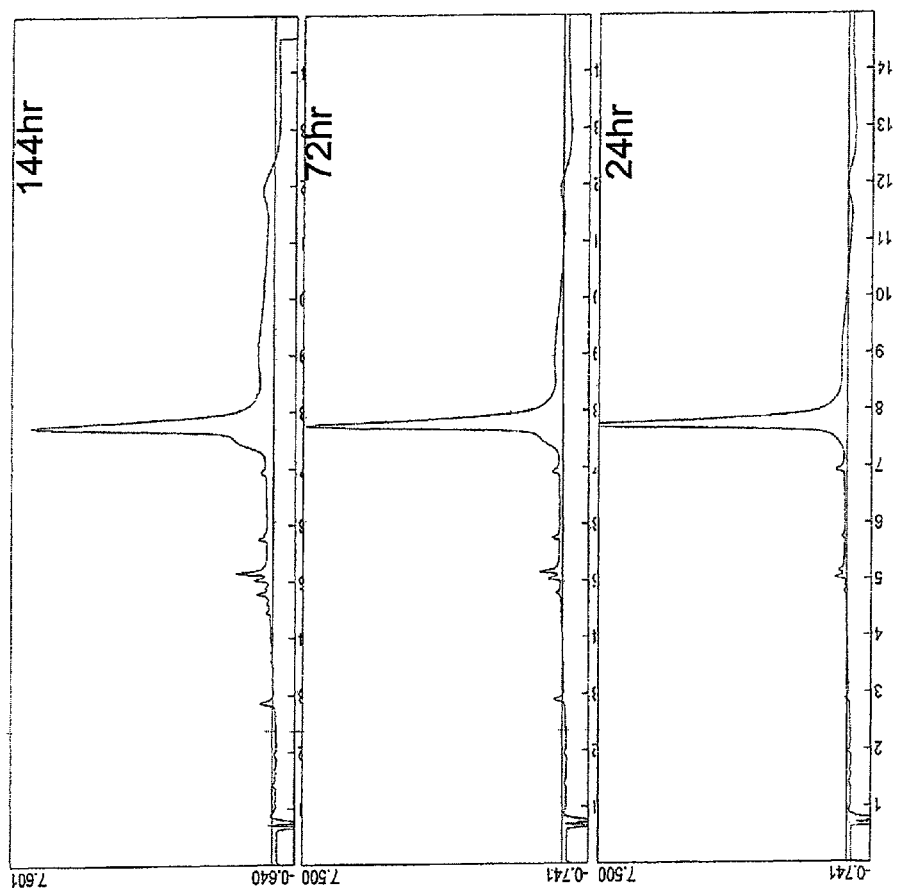

Fig. 4 Glucagon(6-29) peptides with 6 position modification

| Peptide | Residue 6 | IC$_{50}$ (nM) (Receptor binding) | cAMP pA$_2$ | cAMP IC$_{50}$(nM)* |
|---|---|---|---|---|
| [E$^9$]G(6-29)-NH$_2$ | phenylalanine structure | 36.35 ± 5.23 | 7.16 ± 0.27 | 97.2 |
| [3,4-2(F)-F$^6$, E$^9$]G(6-29)-NH$_2$ | 3,4-difluorophenylalanine structure | 36.70 ± 0.54 | 7.35±0.08 | 133.0 |
| [2-Nal$^6$, E$^9$]G(6-29)-NH$_2$ | 2-naphthylalanine structure | 95.16±1.32 | 7.17±0.64 | 41.2 |
| [Ac-F$^6$, E$^9$]G(6-29)-NH$_2$ | N-acetylphenylalanine structure | 37.09±0.26 | 6.67±0.63 | 149.8 |
| [PLA$^6$, E$^9$]G(6-29)-NH$_2$ (PLA: 3-phenyllactic acid) | 3-phenyllactic acid structure | 12.34± 0.13 | 7.67±0.30 | 42.2 |
| [MCA$^6$, E$^9$]G(6-29)-NH$_2$ (MCA: α-methylhydrocinnamic acid) | α-methylhydrocinnamic acid structure | 114.4±5.76 | 6.90±0.83 | 46.6 |
| [BMA$^6$, E$^9$]G(6-29)-NH$_2$ (BMA: benzylmalonic acid) | benzylmalonic acid structure | 80.56±17.91 | 6.43±1.44 | 234.8 |

* Normalized for inhibition of 0.2nM glucagon-induced cAMP release

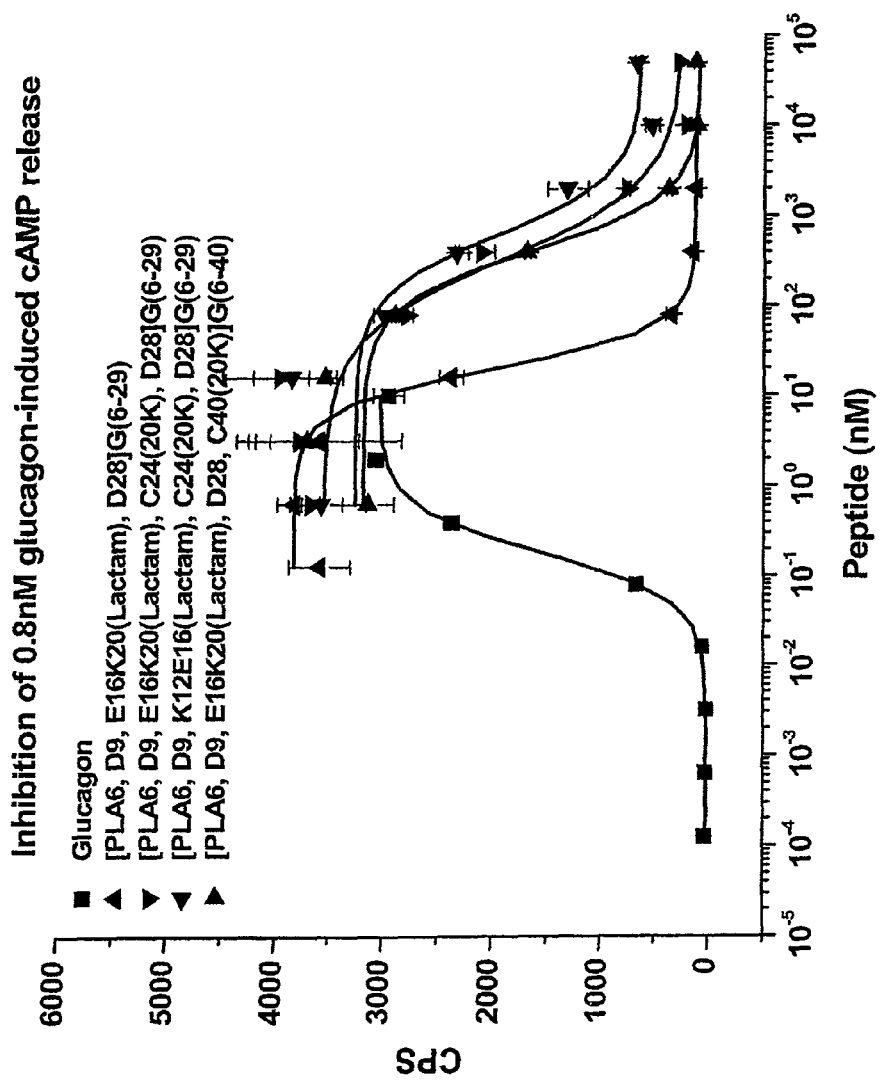
Fig. 8A PEGylated lactam peptides exhibit glucagon antagonism

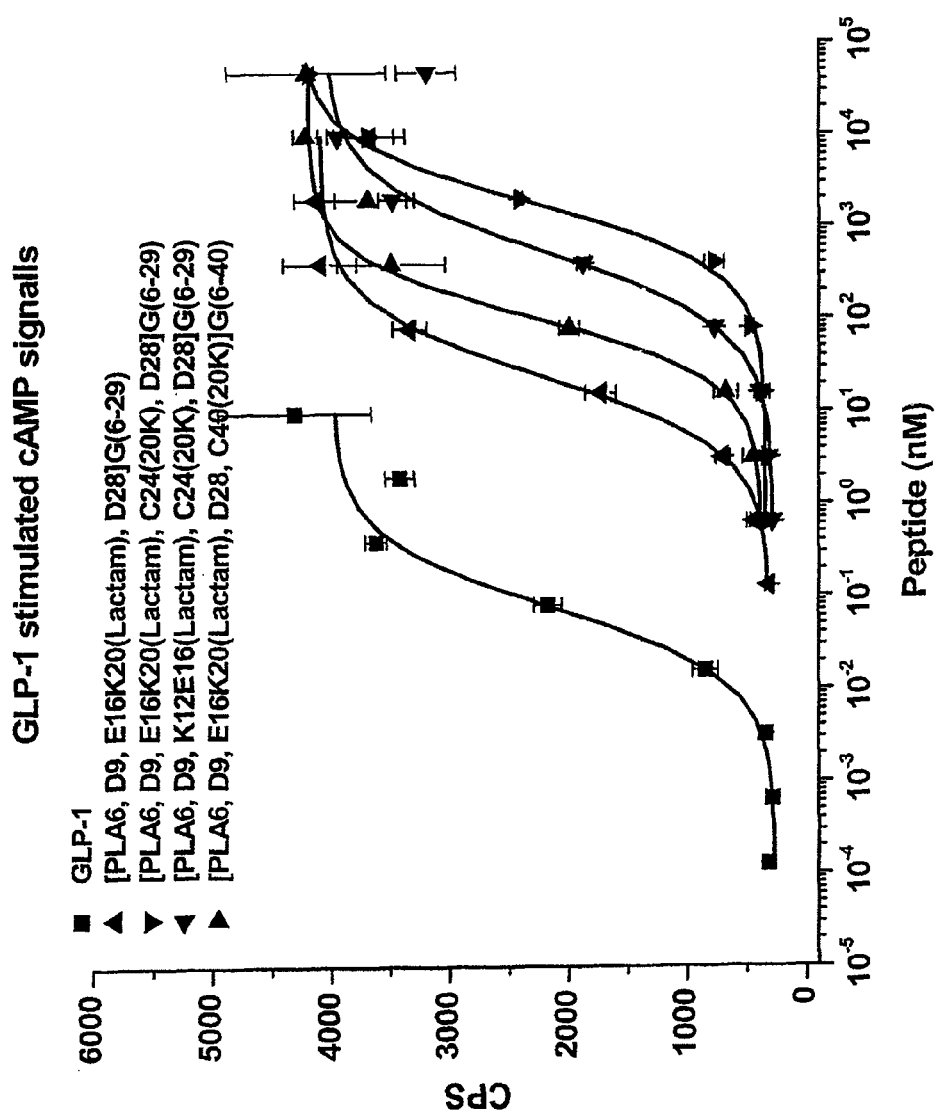
Fig. 8B  PEGylated lactam peptides exhibit GLP-1 agonism

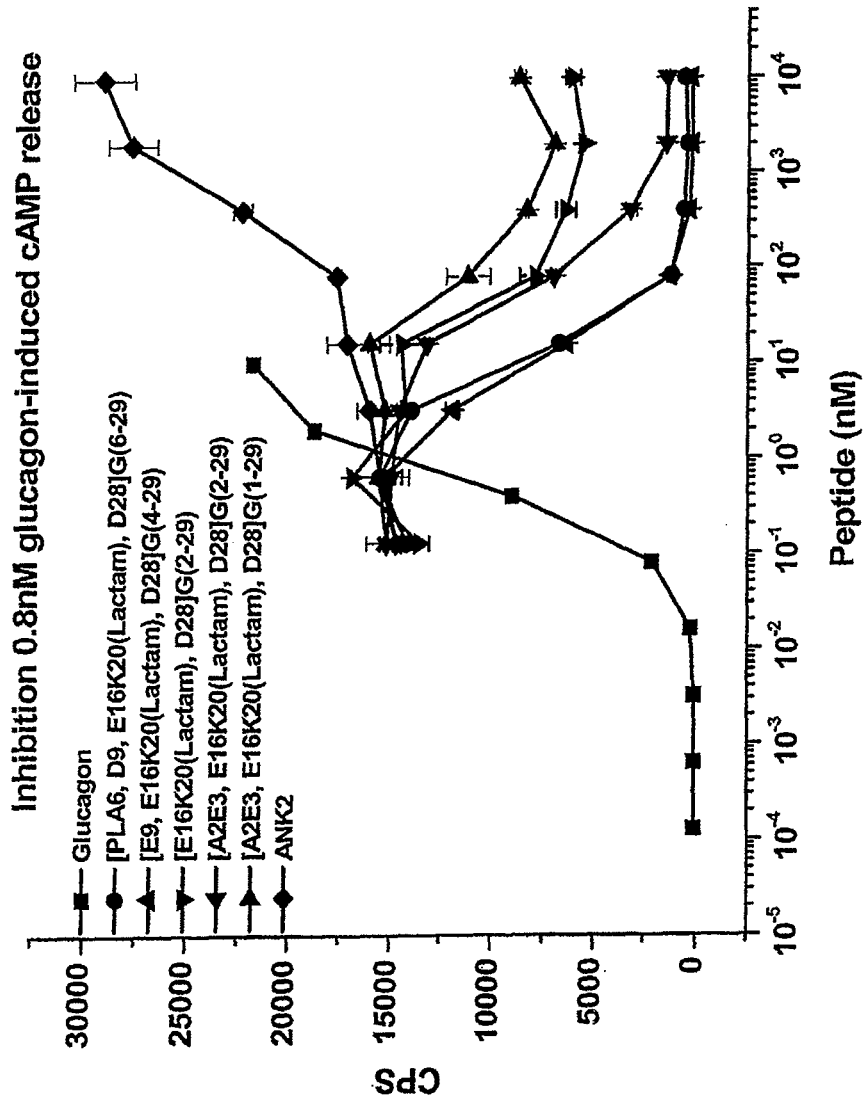
Fig. 9A  Lactam(E16-K20) glucaon(1-29, 2-29 and 4-29) peptides exhibit glucagon antagonism

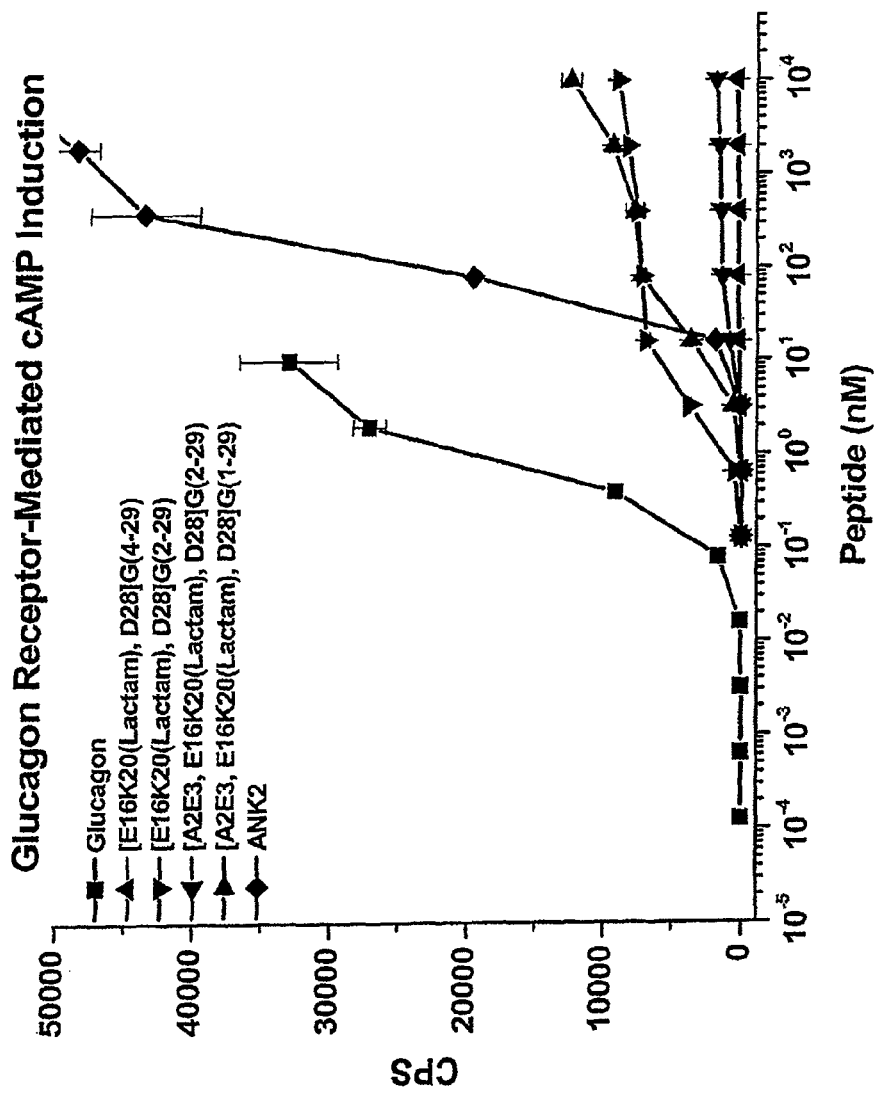
Fig. 9.B  Lactam glucaon(1-29, 2-29 and 4-29) peptides induced cAMP release

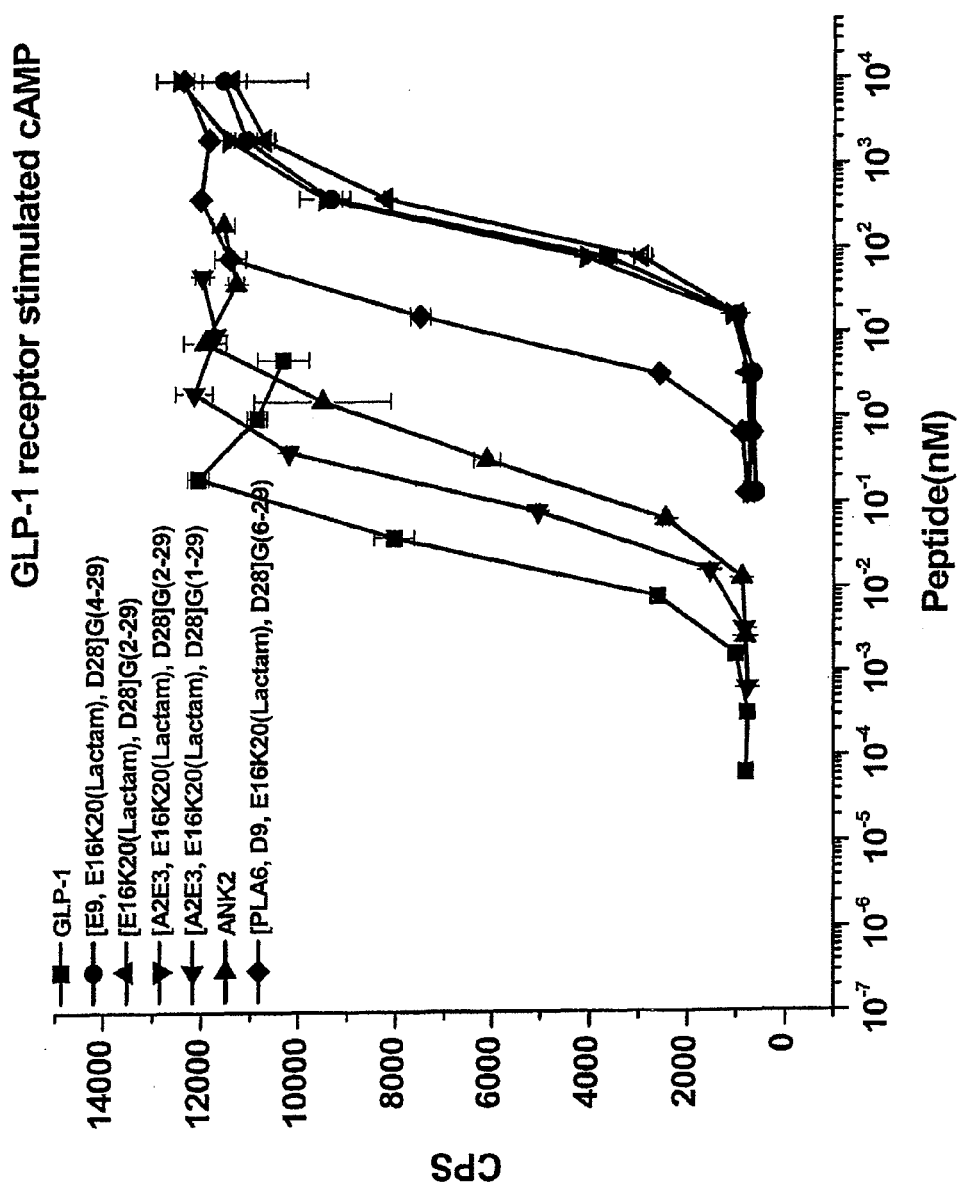
Fig. 9C Lactam(E16-K20) glucaon(1-29, 2-29 and 4-29) peptides exhibit GLP-1 agonism

SEQUENCE LISTING

<160> NUMBER OF SEQ ID NOS: 118

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group

<400> SEQUENCE: 2

Phe Thr Ser Asp Tyr Ser Lys Tyr Leu Asp Ser Arg Arg Ala Gln Asp
1               5                   10                  15

Phe Val Gln Trp Leu Met Asn Thr
            20

<210> SEQ ID NO 3
<211> LENGTH: 31
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 30
<212> TYPE: PRT
<213> ORGANISM: Homo sapiens

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:

```
<221> NAME/KEY: MOD_RES
<222> LOCATION: (1)..(1)
<223> OTHER INFORMATION: N-terminal amino group replaced with hydroxy
      group

<400> SEQUENCE: 5

Phe Thr Ser Asp Tyr Ser Lys Tyr Leu Asp Glu Arg Arg Ala Gln Asp
1               5                   10                  15

Phe Val Gln Trp Leu Met Asn Thr
            20

<210> SEQ ID NO 6
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: N-terminal amino group replaced with hydroxy
      group

<400> SEQUENCE: 6

Phe Thr Ser Asp Tyr Ser Lys Tyr Leu Asp Glu Arg Arg Ala Lys Asp
1               5                   10                  15

Phe Val Gln Trp Leu Met Asn Thr
            20

<210> SEQ ID NO 7
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(11)
<223> OTHER INFORMATION: Xaa is Ser or Glu

<400> SEQUENCE: 7

Phe Thr Ser Asp Tyr Ser Lys Tyr Leu Asp Xaa Arg Arg Ala Lys Asp
1               5                   10                  15

Phe Val Glu Trp Leu Met Asn Thr
            20

<210> SEQ ID NO 8
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
```

```
<222> LOCATION: (11)..(11)
<223> OTHER INFORMATION: Xaa is Ser or Glu

<400> SEQUENCE: 8

Phe Thr Ser Asp Tyr Ser Lys Tyr Leu Asp Xaa Arg Arg Ala Gln Asp
1               5                   10                  15

Phe Val Glu Trp Leu Met Lys Thr
            20

<210> SEQ ID NO 9
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (7)..(7)
<223> OTHER INFORMATION: Xaa at position 7 is Lys or Glu
<220> FEATURE:
<221> NAME/KEY: MISC_FEATURE
<222> LOCATION: (10)..(10)
<223> OTHER INFORMATION: Xaa is Asp, Glu, homoglutamic acid, cysteic
      acid or homocysteic acid
<220> FEATURE:
<221> NAME/KEY: MISC_FEATURE
<222> LOCATION: (11)..(11)
<223> OTHER INFORMATION: Xaa is Ala, Ser, Glu, Lys, homoglutamic acid or
      homocysteic acid
<220> FEATURE:
<221> NAME/KEY: MISC_FEATURE
<222> LOCATION: (15)..(15)
<223> OTHER INFORMATION: Xaa is Gln, Glu or Lys
<220> FEATURE:
<221> NAME/KEY: MISC_FEATURE
<222> LOCATION: (19)..(19)
<223> OTHER INFORMATION: Xaa is Ala, Gln, Lys or Glu
<220> FEATURE:
<221> NAME/KEY: MISC_FEATURE
<222> LOCATION: (23)..(23)
<223> OTHER INFORMATION: Xaa is Asn, Lys or an acidic amino acid
<220> FEATURE:
<221> NAME/KEY: MISC_FEATURE
<222> LOCATION: (24)..(24)
<223> OTHER INFORMATION: Xaa is Thr or an acidic amino acid

<400> SEQUENCE: 9

Phe Thr Ser Asp Tyr Ser Xaa Tyr Leu Xaa Xaa Arg Arg Ala Xaa Asp
1               5                   10                  15

Phe Val Xaa Trp Leu Met Xaa Xaa
            20

<210> SEQ ID NO 10
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
```

```
         group
<220> FEATURE:
<221> NAME/KEY: MISC_FEATURE
<222> LOCATION: (11)..(11)
<223> OTHER INFORMATION: Xaa is Ala, Ser, Glu, Gln, homoglutamic acid or
      homocysteic acid
<220> FEATURE:
<221> NAME/KEY: MISC_FEATURE
<222> LOCATION: (15)..(15)
<223> OTHER INFORMATION: Xaa is Gln or Lys
<220> FEATURE:
<221> NAME/KEY: MISC_FEATURE
<222> LOCATION: (19)..(19)
<223> OTHER INFORMATION: Xaa is Ala, Gln or Glu
<220> FEATURE:
<221> NAME/KEY: MISC_FEATURE
<222> LOCATION: (23)..(23)
<223> OTHER INFORMATION: Xaa is Asn, Lys or an acidic amino acid

<400> SEQUENCE: 10

Phe Thr Ser Asp Tyr Ser Lys Tyr Leu Asp Xaa Arg Arg Ala Xaa Asp
1               5                   10                  15

Phe Val Xaa Trp Leu Met Xaa Thr
            20

<210> SEQ ID NO 11
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(11)
<223> OTHER INFORMATION: Xaa is Ala, Ser, Glu, Gln, homoglutamic acid or
      homocysteic acid
<220> FEATURE:
<221> NAME/KEY: MISC_FEATURE
<222> LOCATION: (15)..(15)
<223> OTHER INFORMATION: Xaa is Gln or Lys

<400> SEQUENCE: 11

Phe Thr Ser Asp Tyr Ser Lys Tyr Leu Asp Xaa Arg Arg Ala Xaa Asp
1               5                   10                  15

Phe Val Gln Trp Leu Met Asn Thr
            20

<210> SEQ ID NO 12
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
```

```
             acid or homocysteic acid
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (15)..(15)
<223> OTHER INFORMATION: Xaa is Lys or Gln
<220> FEATURE:
<221> NAME/KEY: MISC_FEATURE
<222> LOCATION: (16)..(16)
<223> OTHER INFORMATION: Xaa is Lys, Cys, Orn, homocysteine or acetyl
      phenylalanine
<220> FEATURE:
<221> NAME/KEY: MOD_RES
<222> LOCATION: (16)..(16)
<223> OTHER INFORMATION: Pegylated
<220> FEATURE:
<221> NAME/KEY: MISC_FEATURE
<222> LOCATION: (19)..(19)
<223> OTHER INFORMATION: Xaa is Lys, Cys, Orn, homocysteine or acetyl
      phenylalanine
<220> FEATURE:
<221> NAME/KEY: MOD_RES
<222> LOCATION: (19)..(19)
<223> OTHER INFORMATION: Pegylated
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 12

Phe Thr Ser Xaa Tyr Ser Xaa Tyr Leu Asp Glu Arg Arg Ala Xaa Xaa
1               5                   10                  15

Phe Val Xaa Trp Leu Xaa Asn Thr
            20

<210> SEQ ID NO 13
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (15)..(15)
<223> OTHER INFORMATION: Xaa is Lys or Gln
<220> FEATURE:
<221> NAME/KEY: MISC_FEATURE
<222> LOCATION: (16)..(16)
<223> OTHER INFORMATION: Xaa is Cys, Orn, homocysteine or acetyl
      phenylalanine
<220> FEATURE:
<221> NAME/KEY: MOD_RES
<222> LOCATION: (16)..(16)
<223> OTHER INFORMATION: Pegylated
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 13
```

-continued

```
Phe Thr Ser Xaa Tyr Ser Lys Tyr Leu Asp Glu Arg Arg Ala Xaa Xaa
1               5                   10                  15

Phe Val Gln Trp Leu Xaa Asn Thr
            20
```

<210> SEQ ID NO 14
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (15)..(15)
<223> OTHER INFORMATION: Xaa is Lys or Gln
<220> FEATURE:
<221> NAME/KEY: MISC_FEATURE
<222> LOCATION: (19)..(19)
<223> OTHER INFORMATION: Xaa is Cys, Orn, homocysteine or acetyl
      phenylalanine
<220> FEATURE:
<221> NAME/KEY: MOD_RES
<222> LOCATION: (19)..(19)
<223> OTHER INFORMATION: Pegylated
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 14

```
Phe Thr Ser Xaa Tyr Ser Lys Tyr Leu Asp Glu Arg Arg Ala Xaa Asp
1               5                   10                  15

Phe Val Xaa Trp Leu Xaa Asn Thr
            20
```

<210> SEQ ID NO 15
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid, homoglutamic acid or homocysteic acid
<220> FEATURE:
<221> NAME/KEY: MISC_FEATURE
<222> LOCATION: (7)..(7)
<223> OTHER INFORMATION: Xaa is Lys or Glu
<220> FEATURE:
<221> NAME/KEY: MISC_FEATURE

```
<222> LOCATION: (10)..(10)
<223> OTHER INFORMATION: Xaa is Asp, Glu, cysteic acid, homoglutamic
      acid or homocysteic acid
<220> FEATURE:
<221> NAME/KEY: MISC_FEATURE
<222> LOCATION: (11)..(11)
<223> OTHER INFORMATION: Xaa is Ala, Ser, Glu, Lys Gln, homoglutamic
      acid or homocysteic acid
<220> FEATURE:
<221> NAME/KEY: MISC_FEATURE
<222> LOCATION: (15)..(15)
<223> OTHER INFORMATION: Xaa is Arg, Gln, Glu or Lys
<220> FEATURE:
<221> NAME/KEY: MISC_FEATURE
<222> LOCATION: (19)..(19)
<223> OTHER INFORMATION: Xaa is Ala, Gln, Lys or Glu
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn, Lys or an acidic amino acid
<220> FEATURE:
<221> NAME/KEY: MISC_FEATURE
<222> LOCATION: (24)..(24)
<223> OTHER INFORMATION: Xaa is Thr or an acidic amino acid

<400> SEQUENCE: 15

Phe Thr Ser Xaa Tyr Ser Xaa Tyr Leu Xaa Xaa Arg Arg Ala Xaa Asp
1               5                   10                  15

Phe Val Xaa Trp Leu Xaa Xaa Xaa
            20

<210> SEQ ID NO 16
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (7)..(11)
<223> OTHER INFORMATION: Lactam bridge connecting residues 7 and 11
<220> FEATURE:
<221> NAME/KEY: MISC_FEATURE
<222> LOCATION: (10)..(10)
<223> OTHER INFORMATION: Xaa is Glu or Asp
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn, Asp or Glu
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 16

Phe Thr Ser Asp Tyr Ser Lys Tyr Leu Xaa Glu Arg Arg Ala Gln Asp
1               5                   10                  15
```

Phe Val Gln Trp Leu Xaa Xaa Thr
            20

<210> SEQ ID NO 17
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (10)..(10)
<223> OTHER INFORMATION: Xaa is Asp or Glu
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn, Asp or Glu
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 17

Phe Thr Ser Asp Tyr Ser Lys Tyr Leu Xaa Glu Arg Arg Ala Lys Asp
1               5                   10                  15

Phe Val Gln Trp Leu Xaa Xaa Thr
            20

<210> SEQ ID NO 18
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (10)..(10)
<223> OTHER INFORMATION: Xaa is Asp or Glu
<220> FEATURE:
<221> NAME/KEY: MISC_FEATURE
<222> LOCATION: (11)..(11)
<223> OTHER INFORMATION: Xaa is Ser or Glu
<220> FEATURE:
<221> NAME/KEY: MISC_FEATURE
<222> LOCATION: (15)..(19)
<223> OTHER INFORMATION: Lactam bridge connecting residues 15 and 19
<220> FEATURE:
<221> NAME/KEY: MISC_FEATURE
<222> LOCATION: (22)..(22)
<223> OTHER INFORMATION: Xaa is Met, Leu or Nle

```
<220> FEATURE:
<221> NAME/KEY: MISC_FEATURE
<222> LOCATION: (23)..(23)
<223> OTHER INFORMATION: Xaa is Asn, Asp or Glu
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 18

Phe Thr Ser Asp Tyr Ser Lys Tyr Leu Xaa Xaa Arg Arg Ala Lys Asp
1               5                   10                  15

Phe Val Glu Trp Leu Xaa Xaa Thr
            20

<210> SEQ ID NO 19
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (10)..(10)
<223> OTHER INFORMATION: Xaa is Asp or Glu
<220> FEATURE:
<221> NAME/KEY: MISC_FEATURE
<222> LOCATION: (11)..(11)
<223> OTHER INFORMATION: Xaa is Ser or Glu
<220> FEATURE:
<221> NAME/KEY: MISC_FEATURE
<222> LOCATION: (19)..(23)
<223> OTHER INFORMATION: Lactam bridge connecting residues 19 and 23
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (24)..(24)
<223> OTHER INFORMATION: Xaa is Thr or Glu
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 19

Phe Thr Ser Asp Tyr Ser Lys Tyr Leu Xaa Xaa Arg Arg Ala Gln Asp
1               5                   10                  15

Phe Val Glu Trp Leu Xaa Lys Xaa
            20

<210> SEQ ID NO 20
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
```

```
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(7)
<223> OTHER INFORMATION: Xaa is Lys or Glu
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid or homocysteic acid
<220> FEATURE:
<221> NAME/KEY: MISC_FEATURE
<222> LOCATION: (11)..(11)
<223> OTHER INFORMATION: Xaa is Ala, Ser, Glu, Lys Gln, homoglutamic
      acid or homocysteine
<220> FEATURE:
<221> NAME/KEY: MISC_FEATURE
<222> LOCATION: (15)..(15)
<223> OTHER INFORMATION: Xaa is Arg, Gln, Glu or Lys
<220> FEATURE:
<221> NAME/KEY: MISC_FEATURE
<222> LOCATION: (19)..(19)
<223> OTHER INFORMATION: Xaa is Ala, Gln, Lys or Glu
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn, Lys, Asp, Glu, cysteic acid or
      homocysteic acid
<220> FEATURE:
<221> NAME/KEY: MISC_FEATURE
<222> LOCATION: (24)..(24)
<223> OTHER INFORMATION: Xaa is Thr, Asp, Glu, cysteic acid and
      homocysteic acid

<400> SEQUENCE: 20

Phe Thr Ser Xaa Tyr Ser Xaa Tyr Leu Xaa Xaa Arg Arg Ala Xaa Asp
1               5                   10                  15

Phe Val Xaa Trp Leu Xaa Xaa Xaa
            20

<210> SEQ ID NO 21
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide fragment representing the carboxy
      terminal 10 amino acids of Exendin-4

<400> SEQUENCE: 21

Gly Pro Ser Ser Gly Ala Pro Pro Pro Ser
1               5                   10

<210> SEQ ID NO 22
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

```
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(11)
<223> OTHER INFORMATION: Lactam bridge connecting residues 7 and 11
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid and homocysteic acid
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 22

Phe Thr Ser Xaa Tyr Ser Lys Tyr Leu Xaa Glu Arg Arg Ala Gln Asp
1               5                   10                  15

Phe Val Gln Trp Leu Xaa Asn Thr
            20

<210> SEQ ID NO 23
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid and homocysteic acid
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 23

Phe Thr Ser Xaa Tyr Ser Lys Tyr Leu Xaa Glu Arg Arg Ala Lys Asp
1               5                   10                  15

Phe Val Gln Trp Leu Xaa Asn Thr
            20

<210> SEQ ID NO 24
<211> LENGTH: 24
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid and homocysteic acid
<220> FEATURE:
<221> NAME/KEY: MISC_FEATURE
<222> LOCATION: (15)..(19)
<223> OTHER INFORMATION: Lactam bridge connecting residues 15 and 19
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 24

Phe Thr Ser Xaa Tyr Ser Lys Tyr Leu Xaa Glu Arg Arg Ala Lys Asp
 1               5                  10                  15

Phe Val Glu Trp Leu Xaa Asn Thr
                20

<210> SEQ ID NO 25
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid and homocysteic acid
<220> FEATURE:
<221> NAME/KEY: MISC_FEATURE
<222> LOCATION: (19)..(24)
<223> OTHER INFORMATION: Lactam bridge connecting residues 19 and 24
<220> FEATURE:
<221> NAME/KEY: MISC_FEATURE
<222> LOCATION: (22)..(22)
<223> OTHER INFORMATION: Xaa is Met, Leu or Nle

<400> SEQUENCE: 25

Phe Thr Ser Xaa Tyr Ser Lys Tyr Leu Xaa Glu Arg Arg Ala Gln Asp
 1               5                  10                  15

Phe Val Glu Trp Leu Xaa Lys Thr
                20
```

```
<210> SEQ ID NO 26
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide fragment representing the carboxy
      terminal 8 amino acids of oxyntomodulin

<400> SEQUENCE: 26

Lys Arg Asn Arg Asn Asn Ile Ala
1               5

<210> SEQ ID NO 27
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide fragment representing the carboxy 4
      amino acids of oxyntomodulin carboxy terminus

<400> SEQUENCE: 27

Lys Arg Asn Arg
1

<210> SEQ ID NO 28
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue

<400> SEQUENCE: 28

Phe Thr Ser Glu Tyr Ser Lys Tyr Leu Asp Glu Arg Arg Ala Gln Asp
1               5                   10                  15

Phe Val Gln Trp Leu Met Asn Thr Gly Pro Ser Ser Gly Ala Pro Pro
            20                  25                  30

Pro Ser

<210> SEQ ID NO 29
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(11)
<223> OTHER INFORMATION: Lactam bridge connecting residues 7 and 11

<400> SEQUENCE: 29

Phe Thr Ser Glu Tyr Ser Lys Tyr Leu Asp Glu Arg Arg Ala Gln Asp
1               5                   10                  15

Phe Val Gln Trp Leu Met Asn Thr Gly Pro Ser Ser Gly Ala Pro Pro
            20                  25                  30

Pro Ser
```

```
<210> SEQ ID NO 30
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (11)..(15)
<223> OTHER INFORMATION: Lactam bridge connecting residues 11 and 15

<400> SEQUENCE: 30

Phe Thr Ser Glu Tyr Ser Lys Tyr Leu Asp Glu Arg Arg Ala Lys Asp
1               5                   10                  15

Phe Val Gln Trp Leu Met Asn Thr Gly Pro Ser Ser Gly Ala Pro Pro
            20                  25                  30

Pro Ser

<210> SEQ ID NO 31
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (7)..(11)
<223> OTHER INFORMATION: Lactam bridge connecting residues 7 and 11

<400> SEQUENCE: 31

Phe Thr Ser Asp Tyr Ser Lys Tyr Leu Asp Glu Arg Arg Ala Gln Asp
1               5                   10                  15

Phe Val Gln Trp Leu Met Asn Thr Gly Pro Ser Ser Gly Ala Pro Pro
            20                  25                  30

Pro Ser

<210> SEQ ID NO 32
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (7)..(11)
<223> OTHER INFORMATION: Lactam bridge connecting residues 7 and 11

<400> SEQUENCE: 32

Phe Thr Ser Glu Tyr Ser Lys Tyr Leu Asp Glu Arg Arg Ala Gln Asp
1               5                   10                  15

Phe Val Gln Trp Leu Met Asn Thr Gly Pro Ser Ser Gly Ala Pro Pro
            20                  25                  30

Pro Ser
```

```
<210> SEQ ID NO 33
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15

<400> SEQUENCE: 33

Phe Thr Ser Glu Tyr Ser Lys Tyr Leu Asp Glu Arg Arg Ala Lys Asp
1               5                   10                  15

Phe Val Gln Trp Leu Met Asn Thr Gly Pro Ser Ser Gly Ala Pro Pro
            20                  25                  30

Pro Ser

<210> SEQ ID NO 34
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group

<400> SEQUENCE: 34

Phe Thr Ser Asp Tyr Ser Lys Tyr Leu Asp Ser Arg Arg Ala Gln Asp
1               5                   10                  15

Phe Val Gln Trp Leu Met Asp Thr
            20

<210> SEQ ID NO 35
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (7)..(11)
<223> OTHER INFORMATION: Lactam bridge connecting residues 7 and 11

<400> SEQUENCE: 35

Phe Thr Ser Glu Tyr Ser Lys Tyr Leu Asp Glu Arg Arg Ala Gln Asp
1               5                   10                  15
```

```
Phe Val Gln Trp Leu Met Asn Thr
            20
```

<210> SEQ ID NO 36
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15

<400> SEQUENCE: 36

```
Phe Thr Ser Glu Tyr Ser Lys Tyr Leu Asp Glu Arg Arg Ala Lys Asp
1               5                   10                  15
Phe Val Gln Trp Leu Met Asn Thr
            20
```

<210> SEQ ID NO 37
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue

<400> SEQUENCE: 37

```
His Ser Gln Gly Thr Phe Thr Ser Asp Tyr Ala Arg Tyr Leu Asp Ala
1               5                   10                  15
Arg Arg Ala Arg Glu Phe Ile Lys Trp Leu Val Arg Gly Arg Gly
            20                  25                  30
```

<210> SEQ ID NO 38
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 38

```
Phe Thr Ser Asp Tyr Ser Lys Tyr Leu Asp Glu Arg Arg Ala Gln Asp
1               5                   10                  15
Phe Val Gln Trp Leu Met Asn Thr
            20
```

```
<210> SEQ ID NO 39
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid or homocysteic acid
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 39

Phe Thr Ser Xaa Tyr Ser Lys Tyr Leu Xaa Glu Arg Arg Ala Lys Asp
1               5                   10                  15

Phe Val Gln Trp Leu Xaa Asn Thr
            20

<210> SEQ ID NO 40
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue

<400> SEQUENCE: 40

His Ser Gln Gly Thr Phe Thr Ser Asp Tyr Ser Lys Tyr Leu Asp Ser
1               5                   10                  15

Cys Arg Ala Gln Asp Phe Val Gln Trp Leu Met Asn Thr
            20                  25

<210> SEQ ID NO 41
<211> LENGTH: 39
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon Analogue

<400> SEQUENCE: 41

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Gly Pro Ser
```

```
                 20                  25                  30

Ser Gly Ala Pro Pro Ser
        35

<210> SEQ ID NO 42
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (24)..(24)
<223> OTHER INFORMATION: 2-butyrolactone bound through thiol group of
      Cysteine

<400> SEQUENCE: 42

His Ser Gln Gly Thr Phe Thr Ser Asp Tyr Ser Lys Tyr Leu Asp Ser
1               5                  10                  15

Arg Arg Ala Gln Cys Phe Val Gln Trp Leu Met Asn Thr
            20                  25

<210> SEQ ID NO 43
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon Analogue
<220> FEATURE:
<221> NAME/KEY: MOD_RES
<222> LOCATION: (21)..(21)
<223> OTHER INFORMATION: Carboxymethyl group bound through thiol group
      of Cysteine

<400> SEQUENCE: 43

His Ser Gln Gly Thr Phe Thr Ser Asp Tyr Ser Lys Tyr Leu Asp Ser
1               5                  10                  15

Arg Arg Ala Gln Cys Phe Val Gln Trp Leu Met Asn Thr
            20                  25

<210> SEQ ID NO 44
<211> LENGTH: 39
<212> TYPE: PRT
<213> ORGANISM: Homo sapiens

<400> SEQUENCE: 44

His Ser Gln Gly Thr Phe Thr Ser Asp Tyr Ser Arg Tyr Leu Asp Ser
1               5                  10                  15

Arg Arg Ala Gln Asp Phe Val Gln Trp Leu Arg Asn Thr Gly Pro Ser
            20                  25                  30

Ser Gly Ala Pro Pro Ser
        35

<210> SEQ ID NO 45
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

```
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (7)..(11)
<223> OTHER INFORMATION: Lactam bridge connecting residues 7 and 11
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid or homocysteic acid
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn, Lys, Asp, Glu, cysteic acid and
      homocysteic acid
<220> FEATURE:
<221> NAME/KEY: MISC_FEATURE
<222> LOCATION: (24)..(24)
<223> OTHER INFORMATION: Xaa is Thr, Asp, Glu, cysteic acid and
      homocysteic acid
<220> FEATURE:
<221> NAME/KEY: MISC_FEATURE
<222> LOCATION: (25)..(25)
<223> OTHER INFORMATION: Xaa is Cys, Orn, homocysteine or acetyl
      phenylalanine
<220> FEATURE:
<221> NAME/KEY: MOD_RES
<222> LOCATION: (25)..(25)
<223> OTHER INFORMATION: Pegylated

<400> SEQUENCE: 45

Phe Thr Ser Xaa Tyr Ser Lys Tyr Leu Xaa Ser Arg Arg Ala Gln Asp
1               5                   10                  15

Phe Val Gln Trp Leu Xaa Xaa Xaa Xaa Gly Pro Ser Ser Gly Ala Pro
            20                  25                  30

Pro Pro Ser
        35

<210> SEQ ID NO 46
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid or homocysteic acid
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
```

```
        acid or homocysteic acid
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn, Lys, Asp, Glu, cysteic acid and
        homocysteic acid
<220> FEATURE:
<221> NAME/KEY: MISC_FEATURE
<222> LOCATION: (24)..(24)
<223> OTHER INFORMATION: Xaa is Thr, Asp, Glu, cysteic acid and
        homocysteic acid
<220> FEATURE:
<221> NAME/KEY: MISC_FEATURE
<222> LOCATION: (35)..(35)
<223> OTHER INFORMATION: Xaa is Cys, Orn, homocysteine or acetyl
        phenyalanine
<220> FEATURE:
<221> NAME/KEY: MOD_RES
<222> LOCATION: (35)..(35)
<223> OTHER INFORMATION: Pegylated

<400> SEQUENCE: 46

Phe Thr Ser Xaa Tyr Ser Lys Tyr Leu Xaa Ser Arg Arg Ala Gln Asp
1               5                   10                  15

Phe Val Gln Trp Leu Xaa Xaa Xaa Gly Pro Ser Ser Gly Ala Pro Pro
            20                  25                  30

Pro Ser Xaa
        35

<210> SEQ ID NO 47
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (4)..(4)
<223> OTHER INFORMATION: Xaa is glutamic acid, homoglutamic acid,
        cysteic acid or homocysteic acid
<220> FEATURE:
<221> NAME/KEY: MISC_FEATURE
<222> LOCATION: (7)..(11)
<223> OTHER INFORMATION: Lactam bridge connecting residues 7 and 11
<220> FEATURE:
<221> NAME/KEY: MISC_FEATURE
<222> LOCATION: (10)..(10)
<223> OTHER INFORMATION: Xaa is Glu or Asp
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn, Asp or Glu

<400> SEQUENCE: 47

Phe Thr Ser Xaa Tyr Ser Lys Tyr Leu Xaa Glu Arg Arg Ala Gln Asp
1               5                   10                  15

Phe Val Gln Trp Leu Xaa Xaa Thr
            20
```

```
<210> SEQ ID NO 48
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MISC_FEATURE
<222> LOCATION: (4)..(4)
<223> OTHER INFORMATION: Xaa is glutamic acid, homoglutamic acid,
      cysteic acid or homocysteic acid
<220> FEATURE:
<221> NAME/KEY: MISC_FEATURE
<222> LOCATION: (10)..(10)
<223> OTHER INFORMATION: Xaa is Asp or Glu
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn, Asp or Glu

<400> SEQUENCE: 48

Phe Thr Ser Xaa Tyr Ser Lys Tyr Leu Xaa Glu Arg Arg Ala Lys Asp
1               5                   10                  15

Phe Val Gln Trp Leu Xaa Xaa Thr
            20

<210> SEQ ID NO 49
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue

<400> SEQUENCE: 49

Thr Ser Asp Tyr Ser Lys Tyr Leu Asp Glu Arg Arg Ala Lys Asp Phe
1               5                   10                  15

Val Gln Trp Leu Met Asp Thr
            20

<210> SEQ ID NO 50
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide fragment representing the carboxy
      terminal 10 amino acids of Exendin-4 plus one additional amino
      acid
<220> FEATURE:
<221> NAME/KEY: MISC_FEATURE
<222> LOCATION: (11)..(11)
<223> OTHER INFORMATION: Xaa is selected form the group consisting of
      Cys, Orn, Lys, homocysteine and acetyl phenylalanine

<400> SEQUENCE: 50
```

```
Gly Pro Ser Ser Gly Ala Pro Pro Ser Xaa
1               5                   10
```

<210> SEQ ID NO 51
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Glucagon analogue
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (4)..(4)
<223> OTHER INFORMATION: Xaa is aspartic acid, glutamic acid, cysteic
      acid, homoglutamic acid or homocysteic acid
<220> FEATURE:
<221> NAME/KEY: MISC_FEATURE
<222> LOCATION: (7)..(7)
<223> OTHER INFORMATION: Xaa is Lys or Glu
<220> FEATURE:
<221> NAME/KEY: MISC_FEATURE
<222> LOCATION: (10)..(10)
<223> OTHER INFORMATION: Xaa is Asp, Glu, cysteic acid, homoglutamic
      acid or homocysteic acid
<220> FEATURE:
<221> NAME/KEY: MISC_FEATURE
<222> LOCATION: (11)..(11)
<223> OTHER INFORMATION: Xaa is Ala, Ser, Glu, Lys Gln, homoglutamic
      acid or homocysteic acid
<220> FEATURE:
<221> NAME/KEY: MISC_FEATURE
<222> LOCATION: (15)..(15)
<223> OTHER INFORMATION: Xaa is Arg, Gln, Glu or Lys
<220> FEATURE:
<221> NAME/KEY: MISC_FEATURE
<222> LOCATION: (19)..(19)
<223> OTHER INFORMATION: Xaa is Ala, Gln, Lys or Glu
<220> FEATURE:
<221> NAME/KEY: MISC_FEATURE
<222> LOCATION: (22)..(22)
<223> OTHER INFORMATION: Xaa is Met, Leu or Nle
<220> FEATURE:
<221> NAME/KEY: MISC_FEATURE
<222> LOCATION: (23)..(23)
<223> OTHER INFORMATION: Xaa is Asn, Lys or an acidic amino acid
<220> FEATURE:
<221> NAME/KEY: MISC_FEATURE
<222> LOCATION: (24)..(24)
<223> OTHER INFORMATION: Xaa is Thr, Gly or an acidic amino acid

<400> SEQUENCE: 51

```
Phe Thr Ser Xaa Tyr Ser Xaa Tyr Leu Xaa Xaa Arg Arg Ala Xaa Asp
1               5                   10                  15

Phe Val Xaa Trp Leu Xaa Xaa Xaa
            20
```

<210> SEQ ID NO 52
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is phenyl lactic acid

```
<400> SEQUENCE: 52

His Ser Gln Gly Thr Xaa
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (5)..(5)
<223> OTHER INFORMATION: Xaa is phenyl lactic acid

<400> SEQUENCE: 53

Ser Gln Gly Thr Xaa
1               5

<210> SEQ ID NO 54
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: Xaa is phenyl lactic acid

<400> SEQUENCE: 54

Gln Gly Thr Xaa
1

<210> SEQ ID NO 55
<211> LENGTH: 3
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is phenyl lactic acid

<400> SEQUENCE: 55

Gly Thr Xaa
1

<210> SEQ ID NO 56
<211> LENGTH: 2
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa is phenyl lactic acid

<400> SEQUENCE: 56

Thr Xaa
1

<210> SEQ ID NO 57
<211> LENGTH: 6
<212> TYPE: PRT
<213> ORGANISM: Artificial Sequence
<220> FEATURE:
```

```
-continued

<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is selected from a group consisting of His,
      D-histidine, alpha, alpha-dimethyl imidiazole acetic acid (DMIA),
      N-methyl histidine, alpha-methyl histidine, imidazole acetic acid,
      desaminohistidine, hydroxyl-histidine, acetyl-histidine and
<220> FEATURE:
<221> NAME/KEY: MISC_FEATURE
<222> LOCATION: (2)..(2)
<223> OTHER INFORMATION: Xaa is selected from a group consisting of Ser,
      D-serine, D-alanine, Val, Gly, N-methyl serine, N-methyl alanine,
      and aminoisobutyric acid (AIB)
<220> FEATURE:
<221> NAME/KEY: MISC_FEATURE
<222> LOCATION: (3)..(3)
<223> OTHER INFORMATION: Xaa is selected from a group consisting of Glu
      or Gln
<220> FEATURE:
<221> NAME/KEY: MISC_FEATURE
<222> LOCATION: (6)..(6)
<223> OTHER INFORMATION: Xaa is phenyl lactic acid

<400> SEQUENCE: 57

Xaa Xaa Xaa Gly Thr Xaa
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is selected from a group consisting of Ser,
      D-serine, D-alanine, Val, Gly, N-methyl serine, N-methyl alanine,
      and aminoisobutyric acid (AIB)
<220> FEATURE:
<221> NAME/KEY: MISC_FEATURE
<222> LOCATION: (2)..(2)
<223> OTHER INFORMATION: Xaa is selected from a group consisting of Glu
      or Gln
<220> FEATURE:
<221> NAME/KEY: MISC_FEATURE
<222> LOCATION: (5)..(5)
<223> OTHER INFORMATION: Xaa is phenyl lactic acid

<400> SEQUENCE: 58

Xaa Xaa Gly Thr Xaa
1               5

<210> SEQ ID NO 59
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is selected from a group consisting of Glu
      or Gln
<220> FEATURE:
<221> NAME/KEY: MISC_FEATURE
<222> LOCATION: (4)..(4)
<223> OTHER INFORMATION: Xaa is phenyl lactic acid

<400> SEQUENCE: 59

Xaa Gly Thr Xaa
1
```

```
<210> SEQ ID NO 60
<211> LENTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide A
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 60

Phe Thr Ser Asp Tyr Ser Lys Tyr Leu Asp Glu Arg Arg Ala Lys Asp
1               5                   10                  15

Phe Val Gln Trp Leu Met Asp Thr
            20

<210> SEQ ID NO 61
<211> LENTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide B
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 61

Phe Thr Ser Glu Tyr Ser Lys Tyr Leu Asp Ser Arg Arg Ala Gln Asp
1               5                   10                  15

Phe Val Gln Trp Leu Met Asn Thr
            20

<210> SEQ ID NO 62
<211> LENTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide C
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
```

```
<222> LOCATION: (4)..(7)
<223> OTHER INFORMATION: Lactam bridge connecting residues 4 and 7
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 62

Phe Thr Ser Glu Tyr Ser Lys Tyr Leu Asp Ser Arg Arg Ala Gln Asp
1               5                   10                  15

Phe Val Gln Trp Leu Met Asn Thr
            20

<210> SEQ ID NO 63
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide D
<220> FEATURE:
<221> NAME/KEY: MISC_FEATURE
<222> LOCATION: (15)..(19)
<223> OTHER INFORMATION: Lactam bridge connecting residues 15 and 19
<220> FEATURE:
<221> NAME/KEY: MOD_RES
<222> LOCATION: (28)..(28)
<223> OTHER INFORMATION: C-terminal alpha carboxylate replaced with
      amide

<400> SEQUENCE: 63

Ala Glu Gly Thr Phe Thr Ser Glu Tyr Ser Lys Tyr Leu Asp Glu Arg
1               5                   10                  15

Arg Ala Lys Asp Phe Val Gln Trp Leu Met Asp Thr
            20                  25

<210> SEQ ID NO 64
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide E
<220> FEATURE:
<221> NAME/KEY: MISC_FEATURE
<222> LOCATION: (4)..(5)
<223> OTHER INFORMATION: Threonine in position 4 and phenyl lactic acid
      in position 5 are linked via ester bond
<220> FEATURE:
<221> NAME/KEY: MISC_FEATURE
<222> LOCATION: (5)..(5)
<223> OTHER INFORMATION: Xaa is phenyl lactic acid
<220> FEATURE:
<221> NAME/KEY: MISC_FEATURE
<222> LOCATION: (15)..(19)
<223> OTHER INFORMATION: Lactam bridge connecting residues 15 and 19
<220> FEATURE:
<221> NAME/KEY: MOD_RES
<222> LOCATION: (28)..(28)
<223> OTHER INFORMATION: C-terminal alpha carboxylate replaced with
      amide

<400> SEQUENCE: 64

Ala Glu Gly Thr Xaa Thr Ser Asp Tyr Ser Lys Tyr Leu Asp Glu Arg
1               5                   10                  15

Arg Ala Lys Asp Phe Val Gln Trp Leu Met Asp Thr
```

<210> SEQ ID NO 65
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide F
<220> FEATURE:
<221> NAME/KEY: MISC_FEATURE
<222> LOCATION: (15)..(19)
<223> OTHER INFORMATION: Lactam bridge connecting residues 15 and 19
<220> FEATURE:
<221> NAME/KEY: MOD_RES
<222> LOCATION: (28)..(28)
<223> OTHER INFORMATION: C-terminal alpha carboxylate replaced with amide

<400> SEQUENCE: 65

Ser Gln Gly Thr Phe Thr Ser Glu Tyr Ser Lys Tyr Leu Asp Glu Arg
1               5                   10                  15

Arg Ala Lys Asp Phe Val Gln Trp Leu Met Asp Thr
            20                  25

<210> SEQ ID NO 66
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide G
<220> FEATURE:
<221> NAME/KEY: MISC_FEATURE
<222> LOCATION: (4)..(5)
<223> OTHER INFORMATION: Threonine in position 4 and phenyl lactic acid in position 5 are linked via ester bond
<220> FEATURE:
<221> NAME/KEY: MISC_FEATURE
<222> LOCATION: (5)..(5)
<223> OTHER INFORMATION: Xaa is phenyl lactic acid
<220> FEATURE:
<221> NAME/KEY: MISC_FEATURE
<222> LOCATION: (15)..(19)
<223> OTHER INFORMATION: Lactam bridge connecting residues 15 and 19
<220> FEATURE:
<221> NAME/KEY: MOD_RES
<222> LOCATION: (28)..(28)
<223> OTHER INFORMATION: C-terminal alpha carboxylate replaced with amide

<400> SEQUENCE: 66

Ser Gln Gly Thr Xaa Thr Ser Asp Tyr Ser Lys Tyr Leu Asp Glu Arg
1               5                   10                  15

Arg Ala Lys Asp Phe Val Gln Trp Leu Met Asp Thr
            20                  25

<210> SEQ ID NO 67
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide H
<220> FEATURE:
<221> NAME/KEY: MOD_RES

```
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (5)..(5)
<223> OTHER INFORMATION: Covalently linked to a cholesterol acid moiety
<220> FEATURE:
<221> NAME/KEY: MISC_FEATURE
<222> LOCATION: (11)..(15)
<223> OTHER INFORMATION: Lactam bridge connecting residues 11 to 15
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 67

Phe Thr Ser Asp Lys Ser Lys Tyr Leu Asp Glu Arg Arg Ala Lys Asp
1               5                   10                  15

Phe Val Gln Trp Leu Met Asp Thr
            20

<210> SEQ ID NO 68
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide I
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MISC_FEATURE
<222> LOCATION: (25)..(25)
<223> OTHER INFORMATION: Covalently linked to a cholesterol acid moiety
<220> FEATURE:
<221> NAME/KEY: MOD_RES
<222> LOCATION: (25)..(25)
<223> OTHER INFORMATION: C-terminal alpha carboxylate replaced with
      amide

<400> SEQUENCE: 68

Phe Thr Ser Asp Tyr Ser Lys Tyr Leu Asp Glu Arg Arg Ala Lys Asp
1               5                   10                  15

Phe Val Gln Trp Leu Met Asp Thr Lys
            20                  25

<210> SEQ ID NO 69
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide J
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
```

```
<222> LOCATION: (11)..(15)
<223> OTHER INFORMATION: Lactam bridge connectiong residues 11 and 15
<220> FEATURE:
<221> NAME/KEY: MISC_FEATURE
<222> LOCATION: (35)..(35)
<223> OTHER INFORMATION: Covalently linked to a cholesterol acid moiety
<220> FEATURE:
<221> NAME/KEY: MOD_RES
<222> LOCATION: (35)..(35)
<223> OTHER INFORMATION: C-terminal alpha carboxylate replaced with
      amide

<400> SEQUENCE: 69

Phe Thr Ser Asp Tyr Ser Lys Tyr Leu Asp Glu Arg Arg Ala Lys Asp
1               5                   10                  15

Phe Val Gln Trp Leu Met Asp Thr Gly Pro Ser Ser Gly Ala Pro Pro
            20                  25                  30

Pro Ser Lys
        35

<210> SEQ ID NO 70
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide K
<220> FEATURE:
<221> NAME/KEY: MISC_FEATURE
<222> LOCATION: (1)..(1)
<223> OTHER INFORMATION: Xaa is amino isobutyric acid
<220> FEATURE:
<221> NAME/KEY: MISC_FEATURE
<222> LOCATION: (4)..(5)
<223> OTHER INFORMATION: Threonine in position 4 and phenyl lactic acid
      in position 5 are linked via ester bond
<220> FEATURE:
<221> NAME/KEY: MISC_FEATURE
<222> LOCATION: (5)..(5)
<223> OTHER INFORMATION: Xaa is phenyl lactic acid
<220> FEATURE:
<221> NAME/KEY: MISC_FEATURE
<222> LOCATION: (15)..(19)
<223> OTHER INFORMATION: Lactam bridge connectiong residues 15 and 19
<220> FEATURE:
<221> NAME/KEY: MOD_RES
<222> LOCATION: (28)..(28)
<223> OTHER INFORMATION: C-terminal alpha carboxylate replaced with
      amide

<400> SEQUENCE: 70

Xaa Glu Gly Thr Xaa Thr Ser Asp Tyr Ser Lys Tyr Leu Asp Glu Arg
1               5                   10                  15

Arg Ala Lys Asp Phe Val Gln Trp Leu Met Asp Thr
            20                  25

<210> SEQ ID NO 71
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide L
<220> FEATURE:
<221> NAME/KEY: MOD_RES
<222> LOCATION: (34)..(34)
<223> OTHER INFORMATION: C-terminal alpha carboxylate replaced with
      amide
```

```
<400> SEQUENCE: 71

Phe Thr Ser Glu Tyr Ser Lys Tyr Leu Asp Glu Arg Arg Ala Gln Asp
1               5                   10                  15

Phe Val Gln Trp Leu Met Asn Thr Gly Pro Ser Ser Gly Ala Pro Pro
            20                  25                  30

Pro Ser

<210> SEQ ID NO 72
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide M
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MOD_RES
<222> LOCATION: (34)..(34)
<223> OTHER INFORMATION: C-terminal alpha carboxylate replaced with
      amide

<400> SEQUENCE: 72

Phe Thr Ser Glu Tyr Ser Lys Tyr Leu Asp Glu Arg Arg Ala Gln Asp
1               5                   10                  15

Phe Val Gln Trp Leu Met Asn Thr Gly Pro Ser Ser Gly Ala Pro Pro
            20                  25                  30

Pro Ser

<210> SEQ ID NO 73
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide N
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MOD_RES
<222> LOCATION: (34)..(34)
<223> OTHER INFORMATION: C-terminal alpha carboxylate replaced with
      amide

<400> SEQUENCE: 73

Phe Thr Ser Glu Tyr Ser Lys Tyr Leu Asp Glu Arg Arg Ala Lys Asp
1               5                   10                  15

Phe Val Gln Trp Leu Met Asn Thr Gly Pro Ser Ser Gly Ala Pro Pro
            20                  25                  30

Pro Ser

<210> SEQ ID NO 74
<211> LENGTH: 34
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<223> OTHER INFORMATION: Peptide O
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MOD_RES
<222> LOCATION: (34)..(34)
<223> OTHER INFORMATION: C-termincal alpha carboxylate replaced with
      amide

<400> SEQUENCE: 74

Phe Thr Ser Glu Tyr Ser Lys Tyr Leu Asp Glu Arg Arg Ala Lys Asp
1               5                   10                  15

Phe Val Gln Trp Leu Met Asn Thr Gly Pro Ser Ser Gly Ala Pro Pro
            20                  25                  30

Pro Ser

<210> SEQ ID NO 75
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide P
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (7)..(11)
<223> OTHER INFORMATION: Lactam bridge connecting residues 7 and 11
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 75

Phe Thr Ser Asp Tyr Ser Lys Tyr Leu Asp Glu Arg Arg Ala Gln Asp
1               5                   10                  15

Phe Val Gln Trp Leu Met Asp Thr
            20

<210> SEQ ID NO 76
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide Q
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
```

```
<223> OTHER INFORMATION: Lactam bridge connecting residues 11 and 15
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 76

Phe Thr Ser Asp Tyr Ser Lys Tyr Leu Asp Glu Arg Arg Ala Lys Asp
1               5                   10                  15

Phe Val Gln Trp Leu Met Asp Thr
            20

<210> SEQ ID NO 77
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide R
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (15)..(19)
<223> OTHER INFORMATION: Lactam bridge connecting residues 15 and 19
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 77

Phe Thr Ser Asp Tyr Ser Lys Tyr Leu Asp Glu Arg Arg Ala Lys Asp
1               5                   10                  15

Phe Val Glu Trp Leu Met Asp Thr
            20

<210> SEQ ID NO 78
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide S
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (19)..(23)
<223> OTHER INFORMATION: Lactam bridge connecting residues 19 and 23
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 78

Phe Thr Ser Asp Tyr Ser Lys Tyr Leu Asp Glu Arg Arg Ala Gln Asp
1               5                   10                  15

Phe Val Glu Trp Leu Met Lys Thr
```

```
                          20

<210> SEQ ID NO 79
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide T
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (7)..(11)
<223> OTHER INFORMATION: Lactam bridge connecting residues 7 and 11
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 79

Phe Thr Ser Asp Tyr Ser Lys Tyr Leu Asp Glu Gln Ala Ala Lys Asp
1               5                   10                  15

Phe Ile Ala Trp Leu Met Asp Thr
            20

<210> SEQ ID NO 80
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide U
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 80

Phe Thr Ser Asp Tyr Ser Lys Tyr Leu Asp Glu Gln Ala Ala Lys Glu
1               5                   10                  15

Phe Ile Ala Trp Leu Met Asp Thr
            20

<210> SEQ ID NO 81
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide V
<220> FEATURE:
```

```
<221> NAME/KEY: MISC_FEATURE
<222> LOCATION: (15)..(19)
<223> OTHER INFORMATION: Lactam bridge connecting residues 15 and 19
<220> FEATURE:
<221> NAME/KEY: MOD_RES
<222> LOCATION: (28)..(28)
<223> OTHER INFORMATION: C-terminal alpha carboxylate replaced with
      amide

<400> SEQUENCE: 81

Ala Glu Gly Thr Phe Thr Ser Glu Tyr Ser Lys Tyr Leu Asp Glu Arg
1               5                   10                  15

Arg Ala Lys Asp Phe Val Gln Trp Leu Met Asp Thr
            20                  25

<210> SEQ ID NO 82
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide W
<220> FEATURE:
<221> NAME/KEY: MISC_FEATURE
<222> LOCATION: (15)..(19)
<223> OTHER INFORMATION: Lactam bridge connecting residues 15 and 19
<220> FEATURE:
<221> NAME/KEY: MOD_RES
<222> LOCATION: (28)..(28)
<223> OTHER INFORMATION: C-terminal alpha carboxylate replaced with
      amide

<400> SEQUENCE: 82

Ala Glu Gly Thr Phe Thr Ser Glu Tyr Ser Lys Tyr Leu Asp Glu Gln
1               5                   10                  15

Ala Ala Lys Glu Phe Ile Ala Trp Leu Met Asp Thr
            20                  25

<210> SEQ ID NO 83
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide X
<220> FEATURE:
<221> NAME/KEY: MISC_FEATURE
<222> LOCATION: (16)..(20)
<223> OTHER INFORMATION: Lactam bridge connection residues 16 and 20
<220> FEATURE:
<221> NAME/KEY: MOD_RES
<222> LOCATION: (29)..(29)
<223> OTHER INFORMATION: C-terminal alpha carboxylate replaced with
      amide

<400> SEQUENCE: 83

His Ala Glu Gly Thr Phe Thr Ser Glu Tyr Ser Lys Tyr Leu Asp Glu
1               5                   10                  15

Arg Arg Ala Lys Asp Phe Val Gln Trp Leu Met Asp Thr
            20                  25

<210> SEQ ID NO 84
<211> LENGTH: 29
<212> TYPE: PRT
<213> ORGANISM: Artificial Sequence
<220> FEATURE:
```

```
<223> OTHER INFORMATION: Synthetic Polypeptide
<220> FEATURE:
<221> NAME/KEY: MISC_FEATURE
<223> OTHER INFORMATION: Peptide Y
<220> FEATURE:
<221> NAME/KEY: MISC_FEATURE
<222> LOCATION: (16)..(20)
<223> OTHER INFORMATION: Lactam bridge connecting bridges 16 and 20
<220> FEATURE:
<221> NAME/KEY: MOD_RES
<222> LOCATION: (29)..(29)
<223> OTHER INFORMATION: C-terminal alpha carboxylate replaced with
      amide

<400> SEQUENCE: 84

His Ala Glu Gly Thr Phe Thr Ser Glu Tyr Ser Lys Tyr Leu Asp Glu
1               5                   10                  15

Gln Ala Ala Lys Glu Phe Ile Ala Trp Leu Met Asp Thr
            20                  25

<210> SEQ ID NO 85
<211> LENGTH: 26
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide Z
<220> FEATURE:
<221> NAME/KEY: MISC_FEATURE
<222> LOCATION: (13)..(17)
<223> OTHER INFORMATION: Lactam bridge connecting residues 13 and 17
<220> FEATURE:
<221> NAME/KEY: MOD_RES
<222> LOCATION: (26)..(26)
<223> OTHER INFORMATION: C-terminal alpha carboxylate replaced with
      amide

<400> SEQUENCE: 85

Gly Thr Phe Thr Ser Glu Tyr Ser Lys Tyr Leu Asp Glu Arg Arg Ala
1               5                   10                  15

Lys Asp Phe Val Gln Trp Leu Met Asp Thr
            20                  25

<210> SEQ ID NO 86
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AA
<220> FEATURE:
<221> NAME/KEY: MISC_FEATURE
<222> LOCATION: (5)..(6)
<223> OTHER INFORMATION: Threonine in position 5 and phenyl lactic acid
      in position 6 linked via ester bond
<220> FEATURE:
<221> NAME/KEY: MISC_FEATURE
<222> LOCATION: (15)..(19)
<223> OTHER INFORMATION: Lactam bridge connecting residues 15 and 19
<220> FEATURE:
<221> NAME/KEY: MOD_RES
<222> LOCATION: (28)..(28)
<223> OTHER INFORMATION: C-terminal alpha carboxylate replaced with
      amide

<400> SEQUENCE: 86

Ser Gln Gly Thr Phe Thr Ser Glu Tyr Ser Lys Tyr Leu Asp Glu Arg
1               5                   10                  15
```

```
Arg Ala Lys Asp Phe Val Gln Trp Leu Met Asp Thr
            20                  25
```

<210> SEQ ID NO 87
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AB
<220> FEATURE:
<221> NAME/KEY: MISC_FEATURE
<222> LOCATION: (5)..(6)
<223> OTHER INFORMATION: Threonine at position 5 and phenyl lactic acid
      at position 6 linked via ester bond
<220> FEATURE:
<221> NAME/KEY: MISC_FEATURE
<222> LOCATION: (6)..(6)
<223> OTHER INFORMATION: Xaa is phenyl lactic acid
<220> FEATURE:
<221> NAME/KEY: MISC_FEATURE
<222> LOCATION: (16)..(20)
<223> OTHER INFORMATION: Lactam bridge connecting residues 16 and 20
<220> FEATURE:
<221> NAME/KEY: MOD_RES
<222> LOCATION: (29)..(29)
<223> OTHER INFORMATION: C-terminal alpha carboxylate replaced with
      amide

<400> SEQUENCE: 87

```
His Ala Glu Gly Thr Xaa Thr Ser Asp Tyr Ser Lys Tyr Leu Asp Glu
1               5                   10                  15

Arg Arg Ala Lys Asp Phe Val Gln Trp Leu Met Asp Thr
            20                  25
```

<210> SEQ ID NO 88
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AC
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (7)..(11)
<223> OTHER INFORMATION: Lactam bridge connecting residues 7 and 11
<220> FEATURE:
<221> NAME/KEY: MOD_RES
<222> LOCATION: (19)..(19)
<223> OTHER INFORMATION: Pegylated
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 88

```
Phe Thr Ser Asp Tyr Ser Lys Tyr Leu Asp Glu Arg Arg Ala Gln Asp
1               5                   10                  15

Phe Val Cys Trp Leu Met Asp Thr
            20
```

```
<210> SEQ ID NO 89
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AD
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (7)..(11)
<223> OTHER INFORMATION: Lactam bridge connecting residues 7 and 11
<220> FEATURE:
<221> NAME/KEY: MOD_RES
<222> LOCATION: (35)..(35)
<223> OTHER INFORMATION: Pegylated
<220> FEATURE:
<221> NAME/KEY: MOD_RES
<222> LOCATION: (35)..(35)
<223> OTHER INFORMATION: C-terminal alpha carboxylate replaced with
      amide

<400> SEQUENCE: 89

Phe Thr Ser Asp Tyr Ser Lys Tyr Leu Asp Glu Arg Arg Ala Gln Asp
1               5                   10                  15

Phe Val Gln Trp Leu Met Asp Thr Gly Pro Ser Ser Gly Ala Pro Pro
            20                  25                  30

Pro Ser Cys
        35

<210> SEQ ID NO 90
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AE
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MOD_RES
<222> LOCATION: (19)..(19)
<223> OTHER INFORMATION: Pegylated
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 90

Phe Thr Ser Asp Tyr Ser Lys Tyr Leu Asp Glu Arg Arg Ala Lys Asp
1               5                   10                  15

Phe Val Cys Trp Leu Met Asp Thr
            20

<210> SEQ ID NO 91
<211> LENGTH: 35
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AF
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MOD_RES
<222> LOCATION: (35)..(35)
<223> OTHER INFORMATION: Pegylated
<220> FEATURE:
<221> NAME/KEY: MOD_RES
<222> LOCATION: (35)..(35)
<223> OTHER INFORMATION: C-terminal alpha carboxylate replaced with
      amide

<400> SEQUENCE: 91

Phe Thr Ser Asp Tyr Ser Lys Tyr Leu Asp Glu Arg Arg Ala Lys Asp
1               5                   10                  15

Phe Val Gln Trp Leu Met Asp Thr Gly Pro Ser Ser Gly Ala Pro Pro
            20                  25                  30

Pro Ser Cys
        35

<210> SEQ ID NO 92
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AG
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MOD_RES
<222> LOCATION: (1)..(1)
<223> OTHER INFORMATION: Covalently attached to a C16 fatty acid
<220> FEATURE:
<221> NAME/KEY: MISC_FEATURE
<222> LOCATION: (11)..(15)
<223> OTHER INFORMATION: Lactam bridge connection residues 11 and 15
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 92

Phe Thr Ser Asp Tyr Ser Lys Tyr Leu Asp Glu Arg Arg Ala Lys Asp
1               5                   10                  15

Phe Val Gln Trp Leu Met Asp Thr
            20

<210> SEQ ID NO 93
<211> LENGTH: 24
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<223> OTHER INFORMATION: Peptide AH
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MOD_RES
<222> LOCATION: (5)..(5)
<223> OTHER INFORMATION: Linked to a C16 fatty acid via Glu residue
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MISC_FEATURE
<222> LOCATION: (15)..(15)
<223> OTHER INFORMATION: Linked to a C16 fatty acid via Glu residue
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 93

Phe Thr Ser Asp Lys Ser Lys Tyr Leu Asp Glu Arg Arg Ala Lys Asp
1               5                   10                  15

Phe Val Gln Trp Leu Met Asp Thr
            20

<210> SEQ ID NO 94
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AI
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (15)..(15)
<223> OTHER INFORMATION: Linked to C16 fatty acid via Glu residue
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 94

Phe Thr Ser Asp Tyr Ser Lys Tyr Leu Asp Glu Arg Arg Ala Lys Asp
1               5                   10                  15

Phe Val Gln Trp Leu Met Asp Thr
            20

<210> SEQ ID NO 95
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AJ
```

```
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MISC_FEATURE
<222> LOCATION: (19)..(19)
<223> OTHER INFORMATION: Linked to a C16 fatty acid via Glu residue
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 95

Phe Thr Ser Asp Tyr Ser Lys Tyr Leu Asp Glu Arg Arg Ala Lys Asp
1               5                   10                  15

Phe Val Lys Trp Leu Met Asp Thr
            20

<210> SEQ ID NO 96
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AK
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MISC_FEATURE
<222> LOCATION: (24)..(24)
<223> OTHER INFORMATION: Linked to a C16 fatty acid via Glu residue
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 96

Phe Thr Ser Asp Tyr Ser Lys Tyr Leu Asp Glu Arg Arg Ala Lys Asp
1               5                   10                  15

Phe Val Gln Trp Leu Met Asp Lys
            20

<210> SEQ ID NO 97
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AP
<220> FEATURE:
<221> NAME/KEY: MOD_RES
<222> LOCATION: (1)..(1)
<223> OTHER INFORMATION: N-terminal amino group replaced with hydroxy
      group
```

```
<220> FEATURE:
<221> NAME/KEY: MISC_FEATURE
<222> LOCATION: (11)..(11)
<223> OTHER INFORMATION: Xaa is amino isobutyric acid
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 97

Phe Thr Ser Asp Tyr Ser Lys Tyr Leu Asp Xaa Arg Arg Ala Gln Asp
1               5                   10                  15

Phe Val Gln Trp Leu Met Asn Thr
            20

<210> SEQ ID NO 98
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AR
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(11)
<220> FEATURE:
<221> NAME/KEY: MISC_FEATURE
<222> LOCATION: (15)..(15)
<223> OTHER INFORMATION: Xaa is alpha isobutyric acid
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 98

Phe Thr Ser Asp Lys Ser Lys Tyr Leu Asp Xaa Arg Arg Ala Xaa Asp
1               5                   10                  15

Phe Val Cys Trp Leu Met Asn Thr
            20

<210> SEQ ID NO 99
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AS
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 99

Phe Thr Ser Asp Tyr Ser Lys Tyr Leu Asp Glu Arg Arg Ala Gln Asp
1               5                   10                  15
```

```
Phe Val Gln Trp Leu Met Asn Thr
            20

<210> SEQ ID NO 100
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AU
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 100

Phe Thr Ser Asp Lys Ser Lys Tyr Leu Asp Glu Arg Arg Ala Gln Asp
1               5                   10                  15

Phe Val Cys Trp Leu Met Asn Thr
            20

<210> SEQ ID NO 101
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AV
<220> FEATURE:
<221> NAME/KEY: MISC_FEATURE
<222> LOCATION: (4)..(7)
<223> OTHER INFORMATION: Lactam bridge connecting residues 4 and 7
<220> FEATURE:
<221> NAME/KEY: MOD_RES
<222> LOCATION: (11)..(11)
<223> OTHER INFORMATION: Xaa is alpha isobutyric acid
<220> FEATURE:
<221> NAME/KEY: MOD_RES
<222> LOCATION: (24)..(24)
<223> OTHER INFORMATION: C-terminal carboxylate replaced with amide

<400> SEQUENCE: 101

Phe Thr Ser Glu Tyr Ser Lys Tyr Leu Asp Xaa Arg Arg Ala Gln Asp
1               5                   10                  15

Phe Val Gln Trp Leu Met Asn Thr
            20

<210> SEQ ID NO 102
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AW
<220> FEATURE:
<221> NAME/KEY: MISC_FEATURE
<222> LOCATION: (4)..(7)
<223> OTHER INFORMATION: Lactam bridge connecting residues 4 and 7
<220> FEATURE:
```

```
<221> NAME/KEY: MOD_RES
<222> LOCATION: (11)..(11)
<223> OTHER INFORMATION: Xaa is alpha isobutyric acid
<220> FEATURE:
<221> NAME/KEY: MOD_RES
<222> LOCATION: (24)..(24)
<223> OTHER INFORMATION: C-terminal carboxylate replaced with amide

<400> SEQUENCE: 102

Phe Thr Ser Glu Tyr Ser Lys Tyr Leu Asp Xaa Arg Arg Ala Gln Asp
1               5                   10                  15

Phe Val Gln Trp Leu Met Asn Thr
            20

<210> SEQ ID NO 103
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AX
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 103

Phe Thr Ser Asp Tyr Ser Lys Tyr Leu Asp Glu Arg Arg Ala Lys Glu
1               5                   10                  15

Phe Val Gln Trp Leu Met Asp Thr
            20

<210> SEQ ID NO 104
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AY
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 104

Phe Thr Ser Asp Tyr Ser Lys Tyr Leu Asp Glu Gln Ala Ala Lys Glu
1               5                   10                  15

Phe Ile Ala Trp Leu Met Asn Thr
            20
```

```
<210> SEQ ID NO 105
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AZ
<220> FEATURE:
<221> NAME/KEY: MOD_RES
<222> LOCATION: (34)..(34)
<223> OTHER INFORMATION: C-terminal alpha carboxylate replaced with
      amide

<400> SEQUENCE: 105

Phe Thr Ser Glu Tyr Ser Lys Tyr Leu Asp Glu Arg Arg Ala Lys Asp
1               5                   10                  15

Phe Val Gln Trp Leu Met Asn Thr Gly Pro Ser Ser Gly Ala Pro Pro
            20                  25                  30

Pro Ser

<210> SEQ ID NO 106
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide BA
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (5)..(5)
<223> OTHER INFORMATION: Linked to a C16 fatty acid via Glu residue
<220> FEATURE:
<221> NAME/KEY: MISC_FEATURE
<222> LOCATION: (7)..(7)
<223> OTHER INFORMATION: Linked to a C16 fatty acid via Glu residue
<220> FEATURE:
<221> NAME/KEY: MOD_RES
<222> LOCATION: (24)..(24)
<223> OTHER INFORMATION: C-terminal carboxylate replaced with amide

<400> SEQUENCE: 106

Phe Thr Ser Asp Lys Ser Lys Tyr Leu Asp Glu Arg Arg Ala Lys Asp
1               5                   10                  15

Phe Val Gln Trp Leu Met Asp Thr
            20

<210> SEQ ID NO 107
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa1 is selected from a group consisting of
      His, D-histidine, alpha, alpha-dimethyl imidiazole acetic acid
      (DMIA), N-methyl histidine, alpha-methyl histidine, imidazole
      acetic acid, desaminohistidine, hydroxyl-histidine,
      acetyl-histidine and
<220> FEATURE:
<221> NAME/KEY: MISC_FEATURE
<222> LOCATION: (2)..(2)
```

-continued

<223> OTHER INFORMATION: Xaa is selected from a group consisting of Ser,
      D-serine, D-alanine, valine, glycine, N-methyl serine, and
      aminoisobutyric acid (AIB)
<220> FEATURE:
<221> NAME/KEY: MISC_FEATURE
<222> LOCATION: (3)..(3)
<223> OTHER INFORMATION: Xaa is selected from a group consisting of Glu
      or Gln

<400> SEQUENCE: 107

Xaa Xaa Xaa Thr Gly Phe
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is selected from a group consisting of Ser,
      D-serine, D-alanine, valine, glycine, N-methyl serine, and
      aminoisobutyric acid (AIB)
<220> FEATURE:
<221> NAME/KEY: MISC_FEATURE
<222> LOCATION: (2)..(2)
<223> OTHER INFORMATION: Xaa is selected from a group consisting of Glu
      or Gln

<400> SEQUENCE: 108

Xaa Xaa Thr Gly Phe
1               5

<210> SEQ ID NO 109
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is selected from a group consisting of Glu
      or Gln

<400> SEQUENCE: 109

Xaa Thr Gly Phe
1

<210> SEQ ID NO 110
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AL
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 110

```
Phe Thr Ser Asp Tyr Ser Lys Tyr Leu Asp Ser Arg Arg Ala Gln Asp
1               5                   10                  15

Phe Val Gln Trp Leu Met Asp Thr
            20
```

```
<210> SEQ ID NO 111
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AM
<220> FEATURE:
<221> NAME/KEY: MOD_RES
<222> LOCATION: (28)..(28)
<223> OTHER INFORMATION: C-terminal alpha carboxylate replaced with
      amide

<400> SEQUENCE: 111

Ser Gln Gly Thr Phe Thr Ser Glu Tyr Ser Lys Tyr Leu Asp Ser Arg
1               5                   10                  15

Arg Ala Gln Asp Phe Val Gln Trp Leu Met Asn Thr
            20                  25
```

```
<210> SEQ ID NO 112
<211> LENGTH: 28
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AN
<220> FEATURE:
<221> NAME/KEY: MISC_FEATURE
<222> LOCATION: (4)..(5)
<223> OTHER INFORMATION: Threonine at position 4 and phenyl lactic acid
      at position 5 linked via ester bond
<220> FEATURE:
<221> NAME/KEY: MISC_FEATURE
<222> LOCATION: (5)..(5)
<223> OTHER INFORMATION: Xaa is phenyl lactic acid
<220> FEATURE:
<221> NAME/KEY: MOD_RES
<222> LOCATION: (28)..(28)
<223> OTHER INFORMATION: C-terminal alpha carboxylate replaced with
      amide

<400> SEQUENCE: 112

Ser Gln Gly Thr Xaa Thr Ser Glu Tyr Ser Lys Tyr Leu Asp Ser Arg
1               5                   10                  15

Arg Ala Gln Asp Phe Val Gln Trp Leu Met Asn Thr
            20                  25
```

```
<210> SEQ ID NO 113
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Peptide AO
<220> FEATURE:
<221> NAME/KEY: MISC_FEATURE
<222> LOCATION: (5)..(6)
<223> OTHER INFORMATION: Threorine at position 5 and phenyl lactic acid
      at position 6 linked via ester bond
<220> FEATURE:
```

```
<221> NAME/KEY: MISC_FEATURE
<222> LOCATION: (6)..(6)
<223> OTHER INFORMATION: Xaa is phenyl lactic acid
<220> FEATURE:
<221> NAME/KEY: MOD_RES
<222> LOCATION: (29)..(29)
<223> OTHER INFORMATION: C-terminal alpha carboxylate replaced with
      amide

<400> SEQUENCE: 113

His Ser Gln Gly Thr Xaa Thr Ser Glu Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 114
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MOD_RES
<222> LOCATION: (19)..(19)
<223> OTHER INFORMATION: Pegylated
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 114

Phe Thr Ser Glu Tyr Ser Lys Tyr Leu Asp Glu Arg Arg Ala Lys Asp
1               5                   10                  15

Phe Val Cys Trp Leu Met Asn Thr
            20

<210> SEQ ID NO 115
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MISC_FEATURE
<222> LOCATION: (19)..(19)
<223> OTHER INFORMATION: Pegylated via spacer
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 115
```

```
Phe Thr Ser Asp Tyr Ser Lys Tyr Leu Asp Glu Arg Arg Ala Lys Asp
1               5                   10                  15

Phe Val Lys Trp Leu Met Asp Thr
            20

<210> SEQ ID NO 116
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MOD_RES
<222> LOCATION: (19)..(19)
<223> OTHER INFORMATION: Pegylated via rigid spacer
<220> FEATURE:
<221> NAME/KEY: MOD_RES
<222> LOCATION: (24)..(24)
<223> OTHER INFORMATION: C-terminal alpha carboxylate replaced with
      amide

<400> SEQUENCE: 116

Phe Thr Ser Asp Tyr Ser Lys Tyr Leu Asp Glu Arg Arg Ala Lys Asp
1               5                   10                  15

Phe Val Lys Trp Leu Met Asp Thr
            20

<210> SEQ ID NO 117
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MOD_RES
<222> LOCATION: (35)..(35)
<223> OTHER INFORMATION: Pegylated
<220> FEATURE:
<221> NAME/KEY: MOD_RES
<222> LOCATION: (35)..(35)
<223> OTHER INFORMATION: C-terminal alpha carboxylate replaced with
      amide

<400> SEQUENCE: 117

Phe Thr Ser Asp Tyr Ser Lys Tyr Leu Asp Glu Arg Arg Ala Lys Asp
1               5                   10                  15

Phe Val Gln Trp Leu Met Asp Thr Gly Pro Gly Pro Gly Pro Gly Pro
            20                  25                  30

Gly Pro Cys
        35

<210> SEQ ID NO 118
```

```
<211> LENGTH: 35
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: N-terminal amino group replaced with hydroxy
      group
<220> FEATURE:
<221> NAME/KEY: MISC_FEATURE
<222> LOCATION: (11)..(15)
<223> OTHER INFORMATION: Lactam bridge connecting residues 11 and 15
<220> FEATURE:
<221> NAME/KEY: MOD_RES
<222> LOCATION: (35)..(35)
<223> OTHER INFORMATION: Pegylated
<220> FEATURE:
<221> NAME/KEY: MOD_RES
<222> LOCATION: (35)..(35)
<223> OTHER INFORMATION: C-terminal alpha carboxylate reaplaced with
      amide

<400> SEQUENCE: 118

Phe Thr Ser Asp Tyr Ser Lys Tyr Leu Asp Glu Arg Arg Ala Lys Asp
1               5                   10                  15

Phe Val Gln Trp Leu Met Asp Gly Gly Pro Ser Ser Gly Ala Pro Pro
            20                  25                  30

Pro Ser Cys
        35
```

PEPTIDE COMPOUNDS EXHIBITING GLUCAGON ANTAGONIST AND GLP-1 AGONIST ACTIVITY

CROSS REFERENCE TO RELATED APPLICATIONS

This application is a U.S. national counterpart application of international application serial No. PCT/US2008/081333 filed Oct. 27, 2008, which claims priority to U.S. Provisional Patent Application No. 60/983,766, filed Oct. 30, 2007 and to U.S. Provisional Patent Application No. 61/090,441, filed Aug. 20, 2008. The entire disclosures of PCT/US2008/081333, U.S. Ser. No. 60/983,766, and U.S. Ser. No. 61/090,441 are hereby incorporated by reference.

BACKGROUND

Pre-proglucagon is a 158 amino acid precursor polypeptide that is processed in different tissues to form a number of different proglucagon-derived peptides, including glucagon, glucagon-like peptide-1 (GLP-1), glucagon-like peptide-2 (GLP-2) and oxyntomodulin (OXM), that are involved in a wide variety of physiological functions, including glucose homeostasis, insulin secretion, gastric emptying, and intestinal growth, as well as the regulation of food intake. Glucagon is a 29-amino acid peptide that corresponds to amino acids 33 through 61 of pre-proglucagon, while GLP-1 is produced as a 37-amino acid peptide that corresponds to amino acids 72 through 108 of pre-proglucagon. GLP-1(7-36) amide or GLP-1(7-37) acid are biologically potent forms of GLP-1, that demonstrate essentially equivalent activity at the GLP-1 receptor.

Glucagon generally functions as a counter-regulatory hormone, opposing the actions of insulin, to maintain the level of blood glucose, particularly in instances of hypoglycemia. Thus, glucagon's general role in glucose regulation is to counteract the action of insulin and maintain blood glucose levels through enhanced synthesis and mobilization of glucose in the liver. However, in some patients with Type 1 or Type 2 diabetes, absolute or relative elevated glucagon levels have been shown to contribute to the hyperglycemic state. Both in healthy control animals as well as in animal models of Type 1 and Type 2 diabetes, removal of circulating glucagon with selective and specific antibodies has resulted in reduction of the glycemic level (Brand et al., Diabetologia 37, 985 (1994); Diabetes 43, [suppl 1], 172A (1994); Am. J. Physiol. 269, E469-E477 (1995); Diabetes 44 [suppl 1], 134A (1995); Diabetes 45, 1076 (1996)). These studies suggest that glucagon antagonism could be useful in glycemic control of diabetes.

Glucagon exerts its action by binding to and activating its receptor, which is part of the glucagon-secretin branch of the 7-transmembrane G-protein coupled receptor family. The receptor functions by an activation of the adenylyl cyclase resulting in increased cAMP levels. Previous reports have identified peptide-based, (see Unson, C. G. et al. (1989) J. Biol. Chem. 264, 789-94, Ahn, J. et al. (2001) J. Peptide Research 58, 151-8 and Ahn J. et al. (2001) J. Med. Chem. 44, 1372-9) as well as nucleotide-based glucagon antagonists (Sloop K. et al. (2004) J. Clinical Invest. 113, 1571-81). Peptide-based inhibition acts at the level of receptor binding while the latter functions by suppressing intracellular mRNA specific to the glucagon receptor.

Inhibitors of the glucagon receptor have been described, and are generally based on the amino acid sequence of glucagon. Several analogues in which one or more amino acids were either deleted or substituted to produce potent antagonists of glucagon receptor have been described, for example, [des His$^1$] [Glu$^9$]-glucagon amide (Unson et al., (1989) Peptides 10, 1171; Post et al., (1993) Proc. Natl. Acad. Sci. USA 90, 1662), des His$^1$, Phe$^6$ [Glu$^9$]-glucagon amide (Azizh et al., (1995) Bioorg. & Med. Chem. Lett. 16, 1849) and Nle$^9$, Ala$^{11,16}$-glucagon amide (Unson et al. (1994) J. Biol. Chem. 269(17), 12548). Other analogues include substitutions at positions 4 (Ahn J M et al. (2001) J. Pept. Res. 58(2):151-8), 1 (Dharanipragada, R. et al. (1993) Int. J. Pept. Res. 42(1): 68-77) and 4, 5, 12, 17 and 18 in the glucagon sequence (Gysin B et al. 1986. Biochemistry. 25(25):8278-84).

GLP-1 has different biological activities compared to glucagon. Its actions include stimulation of insulin synthesis and secretion, inhibition of glucagon secretion, and inhibition of food intake. GLP-1 has been shown to reduce hyperglycemia (elevated glucose levels) in diabetics. Exendin-4, a peptide from lizard venom that shares about 50% amino acid identity with GLP-1, activates the GLP-1 receptor and likewise has been shown to reduce hyperglycemia in diabetics.

There is also evidence that GLP-1 and exendin-4 may reduce food intake and promote weight loss, an effect that would be beneficial not only for diabetics but also for patients suffering from obesity. Patients with obesity have a higher risk of diabetes, hypertension, hyperlipidemia, cardiovascular disease, and musculoskeletal diseases.

As described herein, glucagon analogs are provided that exhibit high potency activity, both as glucagon antagonists and as GLP-1 agonists. More particularly, the novel glucagon antagonist/GLP-1 agonists represent novel chemical modifications of the N-terminus of the native glucagon sequence, and substitutions of the native glucagon sequence that allow for stabilization of the alpha-helix structure in the C-terminal portion of the compound. The novel glucagon antagonist/GLP-1 agonist compounds can be used in any setting where glucagon antagonism concurrent with GLP-1 agonism is desired. In accordance with one embodiment the compounds can be used in the treatment of diabetes or obesity.

SUMMARY

In accordance with one embodiment, analogs of glucagon are provided that demonstrate potent, selective glucagon antagonism and selective glucagon-like peptide (GLP-1) agonism (glucagon antagonist/GLP-1 agonists). These two activities have separately been shown to be highly desirable properties for the treatment of the metabolic syndrome, specifically diabetes and obesity. The glucagon antagonist activity is useful in any setting where the suppression of glucagon agonism is desired. The presence of GLP-1 agonism further suppresses the endogenous secretion of glucagon from the pancreas while stimulating insulin synthesis and secretion. The two pharmacological actions serve in a synergistic fashion to normalize metabolic abnormalities. These glucagon antagonist/GLP-1 agonists can be further modified to improve the solubility and stability of the compounds while maintaining the glucagon antagonist/GLP-1 agonist activity of the parent compound.

In accordance with one embodiment a glucagon antagonist/GLP-1 agonist is provided comprising a glucagon peptide that has been modified by the deletion of the first 1 to 5 amino acids residues (e.g., first amino acid, first two amino acids, first three amino acids, first four amino acids, first five amino acids) from the N-terminus, and stabilization of the alpha-helix structure in the C-terminal portion of the compound (around amino acid positions 12-29 according to the amino acid numbering of wild type glucagon, SEQ ID NO: 1), e.g., by the linkage of the side chains of amino acid pairs, selected from positions 12 and 16, 16 and 20, 20 and 24, and 24 and 28 (relative to the native glucagon peptide sequence), to one another through hydrogen-bonding or ionic interactions, such as the formation of salt bridges, or by covalent bonds. Alternatively, stabilization of the alpha-helix around residues 12-29 is achieved through introduction of one or more α,α-disubstituted amino acids at positions that retain the desired activity. In some embodiments, one, two, three, four or more of positions 16, 17, 18, 19, 20, 21, 24 or 29 (according to the amino acid numbering of wild type glucagon) of the glucagon peptide or analog thereof is substituted with an α,α-disubstituted amino acid. For example, substitution of position 16 (according to the amino acid numbering of wild type glucagon) of a glucagon peptide or analog thereof with amino iso-butyric acid (AIB) provides a stabilized alpha helix in the absence of a salt bridge or lactam. In some embodiments, one, two, three or more of positions 16, 20, 21 or 24 (according to the amino acid numbering of wild type glucagon) are substituted with AIB In accordance with one embodiment the glucagon antagonist/GLP-1 agonist represents a further modification of the glucagon peptide wherein in addition to the N-terminal deletion, the phenylalanine at position 6 of the native glucagon peptide is modified, e.g., to comprise a hydroxyl group in place of the N-terminus amino group. In a further embodiment the natural carboxylic acid of the C-terminal amino acid is replaced with a charge-neutral group, such as an amide or ester. In another embodiment the aspartic acid residue at position four (position 9 of native glucagon peptide) is substituted with an amino acid selected from the group consisting of glutamic acid, homoglutamic acid, β-homoglutamic acid, a sulfonic acid derivative of cysteine, or an alkylcarboxylate derivative of cysteine having the structure of:

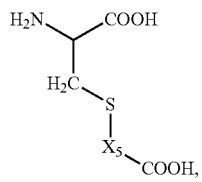

wherein $X_5$ is $C_1$-$C_4$ alkyl, $C_2$-$C_4$ alkenyl, or $C_2$-$C_4$ alkynyl.

In one embodiment, the sulfonic acid derivative of cysteine is cysteic acid or homocysteic acid.

In one embodiment the glucagon antagonist/GLP-1 agonist comprises the sequence of SEQ ID NO: 15 or SEQ ID NO: 51, and more particularly, a sequence selected from the group consisting of SEQ ID NO: 5, SEQ ID NO: 6, SEQ ID NO: 7, SEQ ID NO: 8, SEQ ID NO: 9, SEQ ID NO: 16, SEQ ID NO: 17, SEQ ID NO: 18, SEQ ID NO: 19, SEQ ID NO: 22, SEQ ID NO: 23, SEQ ID NO: 24 and SEQ ID NO: 25.

Also provided herein is a peptide or conjugate thereof comprising (1) an intramolecular bridge, or an alpha, alpha-di-substituted amino acid, or an acidic amino acid at position 16 (according to the numbering of SEQ ID NO:1), or a combination thereof, (2) a C-terminal amide or ester in place of a C-terminal carboxylate, and (3) a general structure of A-B-C,
  wherein A is selected from the group consisting of:
    (i) phenyl lactic acid (PLA);
    (ii) an oxy derivative of PLA;
    (iii) a peptide of 2 to 6 amino acids in which two consecutive amino acids of the peptide are linked via an ester or ether bond;

B represents amino acids i to 26 of SEQ ID NO: 1, wherein i is 3, 4, 5, 6, or 7, optionally comprising one or more amino acid modifications, as further described herein, including, for example, any of the modifications described for glucagon peptides or glucagon analogs or glucagon antagonist/GLP-1 agonists;
  and C is selected from the group consisting of:
    (x) X;
    (xi) X-Y;
    (xii) X-Y-Z; and
    (xiii) X-Y-Z-R10,
wherein X is Met, Leu, or Nle; Y is Asn or a charged amino acid; Z is Thr, Gly, Cys, Lys, ornithine (Orn), homocysteine, acetyl phenylalanine (Ac-Phe), or a charged amino acid; wherein R10 is selected from a group consisting of SEQ ID NOs: 21, 26, 27, and 50.

In one embodiment, the carboxy terminal amino acid of the glucagon antagonist/GLP-1 agonist described herein is covalently bound to a second peptide comprising a sequence selected from the group consisting of SEQ ID NOs: 21, 26, 27, and 50. For example, in one embodiment, the glucagon antagonist/GLP-1 agonist of SEQ ID NO: 15, SEQ ID NO: 51, SEQ ID NO: 5, SEQ ID NO: 6, SEQ ID NO: 7, SEQ ID NO: 8, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 22, SEQ ID NO: 23, SEQ ID NO: 24 and SEQ ID NO: 25 is covalently bound to a second peptide comprising a sequence selected from the group consisting of SEQ ID NO: 21 (GPSSGAPPPS), SEQ ID NO: 26 (KRN-RNNIA), SEQ ID NO: 27 (KRNR) and SEQ ID NO: 50 (GPSSGAPPPSX).

In yet further exemplary embodiments, any of the foregoing compounds can be further modified to improve stability by modifying the amino acid corresponding to position 15 or 16 of native glucagon, to reduce degradation of the peptide over time, especially in acidic or alkaline buffers.

Conjugates of glucagon antagonist/GLP-1 agonists are also provided, in which the glucagon peptide is linked, optionally via covalent bonding and optionally via a linker, to a conjugate moiety.

In another embodiment, the solubility of the glucagon antagonist/GLP-1 agonist is enhanced by the covalent linkage of a hydrophilic moiety to the peptide. In one embodiment the hydrophilic moiety is a polyethylene glycol (PEG) chain. In accordance with one embodiment a glucagon antagonist/GLP-1 agonist is provided, wherein the hydrophilic moiety is covalently bound to an amino acid residue corresponding to position 16, 21 or 24 of native glucagon. In one embodiment the glucagon antagonist/GLP-1 agonist comprises the sequence of SEQ ID NO: 12, SEQ ID NO: 13 or SEQ ID NO: 14 wherein a polyethylene glycol chain is covalently linked to the amino acid at position 16 of SEQ ID NO: 13, at position 19 of SEQ ID NO: 14 or at positions 16 and 19 of SEQ ID NO: 12. In one embodiment the polyethylene glycol chain has a molecular weight selected from the range of about 1,000 to about 5,000 Daltons. In another embodiment the polyethylene glycol chain has a molecular weight of at least about 20,000 Daltons. Alternatively the glucagon antagonist/GLP-1 agonist comprises the sequence of SEQ ID NO: 12 and has a polyethylene glycol chain covalently bound to both amino acid positions 16 and 19 of SEQ ID NO: 12, wherein the combined molecular weight of the two polyethylene chains is either about 1,000 to about 5,000 Daltons or is greater than about 20,000 Daltons.

In another embodiment, the solubility of any of the preceding glucagon antagonist/GLP-1 agonist can be improved by modifying the peptide by substitutions and/or additions that introduce a charged amino acid into the C-terminal portion of the peptide, preferably at a position C-terminal to the amino acid corresponding to position 27 of native glucagon (i.e., C-terminal to position 22 of the glucagon antagonist/GLP-1 agonist). Optionally, one, two or three charged amino acids may be introduced within the C-terminal portion, preferably C-terminal to position 22 of the glucagon antagonist/GLP-1 agonist. In accordance with one embodiment the native amino acid(s) at positions 23 and/or 24 of the glucagon antagonist/GLP-1 agonist are substituted with a charged amino acid, and/or in a further embodiment one to three charged amino acids are also added to the C-terminus of the peptide. In exemplary embodiments, one, two or all of the charged amino acids are negatively charged.

In yet another embodiment, the glucagon antagonist/GLP-1 agonist has been modified by truncation or deletion of one or two amino acids of the C-terminus of the glucagon peptide (i.e., position 29 and/or positions 28 and 29 of the native glucagon peptide).

In one embodiment, the glucagon antagonist/GLP-1 agonist is modified to comprise one or more amino acids of native GLP-1 by substitution of the native glucagon residue(s) at corresponding amino acid positions. For example, the glucagon antagonist may comprise one or more amino acid substitutions at any of positions 2, 3, 17, 18, 21, 23, and 24 (according to the amino acid numbering of native glucagon). In a specific embodiment, the glucagon antagonist/GLP-1 peptide is modified by one or more of the following amino acid substitutions: Ser2 is replaced with Ala, Gln3 is replaced with Glu, Arg17 is replaced with Gln, Arg at position 18 is replaced with Ala, Asp at position 21 is replaced with Glu, Val at position 23 is replaced with Ile, and Gln at position 24 is replaced with Ala (amino acid positions are in accordance with the native glucagon sequence).

Additional modifications, e.g. conservative substitutions, may be made to the glucagon antagonist/GLP-1 agonists that still allow it to retain its activity at the glucagon and GLP-1 receptors. Thus, the invention contemplates that any of the glucagon analogs disclosed herein can be further modified to comprise up to 2, 3, 4, 5, 6, 7, 8 or 9 further amino acid modifications, and still retain the desired level of activity of a glucagon antagonist and GLP-1 agonist at the glucagon and GLP-1 receptors.

Any of the modifications described above can be applied individually or in combination.

Pharmaceutically acceptable salts of the glucagon antagonist/GLP-1 agonist are also encompassed by the present disclosure.

Dimers of the glucagon antagonist/GLP-1 agonists disclosed herein are also encompassed by the present disclosure. In one embodiment a glucagon antagonist/GLP-1 agonist dimer is provided comprising two sequences independently selected form the group consisting of SEQ ID NO: 5, SEQ ID NO: 6, SEQ ID NO: 7, SEQ ID NO: 8, SEQ ID NO: 9, SEQ ID NO: 22, SEQ ID NO: 23, SEQ ID NO: 24 and SEQ ID NO: 25, wherein the two glucagon antagonist/GLP-1 agonists are bound to one another through a linker independently bound to position 16, 19, 24 and 35 (when the extension peptide of SEQ ID NO: 50 is added to the carboxy terminus of the glucagon analog) of the respective peptide chains.

In accordance with one embodiment a pharmaceutical composition is provided comprising the novel glucagon antagonist/GLP-1 agonists disclosed herein. In one embodiment the pharmaceutical compositions comprise solutions that are sterilized and contained within various packages. The pharmaceutical compositions can be further packaged as part of a kit that includes a disposable device for administering the composition to a patient.

In accordance with one embodiment a method of rapidly treating hyperglycemia using a pre-formulated aqueous composition is provided. The method comprises the step of administering an effective amount of an aqueous solution comprising a novel modified glucagon antagonist/GLP-1 agonist of the present disclosure. In one embodiment the glucagon antagonist/GLP-1 agonist is pegylated and the PEG chain has a molecular weight of about 500 to about 5,000 Daltons. In one embodiment the modified glucagon solution is prepackaged in a device that is used to administer the composition to the patient suffering from hyperglycemia.

In accordance with one embodiment an improved method of regulating blood glucose levels in insulin dependent patients is provided. The method comprises the steps of administering insulin in an amount therapeutically effective for the control of diabetes and administering a novel modified glucagon antagonist/GLP-1 agonist of the present disclosure, wherein said administering steps are conducted within twelve hours of each other. In one embodiment the glucagon antagonist/GLP-1 agonist and the insulin are co-administered as a single composition, wherein the glucagon analog is pegylated with a PEG chain having a molecular weight selected from the range of about 5,000 to about 40,000 Daltons. Such methods for treating hyperglycemia are expected to be useful for a variety of types of hyperglycemia, including diabetes, diabetes mellitus type I, diabetes mellitus type II, or gestational diabetes, either insulin-dependent or non-insulin-dependent, and reducing complications of diabetes including nephropathy, retinopathy and vascular disease.

In addition it has been reported that stimulation of GLP-1 will induce weight loss or prevent weight gain. Accordingly, it is believed that the glucagon antagonist/GLP-1 agonists disclosed herein will be effective in inducing weight loss or preventing weight gain. Furthermore, another compound that induces weight loss is oxyntomodulin, a naturally occurring digestive hormone found in the small intestine (see Diabetes 2005; 54:2390-2395). Oxyntomodulin is a 37 amino acid peptide that contains the 29 amino acid sequence of glucagon (i.e. SEQ ID NO: 1) followed by an 8 amino acid carboxy terminal extension of SEQ ID NO: 26 (KRNRNNIA). While it is contemplated that the peptides or glucagon antagonist/GLP-1 agonists described herein may optionally be joined to this 8 amino acid carboxy terminal extension (SEQ ID NO: 26), the invention specifically contemplates analogs lacking the 8 contiguous amino acids of SEQ ID NO: 26. Such methods for reducing appetite or promoting loss of body weight are expected to be useful in reducing body weight, preventing weight gain, or treating obesity of various causes, including drug-induced obesity, and reducing complications associated with obesity including vascular disease (coronary artery disease, stroke, peripheral vascular disease, ischemia reperfusion, etc.), hypertension, onset of diabetes type II, hyperlipidemia and musculoskeletal diseases.

BRIEF DESCRIPTION OF THE DRAWINGS

FIG. 1 is a bar graph representing the stability of Glucagon Cys$^{21}$-maleimidoPEG$_{5K}$ at 37° C. incubated for 24, 48, 72, 96, 144 and 166 hours, respectively.

FIG. 2 represents data generated from HPLC analysis of Glucagon Cys$^{21}$-maleimidoPEG$_{5K}$ at pH 5 incubated at 37° C. for 24, 72 or 144 hours, respectively.

FIG. 3B provides data regarding the inhibitory effect of the same analogs on the induction of the glucagon receptor by 0.2 nM of glucagon. Abbreviations: E9=a substitution of glutamic acid for the amino acid corresponding to position 9 of native glucagon; G(X-29)=native glucagon N-terminally truncated by X-1 amino acids.

FIG. 4 represents data comparing the binding affinity and glucagon receptor activity of glucagon analogs that are modified relative to native glucagon by the deletion of the first 5 native amino acids, and that differ from one another based on modifications to the N-terminal amino acid ("residue 6" of native glucagon).

FIG. 6A represents data generated measuring glucagon receptor antagonism of the listed glucagon analogs in the presence of 0.8 nM of native glucagon, as measure by cAMP production. More particularly, FIG. 6A compares the inhibition of 0.8 nM glucagon-induced cAMP release by glucagon analogs [PLA6, E9]G(6-29) ●, [PLA6, D9, K12E16(L), D28]G(6-29) ▲, [PLA6, D9, E16K20(L), D28]G(6-29) ▼ relative to native glucagon ■. FIG. 6B represents data generated measuring GLP-1-induced cAMP release by glucagon analogs [PLA6, D9, D28]G(6-29) ●, [PLA6, D9, K12E16(L), D28]G(6-29) ▲, [PLA6, D9, E16K20(L), D28]G(6-29) ▼ relative to native glucagon ■. This data demonstrates that the introduction of a backbone lactam into an otherwise glucagon antagonist maintains potent antagonism without residual agonism. Abbreviations: PLA6=phenyl-lactic acid; G(6-29)=native glucagon N-terminally truncated by 5 amino acids; D9=the native Asp corresponding to position 9 of native glucagon; E9=a substitution of glutamic acid for the amino acid corresponding to position 9 of native glucagon; D28=a substitution of aspartic acid for the amino acid corresponding to position 28 of native glucagon; G(6-CEX)=native glucagon N-terminally truncated by 5 amino acids with the additional amino acids of SEQ ID NO: 21 added to the carboxy terminus; K12E16(L)=a lactam bridge formed between the side chains of amino acids corresponding to the lysine at position 12 and the glutamic acid at position 16 of the native glucagon peptide. E16K20(L)=a lactam bridge formed between the side chains of amino acids corresponding to the glutamic acid at position 16 and the lysine at position 20 of the native glucagon peptide.

FIG. 7A represents data generated measuring glucagon receptor antagonism of the listed glucagon analogs in the presence of 0.2 nM of native glucagon, as measure by cAMP production. More particularly, FIG. 7A compares the inhibition of 0.2 nM glucagon-induced cAMP release by glucagon analogs [PLA6, E9]G(6-29) ●, [E9, E16]G(6-CEX) ▲, [E9, K12E16(L)]G(6-CEX) ▼, [PLA6, E9, K12E16(L)]G(6-CEX) ◀, [E9, E16, K20]G(6-CEX) ▶, [E9, E16K20(L)]G(6-CEX) ♦, [PLA6, E9, E16K20(L)]G (6-29) ▲ relative to native glucagon ■. FIG. 7B represents data generated measuring GLP-1-induced cAMP release by glucagon analogs [E9]G(6-CEX) ●, [E9, E16]G(6-CEX) ▲, [D9, K12E16(L)]G(6-CEX) ▼ [E9, K12E16(L)]G (6-CEX) ◀, [PLA6, E9, K12E16(L)]G(6-CEX)) ▶, [E9, E16, K20]G(6-CEX) ♦, [E9, E16K20(L)]G(6-CEX) ▲, [PLA6, E9, E16K20(L)]G(6-CEX) ▲ relative to native glucagon ■. Abbreviations are consistent with those used in FIGS. 6A & 6B.

FIGS. 8A & 8B represents data generated measuring activity of pegylated glucagon lactam derivatives at the glucagon and GLP-1 receptors. FIG. 8A represents data generated measuring glucagon receptor antagonism of the listed glucagon analogs in the presence of 0.8 nM of native glucagon, as measure by cAMP production. More particularly, FIG. 8A compares the inhibition of 0.8 nM glucagon-induced cAMP release by glucagon analogs [PLA6, D9, E16K20(L), D28]G (6-29) ▲, [PLA6, D9, E16K20(L), C24(20K PEG), D28]G (6-29) ▼, [PLA6, D9, K12E16(L), C24(20K PEG), D28]G (6-29) ◀, [PLA6, D9, E16K20(L), D28, C35(20K PEG)]G (6-CEX) ▶, relative to native glucagon ■. FIG. 7B represents data generated measuring GLP-1-induced cAMP release by glucagon analogs [PLA6, D9, E16K20(L), D28]G(6-29) ▲, [PLA6, D9, E16K20(L), C24(20K PEG), D28]G(6-29) ▼, [PLA6, D9, K12E16(L), C24(20K PEG), D28]G(6-29) ◀, [PLA6, D9, E16K20(L), D28, C35(20K PEG)]G(6-CEX) ▶, relative to native GLP-1 ■. Abbreviations are consistent with those used in FIGS. 6A & 6B.

FIGS. 9A-9C represent data generated measuring activity of glucagon lactam derivatives at the glucagon and GLP-1 receptors. FIG. 9A represents data generated measuring glucagon receptor antagonism of the listed glucagon analogs in the presence of 0.8 nM of native glucagon, as measure by cAMP production. More particularly, FIG. 9A compares the inhibition of 0.8 nM glucagon-induced cAMP release by glucagon analogs [PLA6, E16K20(L), D28]G(6-29) ●, [E9, E16K20(L), D28]G(4-29) ▲, [E16K20(L), D28]G(2-29) ▼, [A2, E3, E16K20(L), D28]G(2-29) ◀, [A2, E3, E16K20(L), D28]G(1-29) ▶, ANK2 (SEQ ID NO: 37) ♦ relative to native glucagon ■. FIG. 9B represents data generated measuring glucagon-induced cAMP release by glucagon analogs [E16K20(L), D28]G(4-29) ▲, [E16K20(L), D28]G(2-29) ▼, [A2, E3, E16K20(L), D28]G(2-29) ◀, [A2, E3, E16K20(L), D28]G(1-29) ▶, ANK2 (HSQGTFTSDYARYLDARRAR-EFIKWLVRGRG; SEQ ID NO: 37, a prior art compound) ♦ relative to native GLP-1 ■. FIG. 9C represents data generated measuring GLP-1-induced cAMP release by glucagon analogs [E9, E16K20(L), D28]G(4-29) ●, [E16K20(L), D28]G (2-29) ▲, [A2, E3, E16K20(L), D28]G(2-29) ▼, [A2, E3, E16K20(L), D28]G(1-29) ◀, ANK2 (SEQ ID NO: 37) ▶, [PLA6, E16K20(L), D28]G(6-29) ♦ relative to native GLP-1 ■. Abbreviations are consistent with those used in FIGS. 3, 6A & 6B.

DETAILED DESCRIPTION

Definitions

Figure 3A:
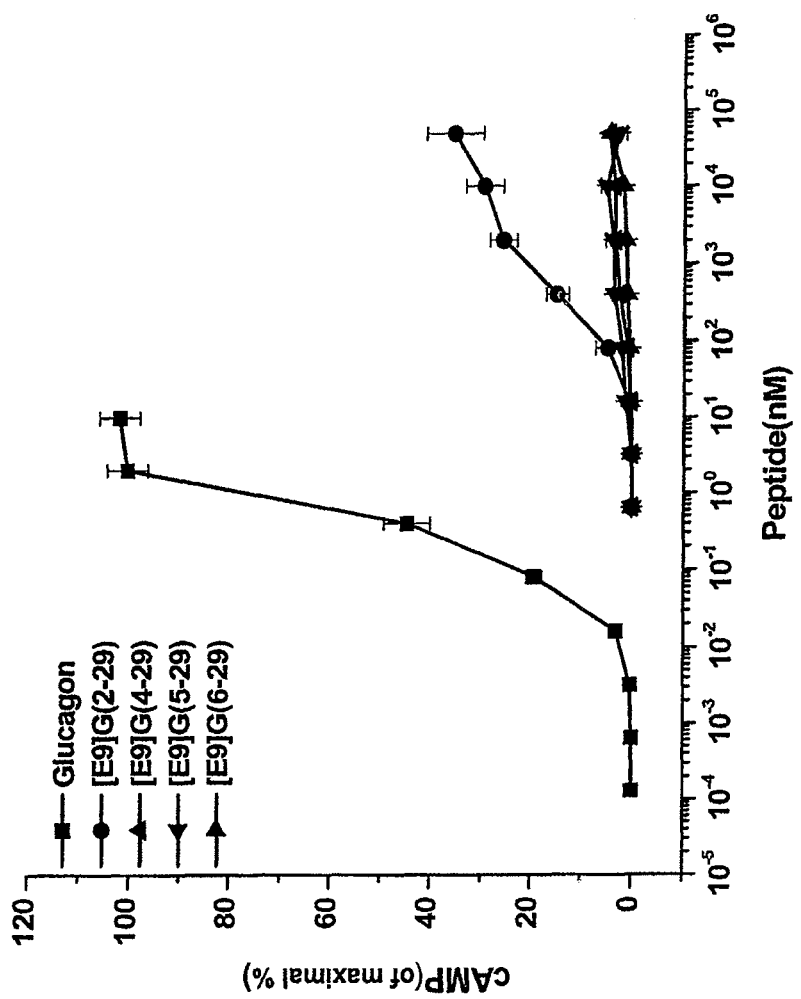
FIGS. 3A & 3B represents data generated measuring glucagon receptor antagonism of the listed glucagon analogs, as measure by cAMP production. The tested analogs have one, three, four or five amino acids removed from the amino terminus of the glucagon peptide and a glutamic acid substitution at position 4. More particularly, FIG. 3A compares induction of the glucagon receptor by glucagon analogs [E9]G(2-29) ●, [E9]G(4-29) ▲, [E9]G(5-29) ▼, [E9]G(6-29) ◀ relative to native glucagon ■.

In describing and claiming the invention, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to maintaining glucose blood levels near normal levels and may include increasing or decreasing blood glucose levels depending on a given situation.

As used herein an "effective" amount or a "therapeutically effective amount" of a glucagon antagonist refers to a nontoxic but sufficient amount of the peptide to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as subcutaneous, intramuscular, intraspinal, or intravenous.

As used herein the term "native glucagon" refers to a peptide consisting of the sequence of SEQ ID NO: 1, and the term "native GLP-1" is a generic term that designates GLP-1(7-36)amide (consisting of the sequence of SEQ ID NO: 4), GLP-1(7-37) acid (consisting of the sequence of SEQ ID NO: 3) or a mixture of those two compounds. As used herein, a general reference to "glucagon" or "GLP-1" in the absence of any further designation is intended to mean native glucagon or native GLP-1, respectively.

A "glucagon analog" as used herein includes any peptide comprising, either the amino acid sequence of SEQ ID NO: 1, or any derivative of the amino acid sequence of SEQ ID NO: 1, including amino acid substitutions, or post translational modifications (e.g. methylation, acylation, ubiquitination and the like) of the peptide, that stimulates glucagon or GLP receptor activity, as measured by cAMP production using the assay described in Example 13.

The term "glucagon antagonist" refers to a compound that counteracts glucagon activity or prevents glucagon function as measured by cAMP production using a validated in vitro model assay, such as that described in Example 13. For example, a glucagon antagonist exhibits at least 50% inhibition (e.g., at least 60%, at least 70% inhibition) and preferably, at least 80% inhibition, of the maximum response achieved by glucagon at the glucagon receptor. In one embodiment, the glucagon antagonist exhibits at least 90% inhibition of the maximum response achieved by glucagon at the glucagon receptor. In a specific embodiment, the glucagon antagonist exhibits 100% inhibition of the maximum response achieved by glucagon at the glucagon receptor.

The term "GLP-1 agonist" refers to a compound that stimulates GLP receptor activity, as measured by cAMP production using a validated in vitro model assay, such as that described in Example 13. A GLP-1 agonist accordingly exhibits GLP-1 agonist activity. The term "GLP-1 agonist activity" refers to maximal activity at the GLP-1 receptor of at least about 10% to about 200% or higher (including at least about 20%, 30%, 40%, 50%, 60%, 75%, 100%, 125%, 150%, or 175%) relative to native GLP-1.

As used herein a "glucagon antagonist/GLP-1 agonist" is a peptide that shares greater than about 65% amino acid sequence identity with the amino acid sequence of native glucagon (SEQ ID NO: 1), but has been modified to exhibit both glucagon antagonist activity as well as GLP-1 agonist activity.

In some embodiments, the peptides described herein exhibit an IC50 at the glucagon receptor that is within a range that is about 100-fold higher or about 100-fold lower than the EC50 at the GLP-1 receptor. For example, a peptide of SEQ ID NO: 1 can be modified such that the peptide exhibits at least about 50% (e.g., at least about 60%, at least about 70%, at least about 80%, at least about 90%, about 100%) of the maximum agonism achieved by native GLP-1 at the GLP-1 receptor and at least about 50% (e.g., at least about 60%, at least about 70%, at least about 80%, at least about 90%, about 100%) inhibition of the maximum response achieved by native glucagon at the glucagon receptor.

In one example, a glucagon antagonist/GLP-1 agonist comprises the glucagon analog of SEQ ID NO: 2 that has been modified to have a glutamic acid substitution at position 11 of SEQ ID NO: 2 or an intramolecular bridge, e.g. a lactam bridge, formed between amino acid residues pairs selected from the group consisting of 7 and 11, 11 and 15, 15 and 19, and 19 and 23 of SEQ ID NO: 2.

Throughout the application, all references to a particular amino acid position by number, absent any further designation or reference to a specific SEQ ID NO: refer to the amino acid position of native glucagon (SEQ ID NO: 1); numbered consecutively starting with the first amino acid of SEQ ID NO: 1 being position number 1, or the corresponding amino acid position in any analogs thereof. However, when a particular amino acid position is designated by number while referring to a specific SEQ ID NO: the designated amino acid position is based on consecutive numbering, starting with the first amino acid, of the referenced SEQ ID NO: For example, the amino acid at position 4 of SEQ ID NO: 2 is aspartic acid.

As used herein an amino acid "modification" refers to a substitution, addition or deletion of an amino acid, and includes substitution with or addition of any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:

Ala, Ser, Thr, Pro, Gly;

II. Polar, negatively charged residues and their amides:

Asp, Asn, Glu, Gln;

III. Polar, positively charged residues:

His, Arg, Lys; Ornithine (Orn)

IV. Large, aliphatic, nonpolar residues:

Met, Leu, Ile, Val, Cys, Norleucine (Nle), homocysteine

V. Large, aromatic residues:

Phe, Tyr, Trp, acetyl phenylalanine

As used herein the general term "polyethylene glycol chain" or "PEG chain", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 500 to 40,000 Daltons. "polyethylene glycol chain" or "PEG chain" is used in combination with a numeric suffix to indicate the approximate average molecular weight thereof. For example, PEG-5,000 refers to polyethylene glycol chain having a total molecular weight average of about 5,000.

As used herein the term "pegylated" and like terms refers to a compound that has been modified from its native state by linking a polyethylene glycol chain to the compound. A "pegylated glucagon analog" is a glucagon analog that has a PEG chain covalently bound to the glucagon analog.

As used herein a general reference to a peptide is intended to encompass peptides that have modified amino and carboxy termini. For example, an amino acid chain comprising an amide group in place of the terminal carboxylic acid is intended to be encompassed by an amino acid sequence designating the standard amino acids.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein a "dimer" is a complex comprising two subunits covalently bound to one another via a linker. The term dimer, when used absent any qualifying language, encompasses both homodimers and heterodimers. A homodimer comprises two identical subunits, whereas a heterodimer comprises two subunits that differ, although the two subunits are substantially similar to one another.

As used herein a "sulfonic acid derivative of cysteine" refers to compounds of the general structure:

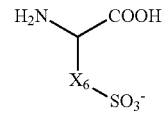

wherein $X_6$ is $C_1$-$C_4$ alkyl, $C_2$-$C_4$ alkene or $C_2$-$C_4$ alkynyl.

The term "$C_1$-$C_n$ alkyl" wherein n can be from 1 through 6, as used herein, represents a branched or linear alkyl group having from one to the specified number of carbon atoms. Typical $C_1$-$C_6$ alkyl groups include, but are not limited to, methyl, ethyl, n-propyl, iso-propyl, butyl, iso-butyl, sec-butyl, tert-butyl, pentyl, hexyl and the like.

The terms "$C_2$-$C_n$ alkenyl" wherein n can be from 2 through 6, as used herein, represents an olefinically unsaturated branched or linear group having from 2 to the specified number of carbon atoms and at least one double bond. Examples of such groups include, but are not limited to, 1-propenyl, 2-propenyl (—CH$_2$—CH═CH$_2$), 1,3-butadienyl, (—CH═CHCH═CH$_2$), 1-butenyl (—CH═CHCH$_2$CH$_3$), hexenyl, pentenyl, and the like.

The term "$C_2$-$C_n$ alkynyl" wherein n can be from 2 to 6, refers to an unsaturated branched or linear group having from 2 to n carbon atoms and at least one triple bond. Examples of such groups include, but are not limited to, 1-propynyl, 2-propynyl, 1-butynyl, 2-butynyl, 1-pentynyl, and the like.

As used herein the term "charged amino acid" refers to an amino acid that comprises a side chain that is negatively charged (i.e., de-protonated) or positively charged (i.e., protonated) in aqueous solution at physiological pH. For example negatively charged amino acids include aspartic acid, glutamic acid, cysteic acid, homocysteic acid, and homoglutamic acid, whereas positively charged amino acids include arginine, lysine and histidine. Charged amino acids include the charged amino acids among the 20 amino acids commonly found in human proteins, as well as atypical or non-naturally occurring amino acids.

As used herein the term "acidic amino acid" refers to an amino acid that comprises a second acidic moiety, including for example, a carboxylic acid or sulfonic acid group.

As used herein the term "patient" without further designation is intended to encompass any warm blooded vertebrate domesticated animal (including for example, but not limited to livestock, horses, cats, dogs and other pets) and humans.

As used herein, the term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

EMBODIMENTS

Disclosed herein are glucagon analogs that function as glucagon antagonists and GLP-1 agonists. Such glucagon antagonists/GLP-1 agonists are utilized in any setting where the suppression of glucagon agonism is desired while simultaneous stimulation of GLP-1 activity is also desired. For example, glucagon antagonist activity in conjunction with GLP-1 stimulation can be used in the treatment of diabetes where glucagon antagonism has been demonstrated in pre-clinical models of hyperglycemia to yield a lowering of blood glucose and GLP-1 activity is associated with insulin production. Compounds demonstrating GLP-1 activity have also been known to be useful for treating obesity and preventing weight gain.

Applicants have discovered that glucagon analogs that have been modified by the removal of the first 1 to 5 amino acids (e.g., first one amino acid, first two amino acids, first three amino acids, first four amino acids, first five amino acids) of the N-terminus and by stabilization of the alpha helix-structure in the C-terminal portion of the peptide, including for example, by formation of an intra-peptide linkage of the side chains of two amino acids to one another, wherein the amino acid pairs are selected from positions 12 and 16, 16 and 20, 20 and 24, and 24 and 28, exhibit activity both as a glucagon antagonist and as a GLP-1 agonist.

In accordance with one embodiment, a glucagon antagonist/GLP-1 agonist peptide is provided wherein the peptide exhibits at least 80% of the maximum agonism achieved by native GLP-1 at the GLP-1 receptor, and exhibits glucagon antagonist activity that reduces the maximum glucagon-induced cAMP production at the glucagon receptor by at least about 50%, as measured by cAMP production in an in vitro assay. In one embodiment, the glucagon antagonist/GLP-1 agonist peptide exhibits at least 90% of the activity of native GLP-1 at the GLP-1 receptor, and exhibits glucagon antagonist activity, that reduces the maximum glucagon-induced cAMP production at the glucagon receptor by at least about 80%.

In accordance with one embodiment the glucagon antagonist/GLP-1 agonist comprises a derivative peptide of SEQ ID NO: 2 wherein the glucagon peptide comprises further amino acid substitutions relative to SEQ ID NO: 2 at one to three amino acid positions selected from positions 1, 2, 4, 5, 6, 7, 8, 9, 10, 11, 12, 13, 14, 15, 16, 19, 22 and 24, and exhibits at least 90% of the activity of native GLP-1 at the GLP-1 receptor, and exhibits glucagon antagonist activity, that reduces the maximum glucagon-induced cAMP production at the glucagon receptor by at least about 80%.

In some embodiments, the alpha-helix structure in the C-terminal portion of the glucagon peptide (around amino acids 12-29 according to the amino acid numbering of wild type glucagon) is stabilized by, e.g., formation of a covalent or non-covalent intramolecular bridge, or substitution and/or insertion of amino acids around positions 12-29 with an alpha helix-stabilizing amino acid (e.g., an α,α-disubstituted amino acid). In one embodiment a lactam ring is formed between the side chains of amino acids 7 and 11 or between amino acids 11 and 15 of SEQ ID NO: 2. In other embodiments, one, two, three or all of positions 16, 20, 21 or 24 (according to the amino acid numbering of wild type glucagon) are substituted with an α,α-disubstituted amino acid, e.g., amino isobutyric acid (AIB). In one embodiment the glucagon antagonist/GLP-1 agonist comprises a derivative peptide of SEQ ID NO: 15 or SEQ ID NO: 51 wherein the glucagon peptide comprises a further amino acid substitution relative to SEQ ID NO: 15 or SEQ ID NO: 51 at one to three amino acid positions selected from positions 1, 2, 5, 6, 8, 9, 12, 13 and 14. In one embodiment the substitutions at positions 1, 2, 5, 6, 8, 9, 12, 13 and 14 are conservative amino acid substitutions. In one embodiment the threonine at position 24 of SEQ ID NO: 5 or SEQ ID NO: 6 is substituted with glycine.

In accordance with one embodiment, specific glucagon analogs have been prepared wherein the first three to five amino acids of native glucagon have been deleted, the amino acid at position 9, relative to the native glucagon peptide, has been substituted with an amino acid selected from the group consisting of glutamic acid, homoglutamic acid, β-homoglutamic acid, a sulfonic acid derivative of cysteine, or an alkylcarboxylate derivative of cysteine having the structure of:

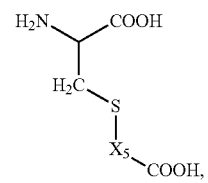

wherein $X_5$ is $C_1$-$C_4$ alkyl, $C_2$-$C_4$ alkenyl, or $C_2$-$C_4$ alkynyl, and the alpha-helix structure in the C-terminal portion of glucagon (around amino acids 12-29 according to the amino acid numbering of wild type glucagon) is stabilized, e.g., via a lactam bridge is formed between the side chains of amino acids 12 and 16 or between amino acids 16 and 20, relative to the native glucagon peptide.

In one embodiment the glucagon peptide comprises a peptide of SEQ ID NO: 47 or SEQ ID NO: 48, and in a further embodiment the glucagon peptide comprises a peptide of SEQ ID NO: 47 or SEQ ID NO: 48 wherein the amino acid at position 4 of those sequences is glutamic acid and an amide group is substituted for the C-terminal carboxylic acid group present on the native amino acid. In a further embodiment the peptide of SEQ ID NO: 47 or SEQ ID NO: 48 is further modified by the addition of the sequence of SEQ ID NO: 21 to the carboxy terminus of the peptide.

In a further embodiment analogs of glucagon have been developed wherein the first five amino acids of native glucagon have been deleted, the amino group of the N-terminal amino acid (phenylalanine) has been replaced with a hydroxyl group (i.e., the first amino acid is phenyl-lactic acid) and the side chains of one or more amino acid pairs selected from positions 12 and 16, 16 and 20, 20 and 24, and 24 and 28 are linked to one another, thus stabilizing the glucagon analog alpha helix.

In accordance with one embodiment a glucagon antagonist/GLP-1 agonist is provided comprising the sequence of SEQ ID NO: 2 that is modified by a substitution of the serine residue at position 11 of SEQ ID NO: 2 (position 16 according to the amino acid numbering of native glucagon) with an amino acid selected from the group consisting of glutamic acid, glutamine, homoglutamic acid, homocysteic acid, threonine or glycine. In accordance with one embodiment the serine residue at position 11 of SEQ ID NO: 2 is substituted with an amino acid selected from the group consisting of glutamic acid, glutamine, homoglutamic acid and homocysteic acid, and in one embodiment the serine residue is substituted with glutamic acid. In accordance with one embodiment the glucagon antagonist/GLP-1 agonist comprises the sequence of SEQ ID NO: 38.

In one embodiment a glucagon antagonist/GLP-1 agonist is provided wherein an intramolecular bridge is formed between two amino acid side chains to stabilize the three dimensional structure of the carboxy terminus of the peptide of SEQ ID NO: 2. More particularly, the side chains of one or more amino acids selected from amino acid pairs 7 and 11, 11 and 15, 15 and 19 or 19 and 23 of SEQ ID NO: 2 are linked to one another, thus stabilizing the glucagon analog alpha helix. The two side chains can be linked to one another through hydrogen-bonding, ionic interactions (such as the formation of salt bridges), or by covalent bonds. In accordance with one embodiment the size of the linker is 7-9 atoms, and in one embodiment the size of the linker is 8 atoms. In one embodiment the glucagon antagonist/GLP-1 agonist is selected from the group consisting of SEQ ID NO: 5, SEQ ID NO: 6, SEQ ID NO: 7 and SEQ ID NO: 8. In one embodiment the C-terminal amino acid of the antagonist/GLP-1 agonists have an amide group substituting for the carboxylic acid group that is present on the native amino acid.

Examples of amino acid pairings that are capable of covalently bonding to form a seven-atom linking bridge include Orn-Glu (lactam); Lys-Asp (lactam); or Homoser-Homoglu (lactone). Examples of amino acid pairings that may form an eight-atom linker include Lys-Glu (lactam); Homolys-Asp (lactam); Orn-Homoglu (lactam); 4-aminoPhe-Asp (lactam); or Tyr-Asp (lactone). Examples of amino acid pairings that may form a nine-atom linker include Homolys-Glu (lactam); Lys-Homoglu (lactam); 4-aminoPhe-Glu (lactam); or Tyr-Glu (lactone). Any of the side chains on these amino acids may be substituted with additional chemical groups, so long as the three-dimensional structure of the alpha-helix is not disrupted. One of ordinary skill in the art can envision alternative pairings or alternative amino acid analogs or derivatives that would create a stabilizing structure of similar size and desired effect. For example, a homocysteine-homocysteine disulfide bridge is 6 atoms in length and may be further modified to provide the desired effect. Even without covalent linkage, the amino acid pairings described above or similar pairings that one of ordinary skill in the art can envision may also provide added stability to the alpha-helix through non-covalent bonds, for example, through formation of salt bridges or hydrogen-bonding interactions.

In accordance with one embodiment a glucagon antagonist/GLP-1 agonist is provided wherein the analog comprises an amino acid sequence of SEQ ID NO: 9. In one embodiment the three dimensional structure of the carboxy terminus of the peptide of SEQ ID NO: 9 is stabilized by the formation of covalent bonds between the side chains of the peptide. In one embodiment two amino acid side chains are bound to one another to form a lactam ring. The size of the lactam ring can vary depending on the length of the amino acid side chains, and in one embodiment the lactam is formed by linking the side chains of a lysine amino acid to a glutamic acid side chain. In one embodiment the C-terminal amino acid of the antagonist/GLP-1 agonists have an amide group substituting for the carboxylic acid group that is present on the native amino acid.

The order of the amide bond in the lactam ring can be reversed (e.g., a lactam ring can be formed between the side chains of a Lys12 and a Glu16 or alternatively between a Glu 12 and a Lys16). In accordance with one embodiment a glucagon analog of SEQ ID NO: 9 is provided wherein at least one lactam ring is formed between the side chains of an amino acid pair selected from the group consisting of amino acid pairs 7 and 11, 11 and 15, 15 and 19 or 19 and 23 of SEQ ID NO: 9. In one embodiment a glucagon antagonist/GLP-1 agonist is provided wherein the peptide comprises the sequence of SEQ ID NO: 10, said sequence further comprising an intramolecular lactam bridge formed between amino acid positions 7 and 11, or between amino acid positions 11 and 15, or between amino acid positions 15 and 19 of SEQ ID NO: 10. In one embodiment a glucagon antagonist/GLP-1 agonist is provided wherein the peptide comprises the sequence of SEQ ID NO: 11, said sequence further comprising an intramolecular lactam bridge formed between amino acid positions 7 and 11, or between amino acid positions 11 and 15 of SEQ ID NO: 11. In one embodiment the glucagon antagonist/GLP-1 agonist comprises the sequence of SEQ ID NO: 17.

Additional glucagon antagonist/GLP-1 agonists are provided comprising derivatives of SEQ ID NO: 5, wherein the aspartic acid at position 10 of SEQ ID NO: 5 (position 15 of native glucagon) has been substituted with glutamic acid, an amino acid of the general structure:

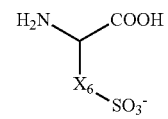

wherein $X_6$ is $C_1$-$C_3$ alkyl, $C_2$-$C_3$ alkene or $C_2$-$C_3$ alkynyl, and in one embodiment $X_6$ is $C_1$-$C_3$ alkyl, and in another embodiment $X_6$ is $C_2$ alkyl. In one embodiment a glucagon antagonist/GLP-1 agonist derivative of SEQ ID NO: 9 is provided wherein position 10 of SEQ ID NO: 9 (position 15 of native glucagon) is substituted with an amino acid selected from the group consisting of glutamic acid, cysteic acid, homocysteic acid and homoglutamic acid. In a further embodiment position 10 of SEQ ID NO: 9 is substituted with an amino acid selected from the group consisting of cysteic acid or homocysteic acid. In one embodiment a glucagon antagonist/GLP-1 agonist derivative of SEQ ID NO: 6, SEQ ID NO: 7 or SEQ ID NO: 8 is provided wherein position 10 of SEQ ID NO: 6, SEQ ID NO: 7 or SEQ ID NO: 8 is substituted with an amino acid selected from the group consisting of glutamic acid, cysteic acid, homocysteic acid and homoglutamic acid. In one embodiment the C-terminal amino acid of the antagonist/GLP-1 agonists have an amide group substituting for the carboxylic acid group that is present on the native amino acid.

The glucagon antagonist/GLP-1 agonist can be further modified to improve the peptide's solubility in aqueous solutions at physiological pH, while retaining the glucagon antagonist and GLP-1 agonist activity. Introduction of hydrophilic groups at positions corresponding to positions 12, 15, 16, 19 and 24 of the peptide of SEQ ID NO: 5, or at positions 12, 16, 19 or 24 of the peptide of SEQ ID NO: 6 can improve the solubility of the resulting peptides in solutions having a physiological pH, while retaining the parent compounds glucagon antagonist and GL P agonist activity. Therefore, in one embodiment the presently disclosed glucagon antagonist/GLP-1 agonists are further modified to comprise one or more hydrophilic groups covalently linked to the side chains of amino acids corresponding to amino acid positions 12, 15, 16, 19 and 24 of the peptide of SEQ ID NO: 5 or SEQ ID NO: 6. In a further embodiment the side chains of amino acids corresponding to amino acid positions 16 and 19 of SEQ ID NO: 5 or SEQ ID NO: 6 are covalently bound to hydrophilic groups, and in one embodiment the hydrophilic group is polyethylene glycol (PEG).

In one embodiment a glucagon antagonist/GLP-1 agonist is provided comprising an amino acid sequence selected from the group consisting of SEQ ID NO: 5, SEQ ID NO: SEQ ID NO: 6, SEQ ID NO: 7, or SEQ ID NO: 8, wherein said peptide comprises a lactam ring formed between the side chains of amino acids 7 and 11 for SEQ ID NO: 5, between 11 and 15 for SEQ ID NO: 6, between positions 15 and 19 for SEQ ID NO: 7 and between positions 19 and 24 for SEQ ID NO: 8, each of said sequences being further modified to comprise a hydrophilic moiety covalently bound to the peptide. More particularly, in one embodiment each of the lactam bearing glucagon antagonist/GLP-1 agonists are modified by covalent attachment of a polyethylene glycol chain. For example, for the glucagon antagonist/GLP-1 agonist comprising SEQ ID NO: 5, the peptide is pegylated at a position selected from the group consisting of 12, 15, 16, 19 and 24; for the glucagon antagonist/GLP-1 agonist comprising SEQ ID NO: 6, the peptide is pegylated at a position selected from the group consisting of 12, 16, 19 and 24; for glucagon antagonist/ GLP-1 agonist of SEQ ID NO: 7, the peptide is pegylated at a position selected from the group consisting of 11, 12, 16 and 24; for the glucagon antagonist/GLP-1 agonist comprising SEQ ID NO: 8, the peptide is pegylated at a position selected from the group consisting of 11, 12, 15 and 16. In accordance with one embodiment glucagon antagonist/GLP-1 agonist comprising SEQ ID NO: 47 or SEQ ID NO: 48 is provided wherein the petide is pegylated at a position selected from the group consisting of 12, 16, 19 and 24, relative to the SEQ ID NO: 47 or SEQ ID NO: 48 sequence.

In one embodiment an amino acid of the glucagon antagonist/GLP-1 agonist is substituted with at least one cysteine residue, wherein the side chain of the cysteine residue is further modified with a thiol reactive reagent, including for example, maleimido, vinyl sulfone, 2-pyridylthio, haloalkyl, and haloacyl. These thiol reactive reagents may contain carboxy, keto, hydroxyl, and ether groups as well as other hydrophilic moieties such as polyethylene glycol units. In an alternative embodiment, an amino acid of the glucagon antagonist/GLP-1 agonist is substituted with lysine, and the side chain of the substituting lysine residue is further modified using amine reactive reagents such as active esters (succinimido, anhydride, etc) of carboxylic acids or aldehydes of hydrophilic moieties such as polyethylene glycol. In accordance with one embodiment the lysine residue corresponding to position 7 of the peptide of SEQ ID NO: 5 is substituted with arginine and a single lysine substitution is inserted for one of the amino acids corresponding to position 12, 15, 16, 19 and 24 of SEQ ID NO: 5.

In another embodiment the methionine residue corresponding to position 22 of the glucagon antagonist/GLP-1 agonist peptides disclosed herein is changed to leucine or norleucine to prevent oxidative degradation of the peptide.

The presently disclosed glucagon antagonist/GLP-1 agonists also encompass amino acid substitutions at positions that are known not to be critical to the function of the glucagon analog. In one embodiment the substitutions are conservative amino acid substitutions at one, two or three positions selected from the group consisting of 2, 5, 6, 7, 8, 9, 12, 13, 14, 15, 16, 19, 22, 23 or 24. In one embodiment the amino acids corresponding to positions 16, 17, 20, 21, 24 or 29 of the native glucagon peptide, and more particularly at position 21 and/or 24 relative to native glucagon are substituted with cysteine or lysine, wherein a PEG chain is covalently attached to the substituted cysteine or lysine residue.

In accordance with one embodiment, a glucagon antagonist/GLP-1 agonist is provided comprising a sequence consisting of SEQ ID NO: 9, further modified by one or more additional amino acid substitutions at positions corresponding to positions 11, 12, 15, 16, 19 and/or 24 of the peptide (including for example substitution with cysteine), wherein the amino acid substitution comprises an amino acid having a side chain suitable for crosslinking with hydrophilic moieties, including for example, PEG. Native glucagon can be substituted with a naturally occurring amino acid or a synthetic (non-naturally occurring) amino acid. Synthetic or non-naturally occurring amino acids refer to amino acids that do not naturally occur in vivo but which, nevertheless, can be incorporated into the peptide structures described herein. In one embodiment a glucagon antagonist/GLP-1 agonist is provided wherein the peptide comprises the sequence of SEQ ID NO: 9 and further comprises a polyethylene chain bound to position 16 or 19 of the peptide. In a further embodiment the C-terminus of the glucagon analog is modified to replace the carboxylic acid group with an amide group.

In those embodiments wherein the glucagon antagonist/GLP-1 agonist comprises a polyethylene glycol chain, the polyethylene chain may be in the form of a straight chain or it may be branched. In accordance with one embodiment the polyethylene glycol chain has an average molecular weight selected from the range of about 500 to about 10,000 Daltons. In one embodiment the polyethylene glycol chain has an average molecular weight selected from the range of about 1,000 to about 5,000 Daltons. In one embodiment the polyethylene glycol chain has an average molecular weight selected from the range of about 1,000 to about 5,000 Daltons. In one embodiment the polyethylene glycol chain has an average molecular weight selected of about 1,000 to about 2,000 Daltons. In one embodiment the polyethylene glycol chain has an average molecular weight of about 1,000 Daltons.

In one embodiment the pegylated glucagon antagonist/GLP-1 agonist comprises a peptide consisting of the sequence of SEQ ID NO: 15 or SEQ ID NO: 51 wherein the polyethylene glycol chain is linked to an amino acid selected from positions 11, 12, 15, 16, 19 and 24 of SEQ ID NO: 15 or SEQ ID NO: 51, and the molecular weight of the PEG chain is about 1,000 to about 5,000 Daltons. In one embodiment the pegylated glucagon antagonist/GLP-1 agonist comprises a peptide consisting of the sequence of SEQ ID NO: 15 or SEQ ID NO: 51 wherein the polyethylene glycol chain is linked to the amino acid at position 16 or 19 of SEQ ID NO: 15 or SEQ ID NO: 51, and the molecular weight of the PEG chain is about 1,000 to about 5,000 Daltons. In a further embodiment the modified glucagon antagonist/GLP-1 agonist comprises two or more polyethylene chains covalently bound to the peptide wherein the total molecular weight of the glucagon chains is about 1,000 to about 5,000 Daltons. In one embodiment the pegylated glucagon antagonist/GLP-1 agonist comprises the sequence of SEQ ID NO: 15 or SEQ ID NO: 51 wherein a polyethylene glycol chain is linked to the amino acid at positions 16 and 19 of SEQ ID NO: 15 or SEQ ID NO: 51 and the combined molecular weight of the two PEG chains is about 1,000 to about 5,000 Daltons.

In accordance with one embodiment a glucagon antagonist/GLP-1 agonist is provided comprising a glucagon analog selected from the group consisting of:

(SEQ ID NO: 39)
$R_1$-Phe-Thr-Ser-Xaa-Tyr-Ser-Lys-Tyr-Leu-Xaa-Glu-

Arg-Arg-Ala-Gln-Asp-Phe-Val-Gln-Trp-Leu-Xaa-Asn-

Thr-$R_2$ (SEQ ID NO: 13)
$R_1$-Phe-Thr-Ser-Xaa-Tyr-Ser-Lys-Tyr-Leu-Asp-Glu-

Arg-Arg-Ala-Gln-Xaa-Phe-Val-Gln-Trp-Leu- Xaa-Asn-

Thr-$R_2$, (SEQ ID NO: 14)
$R_1$-Phe-Thr-Ser-Xaa-Tyr-Ser-Lys-Tyr-Leu-Asp-Glu-

Arg-Arg-Ala-Gln-Asp-Phe-Val-Xaa-Trp-Leu-Xaa-Asn-

Thr-$R_2$ and

-continued (SEQ ID NO: 12)
R₁-Phe- Thr-Ser-Xaa-Tyr-Ser-Lys-Tyr-Leu-Asp-Glu-

Arg-Arg-Ala-Gln-Xaa-Phe-Val-Xaa-Trp-Leu- Xaa-Asn-

Thr-R₂, wherein Xaa at position 4=aspartic acid, glutamic acid, cysteic acid or homocysteic acid, Xaa at position 10=Asp, Glu, cysteic acid, homoglutamic acid and homocysteic acid, Xaa at position 16 is Asp, Cys, Orn, homocysteine or acetyl phenylalanine and the Xaa at position 19 is Gln, Cys, Orn, homocysteine and acetyl phenylalanine, Xaa at position 22=Met, Leu or Nle, R₁ is OH or NH₂, and R₂ is Gly Pro Ser Ser Gly Ala Pro Pro Pro Ser (SEQ ID NO: 21), Gly Pro Ser Ser Gly Ala Pro Pro Pro Ser Xaa (SEQ ID NO: 50; wherein Xaa is Cys, Orn, homocystein or acetyl phenylalanine), COOH or CONH₂, wherein the peptide is optionally pegylated at position 16 of SEQ ID NO: 13, position 19 of SEQ ID NO: 14 and at positions 16 and 19 of SEQ ID NO: 12. In one embodiment the Thr at position 24 of SEq ID NOs: 12-14 and 39 is substituted with Gly. In accordance with one embodiment the peptide comprises the sequence of SEQ ID NO: 13 or SEQ ID NO: 14, wherein R₁ is OH. In accordance with one embodiment the peptide comprises the sequence of SEQ ID NO: 13 or SEQ ID NO: 14, wherein R₁ is OH and R₂ is CONH₂. In accordance with one embodiment the peptide comprises the sequence of SEQ ID NO: 13 or SEQ ID NO: 14, wherein R₁ is OH, R₂ is CONH₂ and the threonine at position 24 is substituted with glycine.

In accordance with one embodiment, a glucagon antagonist/GLP-1 agonist is provided wherein a plasma protein has been covalently linked to an amino acid side chain of the peptide to improve the solubility, stability and/or pharmacokinetics of the glucagon analog. For example, serum albumin can be covalently bound to the glucagon antagonist/GLP-1 agonists presented herein. In one embodiment the plasmid protein is covalently bound to an amino acid corresponding to position 12, 15, 16, 19 or 24 of the peptide of SEQ ID NO: 15, SEQ ID NO: 51 or SEQ ID NO: 5. More particularly, in one embodiment the plasmid protein is bound to an amino acid corresponding to position 16 or 19 of the glucagon analog, wherein the derivative comprises the sequence of SEQ ID NO: 5 and SEQ ID NO: 6, or the plasma protein is bound at position 16 of SEQ ID NO: 13, position 19 of SEQ ID NO: 14 and at positions 16 and 19 of SEQ ID NO: 12.

In accordance with one embodiment, a glucagon antagonist is provided wherein a linear amino acid sequence representing the Fc portion of an immunoglobin molecule has been covalently linked to an amino acid side chain of a glucagon antagonist/GLP-1 agonist disclosed herein to improve the solubility, stability and/or pharmacokinetics of the glucagon analog. For example, the amino acid sequence representing the Fc portion of an immunoglobin molecule can be covalently bound to position 12, 15, 16, 19, 21 or 24 of the peptide of SEQ ID NO: 15, SEQ ID NO: 51 or SEQ ID NO: 5. More particularly, in one embodiment the plasmid protein is bound to an amino acid corresponding to position 16 or 19 of the glucagon analog, wherein the analog comprises the sequence of SEQ ID NO: 5 and SEQ ID NO: 6, or the Fc portion is bound at position 16 for the derivative comprising SEQ ID NO: 13, position 19 for the derivative comprising SEQ ID NO: 14 and at positions 16 and 19 for the derivative comprising SEQ ID NO: 12. The Fc portion is typically one isolated from IgG, but the Fc peptide fragment from any immunoglobin should function equivalently.

The present disclosure also encompasses other conjugates in which glucagon peptides of the invention are linked, optionally via covalent bonding and optionally via a linker, to a conjugate. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

Exemplary conjugates include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. In one embodiment a conjugate is provided comprising a glucagon peptide disclosed herein and a plasma protein, wherein the plasma protein is selected form the group consisting of albumin, transferin, fibrinogen and glubulins. In one embodiment the plasma protein moiety of the conjugate is albumin or transferin. In some embodiments, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

The Asp-Ser sequence at position 15-16 of native glucagon has been identified as a uniquely unstable dipeptide that leads to premature chemical cleavage of the native hormone in aqueous buffers. For example, when maintained at 0.01N HCl at 37° C. for 2 weeks, more than 50% of the native glucagon may be cleaved into fragments. The two liberated cleavage peptides 1-15 and 16-29 are devoid of glucagon-like biological activity and thus represent a limitation on the aqueous pre-formulation of glucagon and its related analogs. The selective chemical substitution of the Asp at position 15 of native glucagon with Glu has been observed to virtually eliminate chemical cleavage of the 15-16 peptide bond.

Accordingly, it is expected that the glucagon antagonists/GLP-1 agonists disclosed herein can be similarly modified to decrease their susceptibility to premature chemical cleavage in aqueous buffers. In accordance with one embodiment the glucagon antagonists/GLP-1 agonists described herein can be further modified to enhance their stability in aqueous solutions by replacing the native aspartic amino acid, located at corresponding position 15 of native glucagon, with an amino acid selected from the group consisting of cysteic acid, glutamic acid, homoglutamic acid and homocysteic acid. In accordance with one embodiment the aspartic acid residue at position 10 of the glucagon antagonists/GLP-1 agonist of SEQ ID NO: 5, SEQ ID NO: 6, SEQ ID NO: 7 or SEQ ID NO: 8 can be substituted with an amino acid selected from the group consisting of cysteic acid, glutamic acid, homo-glutamic acid and homocysteic acid, and in one embodiment the native aspartic acid at position 10 of SEQ ID NO: 5, SEQ ID NO: 6, SEQ ID NO: 7 or SEQ ID NO: 8 is replaced with glutamic acid. In accordance with one embodiment a glucagon antagonist/GLP-1 agonist having improved stability in aqueous solutions is provided wherein the antagonist comprises a modified sequence of SEQ ID NO: 9, wherein the modification comprises substitution of the Asp at position 10 of SEQ ID NO: 9 with Glu. In one embodiment a glucagon antagonist/GLP-1 agonist is provided comprising a sequence selected form the group consisting of SEQ ID NO: 22, SEQ ID NO: 23, SEQ ID NO: 24 and SEQ ID NO: 25. In one embodiment the glucagon antagonist/GLP-1 agonist is amidated.

In accordance with one embodiment, increased stability by way of reduced degradation of the glucagon antagonist/GLP-1 agonist described herein may also be achieved by substitution of the serine at position 16 (according to the numbering of native glucagon) with glutamic acid, cysteic acid, homo-glutamic acid, or homo-cysteic acid. In a specific embodiment, the serine at position 16 (according to the native glucagon sequence numbering) is replaced with glutamic acid.

Applicants have also discovered that native glucagon can be modified by introducing charge at its carboxy terminus to enhance the solubility of the peptide while retaining the agonist properties of the peptide. The enhanced solubility allows for the preparation and storage of glucagon solutions at near neutral pH. Formulating glucagon solutions at relatively neutral pHs (e.g. pH of about 6.0 to about 8.0) improves the long term stability of the glucagon analogs.

Applicants anticipate that the glucagon antagonists/GLP-1 agonists disclosed herein can be similarly modified to enhance their solubility in aqueous solutions at relatively neutral pH (e.g. pH of about 6.0 to about 8.0) while retaining the glucagon antagonist and GLP-1 activities of the parent protein. Accordingly, one embodiment is directed to a glucagon antagonist/GLP-1 of SEQ ID NO: 5, SEQ ID NO: 6, SEQ ID NO: 7 or SEQ ID NO: 8 that has been further modified relative to the native amino acids present at positions 6-29 of the wild type glucagon (SEQ ID NO: 1) to add charge to the peptide by the substitution of native non-charged amino acids with charged amino acids, or the addition of charged amino acids to the carboxy terminus. In accordance with one embodiment, one to three of the non-charged native amino acids of the glucagon antagonist/GLP-1 agonists disclosed herein are replaced with a charged amino acid. In one embodiment the charged amino acid is selected from the group consisting of lysine, arginine, histidine, aspartic acid and glutamic acid. More particularly, applicants have discovered that substituting the normally occurring amino acid corresponding to position 28 and/or 29 (relative to native glucagon) with charged amino acids, and/or the addition of one to two charged amino acids at the carboxy terminus of the peptide, enhances the solubility and stability of the glucagon analog in aqueous solutions at physiologically relevant pHs (i.e., a pH of about 6.5 to about 7.5). Accordingly such modifications of the glucagon antagonist/GLP-1 agonists disclosed herein are anticipated to have a similar effect on the solubility in aqueous solutions, particularly at a pH ranging from about 5.5 to about 8.0, while retaining the parent peptide's biological activity In accordance with one embodiment the glucagon antagonist/GLP-1 agonist of SEQ ID NO: 5, SEQ ID NO: 6, SEQ ID NO: 7 or SEQ ID NO: 8 is modified by the substitution of the native amino acid at position 23 and/or 24 of those sequences with a negatively charged amino acid (e.g., aspartic acid or glutamic acid) and optionally the addition of a negatively charged amino acid (e.g., aspartic acid or glutamic acid) to the carboxy terminus of the peptide. In an alternative embodiment the glucagon antagonis/GLP-1 agonist of SEQ ID NO: 5, SEQ ID NO: 6, SEQ ID NO: 7 or SEQ ID NO: 8 is modified by the substitution of the native amino acid at position 24 of SEQ ID NO: 5, SEQ ID NO: 6, SEQ ID NO: 7 or SEQ ID NO: 8 with a positively charged amino acid (e.g., lysine, arginine or histidine) and optionally the addition of one or two positively charged amino acid (e.g., lysine, arginine or histidine) on the carboxy terminus of the peptide. In accordance with one embodiment a glucagon analog having improved solubility and stability is provided wherein the analog comprises the amino acid sequence of SEQ ID NO: 15 or SEQ ID NO: 51 with the proviso that at least one amino acids at position, 23, or 24 of SEQ ID NO: 15 or SEQ ID NO: 51 is substituted with an acidic amino acid and/or an additional acidic amino acid added at the carboxy terminus of SEQ ID NO: 15 or SEQ ID NO: 51. In one embodiment the acidic amino acids are independently selected from the group consisting of Asp, Glu, cysteic acid and homocysteic acid.

In accordance with one embodiment a glucagon antagonist/GLP-1 agonist having improved solubility and stability is provided wherein the antagonist comprises the amino acid sequence of SEQ ID NO: 16, SEQ ID NO: 17, SEQ ID NO: 18 or SEQ ID NO: 19. In accordance with one embodiment a glucagon agonist is provided comprising the sequence of SEQ ID NO: 16 or SEQ ID NO: 17. In one embodiment the glucagon antagonist/GLP-1 agonist comprises the sequence of SEQ ID NO: 20, with the proviso that when the amino acid at position 23 of SEQ ID NO: 20 is asparagine and the amino acid at position 24 of SEQ ID NO: 20 is threonine, the peptide further comprises one to two amino acids, independently selected from the group consisting of Asp and Glu, added to the carboxy terminus of the glucagon antagonist/GLP-1 agonist.

In accordance with one embodiment a glucagon antagonist/GLP-1 agonist is provided comprising the sequence of SEQ ID NO: 15 or SEQ ID NO: 51. In one embodiment, position 4 of SEQ ID NO: 15 or SEQ ID NO: 51 is aspartic acid, glutamic acid, homoglutamic acid, cysteic acid or homocysteic acid, and in one embodiment position 4 is aspartic acid, glutamic acid, cysteic acid or homocysteic acid, and in a further embodiment position 4 of SEQ ID NO: 15 or SEQ ID NO: 51 is aspartic acid or glutamic acid, and in one embodiment position 4 of SEQ ID NO: 15 or SEQ ID NO: 51 is aspartic acid. In one embodiment a glucagon antagonist/GLP-1 agonist is provided comprising the sequence of SEQ ID NO: 15 or SEQ ID NO: 51 wherein position 4 of SEQ ID NO: 15 is aspartic acid and position 10 of SEQ ID NO: 15 is glutamic acid. In a further embodiment the C-terminal amino acid of SEQ ID NO: 15 or SEQ ID NO: 51 is modified to replace the native carboxylic acid group with a charge-neutral group, such as an amide or ester.

The present disclosure also encompasses glucagon antagonist/GLP-1 agonist fusion peptides wherein a second peptide has been fused to the c-terminus of the glucagon antagonist/GLP-1 agonist. More particularly, the fusion peptide may comprise a glucagon antagonist/GLP-1 agonist peptide of SEQ ID NO: 15 or SEQ ID NO: 51 that further comprises an amino acid sequence selected from the group consisting of SEQ ID NO: 21 (GPSSGAPPPS), SEQ ID NO: 50 (GPSS- GAPPPSX), SEQ ID NO: 26 (KRNRNNIA) and SEQ ID NO: 27 (KRNR) linked to amino acid 24 of the glucagon antagonist/GLP-1 agonist. In one embodiment the amino acid sequence of SEQ ID NO: 21 (GPSSGAPPPS) is bound to amino acid 24 of the glucagon antagonist/GLP-1 agonist of SEQ ID NO: 15 or SEQ ID NO: 51 through a peptide bond. In another embodiment the fusion peptide comprises a glucagon antagonist/GLP-1 agonist peptide of SEQ ID NO: 5, SEQ ID NO: 6, SEQ ID NO: 7, SEQ ID NO: 8, SEQ ID NO: 9, SEQ ID NO: 22, SEQ ID NO: 23, SEQ ID NO: 24 and SEQ ID NO: 25 that further comprises an amino acid sequence of SEQ ID NO: 21 (GPSSGAPPPS) linked to the carboxy terminal amino acid of the glucagon antagonist/GLP-1 agonist. In a further embodiment the C-terminus is modified to replace the carboxylic acid group with an amide group. In one embodiment a glucagon antagonist/GLP-1 agonist dimer is provided comprising two sequences independently selected from the group consisting of SEQ ID NO: 5, SEQ ID NO: 6, SEQ ID NO: 7, SEQ ID NO: 8, SEQ ID NO: 9, SEQ ID NO: 22, SEQ ID NO: 23, SEQ ID NO: 24 and SEQ ID NO: 25 that further comprises an amino acid sequence of SEQ ID NO: 21 (GPSSGAPPPS) linked to the carboxy terminal amino acid of the glucagon antagonist/GLP-1 agonist.

In a further embodiment a glucagon antagonist/GLP-1 agonist fusion peptide is optionally pegylated. In one embodiment a glucagon antagonist/GLP-1 agonist fusion peptide is provided wherein the glucagon antagonist/GLP-1 agonist portion of the fusion peptide is selected from the group consisting of SEQ ID NO: 5, SEQ ID NO: 6, SEQ ID NO: 7, SEQ ID NO: 8, SEQ ID NO: 9, SEQ ID NO: 12, SEQ ID NO: 13, SEQ ID NO: 14, SEQ ID NO: 16, SEQ ID NO: 17, SEQ ID NO: 22, SEQ ID NO: 23, SEQ ID NO: 24 and SEQ ID NO: 25, wherein the sequence of SEQ ID NO: 21 is fused to the carboxy terminus of the glucagon antagonist/GLP-1 agonist portion, and wherein the PEG chain, when present, is selected from the range of 500 to 40,000 Daltons. More particularly, in one embodiment the glucagon antagonist/GLP-1 agonist segment of said fusion peptide is selected from the group consisting of SEQ ID NO: 12, SEQ ID NO: 13 and SEQ ID NO: 14 wherein the PEG chain is selected from the range of about 500 to about 5,000 Daltons, and more particularly, in one embodiment the PEG chain is about 1,000 Daltons. In another embodiment the glucagon antagonist/GLP-1 agonist fusion peptide comprises the sequence of SEQ ID NO: 45 or SEQ ID NO: 46, wherein the PEG chain is selected from the range of about 500 to about 5,000 Daltons, and more particularly, in one embodiment the PEG chain is about 1,000 Daltons. In a further embodiment the C-terminus is modified to replace the carboxylic acid group with an amide group.

In some embodiments, the glucagon antagonists/GLP-1 agonist is further modified by truncation or deletion of one or two amino acids of the C-terminus of the glucagon peptide (i.e., truncation of the amino acid at position 29 or at positions 28 and 29 of native glucagon) without affecting activity and/or potency at the glucagon and GLP-1 receptors. In this regard, the glucagon antagonist described herein can consist essentially of or consist of amino acids 1-27, 1-28, 2-27, 2-28, 3-27, 3-28, 4-27, 4-28, 5-27, 5-28, 6-27, or 6-28 of the native glucagon peptide (SEQ ID NO: 1) with one or more modifications resulting in glucagon antagonistic activity as described herein.

In one embodiment, the glucagon antagonist/GLP-1 agonist is further modified to comprise one or more amino acids of native GLP-1 by substitution of the native glucagon residue(s) at corresponding amino acid positions. For example, the glucagon antagonist/GLP-1 agonist may comprise one or more amino acid substitutions at any of positions 2, 3, 17, 18, 21, 23, and 24 (according to the amino acid numbering of native glucagon). In a specific embodiment, the glucagon antagonist/GLP-1 agonist is modified by one or more of the following amino acid substitutions: Ser2 is replaced with Ala, Gln3 is replaced with Glu, Arg17 is replaced with Gln, Arg at position 18 is replaced with Ala, Asp at position 21 is replaced with Glu, Val at position 23 is replaced with Ile, and Gln at position 24 is replaced with Ala (amino acid positions are in accordance with the native glucagon sequence). In a specific embodiment, the glucagon antagonist/GLP-1 agonist is modified by replacing Ser2 with Ala and Gln3 with Glu (according to the amino acid numbering of native glucagon). In another specific embodiment, the glucagon antagonist/GLP-1 agonist is modified with all of the following amino acid substitutions: Arg17 is replaced with Gln, Arg at position 18 is replaced with Ala, Asp at position 21 is replaced with Glu, Val at position 23 is replaced with Ile, and Gln at position 24 is replaced with Ala (amino acid numbering according to native glucagon). In yet another specific embodiment, the glucagon antagonist/GLP-1 agonist is modified to comprise just Glu at position 21 (according to the numbering of SEQ ID NO: 1). Accordingly, the glucagon antagonist/GLP-1 agonist can comprise the amino acid sequence of any of SEQ ID NOs: 60-70, 73-78, 80-88, 90-96, 103, 104, 106, and 114-118, or comprising the amino acid sequence of any of Peptides 2-6 of Table 13, Peptides 1-8 of Table 14, and Peptides 2-6, 8, and 9 of Table 15.

In a specific embodiment, the above-described glucagon antagonist/GLP-1 agonist comprising PLA is modified to comprise an oxy derivative of PLA, such as, for instance, an ester of PLA or an ether of PLA. For example, the glucagon antagonist/GLP-1 agonist can comprise the amino acid sequence of any of SEQ ID NOs: 2, 5-20, 22-25, 32-36, 38, 39, 45, 46, and 51, wherein the PLA is linked via an ester or ether bond to an amino acid, peptide, polymer, acyl group, or alkyl group. The amino acid, peptide, polymer, acyl group, or alkyl group may be any of those described herein. In the case that the PLA is linked via an ester bond to an amino acid or peptide, the glucagon antagonist/GLP-1 agonist may be considered as a depsipeptide.

Also, in another specific embodiment, the above-described glucagon antagonist/GLP-1 agonist which lacks PLA is modified to comprise at least one ester bond or ether bond between two consecutive amino acids which are N-terminal to the amino acid at position 7 (according to the numbering of native glucagon). In a specific embodiment, the glucagon antagonist/GLP-1 agonist comprises at least one ester or ether bond between the two consecutive amino acids. In a more specific embodiment, the glucagon antagonist/GLP-1 agonist comprises the N-terminal 6 amino acids of SEQ ID NO: 1 and two consecutive amino acids of the N-terminal 6 amino acids are linked via an ester or ether bond.

Also provided herein is a peptide or conjugate thereof comprising (1) a stabilized alpha helix through means described herein (e.g., through an intramolecular bridge, or incorporation of one or more alpha, alpha-di-substituted amino acids, or an acidic amino acid at position 16 (according to the numbering of SEQ ID NO:1), or a combination thereof; (2) a C-terminal amide or ester in place of a C-terminal carboxylate, and (3) a general structure of A-B-C, wherein A is selected from the group consisting of
(i) PLA;
(ii) an oxy derivative of PLA; and
(iii) a peptide of 2 to 6 amino acids in which two consecutive
amino acids of the peptide are linked via an ester or ether bond;

wherein B represents amino acids p to 26 of SEQ ID NO: 1, wherein p is 3, 4, 5, 6, or 7, optionally comprising one or more amino acid modifications selected from the group consisting of:
- (iv) Asp at position 9 (according to the amino acid numbering of SEQ ID NO: 1) is substituted with a Glu, a sulfonic acid derivative of Cys, homoglutamic acid, β-homoglutamic acid, or an alkylcarboxylate derivative of cysteine having the structure of:

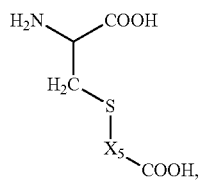

wherein $X_5$ is $C_1$-$C_4$ alkyl, $C_2$-$C_4$ alkenyl, or $C_2$-$C_4$ alkynyl;
- (v) substitution of one or two amino acids at positions 10, 20, and 24, (according to the amino acid numbering of SEQ ID NO: 1) with an amino acid covalently attached to an acyl or alkyl group via an ester, ether, thioether, amide, or alkyl amine linkage;
- (vi) substitution of one or two amino acids at positions 16, 17, 20, 21, and 24 (according to the amino acid numbering of SEQ ID NO: 1) with an amino acid selected from the group consisting of: Cys, Lys, ornithine, homocysteine, and acetyl-phenylalanine (Ac-Phe), wherein the amino acid of the group is covalently attached to a hydrophilic moiety;
- (vii) Asp at position 15 (according to the numbering of SEQ ID NO: 1) is substituted with cysteic acid, glutamic acid, homoglutamic acid, and homocysteic acid;
- (viii) Ser at position 16 (according to the numbering of SEQ ID NO: 1) is substituted with cysteic acid, glutamic acid, homoglutamic acid, and homocysteic acid;
- (ix) Arg at position 17 is replaced with Gln, Arg at position 18 is replaced with Ala, Asp at position 21 is replaced with Glu, Val at position 23 is replaced with Ile, and Gln at position 24 is replaced with Ala (according to amino acid numbering of SEQ ID NO: 1);
- (x) Ser at position 16 is replaced with Glu, Gln at position 20 is replaced with Glu, or Gln at position 24 is replaced with Glu (according to the amino acid numbering of SEQ ID NO: 1);

wherein C is selected from the group consisting of:
- (vii) X;
- (viii) X—Y;
- (ix) X—Y—Z;
- (x) X—Y—Z—R10;

wherein X is Met, Leu, or Nle; Y is Asn or a charged amino acid; Z is Thr, Gly, Cys, Lys, ornithine (Orn), homocysteine, acetyl phenylalanine (Ac-Phe), or a charged amino acid; wherein R10 is selected from a group consisting of SEQ ID NOs: 21, 26, 27, and 50.

In a specific aspect, the peptide comprises an oxy derivative of PLA. As used herein "oxy derivative of PLA" refers to a compound comprising a modified structure of PLA in which the hydroxyl group has been replaced with O—$R_{11}$, wherein $R_{11}$ is a chemical moiety. In this regard, the oxy derivative of PLA can be, for example, an ester of PLA or an ether of PLA.

Methods of making oxy derivatives of PLA are known in the art. For example, when the oxy derivative is an ester of PLA, the ester may be formed by upon reaction of the hydroxyl of PLA with a carbonyl bearing a nucleophile. The nucleophile can be any suitable nucleophile, including, but not limited to an amine or hydroxyl. Accordingly, the ester of PLA can comprise the structure of Formula IV:

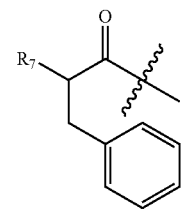

Formula IV wherein R7 is an ester formed upon reaction of the hydroxyl of PLA with a carbonyl bearing a nucleophile.

The carbonyl bearing a nucleophile (which reacts with the hydroxyl of PLA to form an ester) can be, for example, a carboxylic acid, a carboxylic acid derivative, or an activated ester of a carboxylic acid. The carboxylic acid derivative can be, but is not limited to, an acyl chloride, an acid anhydride, an amide, an ester, or a nitrile. The activated ester of a carboxylic acid can be, for example, N-hydroxysuccinimide (NHS), tosylate (Tos), a carbodiimide, or a hexafluorophosphate. In some embodiments, the carbodiimide is 1,3-dicyclohexylcarbodiimide (DCC), 1,1'-carbonyldiimidazole (CDI), 1-ethyl-3-(3-dimethylaminopropyl)carbodiimide hydrochloride (EDC), or 1,3-diisopropylcarbodiimide (DICD). In some embodiments, the hexafluorophosphate is selected from a group consisting of hexafluorophosphate benzotriazol-1-yl-oxy-tris(dimethylamino)phosphonium hexafluorophosphate (BOP), benzotriazol-1-yl-oxytripyrrolidinophosphonium hexafluorophosphate (PyBOP), 2-(1H-7-azabenzotriazol-1-yl)-1,1,3,3-tetramethyl uronium hexafluorophosphate (HATU), and o-benzotriazole-N,N,N',N'-tetramethyl-uronium-hexafluoro-phosphate (HBTU).

Methods of making ethers from reaction with a hydroxyl group (e.g., the hydroxyl of PLA) also are known in the art. For example, the hydroxyl group of PLA may be reacted with a halogenated alkyl or tosylated alkyl alcohol to form an ether bond.

Generally, the chemical moiety of $R_{11}$ is one which does not decrease the activity of the peptide. In some embodiments, the chemical moiety enhances the activity, stability, and/or solubility of the peptide.

In a specific embodiment, the chemical moiety bound to PLA via an oxygen-containing bond (e.g., via an ester or ether bond) is a polymer (e.g., a polyalkylene glycol), a carbohydrate, an amino acid, a peptide, or a lipid, e.g., a fatty acid or a steroid.

In a specific embodiment, the chemical moiety is an amino acid, which, optionally, is a part of a peptide, such that Formula IV is a depsipeptide. In this regard, PLA may be at a position other than the N-terminal amino acid residue of the peptide, such that the peptide comprises one or more (e.g., 1, 2, 3, 4, 5, 6, or more) amino acids N-terminal to the PLA residue. For example, the peptide can comprise PLA at position n, wherein n is 2, 3, 4, 5, or 6 of the peptide.

The amino acids N-terminal to the PLA residue may be synthetic or naturally-occurring. In a specific embodiment, the amino acids which are N-terminal PLA are naturally-occurring amino acids. In one embodiment, the amino acids which are N-terminal to PLA are the N-terminal amino acids of native glucagon. For example, the peptide can comprise at the N-terminus the amino acid sequence of any of SEQ ID NOs: 52-56, wherein PLA is linked to threonine via an ester bond:

```
SEQ ID NO: 52    His-Ser-Gln-Gly-Thr-PLA

SEQ ID NO: 53    Ser-Gln-Gly-Thr-PLA

SEQ ID NO: 54    Gln-Gly-Thr-PLA

SEQ ID NO: 55    Gly-Thr-PLA

SEQ ID NO: 56    Thr-PLA
```

In an alternative embodiment, one or more of the N-terminal amino acids may be substituted with an amino acid other than the amino acid of native glucagon. For example, when the peptide comprises PLA as the amino acid at position 5 or 6, the amino acid at position 1 and/or position 2 may be an amino acid which reduces susceptibility to cleavage by dipeptidyl peptidase IV. More particularly, in some embodiments, position 1 of the peptide is an amino acid selected from the group consisting of D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine. More particularly, in some embodiments, position 2 of the antagonist/agonist peptide is an amino acid selected from the group consisting of D-serine, D-alanine, valine, glycine, N-methyl serine, N-methyl alanine, and aminoisobutyric acid (AIB). Also, for example, when the peptide comprises PLA as the amino acid at position 4, 5, or 6, the amino acid at position 3 of the peptide may be glutamic acid, as opposed to the native glutamine residue of native glucagon. In an exemplary embodiment of the invention, the peptide comprises at the N-terminus the amino acid sequence of any of SEQ ID NOs: 57-59.

With respect to the peptides comprising a compound of Formula IV, the polymer may be any polymer, provided that it can react with the hydroxyl group of PLA. The polymer may be one that naturally or normally comprises a carbonyl bearing a nucleophile. Alternatively, the polymer may be one which was derivatized to comprise the carbonyl bearing the carbonyl. The polymer may be a derivatized polymer of any of: polyamides, polycarbonates, polyalkylenes and derivatives thereof including, polyalkylene glycols, polyalkylene oxides, polyalkylene terephthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

The polymer can be a biodegradable polymer, including a synthetic biodegradable polymer (e.g., polymers of lactic acid and glycolic acid, polyanhydrides, poly(ortho)esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

The polymer can be a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In one embodiment, the polymer is a water-soluble polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof.

In a specific embodiment, the polymer is a polyalkylene glycol, including, for example, polyethylene glycol (PEG).

The carbohydrate may be any carbohydrate provided that it comprises or is made to comprise a carbonyl with an alpha leaving group. The carbohydrate, for example, may be one which has been derivatized to comprise a carbonyl with an alpha leaving group. In this regard, the carbohydrate may be a derivatized form of a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

The lipid may be any lipid comprising a carbonyl with an alpha leaving group. The lipid, for example, may be one which is derivatized to comprise the carbonyl. In this regard, the lipid, may be a derivative of a fatty acid (e.g., a $C_4$-$C_{30}$ fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide.

oil, wax, cholesterol, sterol, fat-soluble vitamin, monoglyceride, diglyceride, triglyceride, a phospholipid.

In one embodiment, R7 has a molecular weight of about 100 kDa or less, e.g., about 90 kDa or less, about 80 kDa or less, about 70 kDa or less, about 60 kDa or less, about 50 kDa or less, about 40 kDa or less. Accordingly, R7 can have a molecular weight of about 35 kDa or less, about 30 kDa or less, about 25 kDa or less, about 20 kDa or less, about 15 kDa or less, about 10 kDa or less, about 5 kDa or less, or about 1 kDa.

In an alternative embodiment, the peptide comprising the general structure of A-B-C comprises, as A, a peptide of 2 to 6 amino acids in which two consecutive amino acids of the peptide of A are linked via an ester or ether bond. The ester or ether bond may be, e.g., between amino acids 2 and 3, 3 and 4, 4 and 5, or 5 and 6. Optionally the peptide of A may be further modified by covalent linkage to another chemical moiety including linkage to a polymer (e.g. a hydrophilic polymer), alkylation, or acylation.

The peptide of A may comprise any amino acids, synthetic or naturally occurring, provided that at least two consecutive amino acids are linked via an ester or ether bond. In a specific embodiment, the peptide of A comprises amino acids of native glucagon. For example, the peptide of A can comprise j to 6 of native glucagon (SEQ ID NO: 1), wherein j is 1, 2, 3, 4, or 5. Alternatively, the peptide of A can comprise an amino acid sequence based on the N-terminus of SEQ ID NO: 1 with one or more amino acid modifications. The amino acid at position 1 and/or position 2 may be an amino acid which reduces susceptibility to cleavage by dipeptidyl peptidase IV. For instance, the peptide of A can comprise at position 1 an amino acid selected from the group consisting of D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine. More particularly, in some embodiments, position 2 of the peptide of A is an amino acid selected from the group consisting of D-serine, D-alanine, valine, glycine, N-methyl serine, N-methyl alanine, and aminoisobutyric acid (AIB). Also, for example, the amino acid at position 3 of the peptide of A may be glutamic acid, as opposed to the native glutamine residue of native glucagon. Accordingly, the peptide of general structure of A-B-C can comprise an amino acid sequence of:

| | |
|---|---|
| Xaa$_1$-Xaa$_2$-Xaa$_3$-Thr-Gly-Phe; | (SEQ ID NO: 107) |
| Xaa$_2$-Xaa$_3$-Thr-Gly-Phe;<br>or | (SEQ ID NO: 108) |
| Xaa$_3$-Thr-Gly-Phe; | (SEQ ID NO: 109) | wherein Xaa$_1$ is selected from a group consisting of: His, D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine; Xaa$_2$ is selected from a group consisting of: Ser, D-serine, D-alanine, valine, glycine, N-methyl serine, N-methyl alanine, and aminoisobutyric acid (AIB); and Xaa$_3$ is Gln or Glu.

With regard to the peptide comprising the general structure A-B-C, B represents amino acids of native glucagon, e.g., i to 26 of SEQ ID NO: 1, wherein i is 3, 4, 5, 6, or 7, optionally comprising one or more amino acid modifications. In a specific embodiment, B represents amino acids 7 to 26 of SEQ ID NO: 1, optionally further modified.

In one embodiment, B is modified by up to three amino acid modifications. For example, B, which represents native amino acid sequence of SEQ ID NO: 1 is modified by one or more conservative amino acid modifications.

In another embodiment, B comprises one or more amino acid modifications selected from the group consisting of (iv) to (x), as described herein. In a specific embodiment, B comprises one or both of the amino acid modifications (v) and (vi). In a further specific embodiment, B comprises one or a combination of amino acid modifications selected from the group consisting of (iv), (vii), (viii), (ix), and (x), in addition to (v) and (vi).

As described herein, the peptide comprising the general structure A-B-C may comprise one or more charged amino acids at the C-terminus, e.g., as Y and/or Z, as described herein. Alternatively or additionally, the peptide comprising the general structure A-B-C may further comprise one to two charged amino acids C-terminal to Z, when C comprises X-Y-Z. The charged amino acids can be, for example, one of Lys, Arg, His, Asp, and Glu. In a specific embodiment, Y is Asp.

In one embodiment, the peptide comprising the general structure A-B-C comprises a hydrophilic moiety covalently bound to an amino acid residue at position 1, 16, 20, 21, or 24 (according to the amino acid numbering of SEQ ID NO: 1), or at the N- or C-terminal residue of the peptide comprising the general structure A-B-C. In a specific embodiment, the hydrophilic moiety is attached to a Cys residue of the peptide comprising the general structure A-B-C. In this regard, the amino acid at position 16, 21, 24, or 29 of native glucagon (SEQ ID NO: 1) may be substituted with a Cys residue. Alternatively, a Cys residue comprising a hydrophilic moiety may be added to the C-terminus of the peptide comprising the general structure A-B-C as position 30 or as position 40, e.g., when the peptide comprising the general structure A-B-C comprises a C-terminal extension (positions according to the amino acid numbering of SEQ ID NO: 1). Alternatively, the hydrophilic moiety may be attached to the PLA of the peptide comprising the general structure A-B-C via the hydroxyl moiety of PLA. The hydrophilic moiety can be any of those described herein, including, for example, polyethylene glycol.

In a specific aspect, the peptide comprising the general structure A-B-C comprises a stabilized alpha helix by virtue of incorporation of an intramolecular bridge. In one embodiment, the intramolecular bridge is a lactam bridge. The lactam bridge may be between the amino acids at positions 9 and 12, the amino acids at positions 12 and 16, the amino acids at positions 16 and 20, the amino acids at positions 20 and 24, or the amino acids at positions 24 and 28 (according to the amino acid numbering of SEQ ID NO: 1). In a specific embodiment, the amino acids at positions 12 and 16 or at positions 16 and 20 (according to the amino acid numbering of SEQ ID NO: 1) are linked via a lactam bridge. Other positions of the lactam bridge are contemplated.

Additionally or alternatively, the peptide comprising the general structure A-B-C can comprise an alpha, alpha di-substituted amino acid at, for example, any of positions 16, 20, 21, or 24 (according to the amino acid numbering of SEQ ID NO: 1). In one embodiment, the alpha, alpha di-substituted amino acid is AIB. In a specific aspect, the AIB is located at position 16 (according to the numbering of SEQ ID NO: 1). Alternatively or additionally, the peptide comprising the general structure A-B-C may be modified to comprise an acidic amino acid at position 16 (according to the numbering of SEQ ID NO: 1), which modification enhances the stability of the alpha helix. The acidic amino acid, in one embodiment, is an amino acid comprising a side chain sulfonic acid or a side chain carboxylic acid. In a more specific embodiment, the acidic amino acid is selected from the group consisting of Glu, Asp, homoglutamic acid, a sulfonic acid derivative of Cys, cysteic acid, homocysteic acid, Asp, and an alkylated derivative of Cys having the structure of

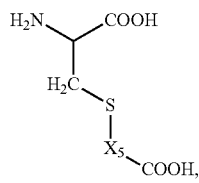

wherein $X_5$ is $C_1$-$C_4$ alkyl, $C_2$-$C_4$ alkenyl, or $C_2$-$C_4$ alkynyl.

In a specific embodiment, the glucagon antagonist/GLP-1 agonist may comprise the amino acid sequence of any of SEQ ID NOs: 60-70, 73-78, 80-88, 90-96, 103, 104, 106, and 114-118, or comprising the amino acid sequence of any of Peptides 2-6 of Table 13, Peptides 1-8 of Table 14, and Peptides 2-6, 8, and 9 of Table 15.

In one embodiment, the peptide comprising the general structure A-B-C is a glucagon antagonist/GLP-1 agonist. In a specific embodiment, the peptide exhibits exhibits at least about 50% of the maximum agonism achieved by native GLP-1 at the GLP-1 receptor and at least about 50% inhibition of the maximum response achieved by native glucagon at the glucagon receptor. In another specific embodiment, the peptide exhibits at least about 55%, at least about 60%, at least about 70%, at least about 80%, at least about 90%, at least about 95%, or about 100% of the maximum agonism achieved by native GLP-1 at the GLP-1 receptor. Alternatively or additionally, the peptide may exhibit at least about 55%, at least about 60%, at least about 70%, at least about 80%, at least about 90%, at least about 95%, or about 100% inhibition of the maximum response achieved by native glucagon at the glucagon receptor.

In some embodiments, a peptide with glucagon antagonist and GLP-1 agonist activity (e.g., a glucagon antagonist, GLP-1 agonist) or conjugate thereof, is provided comprising:
(1) modifications that confer glucagon antagonist activity, including but not limited to:
  (a) substitution of the Phe at position 6 with PLA (according to amino acid numbering of wild type glucagon), optionally with deletion of 1 to 5 amino acids from the N-terminus of wild type glucagon; or
  (b) deletion of 2 to 5 amino acids from the N-terminus of wild type glucagon; optionally with substitution of Asp at position 9 of wild type glucagon with glutamic acid, homoglutamic acid or a sulfonic acid derivative of cysteine (according to amino acid numbering of wild type glucagon);
and
(2) modifications that confer GLP-1 agonist activity, including but not limited to:
  (a) insertion or substitution of α,α-disubstituted amino acid within amino acids 12-29 of wild type glucagon, e.g. at one, two, three, four or more of positions 16, 17, 18, 19, 20, 21, 24 or 29 (according to the amino acid numbering of wild type glucagon); or
  (b) introduction of an intramolecular bridge within amino acids 12-29 of wild type glucagon, e.g. a salt bridge or a lactam bridge or another type of covalent bond; or
  (c) substitution of the amino acid at one or more of positions 2, 3, 17, 18, 21, 23, or 24 (according to the amino acid numbering of native glucagon) with the corresponding amino acid of GLP-1, e.g. Ser2 is replaced with Ala, Gln3 is replaced with Glu, Arg17 is replaced with Gln, Arg at position 18 is replaced with Ala, Asp at position 21 is replaced with Glu, Val at position 23 is replaced with Ile, and/or Gln at position 24 is replaced with Ala; or
  (d) other modifications that stabilize the alpha-helix structure around amino acid positions 12-29 according to the amino acid numbering of wild type glucagon;
and
(3) other modifications that enhance GLP-1 agonist activity, e.g.
  (a) a C-terminal amide or ester in place of a C-terminal carboxylate;
and optionally
(4) one or more of the following modifications:
  (a) covalent attachment to a hydrophilic moiety, such as polyethylene glycol, e.g. at the N-terminus, or at position 6, 16, 17, 20, 21, 24, 29, 40 or at the C-terminal amino acid; and/or
  (b) acylation or alkylation; and optionally
(5) one or more of the following additional modifications:
  (a) covalent linkage of amino acids, to the N-terminus, e.g. 1-5 amino acids to the N-terminus, optionally via an ester bond to PLA at position 6 (according to the numbering of wild type glucagon), optionally together with modifications at position 1 or 2, e.g. as described herein, that improve resistance to DPP-IV cleavage;
  (b) deletion of amino acids at positions 29 and/or 28, and optionally position 27 (according to the numbering of wild type glucagon);
  (c) covalent linkage of amino acids to the C-terminus;
  (d) non-conservative substitutions, conservative substitutions, additions or deletions while retaining desired activity, for example, conservative substitutions at one or more of positions 2, 5, 7, 10, 11, 12, 13, 14, 16, 17, 18, 19, 20, 21, 24, 27, 28 or 29, substitution of Tyr at position 10 with Val or Phe, substitution of Lys at position 12 with Arg, substitution of one or more of these positions with Ala;
  (e) modification of the aspartic acid at position 15, for example, by substitution with glutamic acid, homoglutamic acid, cysteic acid or homocysteic acid, which may reduce degradation; or modification of the serine at position 16, for example, by substitution of threonine, AIB, glutamic acid or with another negatively charged amino acid having a side chain with a length of 4 atoms, or alternatively with any one of glutamine, homoglutamic acid, or homocysteic acid, which likewise may reduce degradation due to cleavage of the Asp15-Ser16 bond;
  (f) modification of the methionine at position 27, for example, by substitution with leucine or norleucine, to reduce oxidative degradation;
  (g) modification of the Gln at position 20 or 24, e.g. by substitution with Ala or AIB, to reduce degradation that occurs through deamidation of Gln
  (h) modification of Asp at position 21, e.g. by substitution with Glu, to reduce degradation that occurs through dehydration of Asp to faun a cyclic succinimide intermediate followed by isomerization to isoaspartate;

(j) homodimerization or heterodimerization as described herein; and
(k) combinations of the above.

It is understood that any of the modifications within the same class may be combined together and/or modifications of different classes are combined. For example, the modifications of (1)(a) may be combined with (2)(a) and (3); (1)(a) may be combined with (2)(b), e.g. lactam bridge or salt bridge, and (3); (1)(a) may be combined with (2)(c) and (3); (1)(b) may be combined with (2)(a) and (3); (1)(b) may be combined with (2)(b), e.g. lactam bridge or salt bridge, and (3); (1)(b) may be combined with (2)(c) and (3); any of the foregoing may be combined with (4)(a) and/or (4)(b); and any of the foregoing may be combined with any of (5)(a) through (5)(k).

In exemplary embodiments, the α,α-disubstituted amino acid AIB is substituted at one, two, three or all of positions 16, 20, 21, or 24 (according to the amino acid numbering of wild type glucagon).

In exemplary embodiments, the intramolecular bridge is a salt bridge.

In other exemplary embodiments, the intramolecular bridge is a covalent bond, e.g. a lactam bridge. In some embodiments, the lactam bridge is between the amino acids at positions 9 and 12, the amino acids at positions 12 and 16, the amino acids at positions 16 and 20, the amino acids at positions 20 and 24, or the amino acids at positions 24 and 28 (according to the amino acid numbering of SEQ ID NO: 1). In exemplary embodiments, acylation or alkylation is at position 6, 10, 20 or 24 or the N-terminus or C-terminus (according to the amino acid numbering of wild type glucagon) SEQ ID NO: 1).

In exemplary embodiments, modifications include:
(i) substitution of Asp at position 15 (according to the numbering of SEQ ID NO: 1) with cysteic acid, glutamic acid, homoglutamic acid, and homocysteic acid;
(ii) substitution of Ser at position 16 (according to the numbering of SEQ ID NO: 1) with cysteic acid, glutamic acid, homoglutamic acid, and homocysteic acid;
(iii) substitution of Asn at position 28 with a charged amino acid;
(iv) substitution of Asn at position 28 with a charged amino acid selected from the group consisting of Lys, Arg, His, Asp, Glu, cysteic acid, and homocysteic acid;
(v) substitution at position 28 with Asn, Asp, or Glu;
(vi) substitution at position 28 with Asp;
(vii) substitution at position 28 with Glu;
(viii) substitution of Thr at position 29 with a charged amino acid;
(ix) substitution of Thr at position 29 with a charged amino acid selected from the group consisting of Lys, Arg, His, Asp, Glu, cysteic acid, and homocysteic acid;
(x) substitution at position 29 with Asp, Glu, or Lys;
(xi) substitution at position 29 with Glu;
(xii) insertion of 1-3 charged amino acids after position 29;
(xiii) insertion after position 29 of Glu or Lys;
(xiv) insertion after position 29 of Gly-Lys or Lys-Lys;
or combinations thereof.

Any of the modifications described above which increase GLP-1 receptor agonist activity, glucagon receptor antagonist activity, peptide solubility, and/or peptide stability can be applied individually or in combination.

The disclosed peptides and glucagon antagonist/GLP-1 agonists are believed to be suitable for any use that has previously been described for other glucagon antagonist/GLP-1 agonists. Accordingly, the glucagon analogs described herein can be used to treat hyperglycemia, or treat other metabolic diseases that result from high blood levels of glucagon or high blood glucose levels. In accordance with one embodiment the patient to be treated using the glucagon antagonist/GLP-1 agonists disclosed herein is a domesticated animal, and in another embodiment the patient to be treated is a human. Studies suggest that lack of glucagon suppression in diabetic patients contributes to postprandial hyperglycemia in part via accelerated glycogenolysis. Analysis of blood glucose during an Oral Glucose Tolerance Test (OGTT), and in the presence or absence of somatostatin-induced glucagon suppression has shown a significant increase in glucose in subjects with higher glucagon levels. Accordingly, the peptides and glucagon antagonist/GLP-1 agonists described herein can be used to treating hyperglycemia, and are expected to be useful for treating a variety of types of diabetes including diabetes mellitus type I, diabetes mellitus type II, or gestational diabetes, either insulin-dependent or non-insulin-dependent, and reducing complications of diabetes including nephropathy, retinopathy and vascular disease.

The method of treating hypoglycemia comprises the steps of administering the presently disclosed peptides or glucagon antagonist/GLP-1 agonists to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the glucagon composition is prepackaged in a syringe.

Exendin-4, is a peptide made up of 39 amino acids. It is a powerful stimulator of a receptor known as GLP-1. This peptide has also been reported to suppress appetite and induce weight loss. Applicants have found that the terminal sequence of Exendin-4 when added at the carboxy terminus of glucagon improves the solubility and stability of glucagon without compromising the bioactivity of glucagon. In accordance with one embodiment the peptides or glucagon antagonist/GLP-1 agonists disclosed herein are administered to patients as a method of reducing appetite or promoting loss of body weight. In accordance with one embodiment the patient is a domesticated animal, and in another embodiment the patient to be treated is a human. In one embodiment the terminal ten amino acids of Exendin-4 (i.e. the sequence of SEQ ID NO: 21 (GPSSGAPPPS)) are linked to the carboxy terminus of a peptide or glucagon antagonist/GLP-1 agonists disclosed herein. These fusion proteins are anticipated to have pharmacological activity for suppressing appetite and inducing weight loss/weight maintenance. In accordance with one embodiment the peptides or glucagon antagonist/GLP-1 agonists disclosed herein can be further modified to include the amino acid sequence of SEQ ID NO: 21 (GPSSGAPPPS), or SEQ ID NO: 50, linked to the carboxy terminal amino acid (position 24) of the peptide or glucagon antagonist/GLP-1 agonist and administered to individuals to induce weight loss or assist in weight maintenance. More particularly, the glucagon antagonist/GLP-1 agonist comprises a sequence selected from the group consisting of SEQ ID NO: 5, SEQ ID NO: 6, SEQ ID NO: 7, SEQ ID NO: 8, SEQ ID NO: 9, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 22, SEQ ID NO: 23, SEQ ID NO: 24 and SEQ ID NO: 25 and further comprising the amino acid sequence of SEQ ID NO: 21 (GPSSGAPPPS), or SEQ ID NO: 50, linked to the carboxy terminal amino acid (position 24) of the peptide or glucagon antagonist/GLP-1 agonist, is used to suppress appetite and inducing weight loss/weight maintenance. In one embodiment the administered peptide or glucagon antagonist/GLP-1 agonist comprises a sequence selected from the group consisting of SEQ ID NO: 16, SEQ ID NO: 17, SEQ ID NO: 18 and SEQ ID NO: 19, further comprising the amino acid sequence of SEQ ID NO: 21 (GPSSGAPPPS) linked to the carboxy terminal amino acid (position 24) of the glucagon antagonist/GLP-1 agonist. In one embodiment the method comprises administering a peptide or glucagon antagonist/GLP-1 agonist comprising the sequence of SEQ ID NO: 45 or SEQ ID NO: 46.

Such methods for reducing appetite or promoting loss of body weight are expected to be useful in reducing body weight, preventing weight gain, or treating obesity of various causes, including drug-induced obesity, and reducing complications associated with obesity including vascular disease (coronary artery disease, stroke, peripheral vascular disease, ischemia reperfusion, etc.), hypertension, onset of diabetes type II, hyperlipidemia and musculoskeletal diseases.

The glucagon peptides of the invention may be administered alone or in combination with other anti-diabetic or anti-obesity agents. Anti-diabetic agents known in the art or under investigation include insulin, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; or 1-BPase (fructose 1,6-bisphosphatase) inhibitors.

Anti-obesity agents known in the art or under investigation include appetite suppressants, including phenethylamine type stimulants, phentermine (optionally with fenfluramine or dexfenfluramine), diethylpropion (Tenuate®), phendimetrazine (Prelu-2®, Bontril®), benzphetamine (Didrex®), sibutramine (Meridia®, Reductil®); rimonabant (Acomplia®), other cannabinoid receptor antagonists; oxyntomodulin; fluoxetine hydrochloride (Prozac); Qnexa (topiramate and phentermine), Excalia (bupropion and zonisamide) or Contrave (bupropion and naltrexone); or lipase inhibitors, similar to xenical (Orlistat) or Cetilistat (also known as ATL-962), or GT 389-255.

The peptides or glucagon antagonist/GLP-1 agonists described herein can also be administered to patients suffering from catabolic wasting. It is estimated that over half of cancer patients experience catabolic wasting which is characterized by unintended and progressive weight loss, weakness, and low body fat and muscle. The syndrome is equally common in AIDS patients and can also be present in bacterial and parasitic diseases, rheumatoid arthritis, and chronic diseases of the bowel, liver, lungs, and heart. It is usually associated with anorexia and can manifest as a condition in aging or as a result of physical trauma. Catabolic wasting is a symptom that diminishes the quality of life, worsens the underlying condition, and is a major cause of death. Applicants anticipate that the peptides or glucagon antagonist/GLP-1 agonists disclosed herein can be administered to patients to treat catabolic wasting.

Pharmaceutical compositions comprising the peptides or glucagon antagonist/GLP-1 agonists disclosed herein can be formulated and administered to patients using standard pharmaeutically acceptable carriers and routes of administration known to those skilled in the art. Accordingly, the present disclosure also encompasses pharmaceutical compositions comprising one or more of the peptides or glucagon antagonist/GLP-1 agonists disclosed herein in combination with a pharmaceutically acceptable carrier. The pharmaceutical compositions may comprise the peptides or glucagon antagonist/GLP-1 agonists as the sole pharmaceutically active component, or the peptides or glucagon antagonist/GLP-1 agonists can be combined with one or more additional active agents. In accordance with one embodiment a composition is provided comprising a peptide or glucagon antagonist/GLP-1 agonist and insulin or an insulin analog. Alternatively, a composition is provided for inducing weight loss or preventing weight gain can be provided that comprises the sequence of SEQ ID NO: 15 or SEQ ID NO: 51 further comprising the amino acid sequence of SEQ ID NO: 21 (GPSSGAPPPS) or SEQ ID NO: 50 linked to amino acid 24 of SEQ ID NO: 15 or SEQ ID NO: 51, and an anti-obesity peptide. Suitable anti-obesity peptides include those disclosed in U.S. Pat. Nos. 5,691,309, 6,436,435 or US Patent application 20050176643.

In accordance with one embodiment a pharmaceutical composition is provided comprising any of the novel peptides or glucagon antagonist/GLP-1 agonists disclosed herein, preferably sterile and preferably at a purity level of at least 90%, 91%, 92%, 93%, 94%, 95%, 96%, 97%, 98% or 99%, and a pharmaceutically acceptable diluent, carrier or excipient. Such compositions may contain a peptide glucagon antagonist/GLP-1 agonist at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored within various containers. The compounds disclosed herein can be used in accordance with one embodiment to prepare pre-formulated solutions ready for injection. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

All therapeutic methods, pharmaceutical compositions, kits and other similar embodiments described herein contemplate that the use of the term peptide or glucagon antagonist/GLP-1 agonist includes all pharmaceutically acceptable salts thereof.

Pegylating peptides or glucagon antagonist/GLP-1 agonists can improve the aqueous solubility of the antagonists. However, increasing the length of the PEG chain, or attaching multiple PEG chains to the peptide, such that the total molecular weight of the linked PEG is greater than 5,000 Daltons, begins to delay the time action of the modified glucagon antagonist/GLP-1 agonist or peptide. In accordance with one embodiment, a peptide or glucagon antagonist/GLP-1 agonist is provided wherein the peptide comprises one or more polyethylene glycol chains, wherein the total molecular weight of the linked PEG is greater than 5,000 Daltons, and in one embodiment is greater than 10,000 Daltons. Such modified glucagon antagonist/GLP-1 agonists or peptides have a delayed time of activity but without loss of bioactivity. Accordingly, such compounds can be administered prophylactically to extend the effect of the administered glucagon antagonist/GLP-1 agonist or peptide.

In one embodiment the pegylated glucagon antagonist/GLP-1 agonist comprises a peptide selected from the group consisting of SEQ ID NO: 5, SEQ ID NO: 6, SEQ ID NO: 7, SEQ ID NO: 8, SEQ ID NO: 9, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 22, SEQ ID NO: 23, SEQ ID NO: 24 and SEQ ID NO: 25, wherein the side chain of one or more amino acid residue at position 16 or 19 of the peptide is covalently bound to a polyethylene glycol chain, wherein the total molecular weight of the PEG chain(s) is greater than about 10,000 Daltons. In one embodiment the molecular weight of the PEG chain(s) is greater than 10,000 and less than or equal to 40,000 Daltons.

Glucagon peptides that have been modified to be covalently bound to a PEG chain having a molecular weight of greater than 10,000 Daltons can be administered in conjunction with insulin to buffer the actions of insulin and help to maintain stable blood glucose levels in diabetics. The modified glucagon peptides of the present disclosure can be co-administered with insulin as a single composition, simultaneously administered as separate solutions, or alternatively, the insulin and the modified glucagon peptide can be administered at different time relative to one another. In one embodiment the composition comprising insulin and the composition comprising the modified glucagon peptide are administered within 12 hours of one another. The exact ratio of the modified glucagon peptide relative to the administered insulin will be dependent in part on determining the glucagon levels of the patient, and can be determined through routine experimentation.

In accordance with one embodiment a composition is provided comprising insulin and a pegylated glucagon antagonist/GLP-1 agonist that comprises the peptide of SEQ ID NO: 13, wherein an amino acid residue at position 16 of SEQ ID NO: 13 is covalently linked to a polyethylene glycol chain having a molecular weight selected from the range of about 10,000 to about 40,000 Daltons. In another embodiment, a composition is provided comprising insulin and a pegylated glucagon antagonist/GLP-1 agonist or peptide that comprises the peptide of SEQ ID NO: 14, wherein an amino acid residue at position 19 of SEQ ID NO:14 is covalently linked to a polyethylene glycol chain having a molecular weight selected from the range of about 10,000 to about 40,000 Daltons. In one embodiment, the pegylated glucagon antagonist/GLP-1 agonist comprises the peptide of SEQ ID NO: 12, wherein an amino acid residue at position16 and 19 of SEQ ID NO: 12 is covalently linked to a polyethylene glycol chain wherein the combined molecular weight of the two polyethylene chains is selected from the range of about 10,000 to about 40,000 Daltons. In another embodiment the pegylated glucagon antagonist/GLP-1 agonist comprises the peptide of SEQ ID NO: 13 or SEQ ID NO. 14, wherein the covalently linked PEG chain has a molecular weight of at least about 10,000 Daltons, and in one embodiment the molecular weight of the PEG is selected from the range of about 20,000 to about 40,000 Daltons.

In accordance with one embodiment the glucagon antagonist/GLP-1 agonists disclosed herein are used to induce temporary paralysis of the intestinal tract. This method has utility for radiological purposes and comprises the step of administering an effective amount of a pharmaceutical composition comprising a pegylated glucagon antagonist/GLP-1 agonist, a glucagon antagonist/GLP-1 agonist comprising a c-terminal extension or a dimer of such glucagon antagonist/GLP-1 agonists.

The present disclosure also encompasses multimers of the peptides or modified glucagon antagonist/GLP-1 agonists disclosed herein. Two or more of the glucagon analogs can be linked together using standard linking agents and procedures known to those skilled in the art. For example, dimers can be formed between two peptides or modified glucagon antagonist/GLP-1 agonists through the use of bifunctional thiol crosslinkers and bi-functional amine crosslinkers, particularly for glucagon antagonist/GLP-1 agonists that have been substituted (at positions 16 or 19, for example) with cysteine, lysine ornithine, homocysteine or acetyl phenylalanine residues (e.g. SEQ ID NO: 13 and SEQ ID NO: 14). The dimer can be a homo dimer or alternatively can be a heterodimer. In one embodiment the dimer is formed between two glucagon antagonist/GLP-1 agonists independently selected from the group consisting of SEQ ID NO: 5, SEQ ID NO: 6, SEQ ID NO: 7, SEQ ID NO: 8, SEQ ID NO: 9, SEQ ID NO: 16, SEQ ID NO: 17, SEQ ID NO: 18, SEQ ID NO: 19, SEQ ID NO: 22, SEQ ID NO: 23, SEQ ID NO: 24, SEQ ID NO: 25, SEQ ID NO: 45, SEQ ID NO: 46, SEQ ID NO: 47 and SEQ ID NO: 48, wherein the two peptides are linked to one another via a linker attached to position 11 of each peptide, 16 of each peptide, or position 19 of each peptide or any combination thereof. In one embodiment the linkage is a disulfide linkage between a Cys16 to Cys16, or a Cys19 to Cys19 or a Cys16 to Cys19, or a Cys 24 to Cys24 or a Cys 35 to Cys 35 residue (for SEQ ID NO: 45 or SEQ ID NO: 46) of the respective glucagon antagonist/GLP-1 agonist peptides.

Similarly, a dimer can be formed between two glucagon antagonist/GLP-1 agonist peptides independently selected from the group consisting of SEQ ID NO: 5, SEQ ID NO: 6, SEQ ID NO: 7, SEQ ID NO: 8, SEQ ID NO: 9, SEQ ID NO: 15, SEQ ID NO: 16, SEQ ID NO: 17, SEQ ID NO: 18, SEQ ID NO: 19, SEQ ID NO: 22, SEQ ID NO: 23, SEQ ID NO: 24, SEQ ID NO: 25, SEQ ID NO: 45, SEQ ID NO: 46, SEQ ID NO: 47, SEQ ID NO: 48 and SEQ ID NO: 51 wherein the linkage is formed between amino acid positions independently selected from positions 11, 16, 19 and 35, relative to the glucagon antagonist/GLP-1 agonists sequence. In accordance with one embodiment a glucagon antagonist/GLP-1 agonist dimer is provided comprising two glucagon antagonist/GLP-1 agonists selected from the group consisting of SEQ ID NO: 16, SEQ ID NO: 17, SEQ ID NO: 18, SEQ ID NO: 19, wherein the two antagonists are linked to one another by a disulfide bond through amino acid position 16 or 19 of SEQ ID NO: 16, SEQ ID NO: 17, SEQ ID NO: 18 or SEQ ID NO: 19. In one embodiment the dimer comprises a homodimer of two glucagon antagonist/GLP-1 agonists. In another embodiment the first and second glucagon analogs of the dimer are independently selected from the group consisting of SEQ ID NO: 5, SEQ ID NO: 6, SEQ ID NO: 7 and SEQ ID NO: 8.

The glucagon analogs or peptides disclosed herein can be provided in accordance with one embodiment as part of a kit. In one embodiment a kit for administering a glucagon agonist to a patient in need thereof is provided wherein the kit comprises a modified glucagon antagonist/GLP-1 agonist selected from the group consisting of 1) a glucagon antagonist/GLP-1 agonist comprising an amino acid sequence selected from the group consisting of SEQ ID NO: 5, SEQ ID NO: 6, SEQ ID NO: 7, SEQ ID NO: 8, SEQ ID NO: 9, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 22, SEQ ID NO: 23, SEQ ID NO: 24, SEQ ID NO: 25 and SEQ ID NO: 51.

2) a pegylated glucagon antagonist/GLP-1 agonist, wherein a polyethylene chain is covalently bound to position 11, 12, 15, 16, 19 or 24 (relative to the amino acid sequence of the analog) of a glucagon antagonist/GLP-1 agonist disclosed herein, wherein the PEG chain has a molecular weight of about 500 to about 40,000 Daltons;

3) a fusion peptide comprising a glucagon antagonist/GLP-1 agonist disclosed herein further comprising the peptide of SEQ ID NO: 21 fused to the terminal amino acid of said glucagon antagonist/GLP-1 agonist; and 4) a pegylated glucagon antagonist/GLP-1 agonist, further comprising an amino acid sequence of SEQ ID NO: 21 (GPSSGAPPPS) or SEQ ID NO: 50 linked to the carboxy terminus of the glucagon antagonist/GLP-1 agonist, wherein a polyethylene chain is covalently bound to position 11, 12, 15, 16, 19, 24 or 35 of the glucagon antagonist/GLP-1 agonist, further wherein the polyethylene chain has a molecular weight of about 500 to about 40,000 Daltons.

In one embodiment the kit is provided with a device for administering the glucagon antagonist/GLP-1 agonist or peptide composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the glucagon antagonist/GLP-1 agonist composition is prepackaged within the syringe.

The following applies to the peptides and glucagon antagonist/GLP-1 agonists disclosed herein.

Stabilization of the Alpha Helix Structure

Stabilization of the alpha-helix structure in the C-terminal portion of the glucagon peptide (around amino acids 12-29, according to the amino acid numbering of wild type glucagon, SEQ ID NO: 1) can be carried out by, e.g., formation of a covalent or non-covalent intramolecular bridge, or substitution and/or insertion of amino acids around positions 12-29 (according to the amino acid numbering of wild type glucagon) with an alpha helix-stabilizing amino acid (e.g., an α,α-disubstituted amino acid).

In some embodiments, an intramolecular bridge is formed between two amino acid side chains to stabilize the three dimensional structure of the carboxy terminal portion (e.g., amino acids 12-29 according to the amino acid numbering of wild type glucagon) of the glucagon peptide. The two amino acid side chains can be linked to one another through hydrogen-bonding, ionic interactions, such as the formation of salt bridges, or by covalent bonds.

In some embodiments, the intramolecular bridge is formed between two amino acids that are 3 amino acids apart, e.g., amino acids at positions i and i+4, wherein i is any integer between 12 and 25 (e.g., 12, 13, 14, 15, 16, 17, 18, 19, 20, 21, 22, 23, 24, and 25) according to the amino acid numbering of wild type glucagon. More particularly, the side chains of the amino acid pairs 12 and 16, 16 and 20, 20 and 24 or 24 and 28 (amino acid pairs in which i=12, 16, 20, or 24) according to the amino acid numbering of wild type glucagon are linked to one another and thus stabilize the glucagon alpha helix. Alternatively, i can be 17.

In some specific embodiments, wherein the amino acids at positions i and i+4 are joined by an intramolecular bridge, the size of the linker is about 8 atoms, or about 7-9 atoms.

In other embodiments, the intramolecular bridge is formed between two amino acids that are two amino acids apart, e.g., amino acids at positions j and j+3, wherein j is any integer between 12 and 26 (e.g., 12, 13, 14, 15, 16, 17, 18, 19, 20, 21, 22, 23, 24, 25, and 26) according to the amino acid numbering of wild type glucagon. In some specific embodiments, j is 17.

In some specific embodiments, wherein amino acids at positions j and j+3 are joined by an intramolecular bridge, the size of the linker is about 6 atoms, or about 5 to 7 atoms.

In yet other embodiments, the intramolecular bridge is formed between two amino acids that are 6 amino acids apart, e.g., amino acids at positions k and k+7, wherein k is any integer between 12 and 22 (e.g., 12, 13, 14, 15, 16, 17, 18, 19, 20, 21, and 22) according to the amino acid numbering of wild type glucagon. In some specific embodiments, k is 12, 13, or 17. In an exemplary embodiment, k is 17.

Examples of amino acid pairings that are capable of covalently bonding to form a six-atom linking bridge include Orn and Asp, Glu and an amino acid of Formula I, wherein n is 2, and homoglutamic acid and an amino acid of Formula I, wherein n is 1, wherein Formula I is:

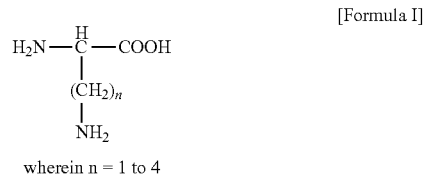

wherein n = 1 to 4

Examples of amino acid pairing that are capable of covalently bonding to form a seven-atom linking bridge include Orn-Glu (lactam ring); Lys-Asp (lactam); or Homoser-Homoglu (lactone). Examples of amino acid pairings that may form an eight-atom linker include Lys-Glu (lactam); Homolys-Asp (lactam); Orn-Homoglu (lactam); 4-aminoPhe-Asp (lactam); or Tyr-Asp (lactone). Examples of amino acid pairings that may form a nine-atom linker include Homolys-Glu (lactam); Lys-Homoglu (lactam); 4-aminoPhe-Glu (lactam); or Tyr-Glu (lactone). Any of the side chains on these amino acids may additionally be substituted with additional chemical groups, so long as the three-dimensional structure of the alpha-helix is not disrupted. One of ordinary skill in the art can envision alternative pairings or alternative amino acid analogs, including chemically modified derivatives, that would create a stabilizing structure of similar size and desired effect. For example, a homocysteine-homocysteine disulfide bridge is 6 atoms in length and may be further modified to provide the desired effect. Even without covalent linkage, the amino acid pairings described above or similar pairings that one of ordinary skill in the art can envision may also provide added stability to the alpha-helix through non-covalent bonds, for example, through formation of salt bridges or hydrogen-bonding interactions.

The size of a lactam ring can vary depending on the length of the amino acid side chains, and in one embodiment the lactam is formed by linking the side chains of a lysine amino acid to a glutamic acid side chain. Further exemplary embodiments (according to the amino acid numbering of wild type glucagon) include the following pairings, optionally with a lactam bridge: Glu at position 12 with Lys at position 16; native Lys at position 12 with Glu at position 16; Glu at position 16 with Lys at position 20; Lys at position 16 with Glu at position 20; Glu at position 20 with Lys at position 24; Lys at position 20 with Glu at position 24; Glu at position 24 with Lys at position 28; Lys at position 24 with Glu at position 28. Alternatively, the order of the amide bond in the lactam ring can be reversed (e.g., a lactam ring can be formed between the side chains of a Lys12 and a Glu 16 or alternatively between a Glu 12 and a Lys16).

Intramolecular bridges other than a lactam bridge can be used to stabilize the alpha helix of the glucagon analog peptides. In one embodiment, the intramolecular bridge is a hydrophobic bridge. In this instance, the intramolecular bridge optionally is between the side chains of two amino acids that are part of the hydrophobic face of the alpha helix of the glucagon analog peptide. For example, one of the amino acids joined by the hydrophobic bridge can be the amino acid at position 10, 14, and 18 (according to the amino acid numbering of wild type glucagon).

In one specific aspect, olefin metathesis is used to cross-link one or two turns of the alpha helix of the glucagon peptide using an all-hydrocarbon cross-linking system. The glucagon peptide in this instance can comprise α-methylated amino acids bearing olefinic side chains of varying length and configured with either R or S stereochemistry at the i and i+4 or i+7 positions. For example, the olefinic side can can comprise $(CH_2)_n$, wherein n is any integer between 1 to 6. In one embodiment, n is 3 for a cross-link length of 8 atoms. Suitable methods of forming such intramolecular bridges are described in the art. See, for example, Schafineister et al., *J. Am. Chem. Soc.* 122: 5891-5892 (2000) and Walensky et al., *Science* 305: 1466-1470 (2004). Alternatively, the glucagon peptide can comprise O-allyl Ser residues located on adjacent helical turns, which are bridged together via ruthenium-catalyzed ring closing metathesis. Such procedures of cross-linking are described in, for example, Blackwell et al., *Angew, Chem., Int. Ed.* 37: 3281-3284 (1998).

In another specific aspect, use of the unnatural thio-dialanine amino acid, lanthionine, which has been widely adopted as a peptidomimetic of cystine, is used to cross-link one turn of the alpha helix. Suitable methods of lanthionine-based cyclization are known in the art. See, for instance, Matteucci et al., *Tetrahedron Letters* 45: 1399-1401 (2004); Mayer et al., *J. Peptide Res.* 51: 432-436 (1998); Polinsky et al., *J. Med. Chem.* 35: 4185-4194 (1992); Osapay et al., *J. Med. Chem.* 40: 2241-2251 (1997); Fukase et al., *Bull. Chem. Soc. Jpn.* 65: 2227-2240 (1992); Harpp et al., *J. Org. Chem.* 36: 73-80 (1971); Goodman and Shao, *Pure Appl. Chem.* 68: 1303-1308 (1996); and Osapay and Goodman, *J. Chem. Soc. Chem. Commun.* 1599-1600 (1993).

In some embodiments, α, ω-diaminoalkane tethers, e.g., 1,4-diaminopropane and 1,5-diaminopentane) between two Glu residues at positions i and i+7 are used to stabilize the alpha helix of the glucagon peptide. Such tethers lead to the formation of a bridge 9-atoms or more in length, depending on the length of the diaminoalkane tether. Suitable methods of producing peptides cross-linked with such tethers are described in the art. See, for example, Phelan et al., *J. Am. Chem. Soc.* 119: 455-460 (1997).

In yet another embodiment of the invention, a disulfide bridge is used to cross-link one or two turns of the alpha helix of the glucagon peptide. Alternatively, a modified disulfide bridge in which one or both sulfur atoms are replaced by a methylene group resulting in an isosteric macrocyclization is used to stabilize the alpha helix of the glucagon peptide. Suitable methods of modifying peptides with disulfide bridges or sulfur-based cyclization are described in, for example, Jackson et al., *J. Am. Chem. Soc.* 113: 9391-9392 (1991) and Rudinger and Jost, *Experientia* 20: 570-571 (1964).

In yet another embodiment, the alpha helix of the glucagon peptide is stabilized via the binding of metal atom by two His residues or a His and Cys pair positioned at i and i+4. The metal atom can be, for example, Ru(III), Cu(II), Zn(II), or Cd(II). Such methods of metal binding-based alpha helix stabilization are known in the art. See, for example, Andrews and Tabor, *Tetrahedron* 55: 11711-11743 (1999); Ghadiri et al., *J. Am. Chem. Soc.* 112: 1630-1632 (1990); and Ghadiri et al., *J. Am. Chem. Soc.* 119: 9063-9064 (1997).

The alpha helix of the glucagon peptide can alternatively be stabilized through other means of peptide cyclizing, which means are reviewed in Davies, *J. Peptide. Sci.* 9: 471-501 (2003). The alpha helix can be stabilized via the formation of an amide bridge, thioether bridge, thioester bridge, urea bridge, carbamate bridge, sulfonamide bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g. suberic acid (octanedioic acid), etc. can introduce a link between two functional groups of an amino acid side chain, such as a free amino, hydroxyl, thiol group, and combinations thereof.

In accordance with one embodiment, the alpha helix of the glucagon peptide is stabilized through the incorporation of hydrophobic amino acids at positions i and i+4. For instance, i can be Tyr and i+4 can be either Val or Leu; i can be Phe and i+4 can be Cys or Met; I can be Cys and i+4 can be Met; or i can be Phe and i+4 can be Ile. It should be understood that, for purposes herein, the above amino acid pairings can be reversed, such that the indicated amino acid at position i could alternatively be located at i+4, while the i+4 amino acid can be located at the i position.

In accordance with other embodiments of the invention, the alpha helix is stabilized through incorporation (either by amino acid substitution or insertion) of one or more alpha helix-stabilizing amino acids at the C-terminal portion of the glucagon peptide (around amino acids 12-29 according to the amino acid numbering of wild type glucagon). In a specific embodiment, the alpha helix-stabilizing amino acid is an α,α-disubstituted amino acid, including, but not limited to any of amino iso-butyric acid (AIB), an amino acid disubstituted with the same or a different group selected from methyl, ethyl, propyl, and n-butyl, or with a cyclooctane or cycloheptane (e.g., 1-aminocyclooctane-1-carboxylic acid). In some embodiments, one, two, three, four or more of positions 16, 17, 18, 19, 20, 21, 24 or 29 (according to the amino acid numbering of wild type glucagon) is substituted with an α,α-disubstituted amino acid. In a specific embodiment, one, two, three or all of positions 16, 20, 21, and 24 (according to the amino acid numbering of wild type glucagon) are substituted with AIB.

Linkage of Hydrophilic Moieties

In another embodiment the solubility of the glucagon peptides disclosed herein are enhanced by the covalent linkage of a hydrophilic moiety to the peptide. Hydrophilic moieties can be attached to the glucagon peptides under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane and 5-pyridyl. If attached to the peptide by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995).

Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly (.beta.-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof.

The hydrophilic moiety, e.g., polyethylene glycol chain in accordance with some embodiments has a molecular weight selected from the range of about 500 to about 40,000 Daltons. In one embodiment the hydrophilic moiety, e.g. PEG, has a molecular weight selected from the range of about 500 to about 5,000 Daltons, or about 1,000 to about 5,000 Daltons. In another embodiment the hydrophilic moiety, e.g., PEG, has a molecular weight of about 10,000 to about 20,000 Daltons. In yet other exemplary embodiments the hydrophilic moiety, e.g., PEG, has a molecular weight of about 20,000 to about 40,000 Daltons.

In one embodiment dextrans are used as the hydrophilic moiety. Dextrans are polysaccharide polymers of glucose subunits, predominantly linked by α1-6 linkages. Dextran is available in many molecular weight ranges, e.g., about 1 kD to about 100 kD, or from about 5, 10, 15 or 20 kD to about 20, 30, 40, 50, 60, 70, 80 or 90 kD.

Linear or branched polymers are contemplated. Resulting preparations of conjugates may be essentially monodisperse or polydisperse, and may have about 0.5, 0.7, 1, 1.2, 1.5 or 2 polymer moieties per peptide.

In one embodiment the hydrophilic moiety is a polyethylene glycol (PEG) chain, optionally linked to the peptide at one or more of positions 1, 16, 17, 20, 21, 24, 29 (according to the amino acid numbering of wild type glucagon), a position within a C-terminal extension, e.g., 30, or at the N- or C-terminal amino acid. In some embodiments, the native amino acid at that position is substituted with an amino acid having a side chain suitable for crosslinking with hydrophilic moieties, to facilitate linkage of the hydrophilic moiety to the peptide. In exemplary embodiments, the native amino acid at that position is substituted with Lys, Cys, Orn, homocysteine, or acetyl-phenylalanine residue. In other embodiments, an amino acid modified to comprise a hydrophilic group is added to the peptide at the N- or C-terminus.

Conjugates and Fusions

The present disclosure also encompasses other conjugates in which glucagon peptides of the invention are linked, optionally via covalent bonding and optionally via a linker, to a conjugate moiety. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

The peptide can be linked to conjugate moieties via direct covalent linkage by reacting targeted amino acid residues of the peptide with an organic derivatizing agent that is capable of reacting with selected side chains or the N- or C-terminal residues of these targeted amino acids. Reactive groups on the peptide or conjugate include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the peptide indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagines or glutamine, acetylation of the N-terminal amine, and/or amidation or esterification of the C-terminal carboxylic acid group.

Another type of covalent modification involves chemically or enzymatically coupling glycosides to the peptide. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Exemplary conjugate moieties that can be linked to any of the glucagon peptides described herein include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. In one embodiment a conjugate is provided comprising a glucagon peptide disclosed herein and a plasma protein, wherein the plasma protein is selected form the group consisting of albumin, transferin, fibrinogen and globulins.

In some embodiments, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

As noted above, in some embodiments, the glucagon peptides are conjugated, e.g., fused to an immunoglobulin or portion thereof (e.g. variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J. Immunol. 175:6694-701, 2005). Amino acid residues involved in IgE receptor binding are described in Sayers et al. (J Biol. Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

The present disclosure also encompasses glucagon fusion peptides or proteins wherein a second peptide or polypeptide has been fused to a terminus, e.g., the carboxy terminus of the glucagon peptide. In some embodiments the second peptide added to the carboxy terminus of the glucagon peptide is GPSSGAPPPS, KRNRNNIA or KRNR linked to amino acid 29 of the glucagon peptide (according to the amino acid numbering of wild type glucagon). In other embodiments, the second peptide is XGPSSGAPPPS, wherein X is selected from one of the 20 common amino acids, e.g., glutamic acid, aspartic acid or glycine. In one embodiment X represents an amino acid, for example Cys, that further comprises a hydrophilic moiety covalently linked to the side chain of that amino acid. Such C-terminal extensions improve solubility and also can improve glucagon or GLP-1 activity. In some embodiments wherein the glucagon peptide further comprises a carboxy terminal extension, the carboxy terminal amino acid of the extension ends in an amide group or an ester group rather than a carboxylic acid.

In some embodiments, e.g., in glucagon peptides which comprise the C-terminal extension, the threonine at position 29 (according to the amino acid numbering of wild type glucagon) is replaced with a glycine. For example, a glucagon peptide having a glycine substitution for threonine at position 29 and comprising the C-terminal extension of GPSSGAPPPS is four times as potent at the GLP-1 receptor as native glucagon modified to comprise the same C-terminal extension. This T29G substitution can be used in conjunction with other modifications disclosed herein to enhance the affinity of the glucagon peptides for the GLP-1 receptor. For example, the T29G substitution can be combined with the S16E and N20K amino acid substitutions (according to the amino acid numbering of wild type glucagon), optionally with a lactam bridge between amino acids 16 and 20, and optionally with addition of a PEG chain as described herein.

In some embodiments an amino acid is added to the C-terminus, and the additional amino acid is selected from the group consisting of glutamic acid, aspartic acid and glycine.

The present disclosure also encompasses multimers of the modified glucagon peptides disclosed herein. Two or more of the modified glucagon peptides can be linked together using standard linking agents and procedures known to those skilled in the art. For example, dimers can be formed between two modified glucagon peptides through the use of bifunctional thiol crosslinkers and bi-functional amine crosslinkers, particularly for the glucagon peptides that have been substituted with cysteine, lysine ornithine, homocysteine or acetyl phenylalanine residues.

Acylation and Alkylation

In accordance with some embodiments, the glucagon peptides disclosed herein are modified to comprise an acyl group or alkyl group. Acylation or alkylation can increase the half-life of the glucagon peptides in circulation. Acylation or alkylation can advantageously delay the onset of action and/or extend the duration of action at the glucagon and/or GLP-1 receptors and/or improve resistance to proteases such as DPP-IV and/or improve solubility. In some embodiments, the potency of the acylated glucagon peptides is comparable to the unacylated versions of the glucagon peptides. Glucagon peptides may be acylated or alkylated at the same amino acid position where a hydrophilic moiety is linked, or at a different amino acid position.

In some embodiments, the invention provides a glucagon peptide modified to comprise an acyl group or alkyl group covalently linked to the amino acid at position 10 of the glucagon peptide (according to the amino acid numbering of wild type glucagon). The glucagon peptide may further comprise a spacer between the amino acid at position 10 of the glucagon peptide and the acyl group or alkyl group. In some embodiments, the acyl group is a fatty acid or bile acid, or salt thereof, e.g. a C4 to C30 fatty acid, a C8 to C24 fatty acid, cholic acid, a C4 to C30 alkyl, a C8 to C24 alkyl, or an alkyl comprising a steroid moiety of a bile acid. The spacer is any moiety with suitable reactive groups for attaching acyl or alkyl groups. In exemplary embodiments, the spacer comprises an amino acid, a dipeptide, or a tripeptide, or a hydrophilic bifunctional spacer. In some embodiments, the spacer is selected from the group consisting of: Trp, Glu, Asp, Cys and a spacer comprising NH$_2$(CH$_2$CH$_2$O)n(CH$_2$)mCOOH, wherein m is any integer from 1 to 6 and n is any integer from 2 to 12. Such acylated or alkylated glucagon peptides may also further comprise a hydrophilic moiety, optionally a polyethylene glycol. Any of the foregoing glucagon peptides may comprise two acyl groups or two alkyl groups, or a combination thereof.

Acylation can be carried out at any positions within the glucagon peptide, including any of positions 1-29, a position within a C-terminal extension, or the C-terminal amino acid, provided that glucagon antagonist activity (and optionally GLP-1 activity) is retained. Nonlimiting examples include positions 5, 10, 11, 12, 13, 14, 16, 17, 18, 19, 20, 21, 24, 27, 28, or 29 (according to the amino acid numbering of wild type glucagon). The acyl group can be covalently linked directly to an amino acid of the glucagon peptide, or indirectly to an amino acid of the glucagon peptide via a spacer, wherein the spacer is positioned between the amino acid of the glucagons peptide and the acyl group. Glucagon peptides may be acylated at the same amino acid position where a hydrophilic moiety is linked, or at a different amino acid position. Nonlimiting examples include acylation at position 10 (according to the amino acid numbering of wild type glucagon) and pegylation at one or more positions in the C-terminal portion of the glucagon peptide, e.g., position 24, 28 or 29 (according to the amino acid numbering of wild type glucagon), within a C-terminal extension, or at the C-terminus (e.g., through adding a C-terminal Cys).

In a specific aspect of the invention, the glucagon peptide is modified to comprise an acyl group by direct acylation of an amine, hydroxyl, or thiol of a side chain of an amino acid of the glucagon peptide. In some embodiments, the glucagon peptide is directly acylated through the side chain amine, hydroxyl, or thiol of an amino acid. In some embodiments, acylation is at position 10, 20, 24, or 29 (according to the amino acid numbering of wild type glucagon). In this regard, the acylated glucagon peptide can comprise the amino acid sequence of SEQ ID NO: 2, or a modified amino acid sequence thereof comprising one or more of the amino acid modifications described herein, with at least one of the amino acids at positions 10, 20, 24, and 29 (according to the amino acid numbering of wild type glucagon) modified to any amino acid comprising a side chain amine, hydroxyl, or thiol. In some specific embodiments of the invention, the direct acylation of the glucagon peptide occurs through the side chain amine, hydroxyl, or thiol of the amino acid at position 10 (according to the amino acid numbering of wild type glucagon).

In some embodiments, the amino acid comprising a side chain amine is an amino acid of Formula I:

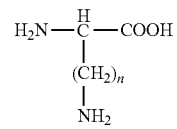

[Formula I]

wherein n = 1 to 4

In some exemplary embodiments, the amino acid of Formula I, is the amino acid wherein n is 4 (Lys) or n is 3 (Orn).

In other embodiments, the amino acid comprising a side chain hydroxyl is an amino acid of Formula II:

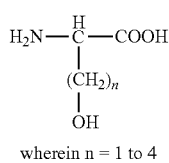

wherein n = 1 to 4

In some exemplary embodiments, the amino acid of Formula II is the amino acid wherein n is 1 (Ser).

In yet other embodiments, the amino acid comprising a side chain thiol is an amino acid of Formula III:

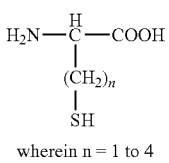

wherein n = 1 to 4

In some exemplary embodiments, the amino acid of Formula II is the amino acid wherein n is 1 (Cys).

In one embodiment of the invention, the acylated glucagon peptide comprises a spacer between the peptide and the acyl group. In some embodiments, the glucagon peptide is covalently bound to the spacer, which is covalently bound to the acyl group. In some exemplary embodiments, the glucagon peptide is modified to comprise an acyl group by acylation of an amine, hydroxyl, or thiol of a spacer, which spacer is attached to a side chain of an amino acid at position 10, 20, 24, or 29 (according to the amino acid numbering of wild type glucagon), or at the C-terminal amino acid of the glucagon peptide. The amino acid to which the spacer is attached can be any amino acid comprising a moiety which permits linkage to the spacer. For example, an amino acid comprising a side chain $NH_2$, —OH, or —COOH (e.g., Lys, Orn, Ser, Asp, or Glu) is suitable. In this respect, the acylated glucagon peptide can comprise the amino acid sequence of SEQ ID NO: 1, or a modified amino acid sequence thereof comprising one or more of the amino acid modifications described herein, with at least one of the amino acids at positions 10, 20, 24, and 29 (according to the amino acid numbering of wild type glucagon) modified to any amino acid comprising a side chain amine, hydroxyl, or carboxylate.

In some embodiments, the spacer is an amino acid comprising a side chain amine, hydroxyl, or thiol, or a dipeptide or tripeptide comprising an amino acid comprising a side chain amine, hydroxyl, or thiol.

When acylation occurs through an amine group of a spacer the acylation can occur through the alpha amine of the amino acid or a side chain amine. In the instance in which the alpha amine is acylated, the spacer amino acid can be any amino acid. For example, the spacer amino acid can be a hydrophobic amino acid, e.g., Gly, Ala, Val, Leu, Ile, Trp, Met, Phe, Tyr. Alternatively, the spacer amino acid can be an acidic residue, e.g., Asp and Glu. In the instance in which the side chain amine of the spacer amino acid is acylated, the spacer amino acid is an amino acid comprising a side chain amine, e.g., an amino acid of Formula I (e.g., Lys or Orn). In this instance, it is possible for both the alpha amine and the side chain amine of the spacer amino acid to be acylated, such that the glucagon peptide is diacylated. Embodiments of the invention include such diacylated molecules.

When acylation occurs through a hydroxyl group of a spacer, the amino acid or one of the amino acids of the dipeptide or tripeptide can be an amino acid of Formula II. In a specific exemplary embodiment, the amino acid is Ser.

When acylation occurs through a thiol group of a spacer, the amino acid or one of the amino acids of the dipeptide or tripeptide can be an amino acid of Formula III. In a specific exemplary embodiment, the amino acid is Cys.

In one embodiment, the spacer comprises a hydrophilic bifunctional spacer. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.).

Suitable methods of peptide acylation via amines, hydroxyls, and thiols are known in the art. See, for example, Example 19 (for methods of acylating through an amine), Miller, *Biochem Biophys Res Commun* 218: 377-382 (1996); Shimohigashi and Stammer, *Int J Pept Protein Res* 19: 54-62 (1982); and Previero et al., *Biochim Biophys Acta* 263: 7-13 (1972) (for methods of acylating through a hydroxyl); and San and Silvius, *J Pept Res* 66: 169-180 (2005) (for methods of acylating through a thiol); *Bioconjugate Chem*. "Chemical Modifications of Proteins: History and Applications" pages 1, 2-12 (1990); Hashimoto et al., *Pharmacuetical Res*. "Synthesis of Palmitoyl Derivatives of Insulin and their Biological Activity" Vol. 6, No: 2 pp. 171-176 (1989).

The acyl group of the acylated glucagon peptide can be of any size, e.g., any length carbon chain, and can be linear or branched. In some specific embodiments of the invention, the acyl group is a C4 to C30 fatty acid. For example, the acyl group can be any of a C4 fatty acid, C6 fatty acid, C8 fatty acid, C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In some embodiments, the acyl group is a C8 to C20 fatty acid, e.g., a C14 fatty acid or a C16 fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

In a specific embodiment, the glucagon antagonist/GLP-1 agonist comprises a cholesterol acid, which is linked to a Lys residue of the glucagon antagonist/GLP-1 agonsit through an alkylated des-amino Cys spacer, i.e., an alkylated 3-mercaptopropionic acid spacer. The alkylated des-amino Cys spacer can be, for example, a des-amino-Cys spacer comprising a dodecaethylene glycol moiety. In one embodiment, the glucagon antagonist/GLP-1 agonist comprises the structure:

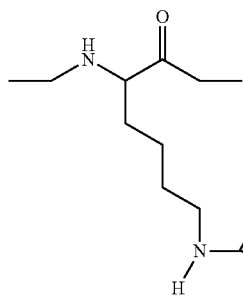
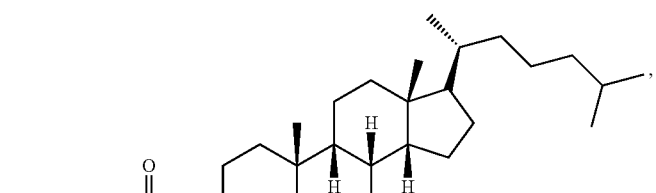

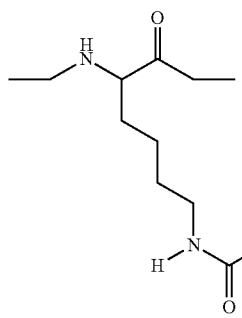
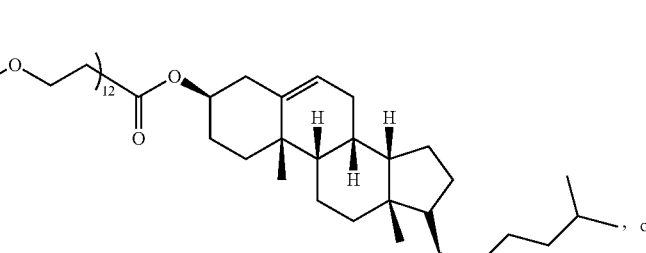

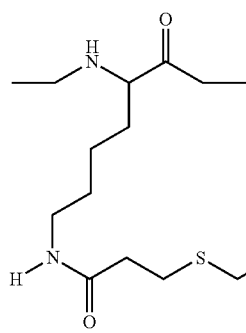
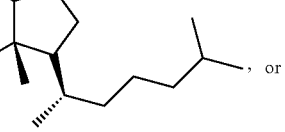

The acylated glucagon peptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the acylated glucagon peptide can comprise SEQ ID NO: 2, including any of the modifications described herein, in which (a) at least one of the amino acids at position 10, 20, 24, and 29 (according to the amino acid numbering of wild type glucagon) comprise an acyl group and (b) at least one of the amino acids at position 16, 17, 21, 24, or 29 (according to the amino acid numbering of wild type glucagon), a position within a C-terminal extension, or the C-terminal amino acid are modified to a Cys, Lys, Orn, homo-Cys, or acetyl phenylalanine (Ac-Phe), and the side chain of the amino acid is covalently bonded to a hydrophilic moiety (e.g., PEG). In some embodiments, the acyl group is attached to position 10 (according to the amino acid numbering of wild type glucagon), optionally via a spacer comprising Cys, Lys, Orn, homo-Cys, or Ac-Phe, and the hydrophilic moiety is incorporated at a Cys residue at position 24 (according to the amino acid numbering of wild type glucagon).

Alternatively, the acylated glucagon peptide can comprise a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

In accordance with one embodiment, the glucagon peptide is modified to comprise an alkyl group which is attached to the glucagon peptide via an ester, ether, thioether, amide, or alkyl amine linkage for purposes of prolonging half-life in circulation and/or delaying the onset of and/or extending the duration of action and/or improving resistance to proteases such as DPP-IV.

Alkylation can be carried out at any positions within the glucagon peptide, including any of positions 1-29, a position within a C-terminal extension, or the C-terminal amino acid, provided that the glucagon antagonist activity (and optionally GLP-1 activity) is retained. Nonlimiting examples include positions 5, 10, 11, 12, 13, 14, 16, 17, 18, 19, 20, 21, 24, 27, 28, or 29 (according to the amino acid numbering of wild type glucagon). The alkyl group can be covalently linked directly to an amino acid of the glucagon peptide, or indirectly to an amino acid of the glucagon peptide via a spacer, wherein the spacer is positioned between the amino acid of the glucagon peptide and the alkyl group. Glucagon peptides may be alkylated at the same amino acid position where a hydrophilic moiety is linked, or at a different amino acid position. Nonlimiting examples include alkylation at position 10 (according to the amino acid numbering of wild type glucagon) and pegylation at one or more positions in the C-terminal portion of the glucagon peptide, e.g., position 24, 28 or 29 (according to the amino acid numbering of wild type glucagon), within a C-terminal extension, or at the C-terminus (e.g., through adding a C-terminal Cys).

In a specific aspect of the invention, the glucagon peptide is modified to comprise an alkyl group by direct alkylation of an amine, hydroxyl, or thiol of a side chain of an amino acid of the glucagon peptide. In some embodiments, the glucagon peptide is directly alkylated through the side chain amine, hydroxyl, or thiol of an amino acid. In some embodiments, alkylation is at position 10, 20, 24, or 29 (according to the amino acid numbering of wild type glucagon). In this regard, the alkylated glucagon peptide can comprise the amino acid sequence of SEQ ID NO: 2, or a modified amino acid sequence thereof comprising one or more of the amino acid modifications described herein, with at least one of the amino acids at positions 10, 20, 24, and 29 (according to the amino acid numbering of wild type glucagon) modified to any amino acid comprising a side chain amine, hydroxyl, or thiol. In some specific embodiments of the invention, the direct alkylation of the glucagon peptide occurs through the side chain amine, hydroxyl, or thiol of the amino acid at position 10 (according to the amino acid numbering of wild type glucagon).

In some embodiments, the amino acid comprising a side chain amine is an amino acid of Formula I. In some exemplary embodiments, the amino acid of Formula I, is the amino acid wherein n is 4 (Lys) or n is 3 (Orn).

In other embodiments, the amino acid comprising a side chain hydroxyl is an amino acid of Formula II. In some exemplary embodiments, the amino acid of Formula II is the amino acid wherein n is 1 (Ser).

In yet other embodiments, the amino acid comprising a side chain thiol is an amino acid of Formula III. In some exemplary embodiments, the amino acid of Formula II is the amino acid wherein n is 1 (Cys).

In one embodiment of the invention, the alkylated glucagon peptide comprises a spacer between the peptide and the alkyl group. In some embodiments, the glucagon peptide is covalently bound to the spacer, which is covalently bound to the alkyl group. In some exemplary embodiments, the glucagon peptide is modified to comprise an alkyl group by alkylation of an amine, hydroxyl, or thiol of a spacer, which spacer is attached to a side chain of an amino acid at position 10, 20, 24, or 29 of the glucagon peptide (according to the amino acid numbering of wild type glucagon). The amino acid to which the spacer is attached can be any amino acid comprising a moiety which permits linkage to the spacer. For example, an amino acid comprising a side chain $NH_2$, —OH, or —COOH (e.g., Lys, Orn, Ser, Asp, or Glu) is suitable. In this respect, the alkylated glucagon peptide can comprise the amino acid sequence of SEQ ID NO: 1, or a modified amino acid sequence thereof comprising one or more of the amino acid modifications described herein, with at least one of the amino acids at positions 10, 20, 24, and 29 (according to the amino acid numbering of wild type glucagon) modified to any amino acid comprising a side chain amine, hydroxyl, or carboxylate.

In some embodiments, the spacer is an amino acid comprising a side chain amine, hydroxyl, or thiol or a dipeptide or tripeptide comprising an amino acid comprising a side chain amine, hydroxyl, or thiol.

When alkylation occurs through an amine group of a spacer the alkylation can occur through the alpha amine of the amino acid or a side chain amine. In the instance in which the alpha amine is alkylated, the spacer amino acid can be any amino acid. For example, the spacer amino acid can be a hydrophobic amino acid, e.g., Gly, Ala, Val, Leu, Ile, Trp, Met, Phe, Tyr. Alternatively, the spacer amino acid can be an acidic residue, e.g., Asp and Glu. In the instance in which the side chain amine of the spacer amino acid is alkylated, the spacer amino acid is an amino acid comprising a side chain amine, e.g., an amino acid of Formula I (e.g., Lys or Orn). In this instance, it is possible for both the alpha amine and the side chain amine of the spacer amino acid to be alkylated, such that the glucagon peptide is dialkylated. Embodiments of the invention include such dialkylated molecules.

When alkylation occurs through a hydroxyl group of a spacer, the amino acid or one of the amino acids of the dipeptide or tripeptide can be an amino acid of Formula II. In a specific exemplary embodiment, the amino acid is Ser.

When alkylation occurs through a thiol group of spacer, the amino acid or one of the amino acids of the dipeptide or tripeptide can be an amino acid of Formula III. In a specific exemplary embodiment, the amino acid is Cys.

In one embodiment, the spacer comprises a hydrophilic bifunctional spacer. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.).

Suitable methods of peptide alkylation via amines, hydroxyls, and thiols are known in the art. For example, a Williamson ether synthesis can be used to form an ether linkage between the glucagon peptide and the alkyl group. Also, a nucleophilic substitution reaction of the peptide with an alkyl halide can result in any of an ether, thioether, or amino linkage.

The alkyl group of the alkylated glucagon peptide can be of any size, e.g., any length carbon chain, and can be linear or branched. In some embodiments of the invention, the alkyl group is a C1 to C30 alkyl. For example, the alkyl group can be any of a C1 alkyl, C2 alkyl, C3 alkyl, C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In some embodiments, the alkyl group is a C8 to C20 alkyl, e.g., a C14 alkyl or a C16 alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

The alkylated glucagon peptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the alkylated glucagon peptide can comprise SEQ ID NO: 2, or a modified amino acid sequence thereof comprising one or more of the amino acid modifications described herein, in which (a) at least one of the amino acids at position 10, 20, 24, and 29 (according to the amino acid numbering of wild type glucagon) comprise an alkyl group and (b) at least one of the amino acids at position 16, 17, 21, 24, and 29 (according to the amino acid numbering of wild type glucagon), a position within a C-terminal extension or the C-terminal amino acid are modified to a Cys, Lys, Orn, homo-Cys, or Ac-Phe, and the side chain of the amino acid is covalently bonded to a hydrophilic moiety (e.g., PEG). In some embodiments, the alkyl group is attached to position 10 (according to the amino acid numbering of wild type glucagon), optionally via a spacer comprising Cys, Lys, Orn, homo-Cys, or Ac-Phe, and the hydrophilic moiety is incorporated at a Cys residue at position 24 (according to the amino acid numbering of wild type glucagon).

Alternatively, the alkylated glucagon peptide can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

EXAMPLES

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

General Synthesis Protocol:

Glucagon analogs were synthesized using HBTU-activated "Fast Boc" single coupling starting from 0.2 mmole of Boc Thr(OBzl)Pam resin on a modified Applied Biosystem 430 A peptide synthesizer. Boc amino acids and HBTU were obtained from Midwest Biotech (Fishers, Ind.). Side chain protecting groups used were: Arg(Tos), Asn(Xan), Asp (OcHex), Cys(pMeBzl), His(Bom), Lys(2Cl—Z), Ser (OBzl), Thr(OBzl), Tyr(2Br—Z), and Trp(CHO). The sidechain protecting group on the N-terminal His was Boc.

Each completed peptidyl resin was treated with a solution of 20% piperidine in dimethylformamide to remove the formyl group from the tryptophan. Liquid hydrogen fluoride cleavages were performed in the presence of p-cresol and dimethyl sulfide. The cleavage was run for 1 hour in an ice bath using an HF apparatus (Pennisula Labs). After evaporation of the HF, the residue was suspended in diethyl ether and the solid materials were filtered. Each peptide was extracted into 30-70 ml aqueous acetic acid and a diluted aliquot was analyzed by HPLC [Beckman System Gold, 0.46×5 cm Zorbax C8, 1 ml/min, 45 C, 214 nm, A buffer=0.1% TFA, B=0.1% TFA/90% acetonitrile, gradient of 10% to 80% B over 10 min].

Purification was done on a FPLC over a 2.2×25 cm Kromasil C18 column while monitoring the UV at 214 nm and collecting 5 minute fractions. The homogeneous fractions were combined and lyophilized to give a product purity of >95%. The correct molecular mass and purity were confirmed using MALDI-mass spectral analysis.

General Pegylation Protocol: (Cys-Maleimido)

Typically, the glucagon Cys analog is dissolved in phosphate buffered saline (5-10 mg/ml) and 0.01M ethylenediamine tetraacetic acid is added (10-15% of total volume). Excess (2-fold) maleimido methoxyPEG reagent (Nektar) is added and the reaction stirred at room temp while monitoring reaction progress by HPLC. After 8-24 hrs, the reaction mixture, is acidified and loaded onto a preparative reverse phase column for purification using 0.1% TFA/acetonitrile gradient. The appropriate fractions were combined and lyophilized to give the desired pegylated derivatives.

Example 1

Synthesis of Glucagon $Cys^{17}$(1-29) and Similar MonoCys Analogs 0.2 mmole Boc Thr(OBzl) Pam resin (SynChem Inc) in a 60 ml reaction vessel and the following sequence was entered and run on a modified Applied Biosystems 430A Peptide Synthesizer using FastBoc HBTU-activated single couplings.

HSQGTFTSDYSKYLDSCRAQDFVQWLMNT (SEQ ID NO: 40)

The following side chain protecting groups were used: Arg (Tos), Asp(OcHex), Asn(Xan), Cys(pMeBzl), Glu(OcHex), His(Boc), Lys(2Cl—Z), Ser(Bzl), Thr(Bzl), Trp(CHO), and Tyr(Br—Z). The completed peptidyl resin was treated with 20% piperidine/dimethylformamide to remove the Trp formyl protection then transferred to an HF reaction vessel and dried in vacuo. 1.0 ml p-cresol and 0.5 ml dimethyl sulfide were added along with a magnetic stir bar. The vessel was attached to the HF apparatus (Pennisula Labs), cooled in a dry ice/methanol bath, evacuated, and aprox. 10 ml liquid hydrogen fluoride was condensed in. The reaction was stirred in an ice bath for 1 hr then the HF was removed in vacuo. The residue was suspended in ethyl ether; the solids were filtered, washed with ether, and the peptide extracted into 50 ml aqueous acetic acid. An analytical HPLC was run [0.46×5 cm Zorbax C8, 1 ml/min, 45 C, 214 nm, A buffer of 0.1% TFA, B buffer of 0.1% TFA/90% ACN, gradient=10% B to 80% B over 10 min.] with a small sample of the cleavage extract. The remaining extract was loaded onto a 2.2×25 cm Kromasil C18 preparative reverse phase column and an acetonitrile gradient was run using a Pharmacia FPLC system. 5 min fractions were collected while monitoring the UV at 214 nm (2.0 A). A=0.1% TFA, B=0.1% TFA/50% acetonitrile. Gradient=30% B to 100% B over 450 min.

The fractions containing the purest product (48-52) were combined frozen, and lyophilized to give 30.1 mg. An HPLC analysis of the product demonstrated a purity of >90% and MALDI mass spectral analysis demonstrated the desired mass of 3429.7. Glucagon $Cys^{21}$, Glucagon $Cys^{24}$, and Glucagon $Cys^{29}$ were similarly prepared.

Example 2

Synthesis of Glucagon-Cex and Other C-Terminal Extended Analogs 285 mg (0.2 mmole) methoxybenzhydrylamine resin (Midwest Biotech) was placed in a 60 ml reaction vessel and the following sequence was entered and run on a modified Applied Biosystems 430A peptide synthesizer using FastBoc HBTU-activated single couplings.

HSQGTFTSDYSKYLDSRRAQDFVQWLMNTGPSSGAPPPS (SEQ ID NO: 41)

The following side chain protecting groups were used: Arg (Tos), Asp(OcHex), Asn(Xan), Cys(pMeBzl), Glu(OcHex), His(Boc), Lys(2Cl—Z), Ser(Bzl), Thr(Bzl), Trp(CHO), and Tyr(Br—Z). The completed peptidyl resin was treated with 20% piperidine/dimethylformamide to remove the Trp formyl protection then transferred to HF reaction vessel and dried in vacuo. 1.0 ml p-cresol and 0.5 ml dimethyl sulfide were added along with a magnetic stir bar. The vessel was attached to the HF apparatus (Pennisula Labs), cooled in a dry ice/methanol bath, evacuated, and aprox. 10 ml liquid hydrogen fluoride was condensed in. The reaction was stirred in an ice bath for 1 hr then the HF was removed in vacuo. The residue was suspended in ethyl ether; the solids were filtered, washed with ether, and the peptide extracted into 50 ml aqueous acetic acid. An analytical HPLC was run [0.46×5 cm Zorbax C8, 1 ml/min, 45 C, 214 nm, A buffer of 0.1% TFA, B buffer of 0.1% TFA/90% ACN, gradient=10% B to 80% B over 10 min.] on an aliquot of the cleavage extract. The extract was loaded onto a 2.2×25 cm Kromasil C18 preparative reverse phase column and an acetonitrile gradient was run for elution using a Pharmacia FPLC system. 5 min fractions were collected while monitoring the UV at 214 nm (2.0 A). A=0.1% TFA, B=0.1% TFA/50% acetonitrile. Gradient=30% B to 100% B over 450 min. Fractions 58-65 were combined, frozen and lyophilized to give 198.1 mg.

HPLC analysis of the product showed a purity of greater than 95%. MALDI mass spectral analysis showed the presence of the desired theoretical mass of 4316.7 with the product as a C-terminal amide. Oxyntomodulin and oxyntomodulin-KRNR were similarly prepared as the C-terminal carboxylic acids starting with the appropriately loaded PAM-resin.

Example 3

Glucagon Cys$^{17}$ Mal-PEG-5K 15.1 mg of Glucagon Cys$^{17}$(1-29) and 27.3 mg methoxy poly(ethyleneglycol) maleimide avg. M.W.5000 (mPEG-Mal-5000, Nektar Therapeutics) were dissolved in 3.5 ml phosphate buffered saline (PBS) and 0.5 ml 0.01M ethylenediamine tetraacetic acid (EDTA) was added. The reaction was stirred at room temperature and the progress of the reaction was monitored by HPLC analysis [0.46×5 cm Zorbax C8, 1 ml/min, 45 C, 214 nm (0.5 A), A=0.1% TFA, B=0.1% TFA/90% ACN, gradient=10% B to 80% B over 10 min.]. After 5 hours, the reaction mixture was loaded onto 2.2×25 cm Kromasil C18 preparastive reverse phase column. An acetonitrile gradient was run on a Pharmacia FPLC while monitoring the UV wavelength at 214 nm and collecting 5 min fractions. A=0.1% TFA, B=0.1% TFA/50% acetonitrile, gradient=30% B to 100% B over 450 min. The fractions corresponding to the product were combined, frozen and lyophilized to give 25.9 mg.

This product was analyzed on HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] which showed a purity of aprox. 90%. MALDI (matrix assisted laser desorption ionization) mass spectral analysis showed a broad mass range (typical of PEG derivatives) of 8700 to 9500. This shows an addition to the mass of the starting glucagon peptide (3429) of approximately 5,000 a.m.u.

Example 4

Glucagon Cys$^{21}$ Mal-PEG-5K 21.6 mg of Glucagon Cys$^{21}$(1-29) and 24 mg mPEG-MAL-5000 (Nektar Therapeutics) were dissolved in 3.5 ml phosphate buffered saline (PBS) and 0.5 ml 0.01M ethylene diamine tetraacetic acid (EDTA) was added. The reaction was stirred at room temp. After 2 hrs, another 12.7 mg of mPEG-MAL-5000 was added. After 8 hrs, the reaction mixture was loaded onto a 2.2×25 cm Vydac C18 preparative reverse phase column and an acetonitrile gradient was run on a Pharmacia FPLC at 4 ml/min while collecting 5 min fractions. A=0.1% TFA, B=0.1% TFA/50% ACN. Gradient=20% to 80% B over 450 min.

The fractions corresponding to the appearance of product were combined frozen and lyophilized to give 34 mg. Analysis of the product by analytical HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] showed a homogeneous product that was different than starting glucagon peptide. MALDI (matrix assisted laser desorption ionization) mass spectral analysis showed a broad mass range (typical of PEG derivatives) of 8700 to 9700. This shows an addition to the mass of the starting glucagon peptide (3470) of approximately 5,000 a.m.u.

Example 5

Glucagon Cys$^{24}$ Mal-PEG-5K 20.1 mg Glucagon C$^{24}$(1-29) and 39.5 mg mPEG-Mal-5000 (Nektar Therapeutics) were dissolved in 3.5 ml PBS with stirring and 0.5 ml 0.01M EDTA was added. The reaction was stirred at room temp for 7 hrs, then another 40 mg of mPEG-Mal-5000 was added. After approximately 15 hr, the reaction mixture was loaded onto a 2.2×25 cm Vydac C18 preparative reverse phase column and an acetonitrile gradient was run using a Pharmacia FPLC. 5 min. fractions were collected while monitoring the UV at 214 nm (2.0 A). A buffer=0.1% TFA, B buffer=0.1% TFA/50% ACN, gradient=30% B to 100% B over 450 min. The fractions corresponding to product were combined, frozen and lyophilized to give 45.8 mg. MALDI mass spectral analysis showed a typical PEG broad signal with a maximum at 9175.2 which is approximately 5,000 a.m.u. more than Glucagon C$^{24}$ (3457.8).

Example 6

Glucagon Cys$^{24}$ Mal-PEG-20K 25.7 mg of Glucagon Cys$^{24}$(1-29) and 40.7 mg mPEG-Mal-20K (Nektar Therapeutics) were dissolved in 3.5 ml PBS with stirring at room temp. and 0.5 ml 0.01M EDTA was added. After 6 hrs, the ratio of starting material to product was aprox. 60:40 as determined by HPLC. Another 25.1 mg of mPEG-Mal-20K was added and the reaction allowed to stir another 16 hrs. The product ratio had not significantly improved, so the reaction mixture was loaded onto a 2.2×25 cm Kromasil C18 preparative reverse phase column and purified on a Pharmacia FPLC using a gradient of 30% B to 100% B over 450 min. A buffer=0.1% TFA, B buffer=0.1% TFA/

50% ACN, flow=4 ml/min, and 5 min fractions were collected while monitoring the UV at 214 nm (2.0 A). The fractions containing homogeneous product were combined, frozen and lyophilized to give 25.7 mg. Purity as determined by analytical HPLC was ~90%. A MALDI mass spectral analysis showed a broad peak from 23,000 to 27,000 which is approximately 20,000 a.m.u. more than starting Glucagon $C^{24}$ (3457.8).

Example 7

Glucagon $Cys^{29}$ Mal-PEG-5K 20.0 mg of Glucagon $Cys^{29}$(1-29) and 24.7 mg mPEG-Mal-5000 (Nektar Therapeutics) were dissolved in 3.5 ml PBS with stirring at room temperature and 0.5 ml 0.01M EDTA was added. After 4 hr, another 15.6 mg of mPEG-Mal-5000 was added to drive the reaction to completion. After 8 hrs, the reaction mixture was loaded onto a 2.2×25 cm Vydac C18 preparative reverse phase column and an acetonitrile gradient was run on a Pharmacia FPLC system. 5 min fractions were collected while monitoring the UV at 214 nm (2.0 A). A=0.1% TFA, B=0.1% TFA/50% ACN. Fractions 75-97 were combined frozen and lyophilized to give 40.0 mg of product that is different than recovered starting material on HPLC (fractions 58-63). Analysis of the product by analytical HPLC [0.46×5 cm Zorbax C8, 1 ml/min, 45 C, 214 nm (0.5 A), A=0.1% TFA, B=0.1% TFA/90% ACN, gradient=10% B to 80% B over 10 min.] showed a purity greater than 95%. MALDI mass spectral analysis showed the presence of a PEG component with a mass range of 8,000 to 10,000 (maximum at 9025.3) which is 5,540 a.m.u. greater than starting material (3484.8).

Example 8

Glucagon $Cys^{24}$ (2-butyrolactone)

To 24.7 mg of Glucagon $Cys^{24}$(1-29) was added 4 ml 0.05M ammonium bicarbonate/50% acetonitrile and 5.5 ul of a solution of 2-bromo-4-hydroxybutyric acid-γ-lactone (100 ul in 900 ul acetonitrile). After 3 hrs of stirring at room temperature, another 105 ul of lactone solution was added to the reaction mixture which was stirred another 15 hrs. The reaction mixture was diluted to 10 ml with 10% aqueous acetic acid and was loaded onto a 2.2×25 cm Kromasil C18 preparative reverse phase column. An acetonitrile gradient (20% B to 80% B over 450 min) was run on a Pharmacia FPLC while collecting 5 min fractions and monitoring the UV at 214 nm (2.0 A). Flow=4 ml/min, A=0.1% TFA, B=0.1% TFA/50% ACN. Fractions 74-77 were combined frozen and lyophilized to give 7.5 mg. HPLC analysis showed a purity of 95% and MALDI mass spect analysis showed a mass of 3540.7 or 84 mass units more than starting material. This result is consistent with the addition of a single butyrolactone moiety.

Example 9

Glucagon $Cys^{24}$(S-carboxymethyl)

18.1 mg of Glucagon $Cys^{24}$(1-29) was dissolved in 9.4 ml 0.1M sodium phosphate buffer (pH=9.2) and 0.6 ml bromoacetic acid solution (1.3 mg/ml in acetonitrile) was added. The reaction was stirred at room temperature and the reaction progress was followed by analytical HPLC. After 1 hr another 0.1 ml bromoacetic acid solution was added. The reaction was stirred another 60 min. then acidified with aqueous acetic acid and was loaded onto a 2.2×25 cm Kromasil C18 preparative reverse phase column for purification. An acetonitrile gradient was run on a Pharmacia FPLC (flow=4 ml/min) while collecting 5 min fractions and monitoring the UV at 214 nm (2.0 A). A=0.1% TFA, B=0.1% TFA/50% ACN. Fractions 26-29 were combined frozen and lyophilized to give several mg of product. Analytical HPLC showed a purity of 90% and MALDI mass spectral analysis confirmed a mass of 3515 for the desired product.

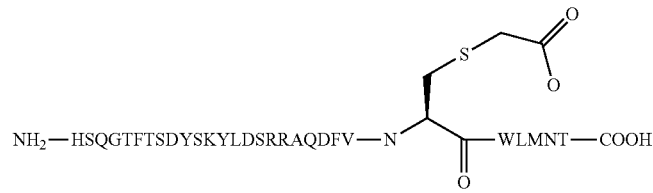

SEQ ID NO: 43

$NH_2$—HSQGTFTSDYSKYLDSRRAQDFV—N—WLMNT—COOH

Molecular Weight = 3515.87
Exact Mass = 3512
Molecular Formula = C153H224N42O50S2

Example 10

Glucagon $Cys^{24}$ maleimido, PEG-3.4K-dimer 16 mg Glucagon $Cys^{24}$ and 1.02 mg Mal-PEG-Mal-3400, poly(ethyleneglycol)-bis-maleimide avg. M.W. 3400, (Nektar Therpeutics) were dissolved in 3.5 phosphate buffered saline and 0.5 ml 0.01M EDTA and the reaction was stirred at room temperature. After 16 hrs, another 16 mg of Glucagon $Cys^{24}$ was added and the stirring continued. After approximately 40 hrs, the reaction mixture was loaded onto a Pharmcia PepRPC 16/10 column and an acetonitrile gradient was run on a Pharmacia FPLC while collecting 2 min fractions and monitoring the UV at 214 nm (2.0 A). Flow=2 ml/min, A=0.1% TFA, B=0.1% TFA/50% ACN. Fractions 69-74 were combined frozen and lyophilized to give 10.4 mg. Analytical HPLC showed a purity of 90% and MALDI mass spectral analysis shows a component in the 9500-11,000 range which is consistent with the desired dimer.

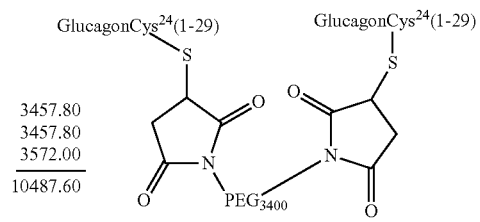

```
GlucagonCys24(1-29)    GlucagonCys24(1-29)
3457.80
3457.80
3572.00
─────────
10487.60
```

Example 11

Glucagon Solubility Assays

A solution (1 mg/ml or 3 mg/ml) of glucagon (or an analog) is prepared in 0.01N HCl. 100 ul of stock solution is diluted to 1 ml with 0.01N HCl and the UV absorbance (276 nm) is determined. The pH of the remaining stock solution is adjusted to pH7 using 200-250 ul 0.1M $Na_2HPO_4$ (pH9.2). The solution is allowed to stand overnight at 4° C. then centrifuged. 100 ul of supernatant is then diluted to 1 ml with 0.01N HCl, and the UV absorbance is determined (in duplicate).

The initial absorbance reading is compensated for the increase in volume and the following calculation is used to establish percent solubility:

$$\frac{\text{Final Absorbance}}{\text{Initial Absorbance}} \times 100 = \text{percent soluble}$$

Results are shown in Table 1 wherein Glucagon-Cex represents wild type glucagon (SEQ ID NO: 1) plus a carboxy terminal addition of SEQ ID NO: 21 and Glucagon-Cex $R^{12}$ represents SEQ ID NO: 44.

TABLE 1

Solubility date for glucagon analogs

| Analog | Percent Soluble |
| --- | --- |
| Glucagon | 16 |
| Glucagon-Cex, R12 | 104 |
| Glucagon-Cex | 87 |
| Oxyntomodulin | 104 |
| Glucagon, Cys17PEG5K | 94 |
| Glucagon, Cys21PEG5K | 105 |
| Glucagon, Cys24PEG5K | 133 |

Example 12

Glucagon Receptor Binding Assay

The affinity of peptides to the glucagon receptor was measured in a competition binding assay utilizing scintillation proximity assay technology. Serial 3-fold dilutions of the peptides made in scintillation proximity assay buffer (0.05 M Tris-HCl, pH 7.5, 0.15 M NaCl, 0.1% w/v bovine serum albumin) were mixed in 96 well white/clear bottom plate (Corning Inc., Acton, Mass.) with 0.05 nM (3-[$^{125}$I]-iodotyrosyl) Tyr10 glucagon (Amersham Biosciences, Piscataway, N.J.), 1-6 micrograms per well, plasma membrane fragments prepared from cells over-expressing human glucagon receptor, and 1 mg/well polyethyleneimine-treated wheat germ agglutinin type A scintillation proximity assay beads (Amersham Biosciences, Piscataway, N.J.). Upon 5 min shaking at 800 rpm on a rotary shaker, the plate was incubated 12 h at room temperature and then read on MicroBeta1450 liquid scintillation counter (Perkin-Elmer, Wellesley, Mass.). Non-specifically bound (NSB) radioactivity was measured in the wells with 4 times greater concentration of "cold" native ligand than the highest concentration in test samples and total bound radioactivity was detected in the wells with no competitor. Percent specific binding was calculated as following: % Specific Binding=((Bound-NSB)/(Total bound-NSB))× 100. $IC_{50}$ values were determined by using Origin software (OriginLab, Northampton, Mass.).

Example 13

Functional Assay—cAMP Synthesis

The ability of glucagon analogs to induce cAMP was measured in a firefly luciferase-based reporter assay. HEK293 cells co-transfected with either glucagon- or GLP receptor and luciferase gene linked to cAMP responsive element were serum deprived by culturing 16 h in DMEM (Invitrogen, Carlsbad, Calif.) supplemented with 0.25% Bovine Growth Serum (HyClone, Logan, Utah) and then incubated with serial dilutions of either glucagon, GLP-1 or novel glucagon analogs for 5 h at 37° C., 5% $CO_2$ in 96 well poly-D-Lysine-coated "Biocoat" plates (BD Biosciences, San Jose, Calif.). At the end of the incubation 100 microliters of LucLite luminescence substrate reagent (Perkin-Elmer, Wellesley, Mass.) were added to each well. The plate was shaken briefly, incubated 10 min in the dark and light output was measured on MicroBeta-1450 liquid scintillation counter (Perkin-Elmer, Wellesley, Mass.). Effective 50% concentrations were calculated by using Origin software (OriginLab, Northampton, Mass. Results are shown in FIG. 3 and in Tables 2 and 3.

TABLE 2 cAMP Induction by Glucagon Analogs with C-Terminus Extension

| | cAMP Induction | | | |
| --- | --- | --- | --- | --- |
| | Glucagon Receptor | | GLP-1 Receptor | |
| Peptide | $EC_{50}$, nM | N* | $EC_{50}$, nM | N* |
| Glucagon | 0.22 ± 0.09 | 14 | 3.85 ± 1.64 | 10 |
| GLP-1 | 2214.00 ± 182.43 | 2 | 0.04 ± 0.01 | 14 |
| Glucagon Cex | 0.25 ± 0.15 | 6 | 2.75 ± 2.03 | 7 |
| Oxyntomodulin | 3.25 ± 1.65 | 5 | 2.53 ± 1.74 | 5 |
| Oxyntomodulin KRNR | 2.77 ± 1.74 | 4 | 3.21 ± 0.49 | 2 |
| Glucagon R12 | 0.41 ± 0.17 | 6 | 0.48 ± 0.11 | 5 |
| Glucagon R12 Cex | 0.35 ± 0.23 | 10 | 1.25 ± 0.63 | 10 |
| Glucagon R12 K20 | 0.84 ± 0.40 | 5 | 0.82 ± 0.49 | 5 |
| Glucagon R12 K24 | 1.00 ± 0.39 | 4 | 1.25 ± 0.97 | 5 |
| Glucagon R12 K29 | 0.81 ± 0.49 | 5 | 0.41 ± 0.24 | 6 |
| Glucagon Amide | 0.26 ± 0.15 | 3 | 1.90 ± 0.35 | 2 |
| Oxyntomodulin C24 | 2.54 ± 0.63 | 2 | 5.27 ± 0.26 | 2 |
| Oxyntomodulin C24 PEG 20K | 0.97 ± 0.04 | 1 | 1.29 ± 0.11 | 1 |

*number of experiments

TABLE 3 cAMP Induction by Pegylated Glucagon Analogs

| Peptide | cAMP Induction | | | |
|---|---|---|---|---|
| | Glucagon Receptor | | GLP-1 Receptor | |
| | EC$_{50}$, nM | N* | EC$_{50}$, nM | N* |
| Glucagon | 0.33 ± 0.23 | 18 | 12.71 ± 3.74 | 2 |
| Glucagon C17 PEG 5K | 0.82 ± 0.15 | 4 | 55.86 ± 1.13 | 2 |
| Glucagon C21 PEG 5K | 0.37 ± 0.16 | 6 | 11.52 ± 3.68 | 2 |
| Glucagon C24 PEG 5K | 0.22 ± 0.10 | 12 | 13.65 ± 2.95 | 4 |
| Glucagon C29 PEG 5K | 0.96 ± 0.07 | 2 | 12.71 ± 3.74 | 2 |
| Glucagon C24 PEG 20K | 0.08 ± 0.05 | 3 | Not determined | |
| Glucagon C24 Dimer | 0.10 ± 0.05 | 3 | Not determined | |
| GLP-1 | >1000 | | 0.05 ± 0.02 | 4 |

*number of experiments

Example 14

Stability Assay for glucagon Cys-maleimido PEG analogs

Each glucagon analog was dissolved in water or PBS and an initial HPLC analysis was conducted. After adjusting the pH (4, 5, 6, 7), the samples were incubated over a specified time period at 37° C. and re-analyzed by HPLC to determine the integrity of the peptide. The concentration of the specific peptide of interest was determined and the percent remaining intact was calculated relative to the initial analysis. Results for Glucagon Cys$^{21}$-maleimidoPEG$_{5K}$ are shown in FIGS. 1 and 2.

Example 15

Glucagon Antagonists/GLP-1 Agonists

The glucagon antagonists/GLP-1 agonists were synthesized using the following general strategies:

General Peptide Synthesis Protocol with Boc-Chemistry Strategy:

Glucagon analogs were synthesized using HBTU-activated "Fast Boc" single coupling starting from 0.2 mmole of MBHA resin or first amino acid attached Pam resin on a modified Applied Biosystem 430A peptide synthesizer. Boc amino acids and HBTU were obtained from Midwest Biotech (Fishers, Ind.). General side chain protecting groups used were: Arg(Tos), Asn(Xan), Asp(OcHex), Cys(pMeBzl), His (Bom), Lys(2Cl—Z), Ser(OBzl), Thr(OBzl), Tyr(2Br—Z), and Trp(CHO). Boc-Glu(OFm)—OH and Boc-Lys(Fmoc)-OH (Chem-Impex, Wood dale, IL) were used in the lactam-bridge formation sites. The N-terminal 3-phenyllacetic acid (PLA) (Aldrich, Milwaukee, Wis.) was coupled manually by BEPBT (3-(Diethoxy-phosphoryloxy)-3H-benzo[d][1,2,3]triazin-4-one (Synchem Inc., Aurora, Ohio) after the automated solid phase synthesis.

After peptide solid phase synthesis, each completed peptidyl resin was treated with 20% piperidine/DMF to remove the Fmoc groups. For the lactam-bridge formation, usually 299 mg (1 mmole, 5-fold) BEPBT were added in 10% DIEA/DMF and reacted for 2~4 h until ninhydrin test shown negative.

Peptides were cleaved by liquid hydrogen fluoride cleavages performed in the presence of p-cresol and dimethyl sulfide. The cleavage was run for 1 hour in an ice bath using an HF apparatus (Penninsula Labs). After evaporation of the HF, the residue was suspended in diethyl ether and the solid materials were filtered and washed with ether. Each peptide was extracted into 30-70 ml aqueous acetic acid and diluted with water and lyophilized. Crude peptide was analyzed by analytical HPLC and peptide molecule weight was checked by ESI or MALDI-TOF mass spectrometry. Peptides were then purified by the general HPLC purification procedure.

General Peptide Synthesis Protocol with Fmoc-Chemistry Strategy:

Peptides were synthesized on an ABI 433A automated peptide synthesizer using standard Fmoc chemistry with Rink MBHA amide resin or first amino acid attached Wang resin (Novabiochem, San Diego, Calif.) using DIC/HOBT as coupling reagent. 3-phenyllacetic acid (PLA) was coupled manually by BEPBT after the automated peptide synthesis. The side chain protecting groups of N$^{\alpha}$-Fmoc [N-(9-fluorenyl) methoxycarbonyl]amino acids were as follows: Arg, Pmc; Asp, OtBu; Cys, Trt; Gln, Trt; His, Trt; Lys, Boc; Ser, tBu, Tyr, tBu; and Trp, Boc (Pmc=2,2,5,7,8-pentamethylchoman-6-sulfonyl, OtBu=tert-butyl ester, Trt=trityl, Boc=tert-butyloxycarbonyl, and tBu=tert-butyl ester). Fmoc-Glu(O-2-PhiPr)—OH and Fmoc-Lys(Mmt)-OH (Novabiochem, San Diego, Calif.) were incorporated in the lactam-bridge formation sites.

After solid phase synthesis, the 2-phenylisopropyl (2-PhiPr) group on the Glu and the 4-methoxytrityl (Mmt) group on the Lys were removed by flashing 1% TFA/DCM though the peptidyl resin. For the lactam-bridge formation, usually 150 mg (0.5 mmole, 5-fold) BEPBT were added in 10% DIEA/DMF and reacted for 2~4 h until ninhydrin test shown negative.

Peptides were cleaved from the resin with cleavage cocktail containing 85% TFA, 5% phenol, 5% water and 5% thioanisole (2.5% EDT was added when peptide contains Cysteine). Crude peptides were precipitated in ether, centrifuged, and lyophilized. Peptides were then analyzed by analytical HPLC and checked by ESI or MALDI-TOF mass spectrometry. Peptides were purified by the general HPLC purification procedure.

General Analytical HPLC Procedure:

Analytical HPLC was performed on a Beckman System Gold HPLC system with a ZORBAX SB-C8 column (0.46×5 cm, 5 μm, Agilent) with a gradient elution at a flow rate of 1.0 mL/min and monitored at 214 nm. The gradients were set up as 10% B to 80% B over 10 min and then 10% B for 5 min. Buffer A=0.1% TFA and B=0.1% TFA/90% acetonitrile.

General Preparative HPLC Purification Procedure:

If not specifically noted, the peptides were usually purified on a Waters 600E connected 486 monitor systems with semi-prepare HPLC column (ZORBAX SB-C8, 21.2×250 mm, 7 μm, Agilent) monitored at 214 nm or 230 nM. Buffer A=0.1% TFA/10% acetonitrile and B=0.1% TFA/90% acetonitrile. The gradients used for the purification were 0-30% B over 40 min, then 30-50% B over 30 min at a flow rate of 12 ml/min if not specifically noted. Fractions were analyzed by analytical HPLC and checked by mass spectrometry. The fractions over 90% pure were collected, lyophilized and stored. The fractions with purity between 60-90% were combined, lyophilized and purified again.

General Pegylation Protocol: (Cys-Maleimido)

Typically, the glucagon Cys analog is dissolved in phosphate buffered saline (5-10 mg/ml) and 0.01M ethylenediamine tetraacetic acid is added (10-15% of total volume). Excess (1.2~2-fold) maleimido methoxy-polyethylene glycol (MAL-m-dPEG) reagent is added and the reaction stirred at room temp while monitoring reaction progress by HPLC. After 2~12 h, the reaction mixture, is acidified and loaded onto a preparative reverse phase column for purification using 0.1% TFA/acetonitrile gradients. The appropriate fractions were combined and lyophilized to give the desired pegylated derivatives.

For peptides that exhibit low solubility in PBS, the peptides were dissolved in 25% acetonitrile water or 4~6M urea buffer with 50~100 mM Tris (adjust pH 8.0~8.5) and reacted with PEG reagents.

Specific examples of compounds synthesized by the methods described above are provided as follows:

Synthesis of [PLA6, D9, E16K20(lactam), D28]glucagon(6-29) amide

A peptide sequence TSDYSKYLDERRAKD-FVQWLMDT (SEQ ID NO: 49) was first solid phase synthesized on ABI 433A automated peptide synthesizer using 0.1 mmole Fmoc/HOBT/DCC chemistry program with 0.1 mmole Rink MBHA amide resin using DIC/HOBT as coupling reagent. The following Fmoc amino acid were used: Ala, Arg(Pmc), Asp(OtBu), Asn(Trt), Glu(O-2-PhiPr), Gln (Trt), Leu, Lys(Boc), Lys(Mmt), Met, PLA, Ser(tBu), Thr (tBu), Trp(Boc), Tyr(tBu), and Val. After the automated synthesis, the peptidyl resin was coupled manually with 3-phenyllacetic acid (83 mg, 0.5 mmole) and DEPBT (150 mg, 0.5 mmole) in 4 ml 5% DIEA/DMF for about 2 h to obtain the peptidyl resin with the following sequence: HO-PLA-Thr-Ser-Asp-Tyr-Ser-Lys-Tyr-Leu-Asp-Glu-Arg-Arg-Ala-Lys-Asp-Phe-Val-Gln-Trp-Leu-Met-Asp-Thr-NH$_2$(SEQ ID NO: 6).

Peptidyl resin was flashed with 50 ml 1% TFA/DCM in 5-10 min and washed with DCM, 5% DIEA/DMF and DMF. The peptidyl resin was then treated with 150 mg (0.5 mmole, 5-fold) DEPBT in 10% DIEA/DMF for 2~4 h until ninhydrin test shown negative.

Peptidyl resin was treated with 8.5 ml TFA with addition of 0.5 g phenol, 0.5 ml water and 0.5 ml thioanisole at room temperature for about 2 h. The peptide dissolved in TFA was filtered and 40 ml ether was added to precipitate the peptide. The crude peptide were centrifuged, dissolved in aqueous acetic acid and lyophilized to get 150-250 mg crude peptide. After purification 20~30 mg (10~15% yield totally) peptide with 95% purity was obtained. The peptide was analyzed in general analytical HPLC showing retention time as 7.63 min and ESI-MS analysis demonstrated the desired mass of 2997.0 corresponding with the peptide molecular weight 2997.3.

Similar procedures were used to synthesize the following peptides: [PLA6, E9, E16K20(lactam)]glucagon(6-39) amide with analytical HPLC 7.17 min and ESI-MS 3444.5 corresponding the calculated MW 3845.2; [PLA6, D9, K12E16(lactam), D28]glucagon(6-29) amide with analytical HPLC 7.71 min and ESI-MS 2997.0 corresponding the calculated MW 2997.3; [PLA6, E9, K12E16(lactam)]glucagon (6-39) amide with analytical HPLC 7.27 min and ESI-MS 3845.5 corresponding the calculated MW 3845.2; [PLA6, D9, E16K20(lactam), C24, D28]glucagon(6-29) amide with analytical HPLC 7.85 min and ESI-MS 2972.0 corresponding the calculated MW 2972.3; [PLA6, D9, K12E16(lactam), C24, D28]glucagon(6-29) amide with analytical HPLC 7.83 min and ESI-MS 2971.5 corresponding the calculated MW 2972.3; [PLA6, D9, E16K20(lactam), D28, C40]glucagon(6-40) amide with analytical HPLC 7.13 min and MALDI-MS 3935.7 corresponding the calculated MW 3935.3.

Synthesis of [PLA6, D9, E16K20(lactam), C24(20K), D28]glucagon (6-29) amide 15 mg (0.005 mmole) [PLA6, D9, E16K20(lactam), C24, D28]glucagon (6-29) amide and 120 mg (0.006 mmole) 20K mPEG-MAL(MW ~20 k, Chirotech Technology Ltd., Cambs CB4 0WG, German) were dissolved in 9 ml 25% acetonitrile water and about 0.5~1 ml 1M Tris base buffer (adjust pH to 8.0~8.5). The reaction was stirred at room temperature and the progress of the reaction was monitored by analytical HPLC. After no initial product was detected on HPLC (2~6 h), the reaction mixture was directly purified by preparative HPLC. The fractions were checked by analytical HPLC at 214 nm and also measured by UV at 280 nm. The fractions with 90% HPLC purity and also with high absorption (A280 nm=1.0~2.0) in UV measurement were combined and lyophilized. About 60~80 mg [PLA6, D9, E16K20(lactam), C24 (20K), D28]glucagon (6-29) amide can be obtained which analytical HPLC analysis shown retention time as 8.5~8.6 min and MALDI-MS shown broad mass spectrometry at 22K~24K.

Similar procedures were used to synthesize [PLA6, D9, K12E16(lactam), C24(20K), D28]glucagon (6-29) amide and [PLA6, D9, E16K20(lactam), D28, C40(20K)]glucagon (6-40) amide.

Synthesis of Dimer[PLA6, D9, E16K20(lactam), C24, D28]glucagon (6-29) amide 20 mg (0.00673 mmole) [PLA6, D9, E16K20(lactam), C24, D28]glucagon (6-29) amide was dissolved in 6 ml PBS buffer, 0.5~1 ml 1M Tris base (adjust pH 8.0~8.5) and 3 ml DMSO. The reaction mixture was stirred in an open air container and monitored by analytical HPLC every 2 h. After the initial product (HPLC RT 7.85 min) was gone and the dimer product (HPLC RT 7.96 min) was the dominate product (~24 h), the mixture was diluted with 0.1% TFA10% acetonitrile water and directly purified by preparative HPLC. After lyophilized about 6-10 mg [PLA6, D9, E16K20(lactam), C24, D28]glucagon (6-29) amide was obtained with ESI-MS 5942.0 corresponding the calculated MW 5942.6.

Example 16

Antagonist Activities of Glucagon Analogs

The receptor binding, cAMP induction and cAMP inhibition of glucagon and various glucagon derivative inhibitors were compared. The assays for measuring receptor binding and cAMP induction and cAMP inhibition were conducted using the assay system essentially as disclosed in Examples 12 and 13, respectively.

Figure 3B:
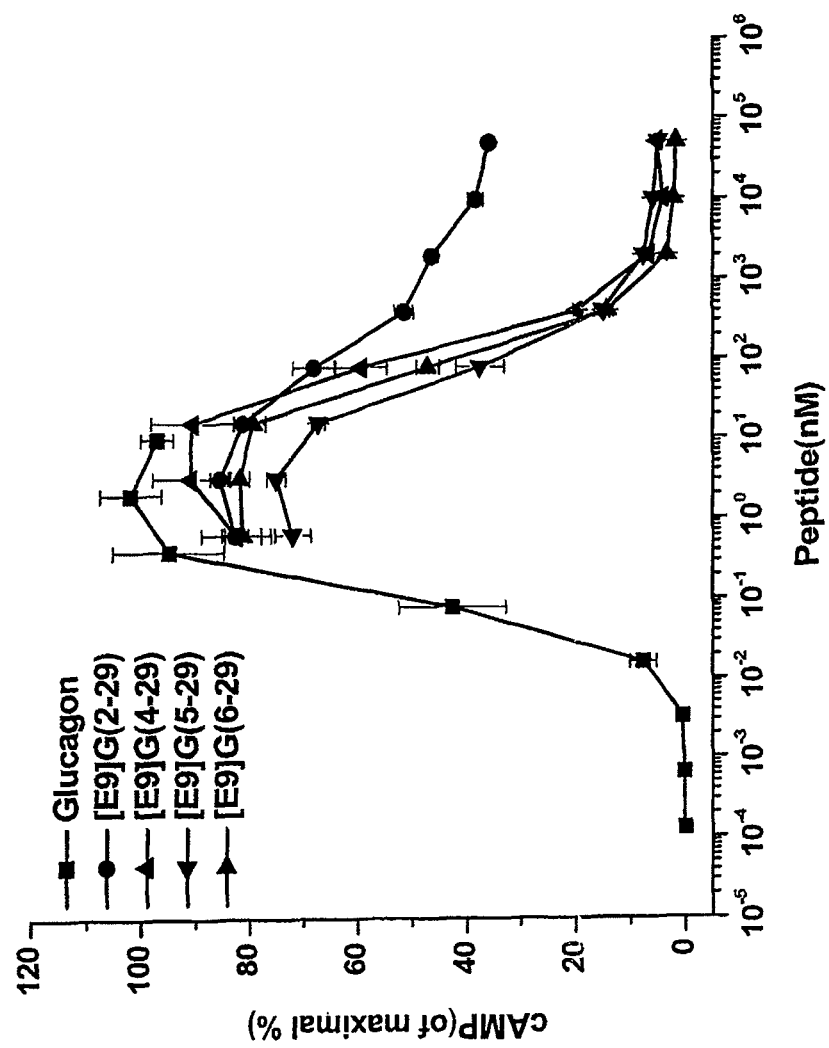

Specific glucagon analogs have been prepared that exhibit glucagon antagonist activity. Such compounds differ from native glucagon in that they do not possess the native N-terminal residues and have a glutamic acid substitution at position 9 relative to native glucagon. Table 4 and FIGS. 3A & 3B provides glucagon receptor affinity and antagonist activity for several specific glucagon analog antagonists.

TABLE 4

Glutamic acid modified N-truncated glucagon analogs and their glucagon antagonism activities

| Peptide | Receptor Binding IC$_{50}$(nM) | cAMP Inhibition IC$_{50}$(nM) |
|---|---|---|
| Glucagon | 1-2.5 | N/A |
| [Glu$^9$]Glucagon(aa2-29)-NH$_2$ | 14 | partial antagonist |
| [Glu$^9$]Glucagon(aa4-29)-NH$_2$ | 136 | 128 |
| [Glu$^9$]Glucagon(aa5-29)-NH$_2$ | 37 | 74 |
| [Glu$^9$]Glucagon(aa6-29)-NH$_2$ | 36 | 97 |

Glu$^9$ is glutamic acid at position 9 according to the numbering of native glucagon.

As the data in Table 5 indicates, a set of hCys9-based antagonists do not perform as potently or selectively as the previously reported Glu9-based antagonists. Compounds 5B and 6B demonstrate some level of antagonism but only at concentrations that are threefold higher than their effective dose as an agonist. However, when additional N-terminal amino acids are removed the potency of the hCys9-based glucagon antagonists is enhanced (See Table 8).

TABLE 5

Receptor Binding and cAMP Inhibition by Glucagon Antagonist Analogs

| Cmpd. # | Peptide | Receptor Binding IC$_{50}$(nM) | cAMP Induction EC$_{50}$(nM) | cAMP Inhibition IC$_{50}$(nM) |
|---|---|---|---|---|
|  | Glucagon | 1.75-0.31 | 0.21 ± 0.11 | N/A |
|  | [desHis$^1$, Glu$^9$]Glucagon-NH$_2$ | 36.90 ± 0.32 | 65 ± 37 | 1862 ± 1234 |
|  | [desHis$^1$, Glu$^9$, Phe$^{25}$, Leu$^{27}$]Glucagon-NH$_2$ | 12.59 ± 0.41 | 81 ± 23 | N/A* |
| 5 | [desHis$^1$, desPhe$^6$] Glucagon-NH$_2$ | 129.55 ± 44.9 | 1178 ± 105 | N/A* |
| 6 | [desHis$^1$, Leu$^4$, Glu$^9$] Glucagon-NH$_2$ | 36.88 ± 0.03 | 318 ± 112 | 102 ± 52 |
| 4B | [desHis$^1$, hCys$^9$(SO$_3$-), Phe$^{25}$, Leu$^{27}$] Glucagon-NH$_2$ | 13.90 ± 0.37 | 430 ± 45 | N/A* |
| 5B | [desHis$^1$, desPhe$^6$, hCys$^9$(SO$_3$-), Phe$^{25}$, Leu$^{27}$] Glucagon-NH$_2$ | 53.32 ± 9.97 | 3212 ± 368 | 9217 ± 3176 |
| 6B | [desHis$^1$, Leu$^4$, hCys$^9$(SO$_3$-), Phe$^{25}$, Leu$^{27}$] Glucagon-NH$_2$ |  | 1614 ± 1132 | 4456 ± 1469 |

*not an antagonist;
amino acid positions according to the numbering of native glucagon indicated by superscripted numbers Glucagon receptor binding affinity of glucagon and glucagon peptides modified by truncation of the first amino acid and by substitution at position 9 (according to the amino acid numbering of native glucagon) was analyzed as essentially described in Example 12, The results are shown in Table 6.

TABLE 6

| peptide no. | peptide | residue 9 | IC$_{50}$ (nM)$^a$ |
|---|---|---|---|
|  | Glucagon | Asp | 1.50 (1.0 ~ 2.5)* |
| 1 | [desHis$^1$, Glu$^9$] Glucagon-NH$_2$ | Glu | 14.08 ± 0.34 |
| 2 | [hGlu$^9$] Glucagon(aa2-29)-NH$_2$ | hGlu | 8.10 ± 0.40 |
| 3 | [(CSA-1)$^9$] Glucagon(aa2-29)-NH$_2$ | CSA-1 | 12.66 ± 0.13 |

TABLE 6-continued

| peptide no. | peptide | residue 9 | IC$_{50}$ (nM)$^a$ |
|---|---|---|---|
| 4 | [(CSA-2)$^9$]Glucagon(aa2-29)-NH$_2$ | CSA-2 | 13.28 ± 0.78 |
| 5 | [β-hGlu$^9$]Glucagon(aa2-29)-NH$_2$ | β-hGlu | 37.10 ± 0.34 |
| 6 | [(NSG-1)$^9$]Glucagon(aa2-29)-NH$_2$ | NSG-1 | 983 ± 82 |
| 7 | [(NSG-2)$^9$]Glucagon(aa2-29)-NH$_2$ | NSG-2 | 2348 ± 382 |

*EC50 (nM); amino acid positions according to the numbering of native glucagon indicated by superscripted numbers Several of the modified glucagon based peptides tested, including the peptides modified at position 9 with Glu, hGlu, CSA-1, CSA-2, and β-hGlu exhibited potent glucagon antagonist activity.

Glucagon peptides comprising a modified amino acid at position 9 (according to the numbering of native glucagon) and having different extents of N-terminal truncation were analyzed for glucagon antagonist activity. The results of the peptides tested are shown in Table 7.

TABLE 7

| | | | | cAMP | | |
|---|---|---|---|---|---|---|
| peptide no. | peptide | residue 9 | IC$_{50}$ (nM)$^a$ | pA$_2$$^b$ | (I/A)$_{50}$$^c$ |
| 8 | [Glu$^9$]Glucagon(aa4-29)-NH$_2$ | Glu | 136.0 ± 17.84 | 7.05 ± 1.01 | 1375 |
| 9 | [Leu$^4$, Glu$^9$]Glucagon(aa4-29)-NH$_2$ | Glu | 36.38 ± 8.69 | NA$^d$ | NA |
| 10 | [Glu$^9$]Glucagon(aa5-29)-NH$_2$ | Glu | 37.38 ± 3.41 | 6.94 ± 0.34 | 390 |
| 11 | [Glu$^9$]Glucagon(aa6-29)-NH$_2$ | Glu | 36.35 ± 5.23 | 7.16 ± 0.27 | 486 |
| 12 | [hGlu$^9$]Glucagon(aa6-29)-NH$_2$ | hGlu | 162.9 ± 70.8 | 6.27 ± 0.11 | 2361 |
| 13 | [(CSA-1)$^9$]Glucagon(aa6-29)-NH$_2$ | CSA-1 | 107.3 ± 5.37 | 6.68 ± 1.05 | 506 |
| 14 | [(CSA-2)$^9$]Glucagon(aa6-29)-NH$_2$ | CSA-2 | 146.4 ± 36.9 | 6.64 ± 0.29 | 580 |
| 15 | Glucagon(aa6-29)-NH$_2$ | Asp | 1894 ± 383 | 6.94 ± 0.63 | 1730 |
| 16 | [Lys$^9$]Glucagon(aa6-29)-NH$_2$ | Lys | 5779 ± 1382 | 6.58 ± 0.60 | 1990 |
| 17 | [Glu$^9$]Glucagon(aa7-29)-NH$_2$ | Glu | >10000 | ND$^e$ | ND | amino acid positions according to the numbering of native glucagon indicated by superscripted numbers
$^a$Data are average ±STD for at least three independent experiments.
$^b$pA$_2$, the negative logarithm of the concentration of the antagonist that reduce the response to 1 unit of the agonist to the response obtained from 0.5 unit of agonist. Data are average ±STD for at least two duplicate experiments.
$^c$(I/A)$_{50}$, the inhibition index, the ratio of inhibitor IC$_{50}$ to the added constant glucagon (0.1-0.2 nM). Data are average of at least three independent experiments and normalized by the EC$_{50}$
$^d$NA, not full antagonist.
$^e$ND, not detected.

Table 8 provides glucagon receptor affinity and antagonist activity for additional glucagon analogs wherein the analogs comprise homocysteic acid modified truncated glucagon fragments. The desHis1-based hCys(SO$_3$H)$^9$-based antagonist performs as potently as the previously reported Glu$^9$-based antagonist [desHis$^1$, Glu9]glucagon peptides. The further shortened hCys(SO$_3$H)$^9$-based glucagon antagonists with removal of three, four or five amino acids were studied. The receptor binding results demonstrate that the removal of the first residue reduces affinity of the compound for the glucagon receptor, but further removal changes the affinity only slightly, and still yields a ligand of nanomolar affinity.

TABLE 8

Homocysteic acid modified truncated glucagon fragment analogs and their glucagon antagonism activities

| Peptide | IC$_{50}$ (nM) | pA$_2$ | cAMP IC$_{50}$ (nM) |
|---|---|---|---|
| Glucagon | 1.0~2.5 | | |
| [desHis$^1$, Glu$^9$]glucagon-NH$_2$ | 14.08 ± 0.34 | NA | 1089 (partial antagonist) |
| [hCys$^9$(SO$_3$H)]Glucagon(aa2-29)-NH$_2$ | 13.16 ± 1.0 | NA | 146.6 (partial antagonist) |
| [hCys$^9$(SO$_3$H)]Glucagon(aa4-29)-NH$_2$ | 41.55 ± 4.79 | 7.22 ± 1.09 | 68.4 |
| [hCys$^9$(SO$_3$H)]Glucagon(aa5-29)-NH$_2$ | 33.85 ± 9.38 | 6.77 ± 0.33 | 98.3 |
| [hCys$^9$(SO$_3$H)]Glucagon(aa6-29)-NH$_2$ | 59.11 ± 18.10 | 7.16 ± 0.51 | 133.4 | amino acid positions according to the numbering of native glucagon indicated by superscripted numbers Specific analogs of glucagon have also been developed where the normally occurring phenylalanine at position six has been substituted with phenyl-lactic acid (PLA), on a 6-29 shortened glucagon amide backbone. PLA is isoelectronic with phenylalanine (Phe) but has no titratable hydrogen. The data presented in Tables 9 & 10 demonstrate that with the PLA6 substitution, the native Asp9 analog exhibits pure antagonism but the potency is reduced relative to that of the Glu9 and hCys(SO$_3$H)$^9$ analogs. The literature has previously indicated that the native Asp9 residue has to be changed to Glu9 or hCys(SO$_3$H)$^9$ for high affinity and potent antagonism of glucagon (2-29) analogs. Accordingly, it is surprising that substitution of Phe with PLA on a 6-29 shortened glucagon amide backbone improves the relative antagonist potency of the analog to a point comparable to that of the Glu9 and hCys(S03H)9 analogs. More specifically, the PLA6 analog increases the affinity of the analog for the glucagon receptor threefold as well as the potency of antagonism relative to the native Phe6 analog.

TABLE 9

Residue 9 substituted glucagon (6-29) analogs and their glucagon antagonism activities

| Peptide | Residue 9 | IC$_{50}$ (nM) receptor binding | pA$_2$ | cAMP IC$_{50}$ (nM) |
|---|---|---|---|---|
| Glucagon | Asp | 1.0~2.5 | | 0.05~0.15 (EC$_{50}$) |
| [E$^9$]Glucagon(aa6-29)-NH$_2$ | Glu | 36.35 ± 5.23 | 7.16 ± 0.27 | 97.2 |
| [hCys(SO$_3$)9]Glucagon(aa6-29)-NH$_2$ | hCys(SO$_3$) | 59.11 ± 18.10 | 7.16 ± 0.51 | 133.4 |
| [hE$^9$]Glucagon(aa6-29)-NH$_2$ | hGlu | 162.9 ± 70.8 | 6.27 ± 0.11 | 472.2 |
| [C$^9$(SCH$_2$COOH)]Glucagon(aa6-29)-NH$_2$ | CSA-1 | 107.3 ± 5.37 | 6.68 ± 1.05 | 101.2 |

TABLE 9-continued

Residue 9 substituted glucagon (6-29) analogs and their glucagon antagonism activities

| Peptide | Residue 9 | IC$_{50}$ (nM) receptor binding | cAMP pA$_2$ | cAMP IC$_{50}$ (nM) |
|---|---|---|---|---|
| [C$^9$(SCH$_2$CH$_2$COOH)]Glucagon (aa6-29)-NH$_2$ | CSA-2 | 146.4 ± 36.9 | 6.64 ± 0.29 | 116 |
| Glucagon(aa6-29)-NH$_2$ | Asp | 1670 ± — | 6.94 ± 0.63 | 346 |
| [K$^9$]Glucagon(aa6-29)-NH$_2$ | Lys | 3236 ± — | 6.58 ± 0.60 | 398 | amino acid positions according to the numbering of native glucagon indicated by superscripted numbers

TABLE 10

Residue 9 substituted [PLA6]glucagon (6-29) analogs and their glucagon antagonism activities

| Peptide | IC$_{50}$ (nM) (Receptor binding) | IC$_{50}$ (nM) (cAMP, inhibit Glucagon) 0.1 nM or | 0.2 nM | Solubility (%, pH 6-8) |
|---|---|---|---|---|
| Glucagon | 1.96 ± 0.61 | 0.09 (EC$_{50}$) | | |
| [PLA$^6$, D$^9$]Glucagon(aa6-29)-NH$_2$ | 13.85 ± 3.22 | 6.90 | | 11 |
| [PLA$^6$, D$^9$]Glucagon(aa6-29)-COOH | 15.51 ± 3.86 | 13.20 | | 96 |
| [PLA$^6$, E$^9$]Glucagon(aa6-29)-NH$_2$ | 12.33 ± 2.24 | 2.39 | 42.40 | 11 |
| [PLA$^6$, hCys(SO$_3$)$^9$]Glucagon(aa6-29)-NH$_2$ | 14.20 ± 0.45 | | 40.20 | |
| [PLA$^6$, D$^9$, D$^{28}$] Glucagon(aa6-29)-NH$_2$ | 9.0 ± 1.24 | 1.32 | | 100 |
| [PLA$^6$, E$^9$]Glucagon (aa6-29 + CEX)-NH$_2$ | 40.28 ± 11.29 | 24.75 | | 16 | amino acid positions according to the numbering of native glucagon indicated by superscripted numbers The effect of the PLA substitution at different positions of glucagon analog, including at positions 4 and 5 was also investigated. The data presented in Table 11 demonstrate that the PLA6 analog is an appreciably more potent antagonist than the slightly lengthened peptides.

TABLE 11

Analogs with PLA substitution at position 4, 5 and 6 and their glucagon antagonism activities

| Peptide | IC$_{50}$ (nM) (Receptor binding) | IC$_{50}$ (nM) (cAMP, inhibit 0.8 mM Glucagon) |
|---|---|---|
| Glucagon | 1.0-2.5 | 1.44 (EC$_{50+}$) |
| [PLA$^6$, E$^9$]Glucagon(aa6-29)-NH$_2$ | 12.34 ± 0.13 | 64.8 ± 3.4 |
| [Ac-PLA$^6$, E$^9$]Glucagon(aa6-29)-NH$_2$ | ND | 38.1 ± 9.2 |
| [PLA$^5$, E$^9$]Glucagon(aa5-29)-NH$_2$ | ND | 328 ± 25 |
| [PLA$^4$, E$^9$]Glucagon(aa4-29)-NH$_2$ | ND | 84.4 ± 19.5 (partial agonist) |

ND: not detected.
amino acid positions according to the numbering of native glucagon indicated by superscripted numbers The data presented in Table 12 demonstrates that the PLA6 substitution not only increases the peptide potency but also serves a role in pegylation. The PLA6 analogs can be selectively pegylated without restoration of glucagon agonism. The native Phe6 analogs surprisingly demonstrate a restoration of agonism when pegylated. However this restoration of agonism is not observed in the Pla6 peptide analogs. Several specific pegylation sites were examined, including amino acid positions 8, 11 and 24 (relative to the native glucagon peptide). Pegylation at position 24 of the Pla6 analog exhibits the most potent and selective glucagon antagonism.

were compared. The assays for measuring receptor binding and cAMP induction and cAMP inhibition were conducted using the assay system essentially as disclosed in Examples 12 and 13, respectively.

Specific glucagon analogs have been prepared that exhibit both glucagon antagonism as well as GLP-1 agonism. More particularly, specific compounds have been prepared wherein the first five amino acids of native glucagon have been removed and the aspartic acid residue at position 9 relative to

TABLE 12

PEGylated N-terminal truncated glucagon analogs and their glucagon antagonism activities

| Peptide | $IC_{50}$ (nM) (Receptor binding) | $IC_{50}$ (nM) (cAMP, inhibit 0.2 mM Glucagon) |
|---|---|---|
| [$C^8$(20kDaPEG), $E^9$]Glucagon(aa6-29)-$NH_2$ | >1000 | no antagonism |
| [$PLA^6$, $C^8$(20kDaPEG), $E^9$]Glucagon(aa6-29)-$NH_2$ | 303 ± 14 | 236 |
| [$E^9$, $C^{11}$(20kDaPEG)]Glucagon(aa6-29)-$NH_2$ | >1000 | no antagonism |
| [$PLA^6$, $E^9$, $C^{11}$(20kDaPEG)]Glucagon(aa6-29)-$NH_2$ | 776 ± 161 | 664 |
| [$E^9$, $C^{24}$(20kDaPEG)]Glucagon(aa6-29)-$NH_2$ | >1000 | no antagonism |
| [$PLA^6$, $E^9$, $C^{24}$(20kDaPEG)]Glucagon(aa6-29)-$NH_2$ | 90 ± 7 | 126 |
| [$MCA^6$, $E^9$, $C^{24}$(20kDaPEG)]Glucagon(aa6-29)-$NH_2$ | 208 ± 57 | no antagonism |
| [$C^5$(1.2kDaPEG), $E^9$]Glucagon(aa5-29)-$NH_2$ | 1081 ± 268 | 2281 |
| [$C^5$(5kDaPEG), $E^9$]Glucagon(aa5-29)-$NH_2$ | 634 ± 174 | 1608 |
| [$C^5$(20kDaPEG), $E^9$]Glucagon(aa5-29)-$NH_2$ | 331 ± 74 | 976 |
| [d-$Cys^5$(20kDaPEG), $E^9$]Glucagon(aa5-29)-$NH_2$ | >10000 | 14764 |
| [$K^5$(CH2CH2S-20kDaPEG), $E^9$]Glucagon(aa5-29)-$NH_2$ | >10000 | no antagonism |
| 3.4kDaPEG-dimer[$C^5$, $E^9$]Glucagon(aa5-29)-$NH_2$ | 435 ± 256 | 1343 |
| [$PLA^6$, $C^8$(1.2kDaPEG), $E^9$]Glucagon(aa6-29)-$NH_2$ | 220 ± 36 | no antagonism |
| [$PLA^6$, $C^8$(5kDaPEG), $E^9$]Glucagon(aa6-29)-$NH_2$ | 948 ± 297 | 216 |
| [$PLA^6$, $C^8$(20kDaPEG), $E^9$]Glucagon(aa6-29)-$NH_2$ | 303 ± 14 | 92 |
| [$PLA^6$, $E^9$, $C^{24}$(1.2 kDaPEG)]Glucagon(aa6-29)-$NH_2$ | 4.7 ± 0.4 | 18 |
| [$PLA^6$, $E^9$, $C^{24}$(20kDaPEG)]Glucagon(aa6-29)-$NH_2$ | 90 ± 7 | 126 |
| [$MCA^6$, $E^9$, $C^{24}$(20kDaPEG)]Glucagon(aa6-29)-$NH_2$ | 208 ± 57 | no antagonism |
| [$Phe^6$, $E^9$, $C^{24}$(20kDaPEG)]Glucagon(aa6-29)-$NH_2$ | >10000 | no antagonism | amino acid positions according to the numbering of native glucagon indicated by superscripted numbers Example 17

All peptides described herein comprised a C-terminal amide in place of the C-terminal carboxylate, unless otherwise noted. The amino acid positions designated in the name of the peptide are in accordance with the numbering of native glucagon.

Activities of the Glucagon Antagonist/GLP-1 Agonists

Figure 5:
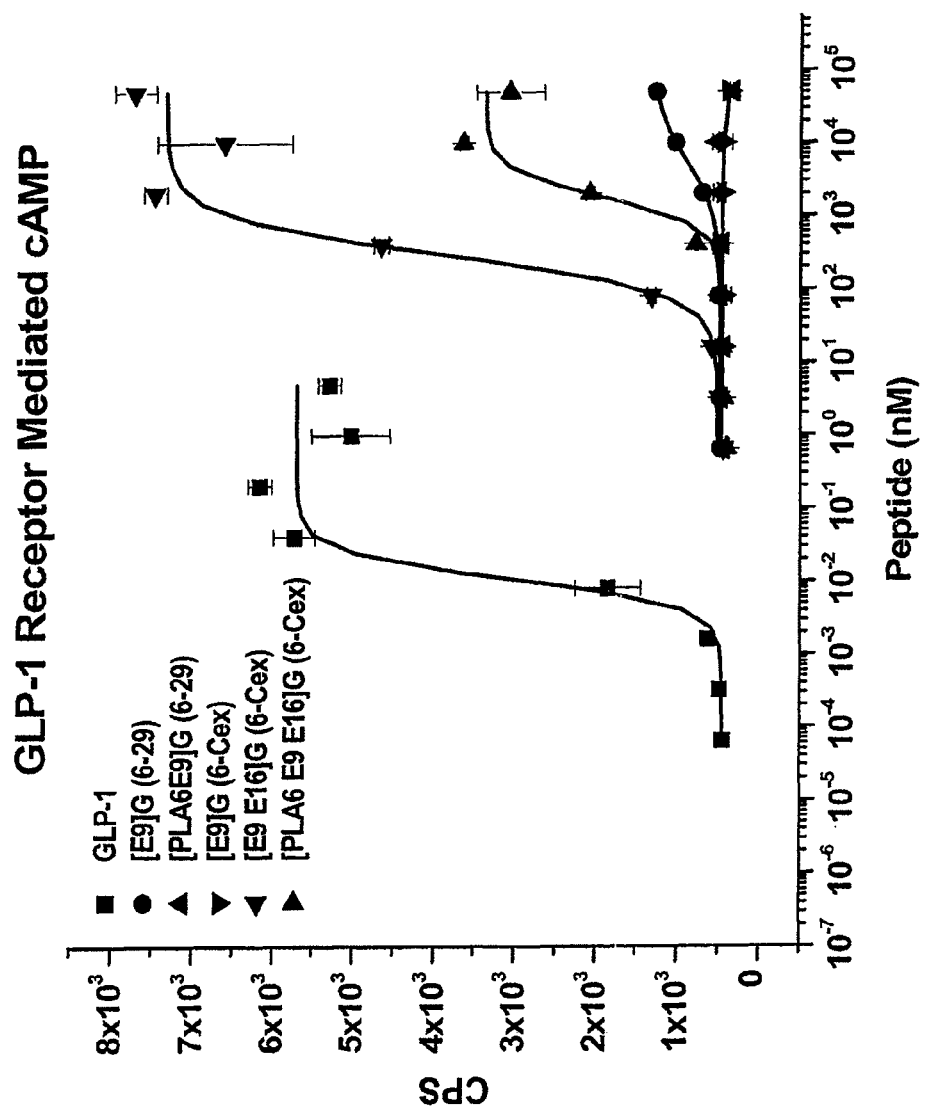
FIG. 5 represents data generated measuring GLP-1 receptor agonism of the listed glucagon analogs, as measure by cAMP production. More particularly, FIG. 5 compares induction of the GLP-1 receptor by glucagon analogs [E9]G(6-29) ●, [PLA6, E9]G(6-29) ▲, [E9]G(6-CEX) ▼, [E9, E16)]G(6-CEX) ◀, [PLA6, E9, E16]G(6-CEX)) ▶ relative to native GLP-1 ■. Abbreviations: PLA6=phenyl-lactic acid; G(6-29)=native glucagon N-terminally truncated by 5 amino acids; E9=a substitution of glutamic acid for the amino acid corresponding to position 9 of native glucagon; G(6-CEX) =native glucagon N-terminally truncated by 5 amino acids with the additional amino acids of SEQ ID NO: 21 added to the carboxy terminus.

The receptor binding, cAMP induction and cAMP inhibition of glucagon and various glucagon derivative inhibitors native glucagon has been substituted with glutamic acid. These compounds exhibit GLP-1 receptor activity that can be enhanced by further modification of the peptide to include a glutamic acid substitution at position 16, relative to native glucagon (see FIG. 5). Furthermore, as indicated in the data presented in Table 13 and FIGS. 6-8, a glucaong analog having the first five amino acids deleted relative to native glucagon and the formation of lactam rings between the side chains of amino acids pairs 7 and 11 or 11 and 15 exhibits both glucagon antagonist and GLP-1 activity.

TABLE 13

Lactam glucagon(6-39) peptides and glucagon antagonist and GLP-1 agonist activity

| | | GLP-1 (nM) | Glu (nM) |
|---|---|---|---|
| 1 E9, K12, E16 | FTSEYSKYLDERRAQDFVQWLMNTGPSSGAPPPS (SEQ ID NO: 28) | 1451 | 762 |
| 2 E9, K12E16(lactam) | FTSEYSKYLDERRAQDFVQWLMNTGPSSGAPPPS (SEQ ID NO: 29) | 63 | 2008 |
| 3 E9, E16K20(lactam) | FTSEYSKYLDERRAKDFVQWLMNTGPSSGAPPPS (SEQ ID NO: 30) | 36 | 42 |
| 4 D9, K12E16(Lactam) | FTSDYSKYLDERRAQDFVQWLMNTGPSSGAPPPS (SEQ ID NO: 31) | 118.7 | 828 |
| 5 [PLA6, E9, K12E16(Lactam)] | PLA-TSEYSKYLDERRAQDFVQWLMNTGPSSGAPPPS (SEQ ID NO: 32) | 6 | 72 |
| 6 [PLA6, E9, E16K20(Lactam)] | PLA-TSEYSKYLDERRAKDFVQWLMNTGPSSGAPPPS (SEQ ID NO: 33) | 20 | 20 |

TABLE 14

Lactam glucagon(1-29, 2-29, 4-29 and 6-29) peptides and their glucagon antagonist and GLP-1 agonist activity (PA = partial antagonist)

| | GLP-1 EC50 (nM) | Glucagon IC50 (nM) |
|---|---|---|
| Glucagon<br>HSQGTFTSDYSKYLDSRRAQDFVQWLMNT (SEQ ID NO: 1) | | 0.2-1.0* |
| GLP-1 (aa 1-30)<br>HAEGTFTSDVSSYLEGQAAKEFIAWLVKGR (SEQ ID NO: 4) | 0.02-0.1 | |
| 1 [PLA6, D9, E16K20(lactam), D28]G(6-29)<br>PLA TSDYSKYLDERRAKDFVQWLMDT (SEQ ID NO: 6) | 5-25 | 10-30 |
| 2 [PLA6, D9, K12E16(Lactam), D28]G(6-29)<br>PLA TSDYSKYLDERRAQDFVQWLMDT (SEQ ID NO: 5) | 177 | 63 |
| 3 [PLA6, D9, E16, K20E24(Lactam), D28]G(6-29)<br>PLA TSDYSKYLDERRAKDFVEWLMDT (SEQ ID NO: 77) | 239 | 74 |
| 4 [PLA6, D9, E16, E24K28(lactam), D28]G(6 ~ 29)<br>PLA TSDYSKYLDERRAQDFVEWLMKT (SEQ ID NO: 78) | 289 | 22 |
| 5 [E9, E16K20(lactam), D28]G(4 ~ 29)<br>GTFTSEYSKYLDERRAKDFVQWLMDT (SEQ ID NO: 85) | 151 | 10-30 |
| 6 [E9, E16K20(lactam), D28]G(2 ~ 29)<br>SQGTFTSEYSKYLDERRAKDFVQWLMDT (SEQ ID NO: 65) | 203 | 49 (PA) |
| 7 [A2E3, E16K20(Lactam), D28]G(2 ~ 29)<br>AEGTFTSEYSKYLDERRAKDFVQWLMDT (SEQ ID NO: 63) | 175 | 63 |
| 8 [A2E3, E16K20(Lactam), D28]G(1 ~ 29)<br>HAEGTFTSEYSKYLDERRAKDFVQWLMDT (SEQ ID NO: 83) | 0.2 | 130 (PA) |
| 9 ANK2 (Bayer peptide)<br>HSQGTFTSDY ARYLDARRAREFIKWL VRGRG (SEQ ID NO: 37) | 0.28 | agonist |

*EC50 at glucagon receptor

Figure 6A:
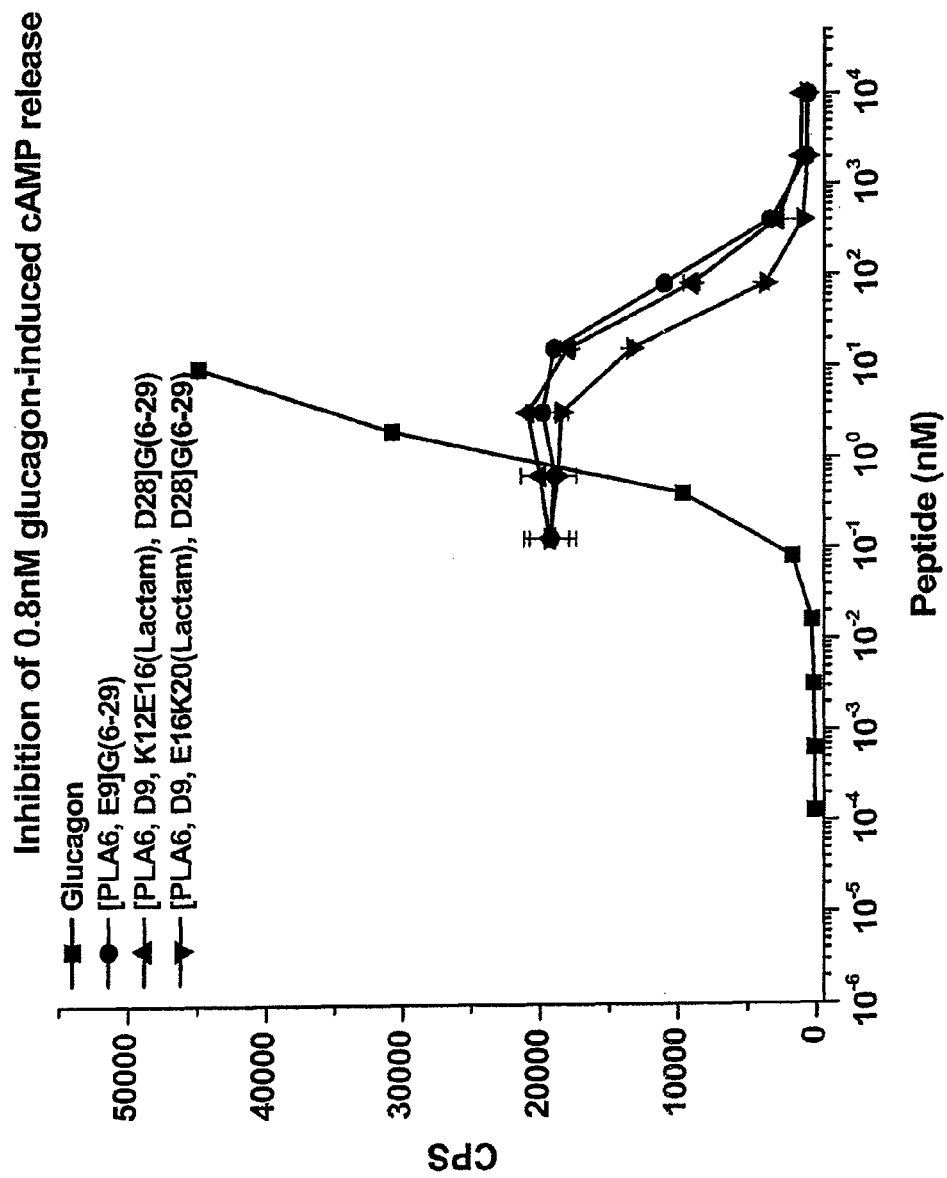
FIGS. 6A and 6B represents data generated measuring activity at the glucagon and GLP-1 receptors.
Figure 6B:
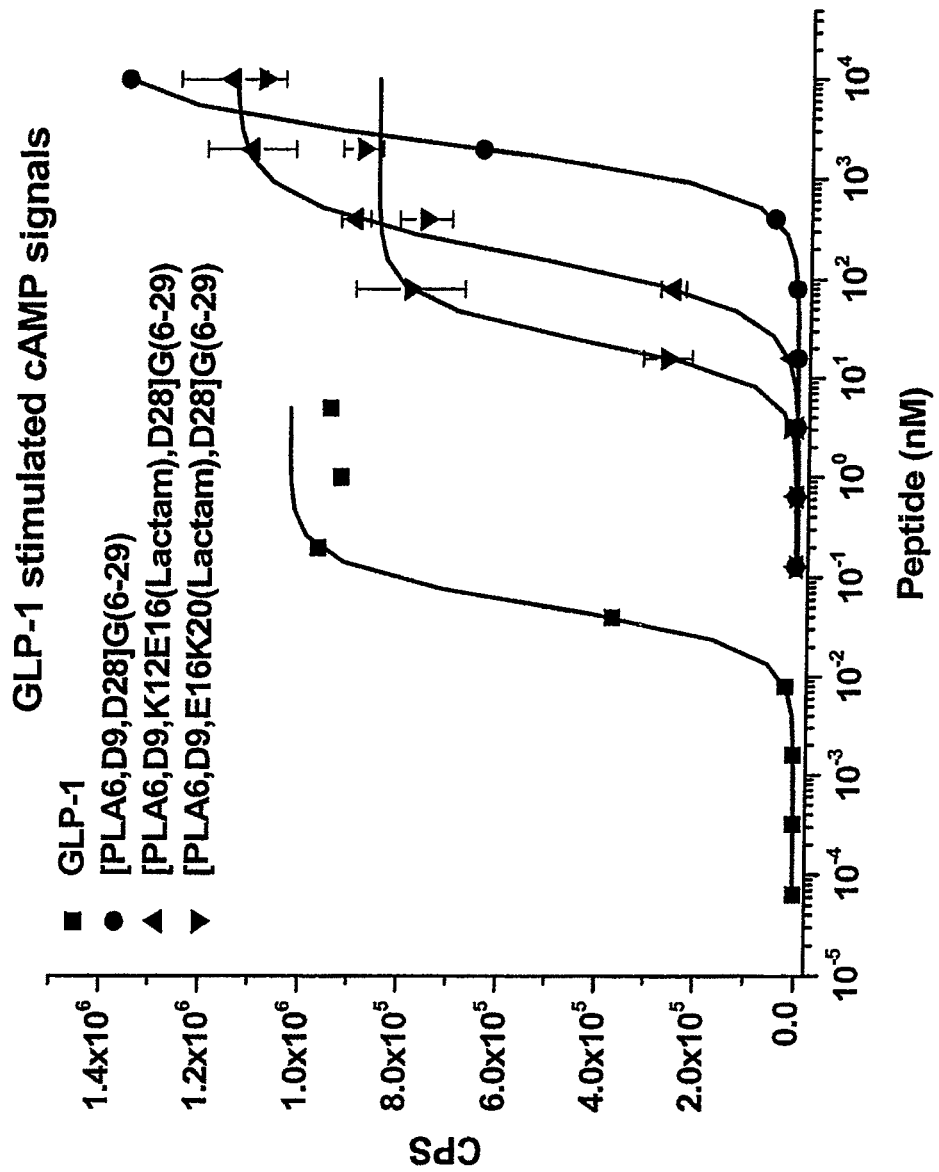
Figure 7A:
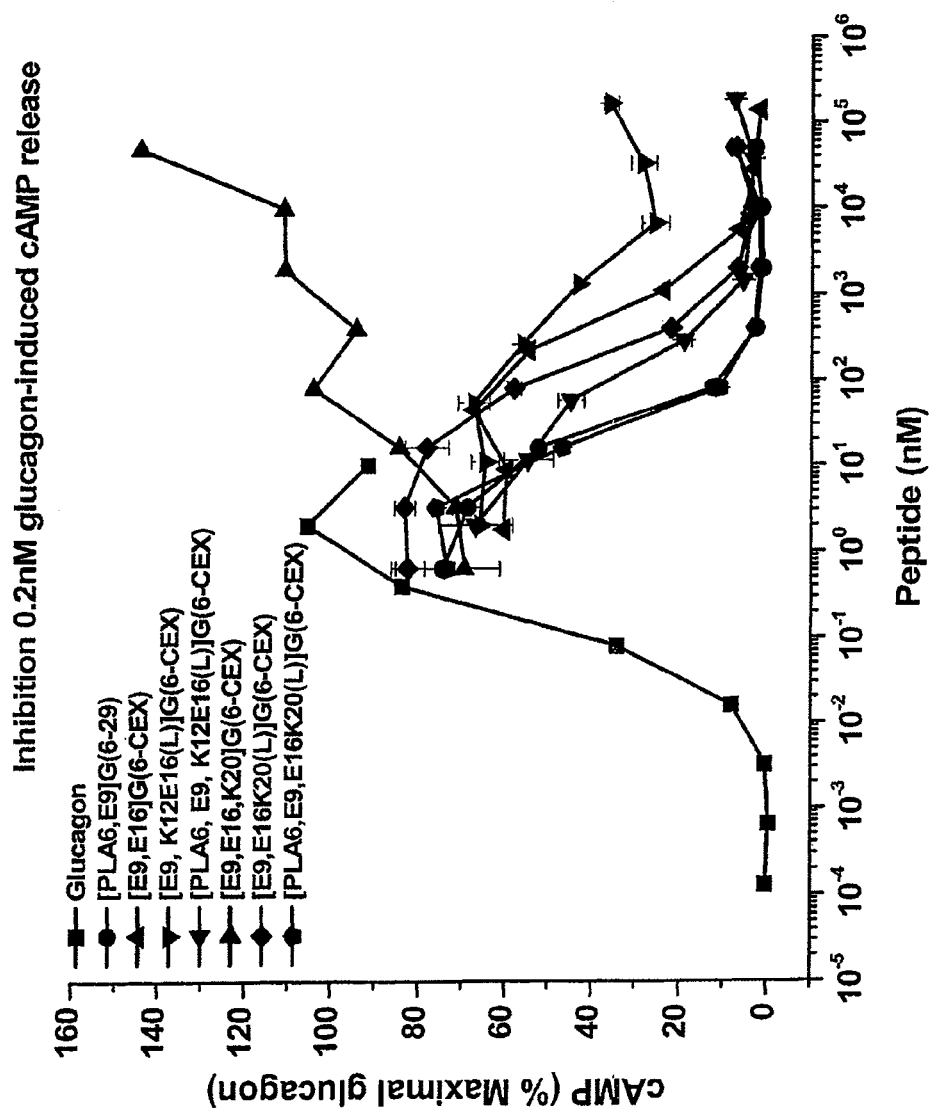
FIGS. 7A and 7B represents data generated measuring activity of glucagon lactam derivatives at the glucagon and GLP-1 receptors.
Figure 7B:
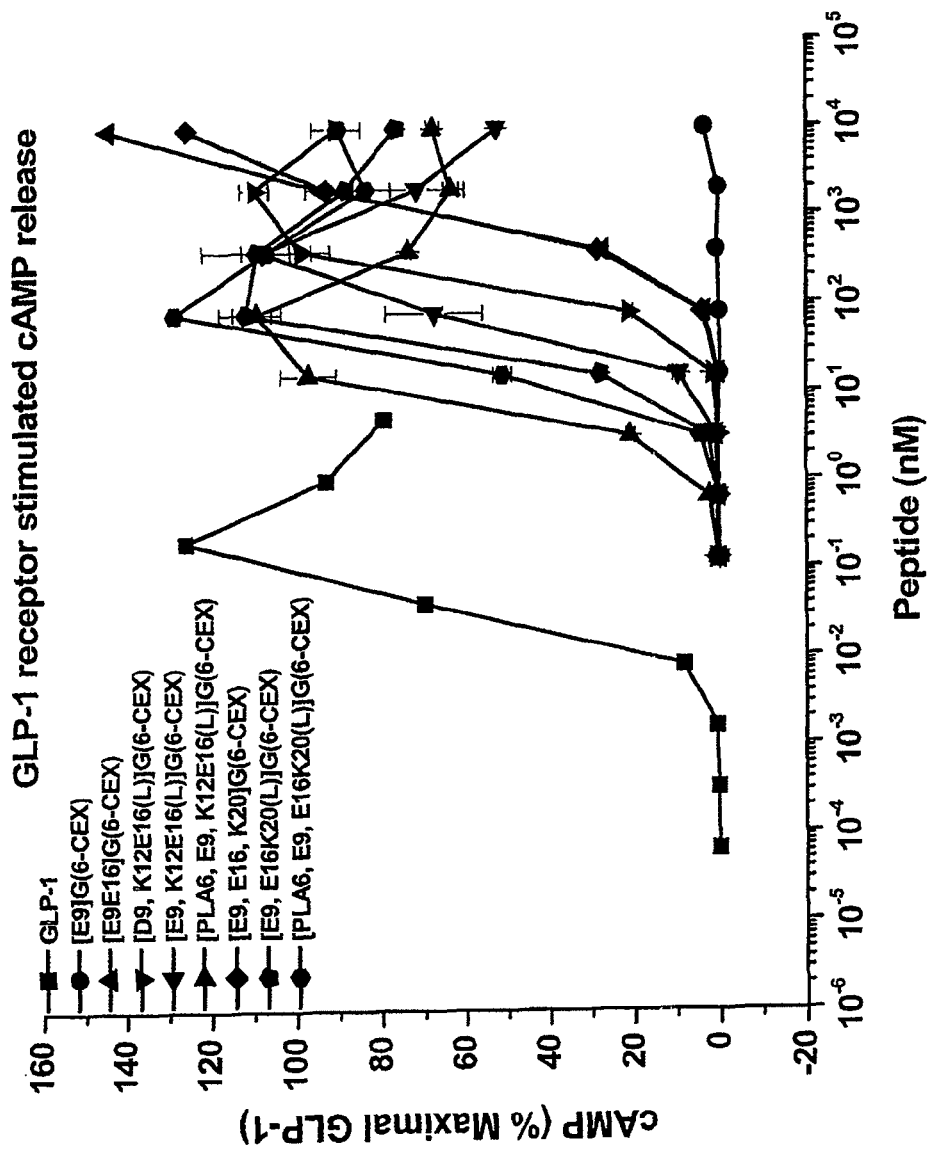

As demonstrated by the data presented in Table 14 and FIGS. 6-8, specific analogs of glucagon have been developed that exhibit glucagon antagonism/GLP-1 agonism, where the normally phenylalanine at position six has been substituted with phenyl-lactic acid (Pla), on a 6-29 shortened glucagon amide backbone (the "PLA6 analogs") and a lactam bridge is formed between the sidechains of the glucagon analog. As demonstrated by FIGS. 6A & 6B the introduction of a backbone lactam into an otherwise glucagon antagonist maintains potent antagonism without residual agonism. FIGS. 7A, 7B, 8A and 8B present data showing that the introduction of a backbone lactam into otherwise glucagon antagonist introduces a full GLP-1 agonism of variable potency, dependent on the specific sequence of the peptide and the location of the lactam.

Table 15 lists a set of different peptides that demonstrate full GLP-1 agonism and full Glucagon antagonism. Two different peptide backbone scaffolds have been developed where the primary difference is the C-terminal extension of the 6-29 glucagon with a CEX nonapeptide (SEQ ID NO: 21).

The glucagon antagonists described herein are acylated as follows:

Acylated and/or PEGylated peptides are prepared as follows. Peptides are synthesized on a solid support resin using either a CS Bio 4886 Peptide Synthesizer or Applied Biosys-

TABLE 15

Profile of Mixed Agonist/Antagonist

Glucagon (6-CEX) Analogs

| | | | | |
|---|---|---|---|---|
| 1 E9, K12, E16 | FTSEYSKY1DERRAQDEVQWlMNTGPSSGAPPPS (SEQ ID NO: 28) | 1451 | 762 | |
| 2 E9, K12E16(lactam) | FTSEYSKY1DERRAQDFVQWlMNTGPSSGAPPPS (SEQ ID NO: 29) | 63 | 2008 | |
| 3 E9, E16K20(lactam) | FTSEYSKY1DERRAKDFVQWlMNTGPSSGAPPPS (SEQ ID NO: 30) | 36 | 42 | |
| 4 D9, K12E20(lactam) | FTSDYSKY1DERRAQDFVQWlMNTGPSSGAPPPS (SEQ ID NO: 31) | 18 | 828 | |
| 5 [PLA6, E9, K12E16(Lactam) | PLA-TSEYSKY1DERRAQDFVQWLMNTGPSSGAPPPS (SEQ ID NO: 32 | 6 | 72 | |
| 6 [PLA6, E9, E16K20(Lactam)] | PLA-TSEYSKYLDERRAKDFVQWLMNTGPSSGAPPPS (SEQ ID NO: 33) | 20 | 20 | |

Glucagon $D^9$(6-29) analogs

| | | GLP-1 EC50 (nM) | Glucagon IC50 (nM) |
|---|---|---|---|
| 7 PLA 6, D9, D28 | PLA-TSDYSKYLDSRRAQDFVQWLMDT (SEQ ID NO: 2) | ~700 | tbd |
| 8 PLA6, D9, K12E16(Lactam) | PLA-TSDYSKYLDERRAQDFVQWLMDT (SEQ ID NO: 75) | 21 | 13 |
| 9 PLA6, D9, E16K20(lactam) | PLA-TSDYSKYLDERRAKDFVQWLMDT (SEQ ID NO: 76) | 4 | 6 |

The systematic introduction of agonism to a peptide that maintains antagonism at a highly homologous receptor is unprecedented in peptide chemistry. There is a report of such a mixed glucagon antagonist/GLP-1 agonist in the literature as contributed by Bayer Research Labs [Journal of Endocrinology (2007) 192:371-80 & Journal of Biological Chemistry (2006) 282:12506-15]. However, analysis of the previously disclosed peptide (ANK2; SEQ ID NO: 37) revealed that the peptide possess no meaningful glucagon antagonism. More particularly, FIGS. 9A-9C present data showing that the Bayer peptide (ANK2; SEQ ID NO: 37), in comparison to the novel glucagon antaongist/GLP-1 agonists disclosed herein, is not a mixed glucagon antagonist/GLP-1 agonist. The ANK2 peptide has very potent GLP-1 agonism but demonstrates a weak, but full glucagon agonism. The peptides disclosed herein are chemically different in that they do not possess the native N-terminal residues, have an unnatural amino at the shortened N-terminus, and possess an internal linkage between the side chains of the analog (e.g., in the form of a salt bridge or a backbone lactam). The peptides can be selectively pegylated to extend the duration of action without changing the mixed agonist/antagonist properties.

Example 18

All peptides described herein comprised a C-terminal amide in place of the C-terminal carboxylate, unless otherwise noted. The amino acid positions designated in the name of the peptide are in accordance with the numbering of native glucagon.

tems 430A Peptide Synthesizer. In situ neutralization chemistry is used as described by Schnolzer et al., *Int. J. Peptide Protein Res.* 40: 180-193 (1992). For acylated peptides, the target amino acid residue to be acylated (e.g., position ten) is substituted with an Nε-FMOC lysine residue. Treatment of the completed N-terminally BOC protected peptide with 20% piperidine in DMF for 30 minutes removes FMOC/formyl groups. Coupling to the free ε-amino Lys residue is achieved by coupling a ten-fold molar excess of either an FMOC-protected spacer amino acid (ex. FMOC-(N—BOC)-Tryptophan-OH) or acyl chain (ex. C17-COOH) and PyBOP or DEPBT coupling reagent in DMF/DIEA. Subsequent removal of the spacer amino acid's FMOC group is followed by repetition of coupling with an acyl chain. Final treatment with 100% TFA results in removal of any side chain protecting groups and the N-terminal BOC group. Peptide resins are neutralized with 5% DIEA/DMF, dried, and then cleaved from the support using HF/p-cresol, 95:5, at 0° C. for one hour. Following ether extraction, a 5% HOAc solution is used to solvate the crude peptide. A sample of the solution is then verified to contain the correct molecular weight peptide by ESI-MS. Correct peptides are purified by RP-HPLC using a linear gradient of 10% CH3CN/0.1% TFA to 0.1% TFA in 100% CH3CN. A Vydac C18 22 mm×250 mm protein column is used for the purification. Acylated peptide analogs generally complete elution by a buffer ratio of 20:80. Portions are pooled together and checked for purity on an analytical RP-HPLC. Pure fractions are lyophilized yielding white, solid peptides.

For peptide pegylation, 40 kDa methoxy poly(ethylene glycol) maleimido-propionamide (Chirotech Technology Ltd.) is reacted with a molar equivalent of peptide in 7M Urea, 50 mM Tris-HCl buffer using the minimal amount of solvent needed to dissolve both peptide and PEG into a clear solution (generally less than 2 mL for a reaction using 2-3 mg peptide). Vigorous stirring at room temperature is commenced for 4-6 hours and the reaction is analyzed by analytical RP-HPLC. PEGylated products appear distinct from the starting material with decreased retention times. Purification is performed on a Vydac C4 column with conditions similar to those used for the initial peptide purification. Elution occurs around buffer ratios of 50:50. Fractions of pure PEGylated peptide are found and lyophilized.

Example 19

All peptides described herein comprised a C-terminal amide in place of the C-terminal carboxylate, unless otherwise noted. The amino acid positions designated in the name of the peptide are in accordance with the numbering of native glucagon.

The depesipeptide was assembled using conventional solid-phase peptide synthesis (SPPS). The PLA derivatized peptide chain was cyclized via a lactam bridge first and then esterified by amino acid using pre-activated symemterical anhydride manually. The classical SPPS was continued to complete the whole sequence. The standard cleavage procedure and purification method were applied to obtain the desired depsipeptide.

Example

Synthesis of lactam-bridge depsipeptide [Aib2, E3, Thr5-O-PLA6, E16K20(lactam), D28]G(2-29) amide A peptidyl resin with sequence HO-PLA-TSDYSKY-LDERRAKDFVQWLMDT (SEQ ID NO: 6) [PLA6, E16, K20, D28]glucagon(6-29) was synthesized by solid-phase Boc-chemistry using an ABI 430A automated peptide synthesizer with 0.2 mmole MBHA amide resin and DEPBT as coupling reagent. The following Boc amino acids were used: Ala, Arg(Tos), Asp(OcHx), Asn(Xan), Glu(OcHx), Gln (Xan), Leu, Lys(2-Cl—Z), Met, PLA, Ser(OBzl), Thr(OBzl), Trp(CHO), Tyr(2.6-di-Cl-Bzl) and Val except the glutamic acid at position 16 was incorporated with Boc-Glu(OFm)-OH and lysine at position 20 was incorporated with Boc-Lys (Fmoc)-OH. After removal of Fm and Fmoc protecting groups at position 16 and 20 with 20% piperidine in DMF, the peptidyl resin was treated with 300 mg (1 mmol) DEPBT in 10% DIEA/DMF for about 4 h to form the lactam bridge. To this lactam-bridged peptidyl resin was added a pre-activated symmetrical anhydride solution composed of Boc-Thr (OBzl)-OH (2 mmol)/DIC (1 mmol)/DMAP (0.2 mmol) in DCM and the reaction was allowed to proceed for 16 h. The remaining amino acids Boc-Gly-OH, Boc-Glu(OcHx)-OH and Boc-Aib-OH were coupled by standard Boc-chemistry again to obtain the depsipeptidyl resin of the following sequence: Aib-Glu-Gly-Thr-O-PLA-Thr-Ser-Asp-Tyr-Ser-Lys-Tyr-Leu-Asp-Glu*-Arg-Arg-Ala-Lys*-Asp-Phe-Val-Gln-Trp-Leu-Met-Asp-Thr-NH$_2$. (SEQ ID NO: 70; * are lactam bridged)

The peptidyl resin was treated with liquid hydrogen fluoride to cleave the crude peptide from the solid support and remove all protecting groups. The depsipeptide was purified by preparative HPLC, and analyzed by MS and analytical HPLC. The purified peptide demonstrated a single peak in analytical RP-HPLC and the ESI-MS analysis yielded the desired mass of 3368.5 which corresponds with the calculated molecular weight of 3369.0 daltons.

Similar procedure were used to synthesize the other lactam-bridge depsipeptides reported in this patent.

Example 20

All peptides described herein comprised a C-terminal amide in place of the C-terminal carboxylate, unless otherwise noted. The amino acid positions designated in the name of the peptide are in accordance with the numbering of native glucagon.

The following peptides were synthesized as generally described above and subsequently tested for the ability to stimulate the GLP-1 receptor by assaying cAMP release from cells expressing the human GLP-1 receptor and for the ability to stimulate the glucagon receptor by assaying cAMP release from cells expressing the human glucagon receptor and stimulated with 0.2-0.8 nM glucagon, as generally described in Example 13.

The effect of lactamization and C-terminal extension on glucagon antagonist/GLP-1 peptides was explored by producing and testing C-terminally extended glucagon antagonist/GLP-1 peptides with and without lactams which bridged the side chains of Glu at position 16 and Lys at position 20 (in accordance with the numbering of native glucagon). The combined results of three separate assays are shown in Table 16.

TABLE 16

| Peptide | SEQ ID NO: | Glucagon antagonism IC50 (nM, inhibit 0.2-0.8 nM glucagon) | GLP-1 agonism EC50 (nM) |
|---|---|---|---|
| Glucagon | 1 | 0.12 ± 0.02 (EC50) | |
| GLP-1 | | | 0.038 ± 0.002 |
| [E9, E16]G(6-39) | 71 | 762 ± 127 | 1451 ± 118 |
| [E9, E16, K20] G(6-39) | 105 | weak agonist | 1042.3 ± 11.9 |
| [PLA6, E9, E16]G(6-39) | 72 | 58.08 | 1756.5 |
| [E9, E16K20(lactam)]G(6-39) | 73 | 42 ± 3.6 | 36.4 ± 3.5 |
| [PLA6, E9, E16K20(Lactam)]G(6-39) | 74 | 20.5 ± 2.5 | 20.0 ± 5.5 |

As shown in Table 16, C-terminally extended peptides comprising a lactam bridge exhibited increased GLP-1 activity as compared to the corresponding peptides lacking a lactam bridge.

The effect of the position of the lactam bridge within the peptide sequence of the glucagon antagonist/GLP-1 agonist was tested by producing and testing peptides with a lactam linking the side chains of amino acids 12 and 16, 16 and 20, 20 and 24, or 24 and 28 (according to the amino acid numbering of native glucagon). The combined results of three separate assays are shown in Table 17.

TABLE 17

| Peptide | SEQ ID NO: | Glucagon antagonism IC50 (nM, inhibit 0.2-0.8 nM glucagon) | GLP-1 agonism EC50 (nM) |
|---|---|---|---|
| Glucagon | 1 | 0.19 ± 0.015 (EC50)a | |
| GLP-1 | | | 0.014 ± 0.003 |
| [PLA6, K12E16(lactam), D28]G(6-29) | 75 | 58.3 ± 3.3 | 38.5 ± 7.6 |
| [PLA6, E16K20(lactam), D28]G(6-29) | 76 | 11.7 ± 2.8 (assay 1), 5.5 ± 0.2 (assay 2) | 6.9 ± 4.6 (assay 1), 4.2 ± 1.6 (assay 2) |
| [PLA6, E16, K20E24(lactam), D28]G(6-29) | 77 | 74.4 ± 8.4 | 239.6 ± 102.2 |
| [PLA6, E16K20(lactam), E21, D28] G(6-29) | 103 | 8.6 ± 0.1 | 11.1 ± 2.6 |
| [PLA6, E16, E24K28(lactam)]G(6-29) | 78 | 22.4 ± 1.7 | 289.2 ± 148.8 |
| [PLA6, E9, E16K20(Lactam)]G(6-39) | 74 | 20.5 ± 2.5 | 20.0 ± 5.5 |

As shown in Table 17, glucagon antagonist/GLP-1 agonist peptides comprising a lactam bridge between amino acids 16 and 20 (according to the numbering of native glucagon) exhibited the highest GLP-1 activity. A lactam bridge between residues 12 and 16 also allowed for the peptide to exhibit potent GLP-1 activity.

Glucagon antagonist/GLP-1 peptides modified to replace native glucagon amino acid sequence with native GLP-1 sequence were synthesized and compared to corresponding peptides lacking GLP-1 sequence replacement. The combined results of three separate assays are shown in Table 18.

TABLE 18

| Peptide | SEQ ID NO: | Glucagon antagonism IC50 (nM, inhibit 0.2-0.8 nM glucagon) | GLP-1 agonism EC50 (nM) |
|---|---|---|---|
| Glucagon | 1 | 0.19 ± 0.015 (EC50) | |
| GLP-1 | | | 0.014 ± 0.003 |
| [PLA6, K12E16(lactam), D28]G(6-29) | 75 | 58.3 ± 3.3 | 38.5 ± 7.6 |
| [PLA6, K12E16(lactam), GLP(23-32)]G(6-29) | 79 | 169 ± — | No agonism |
| [PLA6, E16K20(lactam), D28]G(6-29) | 76 | 11.7 ± 2.8 a, 5.5 ± 0.2 | 6.9 ± 4.6 (assay 1), 4.2 ± 1.6 (assay 2) |
| [PLA6, E16K20(lactam), GLP(23-32)]G(6-29) | 80 | 11.7 ± 0.5 b, 73.5 ± — | 51.2 ± 11.2 |
| [PLA6, E16, GLP(23-32)]G(6-29) | 104 | 64.5 ± 11.4[b] | 85.6 ± 12.7[b] |
| [A2E3, E9, E16K20(Lactam), D28]G(2-29) | 81 | 63.2 ± 2.3 | 175.2 ± 15.7 |
| [A2E3, E9, E16K20(Lactam), GLP(23-32)]G(2-29) | 82 | 423 ± — partial antagonist* | 9.8 ± 4.2* |
| [H1A2E3, E9, E16K20(Lactam), D28]G(1-29) | 83 | 129 ± 106 partial antagonist | 0.11 ± — |
| [H1A2E3, E9, E16K20(Lactam), GLP(23-32)]G(1-29) | 84 | 2148 ± — partial antagonist* | 0.017 ± —* |

As shown in Table 18, the effect of substituting native glucagon sequence for GLP-1 sequence around positions 16-25 (according to the native glucagon sequence) increased GLP-1 agonist activity in most cases. However, for peptides additionally comprising GLP-1 sequence at positions 2 and 3 (according to the native glucagon sequence) and lacking PLA, replacement with GLP-1 sequence around positions 16-25 decreased glucagon antagonist activity.

Glucagon antagonist/GLP-1 peptides lacking PLA with varying N-terminal truncations were made and tested. Some of the peptides also had N-terminal sequence of GLP-1. The combined results of two separate assays are shown in Table 19.

TABLE 19

| Peptide | SEQ ID NO: | Glucagon antagonism IC50 (nM, inhibit 0.8 nM glucagon) | GLP-1 agonism EC50 (nM) |
|---|---|---|---|
| Glucagon | 1 | 0.55 (EC50) | |
| GLP-1 | | | 0.021, 0.0086* |
| [PLA6, E16K20(lactam), D28] G(6-29) | 76 | 13.7 ± 1.2 | 10.6 ± 0.97 |
| [G4T5, E9, E16K20(Lactam), D28] G(4-29) | 85 | 12.7 ± 1.1 | 151.4 ± 8.8 |
| [S2Q3, E9, E16K20(Lactam), D28] G(2-29) | 86 | 48.6 ± 22.3 partial antagonist | 203.2 ± 4.2 |
| [A2E3, E9, E16K20(Lactam), D28] G(2-29) | 81 | 63.2 ± 2.3 | 175.2 ± 15.7 |
| [H1A2E3, E9, E16K20(Lactam), D28] G(1-29) | 83 | 129 ± 106 partial antagonist | 0.11 ± — |
| ANK2 (Bayer peptide)* | * | weak agonist | 0.28 ± — |

* ANK2 described in Pan et al., J Biol Chem 281(18): 12506-12515 (2006).

As shown in Table 19, the glucagon antagonist/GLP-1 peptide comprising PLA is a more potent glucagon antagonist/GLP-1 agonist.

Glucagon antagonist/GLP-1 agonist depsipeptides (comprising PLA at position n (n=5 or 6) linked to Thr at position n−1 via an ester bond) were made and tested for activity. Their potency as glucagon antagonists/GLP-1 agonists were compared to a peptide comprising PLA as the N-terminal amino acid and peptides lacking PLA altogether. The combined results of two separate assays are shown in Table 20.

TABLE 20

| Peptide | SEQ ID NO: | Glucagon antagonism IC50 (nM, inhibit 0.8 nM glucagon) | GLP-1 agonism EC50 (nM) |
|---|---|---|---|
| Glucagon | 1 | 0.55 (EC50) | |
| GLP-1 | | | 0.021, 0.0086* |
| [PLA6, E16K20(lactam), D28] G(6-29) | 76 | 13.7 ± 1.2 | 10.6 ± 0.97 |
| [S2Q3, E9, E16K20(Lactam), D28] G(2-29) | 86 | 48.6 ± 22.3 partial antagonist | 203.2 ± 4.2 |
| [A2E3, E9, E16K20(Lactam), D28] G(2-29) | 81 | 63.2 ± 2.3 | 175.2 ± 15.7 |
| [H1A2E3, E9, E16K20(Lactam), D28] G(1-29) | 83 | 129 ± 106 partial antagonist | 0.11 ± — |
| [S2Q3-O-PLA6, D9, E16K20(Lactam), D28] G(2-29) | 66 | 3.14 ± 1.89 | 45.70 ± 12.34 |
| [A2E3-O-PLA6, D9, E16K20(Lactam), D28] G(2-29) | 64 | 4.68 ± 0.44 | 13.98 ± 1.02 |
| [H1A2E3-O-PLA6, D9, E16K20(Lactam), D28] G(1-29) | 87 | 9.65 ± 0.57 | 6.20 ± 0.91 |

As shown in Table 20, modification of peptides to depsipeptides caused an increase in both GLP-1 agonist activity and glucagon antagonist activity.

The effect of pegylating glucagon antagonist/GLP-1 agonist peptides was explored by synthesizing glucagon antagonist/GLP-1 agonist peptides with 20,000 Dalton PEG moieties attached to the amino acid at position 24 (according to the numbering of native glucagon) or attached to the C-terminal residue of peptides comprising a C-terminal extension. For the peptide "[PLA6, E16K20(Lactam), K24 (COCH$_2$CH$_2$S-20 kDa)]G(6-29)," 3-mercaptopropionic acid was coupled to the side chain amine of Lys at position 24 (according to the numbering of native glucagon) for pegylation. For the peptide "[PLA6,E16K20(Lactam), K24(rigid-S-20 kDa]G(6-29)," 3-aminoprop-1-ynyl-benzoic acid was first coupled to the side chain amine of Lys at position 24 and then 3-mercaptopropionic acid was coupled to the rigid linked for pegylation. The resulting linker had the following structure:

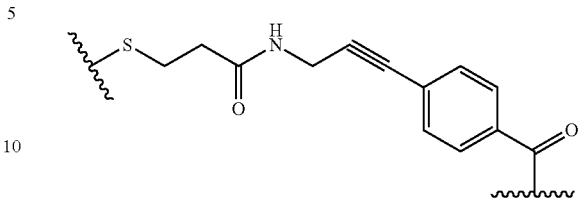

The peptides were then tested for agonist activity at the GLP-1 receptor and antagonist activity at the glucagon receptor as essentially described herein. The results are shown in Table 21.

TABLE 21

| Peptide | SEQ ID NO: | Glucagon antagonism IC50(nM) (inhibit 0.2-0.8 nM glucagon) | GLP-1 agonism EC50 (nM) |
|---|---|---|---|
| Glucagon | 1 | 0.1~0.5 (EC50) | |
| GLP-1 | | | 0.01~0.05 |
| [PLA6, K12E16(lactam), D28]G(6-29) | 75 | 58.3 ± 3.3 a | 38.5 ± 7.6 a |
| [PLA6, K12E16(lactam), C24(20 kDa), D28]G(6-29) | 88 | 628 ± 120 (n = 1) | 550~753 (n = 3) |
| [PLA6, K12E16(Lactam), D28,CEX-C40(20 kDa)]G(6-40) | 89 | Not antagonist (n = 1) | 657 ± 28 (n = 1) |
| [PLA6, E16K20(lactam), D28]G(6-29) | 76 | 5~27 (n = 10) | 5~28 (n = 10) |
| [PLA6, E16K20(Lactam), C24(20 kDa), D28]G(6-29) | 90 | 374~1462 (n = 3) | 450~1842 (n = 4) |
| [PLA6, E9,E16K20(Lactam), C24(20 kDa)]G(6-29) | 114 | Not detect | 825 (n = 1) |
| [PLA6, E16K20(Lactam), D28,CEX-C40(20 kDa)]G(6-40) | 91 | 350~500 (n = 5) | 75~100 (n = 5) |
| [PLA6, E16K20(Lactam), K24(COCH$_2$CH$_2$S-20 kDa)] G(6-29) | 115 | 300~400 (n = 3) | 16~20 (n = 2) |
| [PLA6,E16K20(Lactam), K24(rigid-S-20 kDa)]G(6-29) | 116 | 393~620 (n = 2) | 1362~2675 (n = 2) |
| [PLA6, E16K20(Lactam),D28,GP-C40(20 kDa)]G(6-40) | 117 | 423 ± 133 (n = 1) | 43.6 ± 32 (n = 1) |
| [PLA6, E16K20(Lactam),D28,G29, CEX-C40(20 kDa)]G(6-40) | 118 | 335 ± 86 (n = 1) | 180.2 ± 64 (n = 1) |

As shown in Table 21, pegylation generally increased the IC50 at the glucagon receptor and increased the EC50 at the GLP-1 receptor.

The effect of fatty acid acylation of glucagon antagonist/GLP-1 agonist peptides was explored by making and testing the glucagon antagonist/GLP-1 agonist peptide [PLA6, E16K20(lactam),D28]G(6-29) comprising a C16 fatty acid attached to a Lys residue of the peptide via a glutamic acid residue spacer, wherein the Lys residue varied in amino acid position within the sequence of the glucagon antagonist/GLP-1 agonist peptide. The results are shown in Table 22.

TABLE 22

| Peptide | SEQ ID NO: | Glucagon antagonism IC50 (nM, inhibit 0.4 nM glucagon) | GLP-1 agonism EC50 (nM) |
|---|---|---|---|
| Glucagon | 1 | 0.14 (EC50) | |
| GLP-1 | | | 0.06 |

TABLE 22-continued

| Peptide | SEQ ID NO: | Glucagon antagonism IC50 (nM, inhibit 0.4 nM glucagon) | GLP-1 agonism EC50 (nM) |
|---|---|---|---|
| [PLA6, E16K20(lactam),D28]G(6-29) | 76 | 5~27 (n = 10) | 20.73 ± — |
| [C16FA-O-PLA6, E16K20(lactam),D28]G(6-29) | 92 | 337.8 ± 79.7 | 45.7 ± 13.8 |
| [PLA6, K10(EC16FA), E16K20(lactam),D28]G(6-29) | 93 | 31.1 ± 4.1 | 128.8 ± 38.7 |
| [PLA6, E16, K20(EC16FA), D28]G(6-29) | 94 | 576.5 ± 20.7 | 1290 ± 331 |
| [PLA6, E16K20(lactam), K24(EC16FA), D28]G(6-29) | 95 | 371.9 ± 40.0 | 292.7 ± 40.4 |
| [PLA6, E16K20(lactam), D28, K29(EC16FA)]G(6-29) | 96 | 386.4 ± 26.2 | 1412 ± 407 |
| [PLA6, K10(EC16FA), E16, K20,D28]G(6-29) | 106 | 221.9 ± 41.7 | 105.0 ± 30.3 |

Example 21

All peptides described herein comprised a C-terminal amide in place of the C-terminal carboxylate, unless otherwise noted. The amino acid positions designated in the name of the peptide are in accordance with the numbering of native glucagon.

The cholesterol-modified peptides were prepared by conjugating lactamized peptides with a bromoacetylated cholesterol derivative in solution. The peptides were assembled using conventional solid-phase peptide synthesis (SPPS). The PLA derivatized peptide chain was cyclized via a lactam bridge. The standard cleavage procedure and purification method were applied to obtain the desired depsipeptide.

Example

Synthesis of cholesterol conjugated lactam-bridge peptide [PLA6, K10(COCH2CH2S-Chol), E16K20(lactam), D28]G(6-29) amide A peptidyl resin with sequence HO-PLA-TSDKSKY-LDERRAKDFVQWLMDT (SEQ ID NO: 106) [PLA6, K10, E16, K20, D28]glucagon(6-29) was synthesized by solid-phase Boc-chemistry using an ABI 430A automated peptide synthesizer with 0.2 mmole MBHA amide resin and DEPBT as coupling reagent. The following Boc amino acids were used: Ala, Arg(Tos), Asp(OcHx), Asn(Xan), Glu(OcHx), Gln (Xan), Leu, Lys(2-Cl—Z), Met, PLA, Ser(OBzl), Thr(OBzl), Trp(CHO), Tyr(2.6-di-Cl-Bzl) and Val except the glutamic acid at position 16 was incorporated with Boc-Glu(OFm)-OH, lysine at position 20 was incorporated with Boc-Lys(Fmoc)-OH and lysine at position 10 was incorporated with Boc-Lys(Alloc)-OH. After removal of Fm and Fmoc protecting groups at positions 16 and 20 with 20% piperidine in DMF, the peptidyl resin was treated with 300 mg (1 mmol) DEPBT in 10% DIEA/DMF for about 4 h to form the lactam bridge. This lactam-bridged peptidyl resin was treated a solution composed of 100 mg (0.4 equiv.) Pd(PPh$_3$)$_4$, 120 uL PhSiH$_3$, 0.25 mL N-methylmorpholine and 0.5 mL acetic acid in 10 mL CHCl$_3$ under N$_2$ atmosphere for about 3 h to remove the Alloc group. The 3-tritylthiopropionic acid was then coupled by DEPBT to obtain the peptidyl resin with a sequence of: HO-PLA-Thr-Ser-Asp-Lys(COCH$_2$CH$_2$SH)-Ser-Lys-Tyr-Leu-Asp-Glu*-Arg-Arg-Ala-Lys*-Asp-Phe-Val-Gln-Trp-Leu-Met-Asp-Thr-NH$_2$. (SEQ ID NO: 106; * are lactam bridged)

The peptidyl resin was treated with liquid hydrogen fluoride to cleave the crude peptide from the solid support and remove all protecting groups. The peptide was purified by preparative HPLC, and analyzed by MS and analytical RP-HPLC. The purified peptide demonstrated a single peak in analytical RP-HPLC and the ESI-MS analysis yielded the desired mass of 3050.7 which corresponds with the calculated molecular weight of 3051.0 daltons of the peptide [PLA6, K10(CH2CH2SH), E16K20(lactam), D28]G(6-29) amide.

To synthesize the cholesterol conjugated peptide [PLA6, K10(COCH2CH2S-Chol), E16K20(lactam), D28]G(6-29) amide, 10 mg (3.28 µM) of [PLA6, K10(COCH2CH2SH), E16K20(lactam), D28]G(6-29) amide was dissolved in 2 mL of 7 M urea buffer containing 50 mM Tris-HCl (pH 8.0). To this solution was added 10 mg (9 µM) of cholesterol reagent Br-Oxa$_{12}$-Chol (see the structure below), at room temperature. The reaction was monitored by HPLC. After about 4 h, the reaction solution was purified directly by HPLC. The purified cholesterol conjugated peptide demonstrated a single peak in analytical chromatography and the ESI-MS analysis yielded the desired mass of 4074.13 which corresponds with the calculated molecular weight of 4073.0 of the cholesterol conjugated lactam-bridge peptide [PLA6, K10 (COCH2CH2S-Chol), E16K20(lactam), D28]G(6-29) amide.

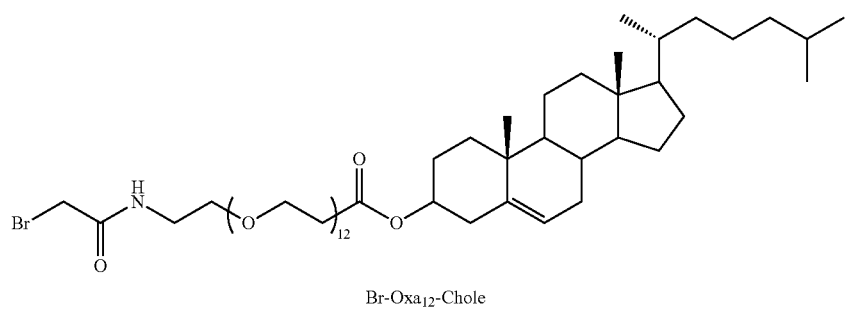

Br-Oxa$_{12}$-Chole

Similar procedures were used to synthesize the other cholesterol conjugated and lactam-bridged peptides such as [PLA6, E16K20(lactam), D28, K30(COCH2CH2S-Chol)]G(6-30) amide and [PLA6, E16K20(lactam), D28, K40(COCH2CH2S-Chol)]G(6-40) amide reported in this patent.

The cholesterolylated peptides were tested for agonist activity at the GLP-1 receptor and antagonist activity at the glucagon receptor as essentially described in Example 13. The EC50 of the peptides at the GLP-1 receptor and the IC50 of the peptide at the glucagon receptor stimulated with 0.4 nM glucagon are shown in Table 23.

16 (according to the numbering of native glucagon) and comprising a C-terminal amide (SEQ ID NO: 97) was made and tested for glucagon antagonist activity and GLP-1 agonist activity. The IC50 at the glucagon receptor in response to 0.2 nM glucagon was 7.04 (0.69) in one assay and 22.0 (2.84) in another (SD provided in parentheses). The EC50 at the GLP-1 receptor was 795 (31.2).

Example 23

All peptides described herein comprised a C-terminal amide in place of the C-terminal carboxylate, unless otherwise noted. The amino acid positions designated in the name of the peptide are in accordance with the numbering of native glucagon.

TABLE 23

| Peptide | SEQ ID NO: | Glucagon antagonism IC50 (nM, inhibit 0.4 nM glucagon) | GLP-1 agonism EC50 (nM) |
|---|---|---|---|
| Glucagon | 1 | 0.118 (0.01) = EC50 | |
| GLP-1 | | | 0.043 (0.003) |
| PLA6D9(E16K20)D28G(6-29) | 60 | 4.14; 7.99* | 47.96 (10.8) |
| Aib depsi lactam G(2-29) | 70 | 11.82 (1.83) | 5.83 (0.9) |
| K10-chol G(6-29) | 67 | 271.49 (60.07) | 35.25 (10.0) |
| K30-chol G(6-30) | 68 | 575.20 (77.91) | 14.38 (2.8) |
| K40-chol G(6-40) | 69 | 311.55 (102.98) | 47.05 (14.6) |

Standard deviation shown in ( ).
*Results of two different assays shown.

Example 22

All peptides described herein comprised a C-terminal amide in place of the C-terminal carboxylate, unless otherwise noted. The amino acid positions designated in the name of the peptide are in accordance with the numbering of native glucagon.

The effect of stabilization of the alpha helix through incorporation of an alpha, alpha di-substituted amino acid on glucagon antagonist/GLP-1 peptides was explored. A peptide comprising amino acids 6-29 of glucagon modified to comprise PLA in place of the Phe at position 6 and AIB at position Glucagon antagonist/GLP-1 agonist peptides were modified to PLA-containing depsipeptides and/or to comprise the native amino acids of GLP-1 at positions 2 and 3 in place of the native amino acids of glucagon at these positions (numbering according to native GLP-1 and glucagon). The peptides were then tested for glucagon antagonist and GLP-1 activities. The results of the assay are shown in Table 24.

TABLE 24

| Peptide | SEQ ID NO: | Glucagon antagonism IC50 (nM, inhibit 0.8 nM glucagon) | GLP-1 agonism EC50 (nM) |
|---|---|---|---|
| Glucagon | 1 | 0.323 (EC50) | |
| GLP-1 | | | 0.057 |
| [PLA6, E16K20(lactam), D28] G(6-29) | 60 | 20.34 ± 1.8 | 18.22 ± 0.56 |
| [PLA6, E9] G(6-29) | 61 | 94.68 ± 17.95 | 900.72 ± 818.56 |
| [PLA6, E9K12(Lactam)] G(6-29) | 62 | 72.47 ± 7.04 | 143.95 ± 21.62 |

TABLE 24-continued

| Peptide | SEQ ID NO: | Glucagon antagonism IC50 (nM, inhibit 0.8 nM glucagon) | GLP-1 agonism EC50 (nM) |
|---|---|---|---|
| [A2E3, E9, E16K20(Lactam), D28] G(2-29) | 63 | 151.46 * | 298.56* |
| [A2E3-O-PLA6, D9, E16K20(Lactam), D28] G(2-29) | 64 | 21.80 ± 6.45 | 18.01 ± 2.14 |
| [S2Q3, E9, E16K20(Lactam), D28] G(2-29) | 65 | 23.37 * | 283.53* |
| [S2Q3-O-PLA6, D9, E16K20(Lactam), D28] G(2-29) | 66 | 20.85 ± 3.09 | 112.21 ± 11.12 |

Example 24

All peptides described herein comprised a C-terminal amide in place of the C-terminal carboxylate, unless otherwise noted. The amino acid positions designated in the name of the peptide are in accordance with the numbering of native glucagon.

The following peptides were synthesized as generally described above and subsequently tested for the ability to stimulate the GLP-1 receptor by assaying cAMP release from cells expressing the human GLP-1 receptor and for the ability to stimulate the glucagon receptor by assaying cAMP release from cells expressing the human glucagon receptor and stimulated with 0.5 nM glucagon, as generally described in Example 13. The results of the assays are shown in Table 25.

TABLE 25

| Peptide | Glucagon antagonism IC50(nM, inhibit 0.5nM G) | GLP-1 agonism EC50(nM) |
|---|---|---|
| Glucagon | 0.005 ± 0.008 | |
| GLP-1 | | 0.005 ± 0.002 |
| [PLA6, E9]Glucagon(6-29) *PLA* TSEYSKYLDSRRAQDFVQWLMNT-NH$_2$ (SEQ ID NO: 61) | 23.75 ± 4.16 | No agonism |
| [PLA6, D9, D28]Glucagon(6-29) *PLA* TSDYSKYLDSRRAQDFVQWLMDT-NH$_2$ (SEQ ID NO: 110) | 9.03 ± 1.54 | 746.0 ± 225.7 |
| [E9]Glucagon (2-29) SQGTFTSEYSKYLDSRRAQDFVQWLMNT-NH$_2$ (SEQ ID NO: 111) | 340.0 ± 149.0 | 2719.8 ± 2136.4 |
| [Thr5-O-PLA6,E9]Glucagon(2-29) SQGT(O*)FTSEYSKYLDSRRAQDFVQWLMNT-NH$_2$ (SEQ ID NO: 112) | 6.49 ± 2.17 | 1305.6 ± 241.5 |
| [Thr5-O-PLA6,E9]Glucagon(1-29) HSQGT(O*)FTSEYSKYLDSRRAQDFVQWLMNT-NH$_2$ (SEQ ID NO: 113) | 14.19 ± 7.89 | 721.0 ± 35.5 |

(O*) represents a depsipeptide bond.

The invention claimed is:

1. A glucagon antagonist/GLP-1 agonist comprising the sequence of SEQ ID NO: 51, wherein the amino acids at positions 4 and 7, positions 7 and 11, positions 11 and 15, positions 15 and 19, or positions 19 and 23 of SEQ ID NO: 51 are linked via a lactam bridge, or an oxy derivative of the glucagon antagonist/GLP-1 agonist.

2. A glucagon antagonist/GLP-1 agonist peptide comprising an intramolecular bridge formed between two amino acid side chains of the glucagon peptide and an amino acid sequence of SEQ ID NO: 51 or a derivative thereof wherein the derivative differs from the peptide of SEQ ID NO: 51 by amino acid substitutions at one to three amino acid positions selected from positions 1, 5, 6, 8, 9, 12, 13 and 14, said peptide exhibiting at least 90% of the maximum agonism of native GLP-1 at the GLP-1 receptor, and exhibiting glucagon antagonist activity, that reduces the maximum glucagon-induced cAMP production by the glucagon receptor by at least about 80%, as measured by cAMP production in an in vitro assay.

3. A peptide comprising (1) an intramolecular bridge, or an alpha, alpha-di-substituted amino acid, or an acidic amino acid at position 16 (according to the numbering of SEQ ID NO: 1), or a combination thereof, (2) a C-terminal amide or ester in place of a C-terminal carboxylate, and (3) a general structure of A-B-C,
  wherein A is selected from the group consisting of
    (i) phenyl lactic acid (PLA);
    (ii) an oxy derivative of PLA; and
    (iii) a peptide of 2 to 6 amino acids in which two consecutive amino acids of the peptide are linked via an ester or ether bond;
  wherein B represents amino acids p to 26 of SEQ ID NO: 1, wherein p is 3, 4, 5, 6, or 7, optionally comprising one or more amino acid modifications selected from the group consisting of:

(iv) Asp at position 9 (according to the amino acid numbering of SEQ ID NO: 1) is substituted with a Glu, a sulfonic acid derivative of Cys, homoglutamic acid, β-homoglutamic acid, or an alkylcarboxylate derivative of cysteine having the structure of:

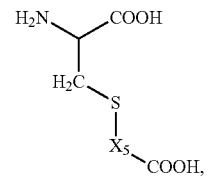

wherein $X_5$ is $C_1$-$C_4$ alkyl, $C_2$-$C_4$ alkenyl, or $C_2$-$C_4$ alkynyl;

(v) substitution of one or two amino acids at positions 10, 20, and 24, (according to the amino acid numbering of SEQ ID NO: 1) with an amino acid covalently attached to an acyl or alkyl group via an ester, ether, thioether, amide, or alkyl amine linkage;

(vi) substitution of one or two amino acids at positions 16, 17, 20, 21, and 24 (according to the amino acid numbering of SEQ ID NO: 1) with an amino acid selected from the group consisting of: Cys, Lys, ornithine, homocysteine, and acetyl-phenylalanine (Ac-Phe), wherein the amino acid of the group is covalently attached to a hydrophilic moiety;

(vii) Asp at position 15 (according to the numbering of SEQ ID NO: 1) is substituted with cysteic acid, glutamic acid, homoglutamic acid, and homocysteic acid;

(viii) Ser at position 16 (according to the numbering of SEQ ID NO: 1) is substituted with cysteic acid, glutamic acid, homoglutamic acid, and homocysteic acid;

(ix) Arg at position 17 is replaced with Gln, Arg at position 18 is replaced with Ala, Asp at position 21 is replaced with Glu, Val at position 23 is replaced with Ile, and Gln at position 24 is replaced with Ala (according to amino acid numbering of SEQ ID NO: 1);

(x) Ser at position 16 is replaced with Glu, Gln at position 20 is replaced with Glu, or Gln at position 24 is replaced with Glu (according to the amino acid numbering of SEQ ID NO: 1);

wherein C is selected from the group consisting of:

(vii) X;

(viii) X-Y;

(ix) X-Y-Z;

(x) X-Y-Z-R10;

wherein X is Met, Leu, or Nle; Y is Asn or a charged amino acid; Z is Thr, Gly, Cys, Lys, ornithine (Orn), homocysteine, acetyl phenylalanine (Ac-Phe), or a charged amino acid; wherein R10 is selected from a group consisting of SEQ ID NOs: 21, 26, 27, and 50.

4. The peptide of claim 3, wherein the oxy derivative of PLA is a depsipeptide comprising PLA covalently linked via an ester bond to an amino acid or a peptide.

5. The peptide of claim 4, wherein the depsipeptide comprises PLA covalently linked via an ester bond to $Xaa_3$, or to a peptide $Xaa_2$-$Xaa_3$ or $Xaa_1$-$Xaa_2$-$Xaa_3$, wherein $Xaa_3$ is Gln or Glu, $Xaa_2$ is selected from a group consisting of: Ser, D-serine, D-alanine, valine, glycine, N-methyl serine, N-methyl alanine, and aminoisobutyric acid (AIB); and $Xaa_1$ is selected from a group consisting of: His, D-histidine, alpha, alpha-dimethyl imidiazole acetic acid (DMIA), N-methyl histidine, alpha-methyl histidine, imidazole acetic acid, desaminohistidine, hydroxyl-histidine, acetyl-histidine and homo-histidine.

6. The peptide of claim 3, wherein B represents amino acids 7 to 26 of SEQ ID NO: 1.

7. The peptide of claim 3, wherein B comprises the amino acid modification designated as (v) or (vi), or a combination thereof.

8. The peptide of claim 7, wherein B further comprises one or more amino acid modifications selected from the group consisting of (iv), (vii), (viii), (ix), (x), and a combination thereof.

9. The peptide of claim 3, comprising a hydrophilic moiety covalently bound to an amino acid residue at position 16, 21, or 24 according to the amino acid numbering of SEQ ID NO: 1, or the C-terminal residue of the peptide.

10. The peptide of claim 3, comprising an amino acid covalently attached to an acyl group or alkyl group via an ester, ether, thioether, amide, or alkyl amine linkage, wherein the amino acid is at position 10, 20, or 24 (according to the amino acid numbering of SEQ ID NO: 1).

11. The peptide of claim 3, wherein the intramolecular bridge is a lactam bridge or a salt bridge.

12. The peptide of claim 11, comprising a lactam bridge between the amino acids at positions 9 and 12, the amino acids at positions 12 and 16, the amino acids at positions 16 and 20, the amino acids at positions 20 and 24, or the amino acids at positions 24 and 28 (according to the amino acid numbering of SEQ ID NO: 1).

13. The peptide of claim 3, comprising AIB at position 16, 20, 21, or 24 (according to the amino acid numbering of SEQ ID NO: 1).

14. The peptide of claim 3, comprising the amino acid sequence of any of SEQ ID NOs: 60-70, 73-78, 80-88, 90-96, 103, 104, 106, and 114-118, or comprising the amino acid sequence of any of Peptides 2-6 of Table 13, Peptides 1-8 of Table 14, and Peptides 2-6, 8, and 9 of Table 15.

15. A multimer or dimer comprising a peptide of claim 3.

16. A conjugate comprising a peptide of claim 3 and a heterologous peptide or polypeptide.

17. A pharmaceutical composition comprising a peptide of claim 3, and a pharmaceutically acceptable carrier.

18. A method of treating hyperglycemia or diabetes in a patient in need thereof, comprising administering to the patient the pharmaceutical composition of claim 17 in an amount effective to treat the hyperglycemia or diabetes.

19. A method of suppressing appetite, reducing weight gain, or inducing weight loss in a patient in need thereof, comprising administering to the patient the pharmaceutical composition of claim 17 in an amount effective to suppress appetite, reduce weight gain, or induce weight loss.

20. A kit comprising a peptide of claim 3 and a set of user instructions.

21. The peptide of claim 14, comprising the amino acid sequence of SEQ ID NO: 76.

22. The peptide of claim 21, comprising a hydrophilic moiety covalently bound to an amino acid residue at position 16, 21, or 24 according to the amino acid numbering of SEQ ID NO: 1, or the C-terminal residue of the peptide, wherein the hydrophilic moiety is a polyethylene glycol chain.

* * * * *